(12) United States Patent
Ueda et al.

(10) Patent No.: US 8,835,411 B2
(45) Date of Patent: Sep. 16, 2014

(54) HIV INTEGRASE INHIBITORS

(75) Inventors: Yasutsuga Ueda, Clinton, CT (US);
Timothy P. Connolly, Portland, CT (US); Barry L. Johnson, Wallingford, CT (US); Chen Li, South Glastonbury, CT (US); B. Narasimhulu Naidu, Durham, CT (US); Manoj Patel, Berlin, CT (US); Kevin Peese, Haddam, CT (US); Margaret E. Sorenson, Meriden, CT (US); Michael A. Walker, Durham, CT (US); Michael S. Bowsher, Prospect, CT (US); Rongti Li, Port Lavaca, TX (US)

(73) Assignee: Bristol-Myers Squibb Company, Princetown, NJ (US)

( * ) Notice: Subject to any disclaimer, the term of this patent is extended or adjusted under 35 U.S.C. 154(b) by 0 days.

(21) Appl. No.: 13/312,483

(22) Filed: Dec. 6, 2011

(65) Prior Publication Data
US 2012/0309698 A1    Dec. 6, 2012

Related U.S. Application Data

(60) Provisional application No. 61/421,843, filed on Dec. 10, 2010.

(51) Int. Cl.
*C07D 519/00* (2006.01)
*C07D 487/08* (2006.01)

(52) U.S. Cl.
CPC ............ *C07D 487/08* (2013.01); *C07D 519/00* (2013.01)
USPC ......... 514/176; 514/210.21; 534/560; 536/53

(58) Field of Classification Search
CPC .......................... C07D 519/00; C07D 487/08
USPC ................. 514/176, 210.21; 534/560; 536/53
See application file for complete search history.

(56) References Cited

U.S. PATENT DOCUMENTS

| | | | |
|---|---|---|---|
| 7,745,453 B2 | 6/2010 | Mikamiyama | |
| 8,129,398 B2 | 3/2012 | Beaulieu | |
| 2012/0022045 A1 * | 1/2012 | Venkatraman et al. | .. 514/214.02 |

OTHER PUBLICATIONS

Muraglia et al. Design and synthesis of bicyclic pyrimidinones as potent and orally bioavailable HIV-1 integrase inhibitors. J Med Chem 51:861-874, 2008.*
Muraglia, *J. Med. Chem.* 2008, 51, 861.

* cited by examiner

*Primary Examiner* — Brandon Fetterolf
*Assistant Examiner* — Yih-Horng Shiao
(74) *Attorney, Agent, or Firm* — James Epperson

(57) ABSTRACT

The disclosure generally relates to the novel compounds of formula I, including their salts, which inhibit HIV integrase and prevent viral integration into human DNA. This action makes the compounds useful for treating HIV infection and AIDS. The invention also encompasses pharmaceutical compositions and methods for treating those infected with HIV.

I

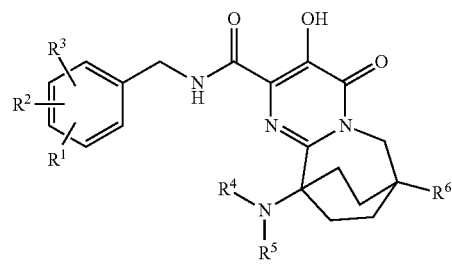

9 Claims, No Drawings

HIV INTEGRASE INHIBITORS

CROSS REFERENCE TO RELATED APPLICATIONS

This patent application claims the benefit of U.S. provisional patent application No. 61/421,843 filed Dec. 10, 2010.

BACKGROUND OF THE INVENTION

The disclosure generally relates to the novel compounds of formula I, including their salts, which inhibit HIV integrase and prevent viral integration into human DNA. This action makes the compounds useful for treating HIV infection and AIDS. The invention also encompasses pharmaceutical compositions and methods for treating those infected with HIV.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into four classes based on the viral protein they target and their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleoside reverse transcriptase inhibitors that behave as substrate mimics to halt viral cDNA synthesis. The non-nucleoside reverse transcriptase inhibitors, nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. Used alone these drugs are effective in reducing viral replication. There are also peptidomimetic protease inhibitors including saquinavir, indinavir, ritonavir, nelfinavir, amprenavir, lopinavir, darunavir, atazanavir, and tipranavir, and integrase inhibitors such as raltegravir. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Further, J.; Satten, G. A.; Aschman, D. J.; Holmberg, S. D. *N. Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly, there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase is a component of the pre-integration complex of the virus that is assembled in the cell shortly after infection (Chiu, T. K.; Davies, D. R. *Curr. Top. Med. Chem.* 2004, 4, 965-977). This enzyme catalyzes the integration of proviral DNA into the host genome and is absolutely required for viral infectivity. Early experiments showed that mutating the active site of integrase within a proviral clone produces virus unable to replicate due to its inability to insert into the host chromosome (Englund, G.; Theodore, T. S.; Freed, E. O.; Engleman, A.; Martin, M. A. *J. Virol.* 1995, 69, 3216-3219). Selective HIV integrase inhibitors have been shown to possess effective anti-HIV activity in cell culture (Hazuda, D. J.; Felock, P.; Witmer, M.; Wolfe, A; Stillmock, K.; Grobler, J. A.; Espeseth, A.; Gabryelski, L.; Schleif, W.; Blau, C.; Miller, M. D. *Science*, 2000, 287, 646-650), and it is clear that this class of inhibitors is very effective as part of a combination regimen containing HIV inhibitors of different classes. An HIV integrase inhibitor, raltegravir (Isentress®), has been approved for use in treatment experienced patients based upon 48 week trial results (Cooper, D. A.; Gatell, J.; Rockstroh, J.; Katlama, C.; Yeni, P.; Lazzarin, A.; Xu, X.; Isaacs, R.; Teppler, H.; Nguyen, B. Y. *15th Conference on Retroviruses and Opportunistic Infections*, Boston, Mass., Feb. 3-6, 2008 Abst. 105LB: Evering, T. H.; Markowitz, M. *Drugs Today*, 2007, 43, 865-877). In addition, a second integrase inhibitor, elvitegravir (GS-9137), completed a successful Phase II trial in combination with ritonavir boosting in naive and treatment experienced patients (Zolopa, A. *14th Conference on Retroviruses and Opportunistic Infections*, Los Angeles, Calif. Feb. 25-28, 2007 Abst. 143LB). Thus, HIV-1 integrase is a promising target for novel anti-HIV-1 therapeutics.

HIV integrase inhibitors have been disclosed. See, for example, PCT patent application publications WO05/061501 and WO2010/088167.

The invention provides technical advantages, for example, the compounds are novel and inhibit HIV integrase. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of formula I

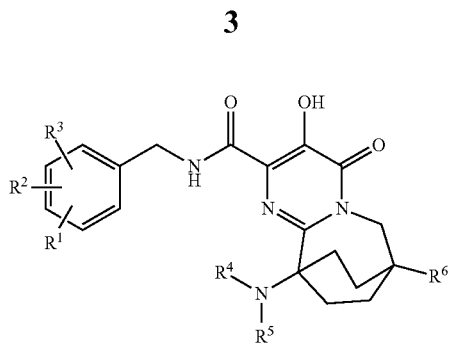

where:
R¹ is hydrogen, halo, or alkyl;
R² is hydrogen, halo, or alkyl;
R³ is hydrogen, halo, or alkyl;
provided that at least one of R¹, R², or R³ is not hydrogen;
R⁴ is alkylCO, (tetrahydropyranyl)CO, CO(Ar¹), CO₂R⁷, CON(R⁸)(R⁹), COCO₂R⁷, or COCON(R⁸)(R⁹);
R⁵ is hydrogen or alkyl;
R⁶ is halo, cyano, N(R⁸)(R⁹), azidoalkyl, haloalkyl, cyanoalkyl, hydroxyalkyl, alkoxyalkyl, (OCO₂R⁷)alkyl, (OCON(R⁸)(R⁹))alkyl, (OCOCO₂R⁷)alkyl, (OCOCON(R⁸)(R⁹))alkyl, (OP(O)(OR⁷)₂)alkyl, (alkylSO₃)alkyl, (phenylSO₃)alkyl, (tolylSO₃)alkyl, (N(R⁸)(R⁹))alkyl, (alkylCONR⁸)alkyl, (pyridinyloxy)alkyl, (alkylthio)alkyl, (N-methylimidazolylthio)alkyl, (N-methyltetrazolylthio)alkyl, (pyridinylthio)alkyl, (alkylSO)alkyl, (alkylSO₂)alkyl, (Ar²)alkyl, or Ar²;
or R⁶ is CO₂R⁷, CO(N(R⁸)(R⁹)), CO(N(R¹⁰)(R¹¹)), CO(N(Ar²)(R¹¹)), or CO(N((Ar²)alkyl)(R¹¹));
or R⁶ is N(R¹¹)CO(R¹²) or N(R¹¹)((CO(R¹²)alkyl);
R⁷ is hydrogen, alkyl, or benzyl;
R⁸ is hydrogen, alkyl, cycloalkyl, haloalkyl, (cycloalkyl)alkyl, hydroxyalkyl, alkoxyalkyl or dialkylaminoalkyl;
R⁹ is hydrogen, alkyl, cycloalkyl, haloalkyl, (cycloalkyl)alkyl, hydroxyalkyl, alkoxyalkyl or dialkylaminoalkyl;
or N(R⁸)(R⁹) taken together is azetidinyl, pyrrolidinyl, piperidinyl, piperazinyl, morpholinyl, or homopiperazinyl, and is substituted with 0-3 substituents selected from halo, alkyl, haloalkyl, hydroxy, alkylcarbonyl, and alkylsulfonyl;
or N(R⁸)(R⁹) taken together is piperazinyl substituted with 1 substituent selected from benzyl, CONMe₂, SO₂NMe₂, tolylSO₂, SO₂NMe₂, Ar³ and COAr³;
or N(R⁸)(R⁹) taken together is selected from the group consisting of

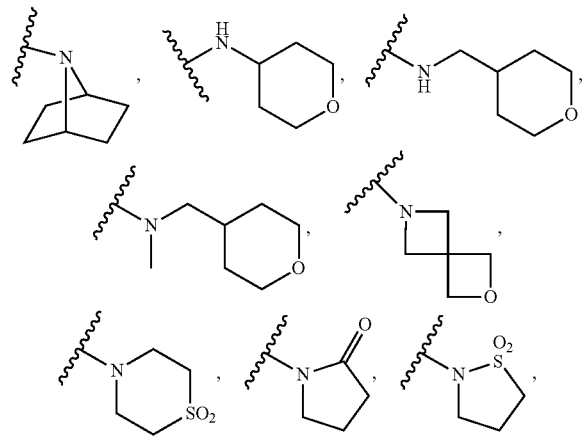

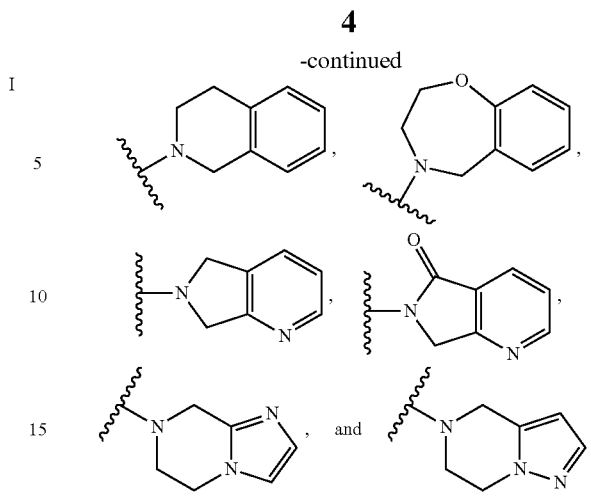

R¹⁰ is azetidinyl, pyrrolidinyl, piperidinyl, piperazinyl, or morpholinyl, and is substituted with 0-3 substituents selected from halo or alkyl;
or R¹⁰ is alkylSO₂ or cycloalkylSO₂;
R¹¹ is hydrogen or alkyl;
or N(R¹⁰)(R¹¹) taken together is azetidinyl, pyrrolidinyl, piperidinyl, piperazinyl, or morpholinyl, and is substituted with 0-3 substituents selected from halo and alkyl;
R¹² is alkyl, alkoxy, N(R⁸)(R⁹), CHO, alkylCO, alkoxyCO, CO₂R⁷, CON(R⁸)(R⁹), alkylSO₂, cycloalkylSO₂, or pyridinyl;
Ar¹ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, pyridinyl, pyridazinyl, pyrimidinyl, pyrazinyl, or hydroxypyridinyl, and is substituted with 0-3 substituents selected from the group consisting of oxo, halo, cyano, benzyl, alkyl, hydroxyl, alkoxy, N(R⁸)(R⁹), CO₂R⁷, and CON(R⁸)(R⁹);
Ar² is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, pyridinyl, pyridazinyl, or imidazolothionyl, and is substituted with 0-3 alkyl substituents; and
Ar³ is triazolyl, imidazolyl, pyrazolyl, pyrrolyl, phenyl, pyridinyl, pyridazinyl, pyrimidinyl, or pyrazinyl:
or a pharmaceutically acceptable salt thereof.

Another aspect of the invention is a compound of Formula I where
R¹ is hydrogen, halo, or alkyl;
R² is hydrogen, halo, or alkyl;
R³ is hydrogen, halo, or alkyl;
provided that at least one of R¹, R², or R³ is not hydrogen;
R⁴ is alkylCO, (tetrahydropyranyl)CO, CO(Ar¹), CO₂R⁷, CON(R⁸)(R⁹), COCO₂R⁷, or COCON(R⁸)(R⁹);
R⁵ is hydrogen or alkyl;
R⁶ is halo, cyano, N(R⁸)(R⁹), azidoalkyl, haloalkyl, cyanoalkyl, hydroxyalkyl, alkoxyalkyl, (OCO₂R⁷)alkyl, (OCON(R⁸)(R⁹))alkyl, (OCOCO₂R⁷)alkyl, (OCOCON(R⁸)(R⁹))alkyl, (OP(O)(OR⁷)₂)alkyl, (alkylSO₃)alkyl, (phenylSO₃)alkyl, (tolylSO₃)alkyl, (N(R⁸)(R⁹))alkyl, (alkylCONR⁸)alkyl, (pyridinyloxy)alkyl, (alkylthio)alkyl, (N-methylimidazolylthio)alkyl, (N-methyltetrazolylthio)alkyl, (pyridinylthio)alkyl, (alkylSO)alkyl, (alkylSO₂)alkyl, (Ar²)alkyl, or Ar²; or R⁶ is CO₂R⁷, CO(N(R⁸)(R⁹)), CO(N(R¹⁰)(R¹¹)), CO(N(Ar²)(R¹¹)), or CO(N((Ar²)alkyl)(R¹¹));
or R⁶ is N(R¹¹)CO(R¹²);
R⁷ is hydrogen, alkyl, or benzyl;
R⁸ is hydrogen, alkyl, cycloalkyl, haloalkyl, hydroxyalkyl, alkoxyalkyl or dialkylaminoalkyl;

$R^9$ is hydrogen, alkyl, cycloalkyl, haloalkyl, hydroxyalkyl, alkoxyalkyl or dialkylaminoalkyl;
or $N(R^8)(R^9)$ taken together is azetidinyl, pyrrolidinyl, piperidinyl, piperazinyl, or morpholinyl, and is substituted with 0-3 substituents selected from halo and alkyl;
$R^{10}$ is azetidinyl, pyrrolidinyl, piperidinyl, piperazinyl, or morpholinyl, and is substituted with 0-3 substituents selected from halo and alkyl;
or $R^{10}$ is alkylSO$_2$ or cycloalkylSO$_2$;
$R^{11}$ is hydrogen or alkyl;
or $N(R^{10})(R^{11})$ taken together is azetidinyl, pyrrolidinyl, piperidinyl, piperazinyl, or morpholinyl, and is substituted with 0-3 substituents selected from halo and alkyl;
$R^{12}$ is alkyl, alkoxy, $N(R^8)(R^9)$, $CO_2R^7$, $CON(R^8)(R^9)$, alkylSO$_2$, cycloalkylSO$_2$, or pyridinyl;
$Ar^1$ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, pyridinyl, pyridazinyl, pyrimidinyl, pyrazinyl, or hydroxypyridinyl, and is substituted with 0-3 substituents selected from the group consisting of oxo, halo, cyano, benzyl, alkyl, alkoxy, $N(R^8)(R^9)$, $CO_2R^7$, and $CON(R^8)(R^9)$; and
$Ar^2$ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, or imidazolothionyl, and is substituted with 0-3 alkyl substituents;
or a pharmaceutically acceptable salt thereof Another aspect of the invention is a compound of Formula I according to the following structure

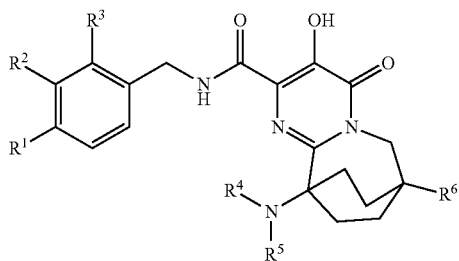

$R^1$ is hydrogen, halo, or alkyl;
$R^2$ is hydrogen, halo, or alkyl;
$R^3$ is hydrogen, halo, or alkyl;
provided that at least one of $R^1$, $R^2$, or $R^3$ is not hydrogen;
$R^4$ is alkylCO, (tetrahydropyranyl)CO, CO(Ar$^1$), $CO_2R^7$, $CON(R^8)(R^9)$, $COCO_2R^7$, or $COCON(R^8)(R^9)$;
$R^5$ is hydrogen or alkyl;
$R^6$ is halo, cyano, $N(R^8)(R^9)$, azidoalkyl, haloalkyl, cyanoalkyl, hydroxyalkyl, alkoxyalkyl, (OC(O)R$^7$)alkyl, (OCON(R$^8$)(R$^9$))alkyl, (OCOCON(R$^8$)(R$^9$))alkyl, (alkylSO$_3$)alkyl, (phenylSO$_3$)alkyl, (tolylSO$_3$)alkyl, (N(R$^8$)(R$^9$))alkyl, (alkylCONR$^8$)alkyl, (pyridinyloxy)alkyl, (alkylthio)alkyl, (N-methylimidazolylthio)alkyl, (N-methyltetrazolylthio)alkyl, (pyridinylthio)alkyl, (alkylSO)alkyl, (alkylSO$_2$)alkyl, (Ar$^2$)alkyl, or Ar$^2$;
or $R^6$ is $CO_2R^7$, $CO(N(R^8)(R^9))$, $CO(N(R^{10})(R^{11}))$, $CO(N(Ar^2)(R^{11}))$, or $CO(N((Ar^2)alkyl)(R^{11}))$;
or $R^6$ is $N(R^{11})CO(R^{12})$;
$R^7$ is hydrogen, alkyl, or benzyl;
$R^8$ is hydrogen, alkyl, cycloalkyl, haloalkyl, hydroxyalkyl, alkoxyalkyl or dialkylaminoalkyl;
$R^9$ is hydrogen, alkyl, cycloalkyl, haloalkyl, hydroxyalkyl, alkoxyalkyl or dialkylaminoalkyl;
or $N(R^8)(R^9)$ taken together is azetidinyl, pyrrolidinyl, piperidinyl, piperazinyl, or morpholinyl, and is substituted with 0-3 substituents selected from halo and alkyl;
$R^{10}$ is azetidinyl, pyrrolidinyl, piperidinyl, piperazinyl, or morpholinyl, and is substituted with 0-3 substituents selected from halo and alkyl;
or $R^{10}$ is alkylSO$_2$ or cycloalkylSO$_2$;
$R^{11}$ is hydrogen or alkyl;
$R^{12}$ is alkyl, alkoxy, $N(R^8)(R^9)$, $CO_2R^7$, $CON(R^8)(R^9)$, alkylSO$_2$, cycloalkylSO$_2$, or pyridinyl;
$Ar^1$ is isoxazolyl, pyridinyl, pyridazinyl, or hydroxypyridinyl, and is substituted with 0-1 substituents selected from the group consisting of alkyl and $CON(R^8)(R^9)$; and
$Ar^2$ is tetrazolyl, triazolyl, oxadiazolyl, imidazolyl, isoxazolyl or imidazolothionyl, and is substituted with 0-1 alkyl substituents;
or a pharmaceutically acceptable salt thereof.

Another aspect of the invention is a compound of Formula I where $R^1$ is hydrogen or fluoro; $R^2$ is hydrogen, fluoro, chloro, bromo, or methyl; $R^3$ is hydrogen, fluoro, or bromo.

Another aspect of the invention is a compound of Formula I where $R^1$ is fluoro, $R^2$ is hydrogen, and $R^3$ is hydrogen; $R^1$ is fluoro, $R^2$ is methyl, and $R^3$ is hydrogen; or $R^1$ is hydrogen, $R^2$ is chloro, and $R^3$ is fluoro.

Another aspect of the invention is a compound of Formula I where $R^4$ is $COCON(R^8)(R^9)$; $R^5$ is hydrogen or methyl; $R^8$ is hydrogen, alkyl, (cycloalkyl)alkyl, cycloalkyl, haloalkyl, hydroxyalkyl, alkoxyalkyl or dialkylaminoalkyl; $R^9$ is hydrogen, alkyl, (cycloalkyl)alkyl, cycloalkyl, haloalkyl, hydroxyalkyl, alkoxyalkyl or dialkylaminoalkyl; or $N(R^8)(R^9)$ taken together is azetidinyl, pyrrolidinyl, piperidinyl, piperazinyl, or morpholinyl, and is substituted with 0-3 substituents selected from halo and alkyl.

Another aspect of the invention is a compound of Formula I where $R^4$ is COCONMe$_2$ and $R^5$ is hydrogen or methyl.

Another aspect of the invention is a compound of Formula I where $R^4$ is COCONMe$_2$, $R^5$ is hydrogen or methyl; $R^6$ is dialkylamino, ((cycloalkyl)alkyl)(alkyl)amino, azetidinyl, pyrrolidinyl, or morpholinyl; $R^1$ is hydrogen or halo; $R^2$ is hydrogen, halo, or alkyl; and $R^3$ is hydrogen or halo.

Another aspect of the invention is a compound of Formula I where $R^6$ is $N(R^8)(R^9)$ or $(N(R^8)(R^9))$alkyl; $R^8$ is hydrogen, alkyl, (cycloalkyl)alkyl, cycloalkyl, haloalkyl, hydroxyalkyl, alkoxyalkyl or dialkylaminoalkyl; $R^9$ is hydrogen, alkyl, (cycloalkyl)alkyl, cycloalkyl, haloalkyl, hydroxyalkyl, alkoxyalkyl or dialkylaminoalkyl; or $N(R^8)(R^9)$ taken together is azetidinyl, pyrrolidinyl, piperidinyl, piperazinyl, or morpholinyl, and is substituted with 0-3 substituents selected from halo and alkyl.

Another aspect of the invention is a compound of Formula I where $R^6$ is $N(R^8)(R^9)$ or $(N(R^8)(R^9))$methyl; $R^8$ is hydrogen, alkyl, (cycloalkyl)alkyl, cycloalkyl, haloalkyl, hydroxyalkyl, alkoxyalkyl or dialkylaminoalkyl; $R^9$ is hydrogen, alkyl, (cycloalkyl)alkyl, cycloalkyl, haloalkyl, hydroxyalkyl, alkoxyalkyl or dialkylaminoalkyl; or $N(R^8)(R^9)$ taken together is azetidinyl, pyrrolidinyl, piperidinyl, piperazinyl, or morpholinyl, and is substituted with 0-3 substituents selected from halo and alkyl.

Another aspect of the invention is a compound of Formula I where $R^6$ is dialkylamino, ((cycloalkyl)alkyl)(alkyl)amino, azetidinyl, pyrrolidinyl, or morpholinyl.

Another aspect of the invention is a compound of Formula I where $R^1$ is hydrogen or halo; $R^2$ is hydrogen, halo, or methyl; and $R^3$ is hydrogen or halo.

Another aspect of the invention is a compound of Formula I where:
$R^1$ is hydrogen, halo, or alkyl;
$R^2$ is hydrogen, halo, or alkyl;

$R^3$ is hydrogen, halo, or alkyl;
provided that at least one of $R^1$, $R^2$, or $R^3$ is not hydrogen;
$R^4$ is alkylCO, (tetrahydropyranyl)CO, CO($Ar^1$), $CO_2R^7$, CON($R^8$)($R^9$), $COCO_2R^7$, or COCON($R^8$)($R^9$);
$R^5$ is hydrogen or alkyl;
$R^6$ is halo, cyano, N($R^8$)($R^9$), azidoalkyl, haloalkyl, cyanoalkyl, hydroxyalkyl, alkoxyalkyl, ($OCO_2R^7$)alkyl, (OCON($R^8$)($R^9$))alkyl, ($OCOCO_2R^7$)alkyl, (OCOCON($R^8$)($R^9$))alkyl, (OP(O)($OR^7$)$_2$)alkyl, ($alkylSO_3$)alkyl, ($phenylSO_3$)alkyl, ($tolylSO_3$)alkyl, (N($R^8$)($R^9$))alkyl, ($alkylCONR^8$)alkyl, (pyridinyloxy)alkyl, (alkylthio)alkyl, (N-methylimidazolylthio)alkyl, (N-methyltetrazolylthio)alkyl, (pyridinylthio)alkyl, (alkylSO)alkyl, ($alkylSO_2$)alkyl, ($Ar^2$)alkyl, or $Ar^2$;
or $R^6$ is $CO_2R^7$, CO(N($R^8$)($R^9$)), CO(N($R^{10}$)($R^{11}$)), CO(N($Ar^2$)($R^{11}$)), or CO(N(($Ar^2$)alkyl)($R^{11}$));
or $R^6$ is N($R^{11}$)CO($R^{12}$);
$R^7$ is hydrogen, alkyl, or benzyl;
$R^8$ is hydrogen, alkyl, cycloalkyl, haloalkyl, hydroxyalkyl, alkoxyalkyl or dialkylaminoalkyl;
$R^9$ is hydrogen, alkyl, cycloalkyl, haloalkyl, hydroxyalkyl, alkoxyalkyl or dialkylaminoalkyl;
or N($R^8$)($R^9$) taken together is azetidinyl, pyrrolidinyl, piperidinyl, piperazinyl, or morpholinyl, and is substituted with 0-3 substituents selected from halo and alkyl;
$R^{10}$ is azetidinyl, pyrrolidinyl, piperidinyl, piperazinyl, or morpholinyl, and is substituted with 0-3 substituents selected from halo and alkyl;
or $R^{10}$ is $alkylSO_2$ or $cycloalkylSO_2$;
$R^{11}$ is hydrogen or alkyl;
or N($R^{10}$)($R^{11}$) taken together is azetidinyl, pyrrolidinyl, piperidinyl, piperazinyl, or morpholinyl, and is substituted with 0-3 substituents selected from halo and alkyl;
$R^{12}$ is alkyl, alkoxy, N($R^8$)($R^9$), $CO_2R^7$, CON($R^8$)($R^9$), $alkylSO_2$, $cycloalkylSO_2$, or pyridinyl;
$Ar^1$ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, pyridinyl, pyridazinyl, pyrimidinyl, pyrazinyl, or hydroxypyridinyl, and is substituted with 0-3 substituents selected from the group consisting of oxo, halo, cyano, benzyl, alkyl, alkoxy, N($R^8$)($R^9$), $CO_2R^7$, and CON($R^8$)($R^9$); and
$Ar^2$ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, or imidazolothionyl, and is substituted with 0-3 alkyl substituents;
or a pharmaceutically acceptable salt thereof.

Another aspect of the invention is a compound of formula I according to the following structure

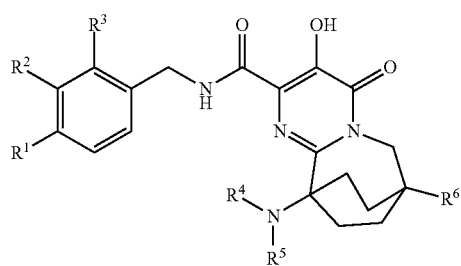

where
$R^1$ is hydrogen, halo, or alkyl;
$R^2$ is hydrogen, halo, or alkyl;
$R^3$ is hydrogen, halo, or alkyl;
provided that at least one of $R^1$, $R^2$, or $R^3$ is not hydrogen;
$R^4$ is alkylCO, (tetrahydropyranyl)CO, CO($Ar^1$), $CO_2R^7$, CON($R^8$)($R^9$), $COCO_2R^7$, or COCON($R^8$)($R^9$);
$R^5$ is hydrogen or alkyl;
$R^6$ is halo, cyano, N($R^8$)($R^9$), azidoalkyl, haloalkyl, cyanoalkyl, hydroxyalkyl, alkoxyalkyl, (OC(O)$R^7$)alkyl, (OCON($R^8$)($R^9$))alkyl, (OCOCON($R^8$)($R^9$))alkyl, ($alkylSO_3$)alkyl, ($phenylSO_3$)alkyl, ($tolylSO_3$)alkyl, (N($R^8$)($R^9$))alkyl, ($alkylCONR^8$)alkyl, (pyridinyloxy)alkyl, (alkylthio)alkyl, (N-methylimidazolylthio)alkyl, (N-methyltetrazolylthio)alkyl, (pyridinylthio)alkyl, (alkylSO)alkyl, ($alkylSO_2$)alkyl, ($Ar^2$)alkyl, or $Ar^2$;
or $R^6$ is $CO_2R^7$, CO(N($R^8$)($R^9$)), CO(N($R^{10}$)($R^{11}$)), CO(N($Ar^2$)($R^{11}$)), or CO(N(($Ar^2$)alkyl)($R^{11}$));
or $R^6$ is N($R^{11}$)CO($R^{12}$);
$R^7$ is hydrogen, alkyl, or benzyl;
$R^8$ is hydrogen, alkyl, cycloalkyl, haloalkyl, hydroxyalkyl, alkoxyalkyl or dialkylaminoalkyl;
$R^9$ is hydrogen, alkyl, cycloalkyl, haloalkyl, hydroxyalkyl, alkoxyalkyl or dialkylaminoalkyl;
or N($R^8$)($R^9$) taken together is azetidinyl, pyrrolidinyl, piperidinyl, piperazinyl, or morpholinyl, and is substituted with 0-3 substituents selected from halo and alkyl;
$R^{10}$ is azetidinyl, pyrrolidinyl, piperidinyl, piperazinyl, or morpholinyl, and is substituted with 0-3 substituents selected from halo and alkyl;
or $R^{10}$ is $alkylSO_2$ or $cycloalkylSO_2$;
$R^{11}$ is hydrogen or alkyl;
$R^{12}$ is alkyl, alkoxy, N($R^8$)($R^9$), $CO_2R^7$, CON($R^8$)($R^9$), $alkylSO_2$, $cycloalkylSO_2$, or pyridinyl;
$Ar^1$ is isoxazolyl, pyridinyl, pyridazinyl, or hydroxypyridinyl, and is substituted with 0-1 substituents selected from the group consisting of alkyl and CON($R^8$)($R^9$); and
$Ar^2$ is tetrazolyl, triazolyl, oxadiazolyl, imidazolyl, isoxazolyl or imidazolothionyl, and is substituted with 0-1 alkyl substituents;
or a pharmaceutically acceptable salt thereof.

Another aspect of the invention is a compound of formula I where $R^1$ is hydrogen or fluoro; $R^2$ is hydrogen, fluoro, chloro, bromo, or methyl; and $R^3$ is hydrogen, fluoro, or bromo.

Another aspect of the invention is a compound of formula I where $R^1$ is fluoro, $R^2$ is methyl, and $R^3$ is hydrogen or where $R^1$ is hydrogen, $R^2$ is fluoro, and $R^3$ is chloro.

Another aspect of the invention is a compound of formula I where $R^4$ is $COCONMe_2$.

Another aspect of the invention is a compound of formula I where $R^6$ is hydroxymethyl.

For a compound of Formula I, the scope of any instance of a variable substituent, including $R^1$, $R^2$, $R^3$, $R^4$, $R^5$, $R^6$, $R^7$, $R^8$, $R^9$, $R^{10}$, $R^{11}$, $R^{12}$, $Ar^1$, $Ar^2$, and $Ar^3$, can be used independently with the scope of any other instance of a variable substituent. As such, the invention includes combinations of the different aspects.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append. For example, substituents $R^1$ and $R^2$ of formula IV are intended to bond to the benzene ring of formula IV and not to the thiophene ring.

"Imidazolothionyl" means

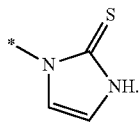

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. An example of a tautomeric pair is shown below.

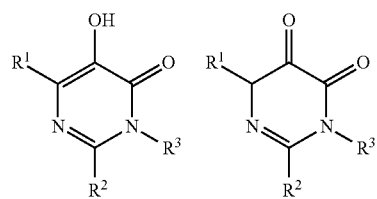

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaH-MDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

11          12
Scheme 1.
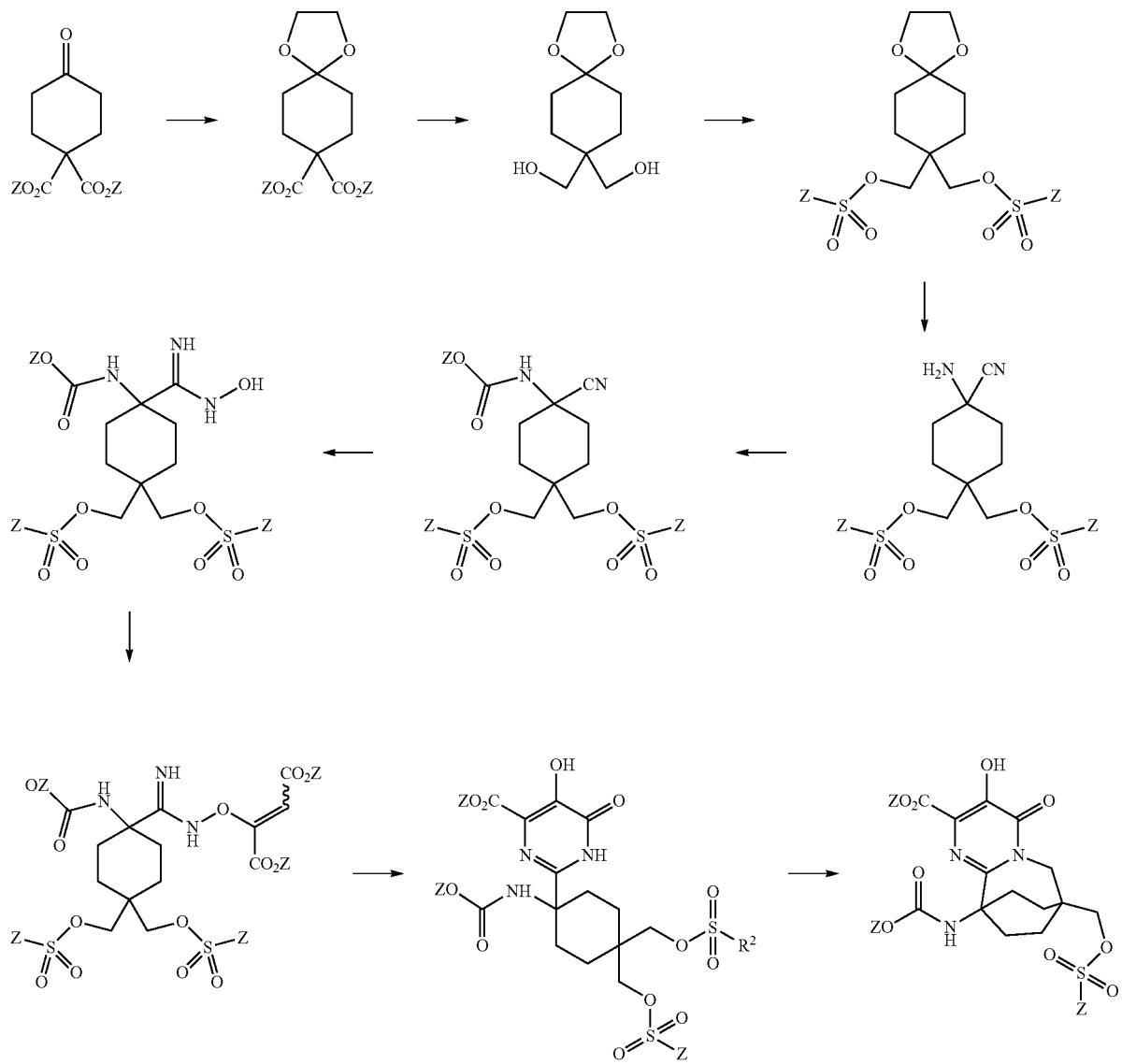
Z = alkyl or aryl
Scheme 2
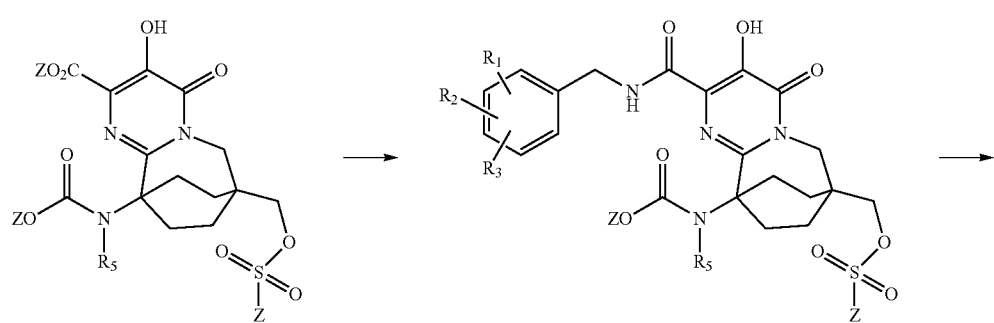

-continued
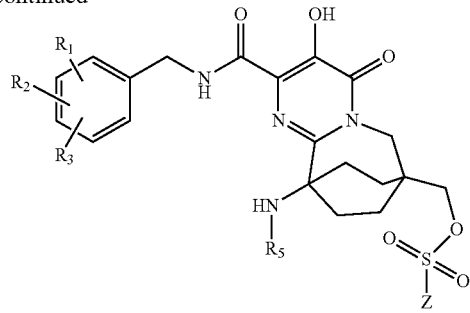
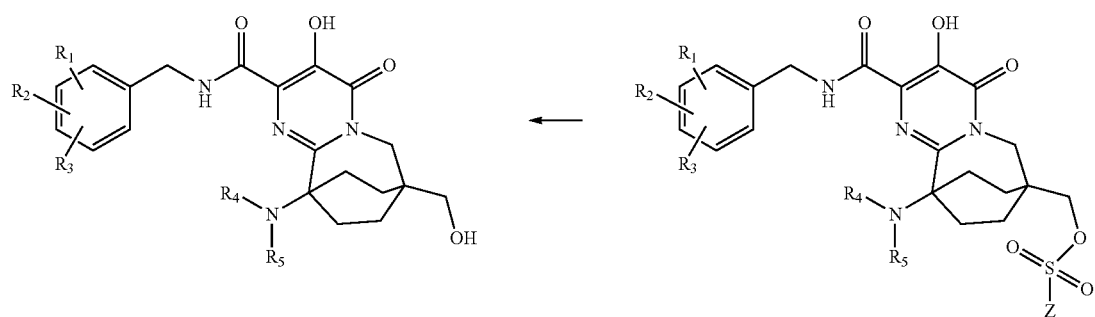
30
Scheme 3
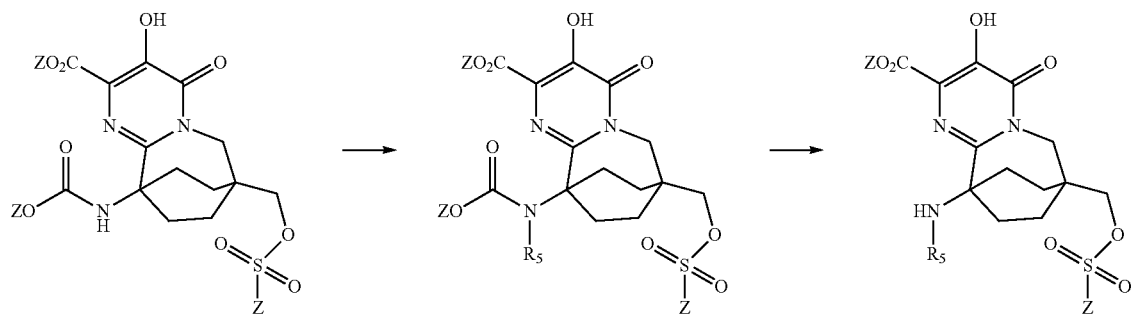
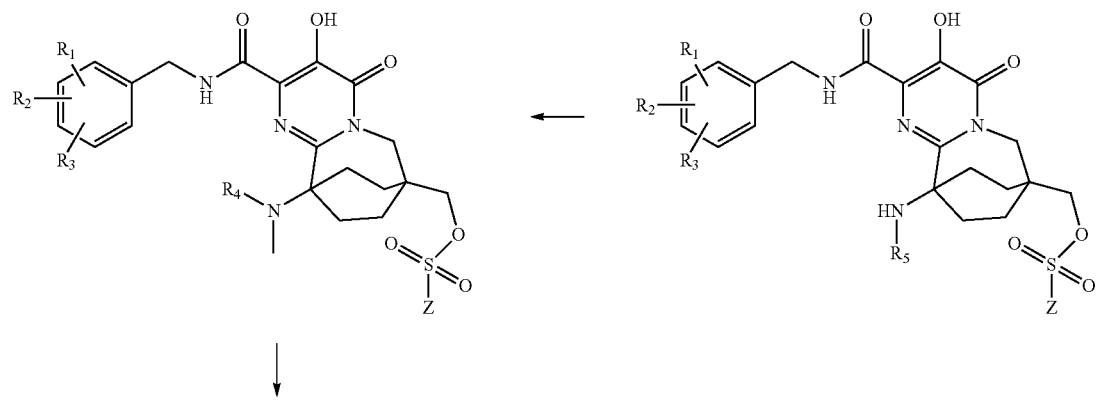

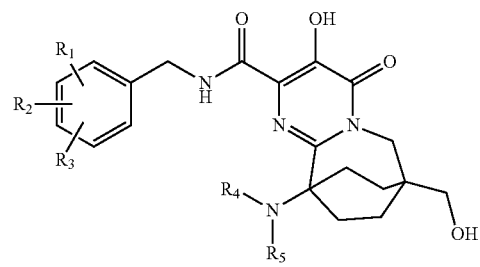
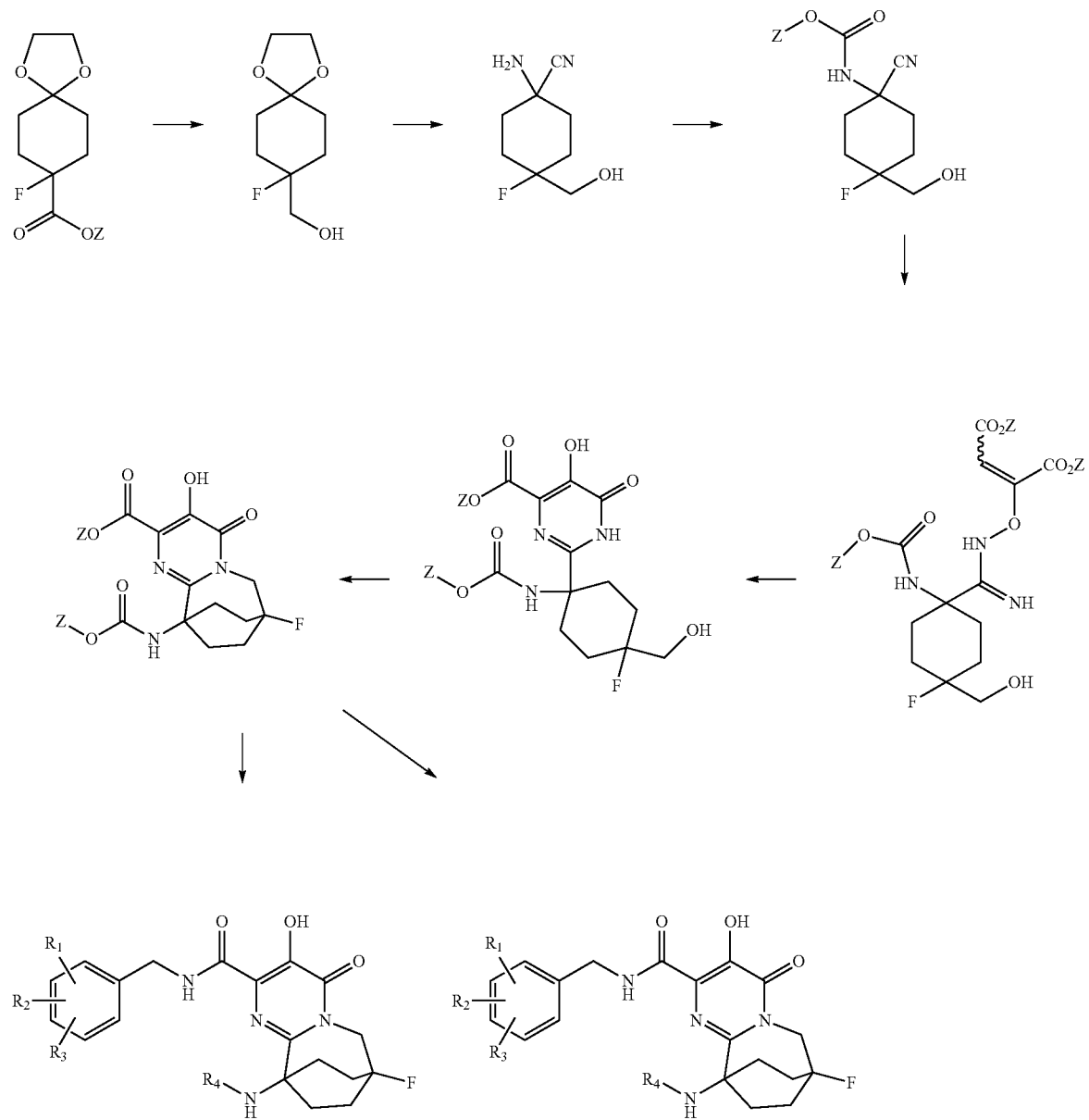
Scheme 4

Scheme 5
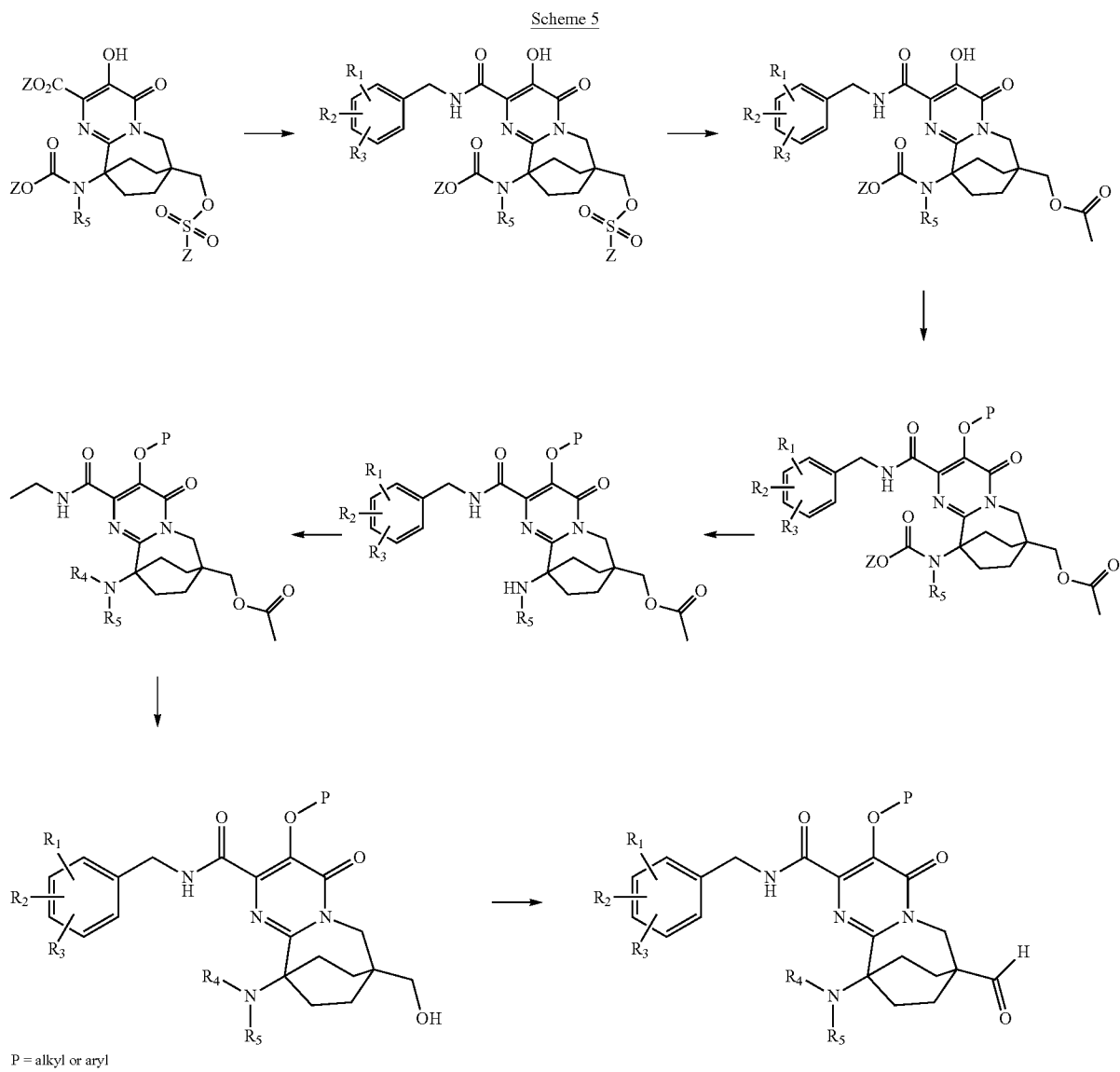
P = alkyl or aryl
Scheme 6
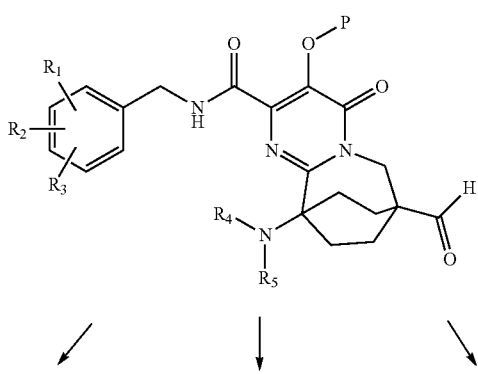

19
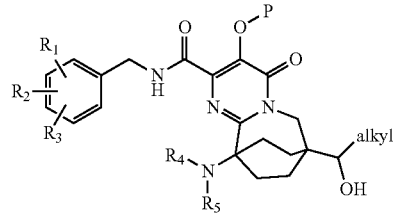
20
-continued
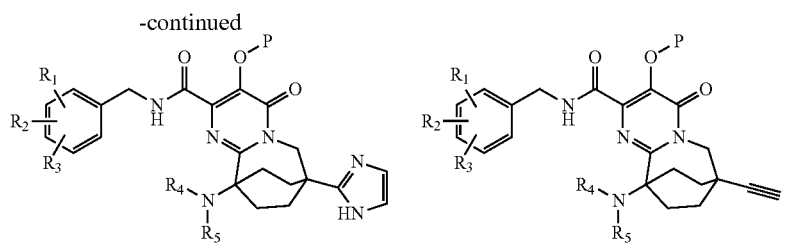
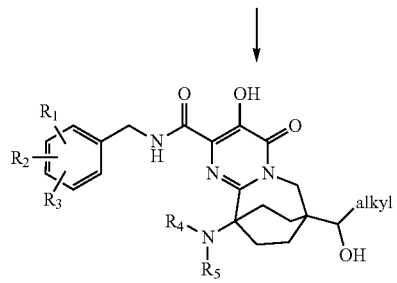 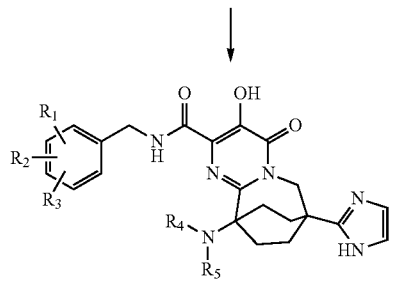 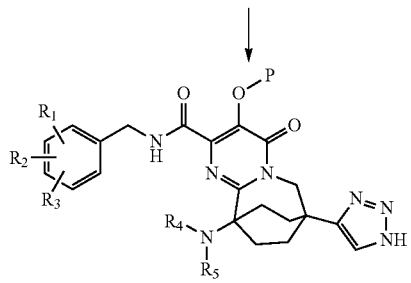
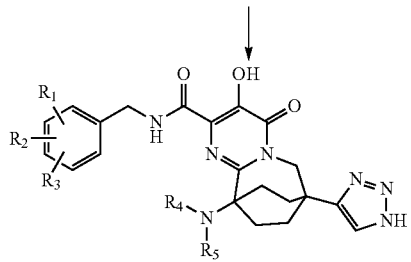
Scheme 7
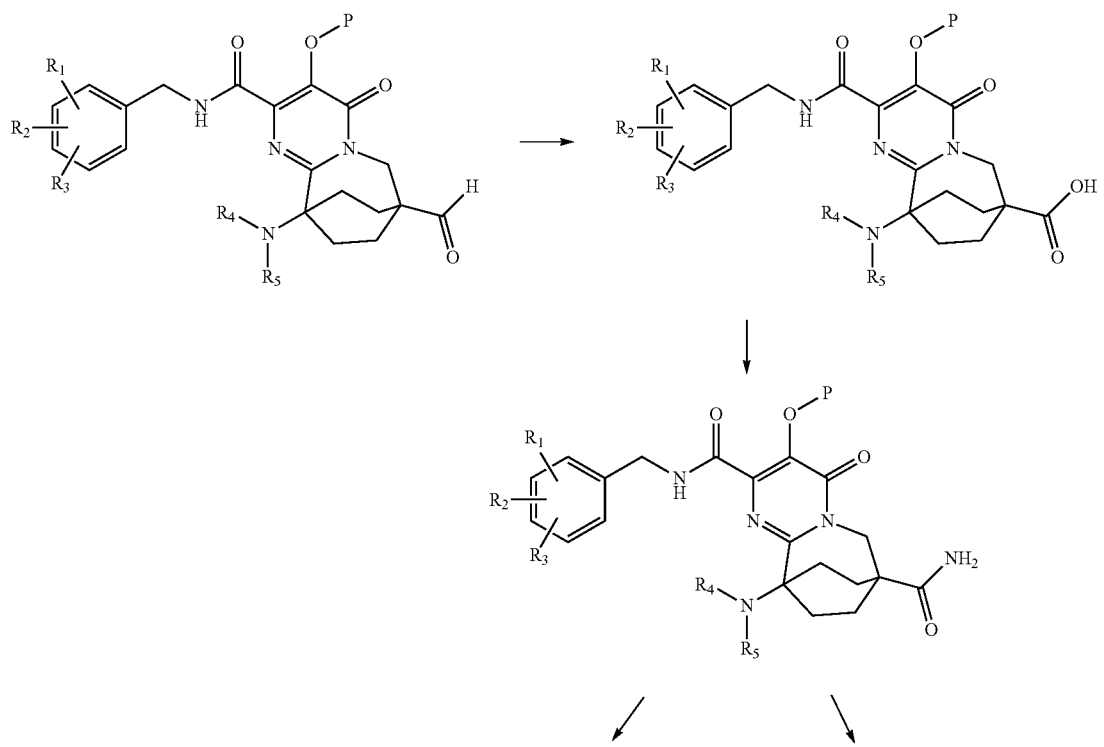

21 22
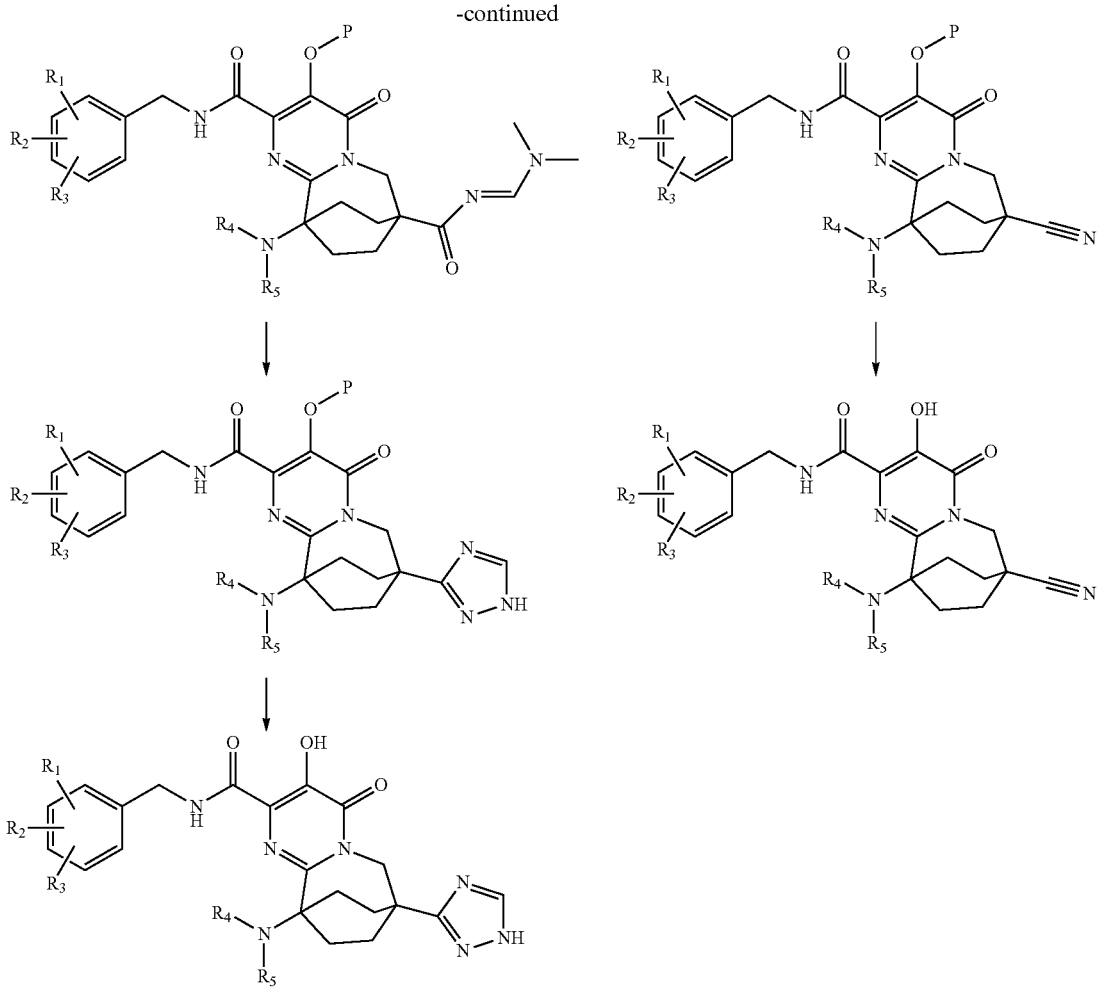
-continued

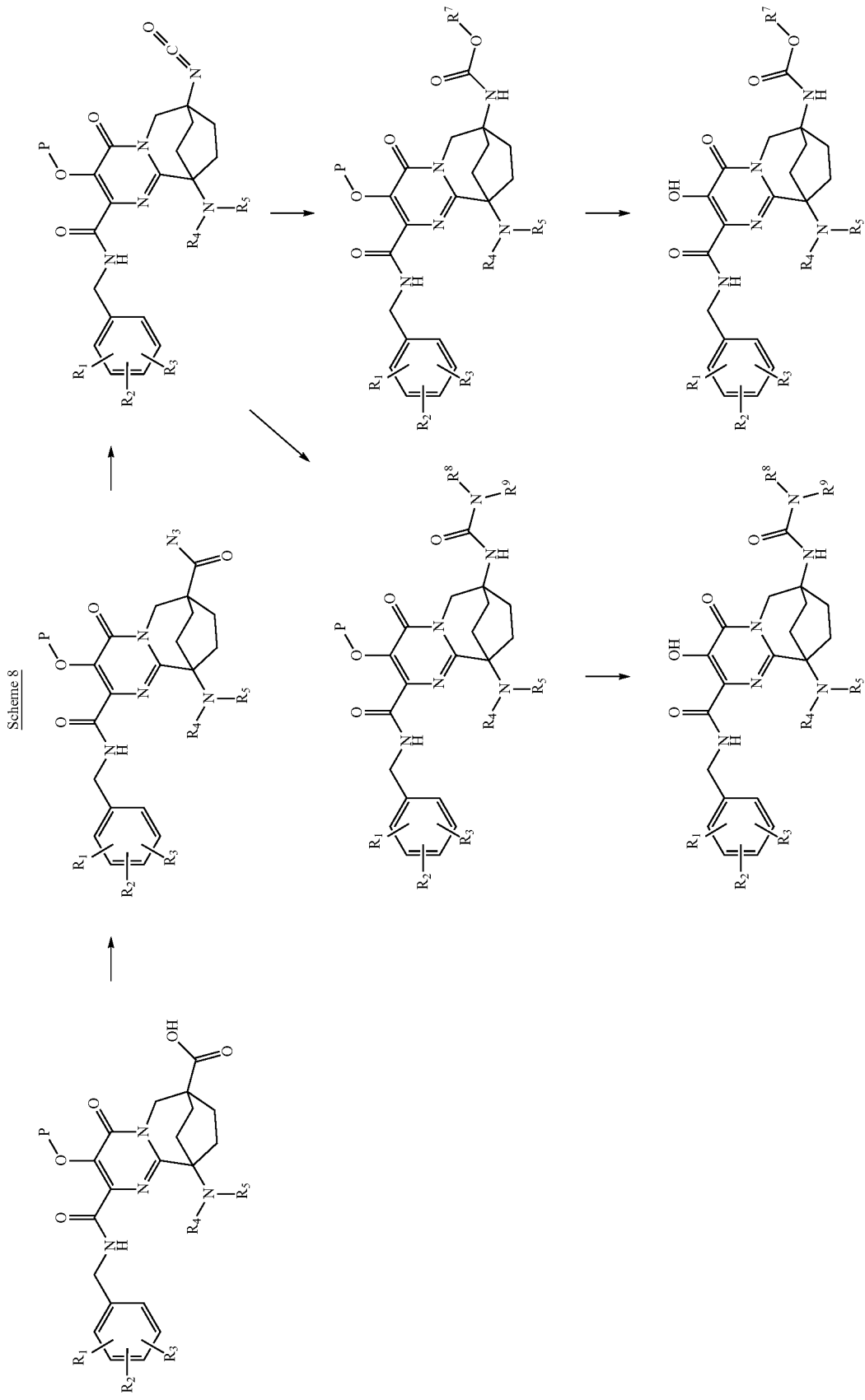
Scheme 8

Scheme 9

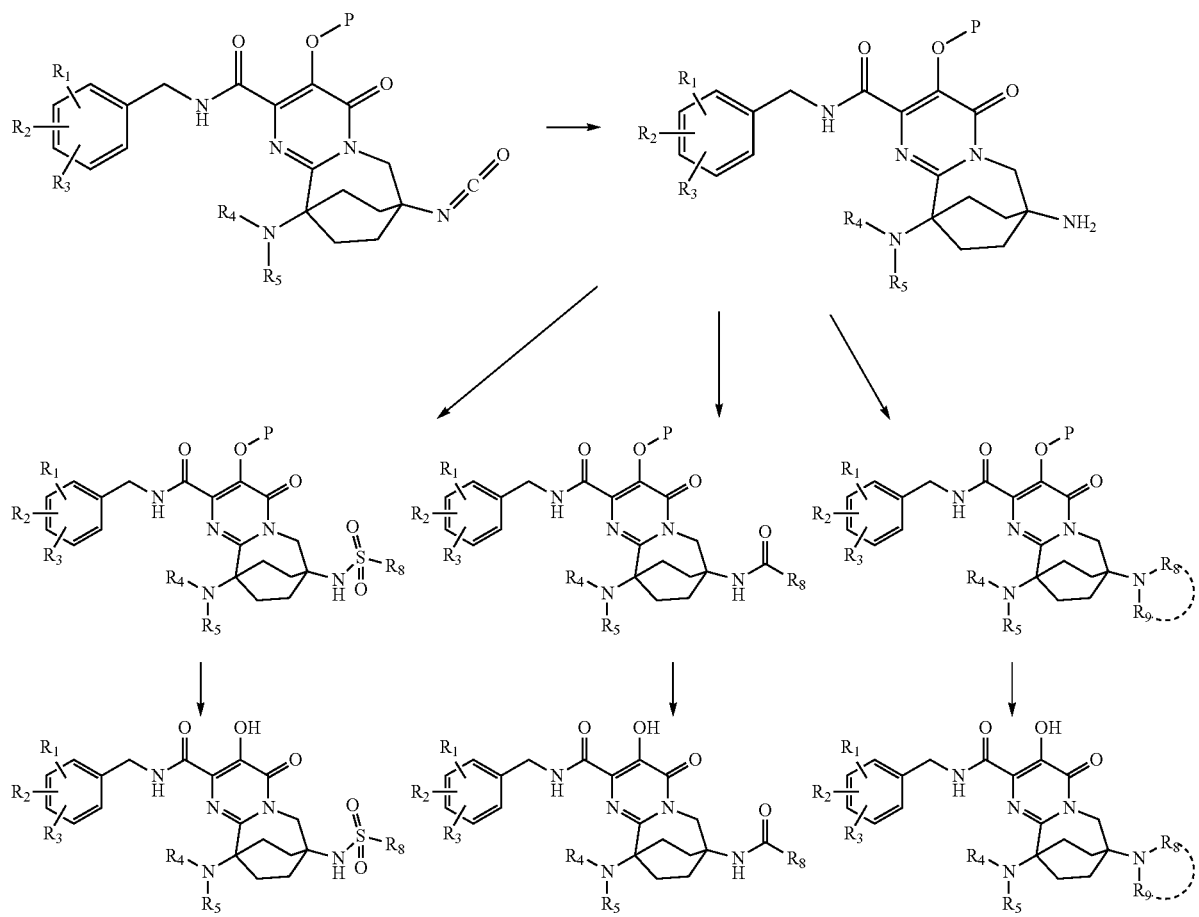

Biological Methods

HIV-Integrase Inhibition Activity.

Radiolabeled integrase inhibitor, N-[(4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide, was used as a known reference ligand to determine the binding constants towards the integrase enzyme of the compounds described in this invention using a method similar to that described in; Dicker et al. *J. Biological Chem.* 2007, 282, 31186-31196; Dicker et al. *J. Biol. Chem.* 2008, 283, 23599-23609 and Dicker et al. *Biochemistry* 2008, 47, 13481-13488. N-[(4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide is a known active-site binding inhibitor as it can be competed off the. Kd values for [$^3$H]N-[(4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide were determined from fitting data to a saturation binding curve using Graphpad Prism, V4.01. The Ki measurement toward integrase was made by measuring the inhibition of binding of [$^3$H]N-[(4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide to enzyme-SPA bead complexes in the presence of serial dilutions of the test compounds. The Ki value was determined from the [$^3$H]N-[(4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide Kd and the inhibition binding curve using Graphpad Prism, V4.03. Results are shown in the Table 1.

TABLE 1

| Example | $K_i$ nM |
|---------|----------|
| Example 1 | 0.0012 |
| Example 2 | 0.0018 |
| Example 3 | 0.0021 |
| Example 4 | 0.0011 |
| Example 5 | 0.0017 |
| Example 6 | 0.0014 |
| Example 7 | 0.0013 |
| Example 8 | 0.0013 |
| Example 9 | 0.0015 |
| Example 10 | 0.0008 |
| Example 11 | 0.0024 |
| Example 12 | 0.0012 |
| Example 13 | 0.0014 |
| Example 14 | 0.0016 |
| Example 15 | 0.0014 |
| Example 16 | 0.0018 |
| Example 17 | 0.0010 |
| Example 18 | 0.0011 |
| Example 19 | 0.0011 |
| Example 20 | 0.0016 |
| Example 21 | 0.0022 |
| Example 22 | 0.0028 |
| Example 23 | 0.0018 |

TABLE 1-continued

| Example | $K_i$ nM |
|---|---|
| Example 24 | 0.0024 |
| Example 25 | 0.0022 |
| Example 26 | 0.0023 |
| Example 27 | 0.0020 |
| Example 28 | 0.0016 |
| Example 29 | 0.0018 |
| Example 30 | 0.0018 |
| Example 31 | 0.0036 |
| Example 32 | 0.0012 |
| Example 33 | 0.0017 |
| Example 34 | 0.0013 |
| Example 35 | 0.0012 |
| Example 36 | 0.0007 |
| Example 37 | 0.0008 |
| Example 38 | 0.0014 |
| Example 39 | 0.0009 |
| Example 40 | 0.0012 |
| Example 41 | 0.0052 |
| Example 42 | 0.0013 |
| Example 43 | 0.0016 |
| Example 44 | 0.0013 |
| Example 45 | 0.0013 |
| Example 46 | 0.0015 |
| Example 47 | 0.0021 |
| Example 48 | 0.0022 |
| Example 49 | 0.0017 |
| Example 50 | 0.0029 |
| Example 51 | 0.0030 |
| Example 52 | 0.0013 |
| Example 53 | 0.0014 |
| Example 54 | 0.0010 |
| Example 55 | 0.0014 |
| Example 56 | 0.0020 |
| Example 57 | 0.0020 |
| Example 58 | 0.0015 |
| Example 59 | 0.0033 |
| Example 60 | 0.0141 |
| Example 61 | 0.0008 |
| Example 62 | 0.0064 |
| Example 63 | 0.0019 |
| Example 64 | 0.0014 |
| Example 65 | 0.0013 |
| Example 66 | 0.0014 |
| Example 67 | 0.0011 |
| Example 68 | 0.0012 |
| Example 69 | 0.0015 |
| Example 70 | 0.0021 |
| Example 71 | 0.0013 |
| Example 72 | 0.0015 |
| Example 73 | 0.0016 |
| Example 74 | 0.0024 |
| Example 75 | 0.0017 |
| Example 76 | 0.0026 |
| Example 77 | 0.0014 |
| Example 78 | 0.0018 |
| Example 79 | 0.0021 |
| Example 80 | 0.0014 |
| Example 81 | 0.0012 |
| Example 82 | 0.0020 |
| Example 83 | 0.0010 |
| Example 84 | 0.0038 |
| Example 85 | 0.0014 |
| Example 86 | 0.0015 |
| Example 87 | 0.0011 |
| Example 88 | 0.0017 |
| Example 89 | 0.0019 |
| Example 90 | 0.0017 |
| Example 91 | 0.0061 |
| Example 94 | 0.007 |
| Example 96 | 0.005 |
| Example 97 | 0.003 |
| Example 98 | 0.004 |
| Example 151 | 0.006 |
| Example 262 | 0.008 |

Inhibition of HIV Replication.

A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in the Table 2. Activity equal to A refers to a compound having $IC_{50}=<10$ nM while B and C denote compounds having $IC_{50}=<10$ nM and $IC_{50}<100$ nM and $IC_{50}>100$ nM respectively.

TABLE 2

| Example | Cell Culture |
|---|---|
| Example 1 | A |
| Example 2 | A |
| Example 3 | A |
| Example 4 | B |
| Example 5 | A |
| Example 6 | A |
| Example 7 | A |
| Example 8 | A |
| Example 9 | A |
| Example 10 | A |
| Example 11 | A |
| Example 12 | A |
| Example 13 | A |
| Example 14 | A |
| Example 15 | A |
| Example 16 | A |
| Example 17 | A |
| Example 18 | A |
| Example 19 | A |
| Example 20 | A |
| Example 21 | A |
| Example 22 | A |
| Example 23 | A |
| Example 24 | A |
| Example 25 | A |
| Example 26 | A |
| Example 27 | A |
| Example 28 | A |
| Example 29 | A |
| Example 30 | A |
| Example 31 | A |
| Example 32 | A |
| Example 33 | B |
| Example 34 | A |
| Example 35 | A |
| Example 36 | A |
| Example 37 | A |
| Example 38 | A |
| Example 39 | A |
| Example 40 | A |
| Example 42 | A |
| Example 43 | A |
| Example 44 | A |
| Example 45 | A |

TABLE 2-continued

| Example | Cell Culture |
|---|---|
| Example 46 | A |
| Example 47 | A |
| Example 48 | A |
| Example 49 | A |
| Example 50 | A |
| Example 51 | A |
| Example 52 | A |
|  | A |
| Example 54 | A |
| Example 55 | A |
| Example 56 | A |
| Example 57 | A |
| Example 58 | A |
| Example 59 | A |
| Example 60 | A |
| Example 61 | A |
| Example 62 | A |
| Example 63 | A |
| Example 64 | A |
| Example 65 | B |
| Example 66 | B |
| Example 67 | A |
| Example 68 | A |
| Example 69 | A |
| Example 70 | A |
| Example 71 | B |
| Example 72 | A |
| Example 73 | A |
| Example 74 | A |
| Example 75 | A |
| Example 76 | C |
| Example 77 | A |
| Example 78 | B |
| Example 79 | B |
| Example 80 | A |
| Example 81 | B |
| Example 82 | A |
| Example 83 | A |
| Example 84 | A |
| Example 85 | A |
| Example 86 | A |
| Example 87 | A |
| Example 88 | B |
| Example 89 | A |
| Example 90 | A |
| Example 93 | A |
| Example 94 | A |
| Example 95 | A |
| Example 96 | A |
| Example 97 | A |
| Example 98 | A |
| Example 99 | A |
| Example 100 | A |
| Example 101 | A |
| Example 102 | A |
| Example 103 | A |
| Example 104 | A |
| Example 105 | A |
| Example 106 | A |
| Example 107 | A |
| Example 108 | A |
| Example 109 | A |
| Example 110 | A |
| Example 111 | A |
| Example 112 | A |
| Example 113 | A |
| Example 114 | A |
| Example 115 | A |
| Example 116 | A |
| Example 117 | A |
| Example 118 | A |
| Example 119 | A |
| Example 120 | A |
| Example 121 | A |
| Example 122 | A |
| Example 123 | A |
| Example 124 | A |
| Example 125 | B |
| Example 126 | A |
| Example 127 | A |
| Example 128 | A |
| Example 129 | A |
| Example 130 | A |
| Example 131 | A |
| Example 132 | A |
| Example 133 | A |
| Example 134 | A |
| Example 135 | A |
| Example 136 | A |
| Example 137 | A |
| Example 138 | A |
| Example 139 | A |
| Example 140 | A |
| Example 141 | A |
| Example 142 | A |
| Example 143 | A |
| Example 144 | A |
| Example 145 | A |
| Example 146 | A |
| Example 147 | A |
| Example 148 | A |
| Example 149 | A |
| Example 150 | A |
| Example 151 | A |
| Example 152 | A |
| Example 153 | A |
| Example 154 | A |
| Example 155 | A |
| Example 156 | A |
| Example 157 | A |
| Example 158 | A |
| Example 159 | B |
| Example 160 | A |
| Example 161 | A |
| Example 162 | A |
| Example 163 | B |
| Example 164 | A |
| Example 165 | A |
| Example 166 | A |
| Example 167 | A |
| Example 168 | C |
| Example 169 | A |
| Example 170 | B |
| Example 171 | A |
| Example 172 | A |
| Example 173 | A |
| Example 174 | A |
| Example 175 | A |
| Example 176 | A |
| Example 177 | A |
| Example 178 | A |
| Example 179 | A |
| Example 180 | A |
| Example 181 | A |
| Example 183 | A |
| Example 184 | A |
| Example 185 | A |
| Example 186 | A |
| Example 187 | A |
| Example 188 | A |
| Example 189 | A |
| Example 190 | A |
| Example 191 | B |
| Example 192 | B |
| Example 194 | B |
| Example 195 | A |
| Example 196 | A |
| Example 197 | A |
| Example 198 | A |
| Example 199 | A |
| Example 200 | A |
| Example 201 | A |
| Example 202 | A |
| Example 203 | A |
| Example 204 | A |
| Example 205 | A |

TABLE 2-continued

| Example | Cell Culture |
| --- | --- |
| Example 206 | A |
| Example 207 | A |
| Example 208 | A |
| Example 209 | C |
| Example 210 | A |
| Example 214 | A |
| Example 215 | A |
| Example 216 | A |
| Example 217 | A |
| Example 218 | A |
| Example 219 | A |
| Example 220 | A |
| Example 221 | A |
| Example 222 | A |
| Example 223 | A |
| Example 224 | A |
| Example 225 | A |
| Example 226 | A |
| Example 227 | A |
| Example 228 | A |
| Example 229 | B |
| Example 230 | A |
| Example 231 | A |
| Example 232 | A |
| Example 233 | A |
| Example 234 | A |
| Example 235 | A |
| Example 236 | A |
| Example 237 | A |
| Example 238 | A |
| Example 239 | A |
| Example 240 | A |
| Example 241 | A |
| Example 242 | B |
| Example 243 | C |
| Example 244 | A |
| Example 245 | C |
| Example 246 | C |
| Example 247 | C |
| Example 248 | B |
| Example 249 | A |
| Example 250 | A |
| Example 251 | A |
| Example 252 | C |
| Example 253 | B |
| Example 254 | A |
| Example 255 | A |
| Example 256 | A |
| Example 257 | A |
| Example 258 | A |
| Example 259 | A |
| Example 260 | A |
| Example 261 | A |
| Example 262 | A |
| Example 263 | A |
| Example 264 | A |
| Example 265 | A |
| Example 266 | A |
| Example 267 | A |
| Example 268 | A |
| Example 269 | A |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently reltegravir, an HIV integrase inhibitor, has been approved by the FDA for treating AIDS and HIV infection.

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences,* 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically.

The specific dosing regime, however, will be determined by a physician using sound medical judgement. A partial list of such agents is shown in the table below.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection ARC, |
| AL-721 | Ethigen (Los Angeles, CA) | PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, Sustiva ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |

-continued

| Drug Name | Manufacturer | Indication |
|---|---|---|
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Emtriva ® (Emtricitabine) (FTC) | Gilead | HIV infection, AIDS, (reverse transcriptase inhibitor) |
| Combivir ® | GSK | HIV infection, AIDS, (reverse transcriptase inhibitor) |
| Abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® | Roche/Trimeris | HIV infection AIDs, |

-continued

| Drug Name | Manufacturer | Indication |
|---|---|---|
| (Enfuvirtide or T-20) | | viral Fusion inhibitor |
| Lexiva ® | GSK/Vertex | HIV infection AIDs, |
| (or Fosamprenavir calcium) | | viral protease inhibitor |
| Selzentry | Pfizer | HIV infection AIDs, |
| Maraviroc; (UK 427857) | | (CCR5 antagonist, |
| | | in development) |
| Trizivir ® | GSK | HIV infection AIDs, |
| | | (three drug combination) |
| Sch-417690 (vicriviroc) | Schering-Plough | HIV infection AIDs, |
| | | (CCR5 antagonist, |
| | | in development) |
| TAK-652 | Takeda | HIV infection AIDs, |
| | | (CCR5 antagonist, |
| | | in development) |
| GSK 873140 | GSK/ONO | HIV infection AIDs, |
| (ONO-4128) | | (CCR5 antagonist, |
| | | in development) |
| Integrase Inhibitor | Merck | HIV infection AIDs |
| MK-0518 | | |
| Raltegravir | | |
| Truvada ® | Gilead | Combination of Tenofovir |
| | | disoproxil fumarate salt |
| | | (Viread ®) and Emtriva ® |
| | | (Emtricitabine) |
| Integrase Inhibitor | Gilead/Japan Tobacco | HIV Infection AIDs |
| GS917/JTK-303 | | in development |
| Elvitegravir | | |
| Triple drug combination | Gilead/Bristol-Myers Squibb | Combination of Tenofovir |
| Atripla ® | | disoproxil fumarate salt |
| | | (Viread ®), Emtriva ® |
| | | (Emtricitabine), and |
| | | Sustiva ® (Efavirenz) |
| Festinavir ® | Oncolys BioPharma | HIV infection AIDs |
| | | in development |
| CMX-157 | Chimerix | HIV infection AIDs |
| Lipid conjugate of | | |
| nucleotide tenofovir | | |
| GSK1349572 | GSK | HIV infection AIDs |
| Integrase inhibitor | | |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. | AIDS, ARC |
| | (Irving, TX) | |
| CL246,738 | Wyeth | AIDS, Kaposi's |
| | Lederle Labs | sarcoma |
| FP-21399 | Fuki ImmunoPharm | Blocks HIV fusion |
| | | with CD4+ cells |
| Gamma Interferon | Genentech | ARC, in combination |
| | | w/TNF (tumor |
| | | necrosis factor) |
| Granulocyte | Genetics Institute | AIDS |
| Macrophage Colony | Sandoz | |
| Stimulating Factor | | |
| Granulocyte | Hoechst-Roussel | AIDS |
| Macrophage Colony | Immunex | |
| Stimulating Factor | | |
| Granulocyte | Schering-Plough | AIDS, combination |
| Macrophage Colony | | w/AZT |
| Stimulating Factor | | |
| HIV Core Particle | Rorer | Seropositive HIV |
| Immunostimulant | | |
| IL-2 | Cetus | AIDS, in combination |
| Interleukin-2 | | w/AZT |
| IL-2 | Hoffman-LaRoche | AIDS, ARC, HIV, in |
| Interleukin-2 | Immunex | combination w/AZT |
| IL-2 | Chiron | AIDS, increase in |
| Interleukin-2 | | CD4 cell counts |
| (aldeslukin) | | |
| Immune Globulin | Cutter Biological | Pediatric AIDS, in |
| Intravenous | (Berkeley, CA) | combination w/AZT |
| (human) | | |
| IMREG-1 | Imreg | AIDS, Kaposi's |
| | (New Orleans, LA) | sarcoma, ARC, PGL |
| IMREG-2 | Imreg | AIDS, Kaposi's |
| | (New Orleans, LA) | sarcoma, ARC, PGL |

| Drug Name | Manufacturer | Indication |
| --- | --- | --- |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

Abbreviations used in the schemes generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

When mentioned, the HPLC conditions specified as System A or System B consist of the following:
HPLC (System A):
Start % B=0%, Final % B=100%
Gradient Time=4 min, Total Time=5 min.
Flow Rate=4 mL/min, Wavelength=254 nm.
Solvent A=90% Water/10% Acetonitrile/0.1% TFA
Solvent B=10% Water/90% Acetonitrile/0.1% TFA
Column=YMC ODS-AQ 4.6×50 mm, 3 micron
LCMS (System B):
Start % B=0, Final % B=100
Gradient Time=2 min, Total Time=3 min.
Flow Rate=1 mL/min, Wavelength=254 nm.
Solvent A=90% Water/10% Acetonitrile/0.1% TFA
Solvent B=10% Water/90% Acetonitrile/0.1% TFA
Column=Phenomenex LUNA C18, 2×30 mm, 3 micron Intermediate 1

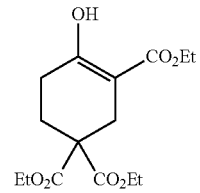

Triethyl 4-hydroxycyclohex-3-ene-1,1,3-tricarboxylate

The title compound was prepared from diethyl malonate and ethyl acrylate using a procedure similar to that described in *J. Org. Chem.*, 2007, 72, 7455. A solution of diethyl malonate (64 g, 400 mmol), and ethyl acrylate (88 g, 879 mmol) in THF (300 mL) in a 2 L 3-neck round bottom flask, equipped with a thermometer, a mechanical stirrer, a N₂ inlet, and a condenser was cooled in a cold water bath (~10° C.). 500 mL of a 1M THF solution of potassium tert-butoxide measured out for addition to the reaction. The reaction was initiated by very slowly introducing 2-5 mL of this solution to the reaction mixture (exothermic reaction) in order to maintain an internal temperature below 35° C. After the initial vigorous reaction subsided, the remainder of the solution was added drop-wise without a cooling bath over 1.5 h. During this period, the internal temp. remained between 20-28° C. The resulting cloudy amber solution was stirred at room temp. under N₂ for 2.5 h, by which time a mass of precipitate had formed. The mixture was diluted with EtOAc (300 mL) and sat'd NH₄Cl (200 mL), and then neutralized by the addition of 3N HCl (170 mL). The organic phase was washed with brine (100 mL), dried (Na₂SO₄), filtered and concentrated to give the title compound (135.2 g, 400 mmol, 100% yield) as an amber oil. HPLC: retention time=3.00 min (AP 81% at λ, = 220 nm). LCMS: m/z 315 (M+H). $^1$H NMR (500 MHz, CDCl₃) δ ppm 1.22 (6H, t, J=7.2 Hz, 12,15-CH₃), 1.28 (3H, t, J=7.2 Hz, 9-CH₃), 2.17 (2H, t, J=6.6 Hz, 5-CH₂), 2.34 (2H, t, J=6.4 Hz, 6-CH₂), 2.76 (2H, s, 3-CH₂), 4.12-4.23 (6H, m, 8,11,14-OCH₂), 12.2 (1H, s, 1-OH). $^{13}$C NMR (126 MHz, CDCl₃) δ ppm 14.1 (12,15-CH₃), 14.3 (9-CH₃), 26.1 (6-CH₂), 26.7 (5-CH₂), 27.9 (3-CH₂), 53.0 (4-C), 60.6 (8-OCH₂), 61.6 (11,14-OCH₂), 95.3 (2-C=), 170.2 (1-OC=), 170.8 (10,13-OC=O), 172.0 (7-OC=O).

Intermediate 2

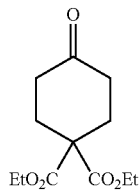

Diethyl 4-oxocyclohexane-1,1-dicarboxylate

The procedure in Sanchez et al., Synth. Comm., 1985, 15, 141 was followed. A mixture of triethyl 4-oxocyclohexane-1,1,3-tricarboxylate, Intermediate 1, (135.2 g, 400 mmol), sodium chloride (70.1 g, 1200 mmol), and H₂O (17.30 mL, 960 mmol) in DMSO (530 mL) was stirred at 160° C. (oil bath) under N₂ for 3.5 h. The cooled mixture was poured into ice-water (3 L) and extracted with EtOAc (400 mL×3). The combined extracts were washed with brine, dried (Na₂SO₄) then concentrated to provide the title compound (103.4 g, 397 mmol, 99% yield) as an amber oil. HPLC: 2.04 min (AP 45% at 220 nm). LCMS: m/z 243 (M+H). $^1$H NMR (500 MHz, CDCl₃) δ ppm 1.27 (6H, t, J=7.0 Hz, 9,12-CH₃), 2.37 (4H, t, J=6.9 Hz, 3,5-CH₂), 2.43 (4H, t, J=6.7 Hz, 2,6-CH₂), 4.23 (4H, q, J=7.2 Hz, 8,11-OCH₂). $^{13}$C NMR (126 MHz, CDCl₃) δ ppm 14.1 (9,12-CH₃), 31.0 (3,5-CH₂), 37.8 (2,6-CH₂), 53.6 (4-C), 61.9 (8,11-OCH₂), 170.7 (7,10-OC=O), 209.4 (1-C=O).

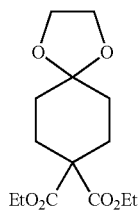

Diethyl 1,4-dioxaspiro[4.5]decane-8,8-dicarboxylate

The procedure described in Pearson at al., *J. Org. Chem.*, 1997, 62, 5284 was followed with a minor modification. A mixture of diethyl 4-oxocyclohexane-1,1-dicarboxylate, Intermediate 2, (120.6 g, 463 mmol), ethane-1,2-diol (110 mL, 1973 mmol), and para-toluene sulfonic acid mono hydrate (1.0 g, 5.26 mmol) in Benzene (250 mL) was stirred at room temp under N₂ for 2 days. The mixture was diluted with Et₂O (1 L) and washed with water (300 mL×3), sat'd NaHCO₃ (100 mL) and then with brine, dried (MgSO₄), and concentrated to dryness to provide the title compound (132.7 g, 463 mmol, 100% yield) as an amber oil HPLC: 2.38 min (AP 70% at 220 nm). LCMS: m/z 287 (M+H). $^1$H NMR (500 MHz, CDCl₃) δ ppm 1.17 (6H, t, J=7.2 Hz, 9,12-CH₃), 1.60 (4H, t, J=6.4 Hz, 2,6-CH₂), 2.09 (4H, t, J=6.4 Hz, 3,5-CH₂), 3.86 (4H, s, 13,14-OCH₂), 4.11 (4H, q, J=7.2 Hz, 8,11-OCH₂). $^{13}$C NMR (126 MHz, CDCl₃) δ ppm 14.1 (9,12-CH₃), 29.0 (3,5-CH₂), 31.6 (2,6-CH₂), 53.9 (4-C), 61.3 (8,11-OCH₂), 64.3 (13,14-OCH₂), 107.7 (1-OCO), 171.2 (7,10-OC=O).

Intermediate 4

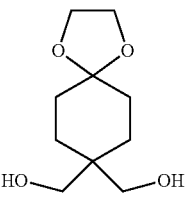

1,4-Dioxaspiro[4.5]decane-8,8-diyldimethanol

A 3-neck 1-L round bottom flask was equipped with a thermometer, dropping funnel and nitrogen inlet. Under an atmosphere of N₂, a solution of 1M lithium aluminum hydride in THF (900 mL, 900 mmol) was added and cooled using a dry ice/acetone bath. To this was added drop-wise a solution of diethyl 1,4-dioxaspiro[4.5]decane-8,8-dicarboxylate, Intermediate 3, (128.7 g, 450 mmol) in THF (75 mL) over a period of 1 h while maintaining the internal temperature at 10-15° C. The mixture was left in the cooling bath and allowed to regain room temperature while stirring overnight. The mixture was then cooled to −5° C. and quenched by the slow addition of water (40 mL) under vigorous stirring over 1.5 hours being careful to maintain the internal temperature below 30° C. To this was added drop-wise 15% NaOH (40 mL) and water (40 mL). The resulting precipitate was filtered over Celite, and washed with THF (300 mL). The filtrate was concentrated in vacuo to dryness to provide the title compound (63.3 g) as a white solid. Further extraction of the white cake with 10% MeOH/CH₂Cl₂ (2×500 mL) gave an additional amount (15.6 g) of the title compound. This constitutes total combined yield of 78.9 g (0.39 mol, Y. 87%). LCMS: m/z 203 (M+H), 225 (M+Na). $^1$HNMR (500 MHz, CD$_3$OD) δ ppm 1.49-1.55 (4H, m, 3,5-CH$_2$), 1.59-1.66 (4H, m, 2,6-CH$_2$), 3.49 (4H, s, 9,10-OCH$_2$), 3.94 (4H, s, 7,8-OCH$_2$). $^{13}$C NMR (126 MHz, CD$_3$OD) δ ppm 26.7 (3,5-CH$_2$), 30.3 (2,6-CH$_2$), 38.3 (4-C), 64.2 (7,8-OCH$_2$), 65.4 (9,10-OCH$_2$), 109.2 (1-OCO).

An alternative route to diethyl 4-oxocyclohexane-1,1-dicarboxylate, Intermediate 2, is described in the following:

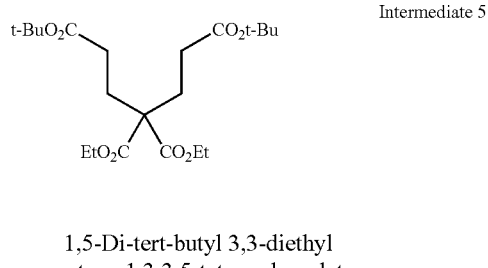

Intermediate 5

1,5-Di-tert-butyl 3,3-diethyl pentane-1,3,3,5-tetracarboxylate (Oosterbaan, W. D., Koper, C., Braam, T. W., Hoogesteger, F. J., Piet, J. J., Jansen, B. A. J., van Walree, C. A., van Ramesdonk, H. J., Goes, M., Verhoeven, J. W., Schuddeboom, W., Warman, J. M., Jenneskens, L. W., *J. Phys. Chem. A.*, 2003, 107 (19), 3612, Supporting Information.) A solution of diethyl malonate (130 g, 812 mmol) and powdered sodium ethoxide (58.4 g, 815 mmol) in absolute EtOH (1600 mL) under an N$_2$ atmosphere was cooled (0° C. ice bath) and treated with tert-butyl acrylate (250 mL, 1704 mmol) by slow addition over 30 min. (Note: addition results in a mildly exothermic reaction). The mixture was stirred at room temperature for 5 h, and then concentrated to approximately half-volume. The resulting solution was poured into 1.0 N HCl (1000 mL) in a 3000 mL separatory funnel, the mixture was saturated with NaCl, and extracted with Et$_2$O (600 mL, then 2×200 mL)). The combined organic phases were dried (MgSO$_4$), filtered and concentrated to provide the title compound (365.7 g, ~815 mmol, ~100% crude yield) as a light amber oil. HPLC: 3.60 min (AP 55% at 220 nm); LCMS: 439.18 (M+Na); $^1$H NMR (500 MHz, CDCl$_3$-d) δ ppm 4.17 (4H, q, J=7.22 Hz), 2.16-2.23 (4H, m), 2.10-2.16 (4H, m), 1.42 (18H, s), 1.24 (6H, t, J=7.02 Hz).

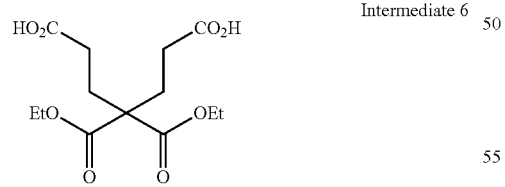

Intermediate 6

4,4-Bis(ethoxycarbonyl)heptanedioic acid

A solution of 1,5-di-tert-butyl 3,3-diethyl pentane-1,3,3,5-tetracarboxylate, Intermediate 5, (812 mmol) in CH$_2$Cl$_2$ (200 mL) was treated with trifluoroacetic acid (270 mL, 3508 mmol). The reaction was stirred a total of 36 h. The mixture was concentrated under reduced pressure, and the resulting oily residue dissolved in CH$_2$Cl$_2$ (200 mL). The solution was washed with 0.1 N HCl (1×100 mL) then sat'd aqueous NaHCO$_3$ (2×75 mL). The combined aq. NaHCO$_3$ fractions were acidified to approximately pH 1, using 6.0 N HCl, and extracted with CH$_2$Cl$_2$ (2×50 mL). The combined organic fractions were dried (Na$_2$SO$_4$), filtered, and concentrated under reduced pressure to afford the crude product as a pale yellow solid. The product was purified by crystallization from benzene (89.75 g, 295 mmol, 36% yield over two steps). HPLC: 1.56 min (AP 68% at 220 nm); LC/MS: 326.90 (M+Na); $^1$H NMR (500 MHz, CDCl$_3$) δ ppm 4.19 (4H, q, J=7.12 Hz), 2.36 (4H, t, J=7.63 Hz), 2.23 (4H, t, J=7.63 Hz), 1.25 (6H, t, J=7.17 Hz); $^{13}$C NMR (126 MHz, CDCl$_3$) δ ppm 179.03, 170.55, 61.82, 56.59, 29.25, 26.56, 14.16.

Diethyl 4-oxocyclohexane-1,1-dicarboxylate, Intermediate 2

(Kutsuma, T., Sugasawa, S., *Tetrahedron*, 3, 175 (1958).) To 100 mL of a pre-mixed solution of 10% (v/v) pyridine and acetic anhydride was added 4,4-bis(ethoxycarbonyl)heptanedioic acid (23.6 g, 78 mmol), and the resulting mixture heated at reflux in a pre-heated oil bath. The reaction was stirred for 3 hrs then cooled to room temperature and concentrated under reduced pressure. The resulting oil was azeotroped twice with CH$_2$Cl$_2$, then dissolved in 95% EtOH (300 mL) and water (300 mL) and treated with solid potassium carbonate (12.9 g, 93.6 mmol). The mixture was stirred for 16 hrs. The reaction was concentrated under reduced pressure to remove EtOH, and the remaining water layer was diluted to re-dissolve the solids, then extracted with Et$_2$O (2×150 mL). The combined extracts were dried (MgSO$_4$), filtered, and concentrated under reduced pressure, to afford the title compound (11.82 g, 48.8 mmol, 62.9% yield), as an amber oil. HPLC: 2.00 min (AP 74%); $^1$H NMR (500 MHz, CDCl$_3$) δ ppm 4.24 (4H, q, J=7.12 Hz), 2.44 (4H, t, J=6.56 Hz), 2.37 (4H, t, J=6.41 Hz), 1.27 (6H, t, J=7.17 Hz).

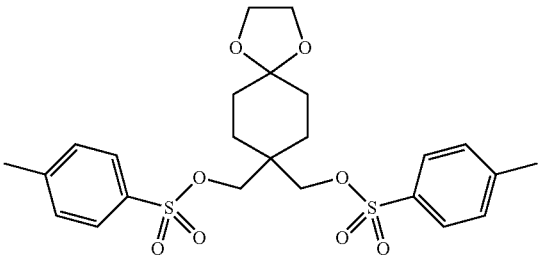

Intermediate 7

1,4-Dioxaspiro[4.5]decane-8,8-diylbis(methylene) bis(4-methylbenzenesulfonate)

A suspension of 1,4-dioxaspiro[4.5]decane-8,8-diyldimethanol, Intermediate 4, (202.8 g, 1003 mmol) was stirred in pyridine (1200 ml) for 5 min. The suspension was treated with para-toluenesulfonyl chloride (406.4 g, 2132 mmol) and N,N-dimethylaminopyridine (6.27 g, 51.3 mmol). The suspension rapidly turned clear, developing a light pink color, and significant precipitate over ~15 min. The mixture was stirred at room temperature for 2 days, after which the reaction was diluted with water (3000 mL). The slurry was stirred for 20 min, after which the solids were collected by vacuum filtration. The solids were rinsed using several portions of water and Et$_2$O. HPLC (system A): 84.5% AP, rt=3.22 min. $^1$H NMR (500 MHz, CDCl$_3$) δ ppm 7.72 (4H, d, J=8.24

Hz), 7.34 (4H, d, J=8.24 Hz), 3.88 (4H, s), 3.83 (4H, s), 2.45 (6H, s), 1.43-1.53 (8H, m). $^{13}$C NMR (126 MHz, CDCl$_3$) δ ppm 145.15, 132.51, 130.11, 128.00, 107.88, 70.87, 64.41, 37.04, 29.81, 26.69, 21.81.

Intermediate 8

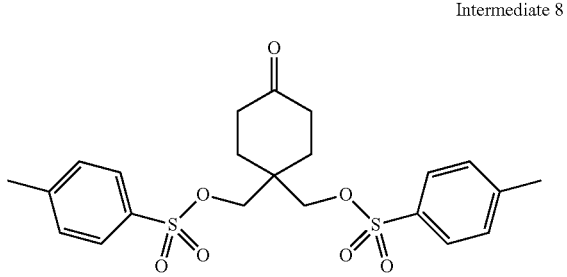

(4-Oxocyclohexane-1,1-diyl)bis(methylene)-bis(4-methylbenzenesulfonate)

To a suspension of 1,4-dioxaspiro[4.5]decane-8,8-diylbis(methylene)bis(4-methylbenzenesulfonate), Intermediate 7, (512 g, 1003 mmol) in THF (1200 mL) was added 6.0 N HCl (1000 mL, 6000 mmol) and the resulting heterogeneous solution heated to an internally measured temperature of 52° C., during which time, the solids dissolved fully. The reaction was stirred for 3.5 hrs, then concentrated to remove the organic solvent and extracted with EtOAc (3×300 mL). The combined organic extracts were washed with sat'd NaHCO$_3$ (200 mL×2), and brine, then dried (Na$_2$SO$_4$), filtered, and concentrated under reduced pressure. The resulting clear oil was diluted with Et$_2$O (~600 mL) and allowed to stand overnight to form a white solid. Et$_2$O (~1500 mL) was added and the solid stirred vigorously. Solids were collected by vacuum filtration, and dried under vacuum overnight to afford 342.3 g (691 mmol) of the title compound as a white powdery solid. HPLC (System A): 94.2% AP, rt=2.94 min. LC/MS (System B): 467.1 (M+H). $^1$H NMR (500 MHz, CDCl$_3$) δ ppm 7.74 (4H, d, J=8.55 Hz), 7.36 (4H, d, J=7.94 Hz), 3.93 (4H, s), 2.47 (6H, s), 2.21 (4H, t, J=7.02 Hz), 1.71 (4H, t, J=7.02 Hz). $^{13}$C NMR (126 MHz, CDCl$_3$) δ ppm 209.20, 145.52, 132.27, 130.22, 128.02, 70.39, 37.23, 35.97, 28.08, 21.84.

Intermediate 9

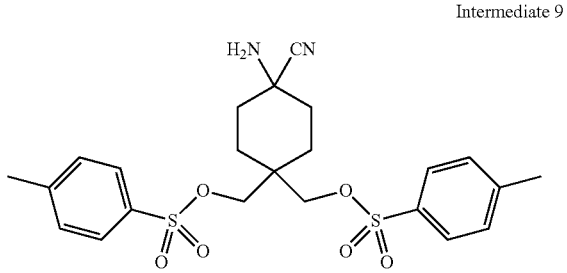

(4-Amino-4-cyanocyclohexane-1,1-diyl)bis(methylene)bis(4-methylbenzenesulfonate)

To a solution of (4-oxocyclohexane-1,1-diyl)bis(methylene)bis(4-methylbenzenesulfonate), Intermediate 8, (383.3 g, 822 mmol) in conc. ammonium hydroxide (1200 mL, 18.0 mol) and MeOH (500 mL) was added solid ammonium chloride (88 g, 1643 mmol) and THF (1000 mL), and the mixture stirred for several minutes. Additional MeOH (500 mL) and THF (300 mL) were added in order to dissolve the remaining solid. To this mixture was added NaCN (81 g, 1643 mmol) and the solution was stirred overnight. A mechanical stirrer was then fitted and the reaction was stirred for 4 hrs, and the reaction was then concentrated to remove all organic solvents. The suspension was further diluted with water, sufficient to allow for suspending all solids prior to filtration. The filtercake was washed with several portions of water and Et$_2$O then air dried for 20 min. The collected solids were then transferred to a 5000 mL round bottom flask for overnight drying under vacuum, affording 430.9 g (797 mmol, 97% yield) as a white, free-flowing powdery solid. HPLC (System A): 94.4% AP, 2.05 min. $^1$H NMR (500 MHz, CDCl$_3$) δ ppm 1.36-1.47 (2H, m), 1.49-1.58 (2H, m), 1.69-1.76 (2H, m), 1.77 (2H, s), 1.79-1.87 (2H, m), 2.49 (6H, s), 3.79 (2H, s), 3.91 (2H, s), 7.38 (4H, dd, J=7.9, 3.7 Hz), 7.75 (4H, t, J=7.9 Hz). $^{13}$C NMR (126 MHz, CDCl$_3$) δ ppm 21.8, 25.1, 32.3, 37.0, 50.6, 68.6, 72.3, 123.4, 128.0, 130.2, 130.2, 132.3, 145.4, 209.2.

Intermediate 10

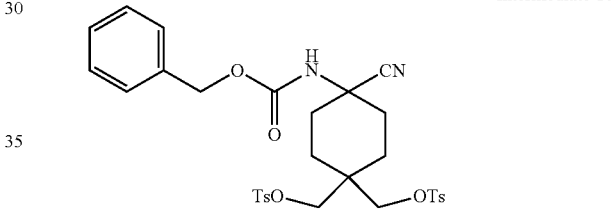

(4-(Benzyloxycarbonylamino)-4-cyanocyclohexane-1,1-diyl)bis(methylene)bis(4-methylbenzenesulfonate)

To a solution of (4-amino-4-cyanocyclohexane-1,1-diyl)bis(methylene)bis(4-methylbenzenesulfonate), Intermediate 9, (430.9 g, 826 mmol) in CH$_2$Cl$_2$ (800 ml) was added a solution of sodium carbonate, monohydrate (102 g, 826 mmol) in ice water (800 mL). To this stirred heterogeneous mixture was added drop-wise CBZ-Cl (124 ml, 826 mmol) over 30 min, and the mixture stirred under a nitrogen atmosphere at room temperature for 2 hrs. The reaction formed a large, non-stirrable mass. A mechanical stirrer was fitted to the reaction vessel, but was unable to fully disperse the solids. The reaction was diluted with additional CH$_2$Cl$_2$ (500 mL), without noticeable improvement. The reaction was diluted with THF (1000 mL), resulting in slow dissolution of the solids to form a biphasic reaction mixture. The reaction was stirred overnight. The mixture was then diluted with water (500 mL) and stirred for 10 min. The organic layer was separated, then washed with brine, and concentrated to dryness to obtain 550 g (~826 mmol, ~100% yield) of the title compound as a clear viscous oil. HPLC (System A): 76.3% AP, rt=3.41 min. LC/MS (System B): 627.2 (M+H).

Intermediate 11

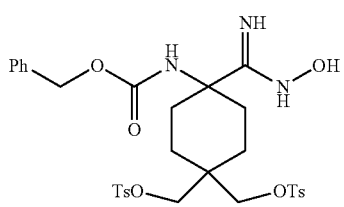

(4-(Benzyloxycarbonylamino)-4-(N-hydroxycarbamimidoyl)cyclohexane-1,1-diyl)bis(methylene)bis(4-methylbenzenesulfonate)

To a solution of (4-(benzyloxycarbonylamino)-4-cyanocyclohexane-1,1-diyl)bis(methylene)bis(4-methylbenzenesulfonate) Intermediate 10, (150 g, 239 mmol) in THF (300 ml) was added 50% aq. hydroxylamine (44 ml, 718 mmol) and the mixture was heated to reflux for 5 h. It was allowed to cool and then concentrated to give crude product. The product was crystallized from EtOH/$H_2O$ as white solid (150 g, 95% yield).

Intermediate 12

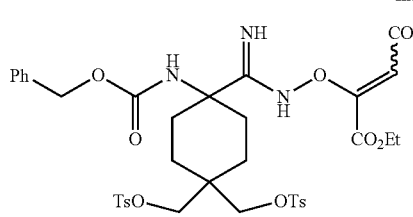

Diethyl 2-(1-(benzyloxycarbonylamino)-4,4-bis(tosyloxymethyl)cyclohexanecarboximidamidooxy)but-2-enedioate A solution of (4-(benzyloxycarbonylamino)-4-(N-hydroxycarbamimidoyl)cyclohexane-1,1-diyl)bis(methylene) bis(4-methylbenzenesulfonate), Intermediate 11, (55 g, 83 mmol) in THF (200 ml) was treated with diethyl but-2-ynedioate (14.7 ml, 92 mmol) at room temperature (Note: mildly exothermic), and heated to reflux overnight. The mixture was allowed to cool and then concentrated under vacuum. The crude product was crystallized from $Et_2O$/EtOH to provide a white solid (53 g, 77%).

Intermediate 13

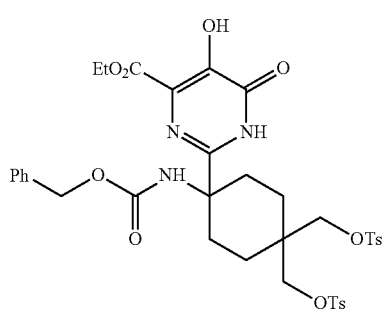

Ethyl 2-(1-(benzyloxycarbonylamino)-4,4-bis(tosyloxymethyl)cyclohexyl)-5-hydroxy-6-oxo-1,6-dihydropyrimidine-4-carboxylate A solution of diethyl 2-(1-(benzyloxycarbonylamino)-4,4-bis-(tosyloxymethyl)-cyclohexane-carboximidamidooxy) but-2-enedioate, Intermediate 12, (51.62 g, 62.2 mmol) was partially dissolved in dichloromethane (100 ml). Added to this was xylene (1600 ml) and the mixture was stirred until fully dissolved. The solution was then heated to an internal temperature of 115° C. for 24 hr. The yellow solution was cooled to ambient temperature, and then concentrated to give 57.5 g (73.4 mmol, 118% yield) of the title compound as an amber oil. HPLC (System A): 3.27 min. LC/MS (System C): 784.4 (M+H).

Intermediate 14

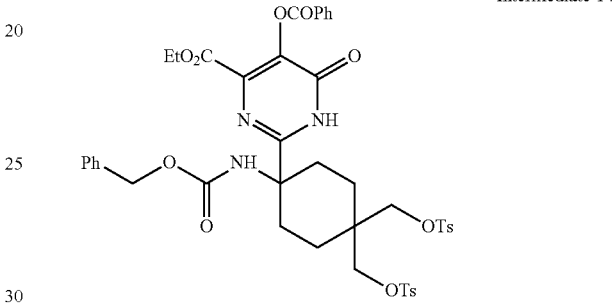

Ethyl 5-(benzoyloxy)-2-(1-(benzyloxycarbonylamino)-4,4-bis(tosyloxymethyl)cyclohexyl)-6-oxo-1,6-dihydropyrimidine-4-carboxylate To a solution of ethyl 2-(1-(benzyloxycarbonylamino)-4,4-bis(tosyloxymethyl)cyclohexyl)-5-hydroxy-6-oxo-1,6-dihydropyrimidine-4-carboxylate, Intermediate 13, (88 g, 112 mmol) in pyridine (500 ml) was added benzoic anhydride (27.1 g, 118 mmol) and the mixture stirred at room temp for 20 hrs. The mixture was concentrated to dryness by rotary evaporator, and the residue, dissolved in EtOAc (700 mL), was washed with 1.0 N HCl, sat'd aq. $NaHCO_3$, and then with brine, dried ($Na_2SO_4$) and concentrated to afford the crude product as an amber gummy solid after azeotroping with $Et_2O$. The reaction was purified by passing through a silica gel pad in a large sintered glass funnel, loading with minimal $CH_2Cl_2$, and eluting with 30%-60% EtOAc in hexanes (2000 mL each step, 10% steps). Product containing fractions were pooled and concentrated, to afford 44.32 g (49.9 mmol, 44.6% yield) of the title compound as a pale yellow oil. HPLC (System A): 3.69 min.

Intermediate 15

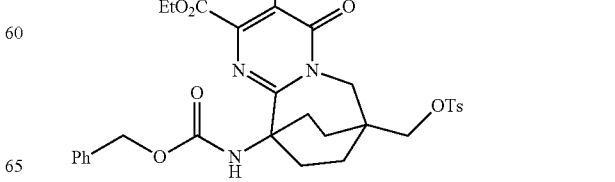

4,6,7,8,9,10-Hexahydro-3-hydroxy-7-[[[(4-methylphenyl)sulfonyl]oxy]methyl]-4-oxo-10-[[(phenylmethoxy)carbonyl]amino]-, 7,10-ethanopyrimido[1,2-a]azepine-2-carboxylic acid ethyl ester A mixture of ethyl 5-(benzoyloxy)-2-(1-(benzyloxycarbonylamino)-4,4-bis(tosyloxymethyl)cyclohexyl)-6-oxo-1,6-dihydropyrimidine-4-carboxylate, Intermediate 14, (60 g, 67.6 mmol), K₂CO₃ (18.68 g, 135 mmol) and DMF (1000 ml) was heated at 90° C. for 16 h. After cooling to room temp, the mixture was diluted with water (100 mL) and washed with ether (300 mL). The aqueous layer was acidified with 1N HCl and extracted with Et₂O (4×500 mL). The Et₂O fractions were combined and allowed to stand overnight. The resulting precipitate was filtered and dried under high vac to afford 13 g of the title compound as an off-white solid. LC/MS (System B): 612.3 (M+H). ¹H NMR (500 MHz, CDCl₃) δ ppm 10.46 (1H, br. s.), 7.84 (2H, d, J=8.24 Hz), 7.32-7.46 (7H, m), 7.15 (1H, br), 5.13 (2H, s), 4.45 (2H, q, J=7.02 Hz), 3.97 (2H, s), 3.82 (2H, s), 2.83-2.97 (2H, m), 2.47-2.53 (3H, m), 1.70-1.89 (4H, m), 1.53-1.67 (2H, m), 1.43 (3H, t, J=7.02 Hz).

Alternative procedure for the synthesis of 4,6,7,8,9,10-Hexahydro-3-hydroxy-7-[[[(4-methylphenyl)sulfonyl]oxy]methyl]-4-oxo-10-[[phenylmethoxy)carbonyl]amino]-, 7,10-ethanopyrimido[1,2-a]azepine-2-carboxylic acid ethyl ester, Intermediate 15:

A solution of diethyl 2-(1-(benzyloxycarbonylamino)-4,4-bis(tosyloxymethyl)cyclohexanecarboximidamidooxy)but-2-enedioate, Intermediate 12, (100 g, 120 mmol, 1 equiv) in toluene (3 L) was refluxed for 94 h. After cooling to ambient temperature, the solution was concentrated in vacuo to provide the intermediate pyrolysis product (99 g) as a yellow foam. To a solution of the intermediate pyrimidone (67.5 g, 86 mmol, 1 equiv) in toluene (1435 mL) was added tetramethyl guanidine (21.6 mL, 172 mmol, 2 equiv). The reaction was refluxed for 1.5 h. The dark brown solution was then removed from heat and concentrated in vacuo. The residue was partitioned between EtOAc (700 mL) and 1 N HCl (700 mL). The EtOAc layer was separated and washed with brine (500 mL), dried (Na₂SO₄), and concentrated in vacuo to provide the crude product as a tan foam. The crude product was recrystallized from MeCN (90 mL). After sitting in the refrigerator overnight, the white solid was filtered, washing with cold MeCN (2×15 mL) to provide the title compound as a white solid (19.7 g, 37%).

Intermediate 16

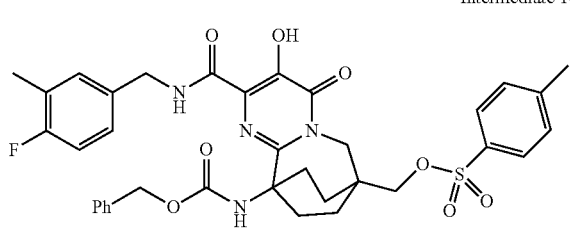

[2-[[[(4-Fluoro-3-methylphenyl)methyl]amino]carbonyl]-6,7,8,9-tetrahydro-3-hydroxy-7-[[[(4-methylphenyl)sulfony]oxy]methyl]-4-oxo-7,10-ethanopyrimido[1,2-a]azepin-10(4H)-yl]-, phenylmethyl ester carbamic acid A mixture of 4,6,7,8,9,10-hexahydro-3-hydroxy-7-[[[(4-methylphenyl)sulfonyl]oxy]methyl]-4-oxo-10-[[(phenylmethoxy)carbonyl]amino]-, 7,10-ethanopyrimido[1,2-a]azepine-2-carboxylic acid ethyl ester, Intermediate 15, (10.0 g, 16.4 mmol) and 4-fluoro-3-methyl-benzylamine (6.84 g, 49.1 mmol) in EtOH (150 ml) was stirred with heating (90° C. oil bath) for 16 hrs, under a nitrogen atmosphere. After cooling to room temperature the reaction was stirred an additional 6 hrs. The mixture was concentrated under reduced pressure. The resulting residue was suspended in EtOAc (100 mL). Addition of aq HCl resulted in precipitation of an off-white solid. The solid was collected by vacuum filtration and washed with a small volume of 1.0 N HCl. The filtrate was separated and the organic layer concentrated under reduced pressure and triturated with Et₂O to provide additional solid which was collected by vacuum filtration. The combined solids were azeotroped under reduced pressure using 1:1 MeOH/CH₂Cl₂, to afford the title compound as a solid. HPLC (System A): 90% AP, rt=3.55 min. LCMS: 705 (M+H). ¹HNMR (500 MHz, CDCl₃) δ ppm 1.51-1.64 (2H, m), 1.76 (2H), 2.04-2.11 (2H, m), 2.24 (3H, s), 2.47-2.50 (2H, m), 2.49 (3H, s), 3.81 (2H, s), 3.95 (2H, s), 4.40 (2H, d, J=6.4 Hz), 4.91 (2H, s), 5.69 (1H, s), 6.88-7.08 (3H, m), 7.23-7.39 (5H, m), 7.42 (2H, d, J=8.2 Hz), 7.58 (1H, br), 7.83 (1H, d, J=8.2 Hz), 12.04 (1H). ¹³C NMR (126 MHz, CDCl₃) δ ppm 14.6, 21.8, 26.0, 30.0, 35.8, 42.4, 53.9, 57.2, 66.7, 75.3, 115.4, 124., 125.5, 126.7, 128.0, 128.5, 128.8, 128.1, 130.3, 131.0, 132.2, 132.7, 136.2, 145.5, 146.9, 152.4, 155.3, 159.3, 161.0, 168.0.

Intermediate 17

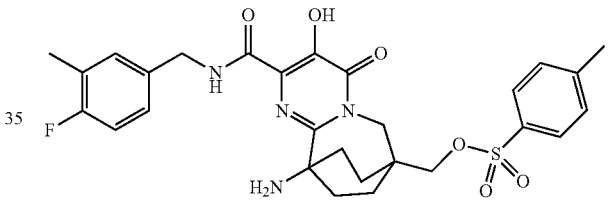

7,10-Amino-N-[(4-fluoro-3-methylphenyl)methyl]-4,6,7,8,9,10-hexahydro-3-hydroxy-7-[[[(4-methylphenyl) sulfonyl]oxy]methyl]-4-oxo-, 10-ethanopyrimido[1,2-a]azepine-2-carboxamide hydrochloride A suspension of [2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-, phenylmethyl ester carbamic acid, Intermediate 16, (11.54 g, 16.38 mmol) in EtOAc (150 mL) and MeOH (150 mL) was treated with 1.0 N HCl (25 mL). The suspension was diluted with THF (100 mL) and CH₂Cl₂ (100 mL), and heated until dissolution occurred. The reaction solution was cooled and a stream of N₂ gas was bubbled through the solution for 20 min, followed by portionwise addition of 10% Pd—C (3.49 g, 3.28 mmol). The mixture was stirred under 1 atm. of H₂ (balloon) at room temp for 16 hrs. The reaction was diluted with MeOH (700 mL) and CH₂Cl₂ (700 mL), and stirred until grey solids appeared to have dissolved. The Pd catalyst was removed by filtration through a celite pad, washing with several portions of 1:1 CH₂Cl₂/MeOH. After concentration under reduced pressure the residue was triturated with Et₂O, and the solids were collected by vacuum filtration, affording 9.45 g of the title compound as a light pink powder. HPLC (System A): 90.2% AP, rt=2.12 min. LC/MS (System C): 571.3 (M+H). ¹H NMR (500 MHz, CD$_3$OD) δ ppm 1.78 (2H, br.s), 2.11-2.30 (2H, m), 2.26 (3H, s), 2.48 (3H, s), 3.94 (2H, s), 4.03 (2H, s), 4.56 (2H, br), 7.00 (1H, br.s), 7.26 (2H, br), 7.50 (2H, d, J=7.3 Hz), 7.84 (1H, d, J=6.9 Hz). $^{13}$C NMR (126 MHz, CD$_3$OD) δ ppm 14.3, 21.6, 26.2, 29.4, 36.7, 55.3, 57.9, 76.7, 115.7, 125.8, 129.1, 131.3, 133.8, 146.9, 148.2, 150.2, 160.7, 162.2, 169.1.

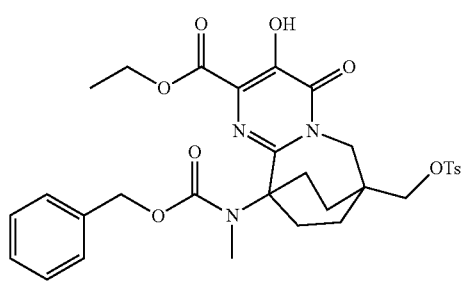

Intermediate 18

7,10-Ethanopyrimido[1,2-a]azepine-2-carboxylic acid, 4,6,7,8,9,10-hexahydro-3-hydroxy-10-[methyl[(phenylmethoxy)carbonyl]amino]-7-[[[(4-methylphenyl)sulfonyl]oxy]methyl]-4-oxo-, ethyl ester To a solution of 4,6,7,8,9,10-hexahydro-3-hydroxy-7-[[[(4-methylphenyl)sulfonyl]oxy]methyl]-4-oxo-10-[[phenylmethoxy)carbonyl]amino]-, 7,10-ethanopyrimido[1,2-a]azepine-2-carboxylic acid ethyl ester, Intermediate 15, (300 mg, 0.490 mmol) in DMF (3 mL) at 0° C. was added NaHMDS (1.079 mL, 1.079 mmol) in THF. After 1 h at room temperature, iodomethane (0.092 mL, 1.471 mmol) was added and the mixture was stirred at room temp for 16 h. The reaction mixture was quenched with water and acidified with 1N HCl. The mixture was then extracted with ethyl acetate (3×50 mL), washed with brine, dried (Na$_2$SO$_4$), filtered and concentrated to afford crude product which was used in the next step without further purification. $^1$H NMR (400 MHz, CDCl$_3$) δ: 10.29 (1H, br. s.), 7.82 (2H, d, J=8.28 Hz), 7.10-7.48 (7H, m), 5.07 (2H, br. s.), 4.29 (2H, d, J=6.53 Hz), 3.80 (2H, br. s.), 3.13 (3H, s), 2.49 (3H, s), 1.95-2.10 (2H, m), 1.17-1.94 (11H, m). LCMS (M+H) calcd for C$_{31}$H$_{36}$N$_3$O$_9$S: 626.21. found: 626.3.

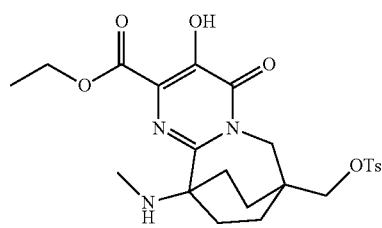

Intermediate 19

7,10-Ethanopyrimido[1,2-a]azepine-2-carboxylic acid, 4,6,7,8,9,10-hexahydro-3-hydroxy-10-(methylamino)-7-[[[(4-methylphenyl)sulfonyl]oxy]methyl]-4-oxo-, ethyl ester The 7,10-ethanopyrimido[1,2-a]azepine-2-carboxylic acid, 4,6,7,8,9,10-hexahydro-3-hydroxy-10-[methyl[(phenylmethoxy)carbonyl]amino]-7-[[[(4-methylphenyl)sulfonyl]oxy]methyl]-4-oxo-, ethyl ester, Intermediate 18, (1.948 g, 3.11 mmol) was dissolved in a mixture of dichloromethane (20 ml) and ethanol (120 ml). 1N HCl (20.00 ml, 20 mmol) was added followed by Pd/C (2.485 g, 2.335 mmol) and the mixture was shaken at room temperature under H$_2$ (60 psi) for 2.5 h. The mixture was filtered over celite rinsing with EtOH and water. The solution was concentrated to give the title compound as an HCl salt (1.41 g, 2.67 mmol, 86% yield) as a pale yellow solid. $^1$H NMR (500 MHz, DMSO-d$_6$) δ: 10.61 (1H, br. s.), 9.22 (1H, d, J=4.27 Hz), 7.83 (2H, d, J=8.24 Hz), 7.52 (2H, d, J=7.93 Hz), 4.29 (2H, q, J=7.02 Hz), 3.94 (2H, s), 3.88 (2H, s), 2.57 (3H, t, J=5.04 Hz), 2.44 (3H, s), 2.02-2.16 (4H, m), 1.54-1.66 (4H, m), 1.30 (3H, t, J=7.17 Hz). LCMS (M+H) calcd for C$_{23}$H$_{30}$N$_3$O$_7$S: 492.18. found: 492.3.

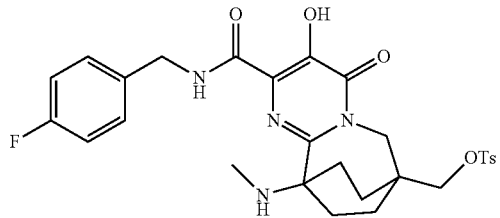

Intermediate 20

7,10-Ethanopyrimido[1,2-a]azepine-2-carboxamide, N-[(4-fluorophenyl)methyl]-4,6,7,8,9,10-hexahydro-3-hydroxy-10-(methylamino)-7-[[[(4-methylphenyl)sulfonyl]oxy]methyl]-4-oxo- To a mixture of 7,10-ethanopyrimido[1,2-a]azepine-2-carboxylic acid, 4,6,7,8,9,10-hexahydro-3-hydroxy-10-(methylamino)-7-[[[(4-methylphenyl)sulfonyl]oxy]methyl]-4-oxo-, ethyl ester, Intermediate 19, (1.2544 g, 2.55 mmol) in ethanol (25 ml) was added (4-fluorophenyl)methanamine (0.348 ml, 3.06 mmol) followed by Et$_3$N (1.067 ml, 7.66 mmol) and the resulting mixture was stirred at 90° C. for 22 h. The mixture was cooled to room temperature and concentrated. The residue was partitioned between EtOAc and 1N HCl and stirred vigorously. The solids were collected by filtration. The organic phase was washed with brine and dried (Na$_2$SO$_4$), filtered and concentrated to give a white solid that was combined with the solid that was collected by filtration to give the title compound (1.38 g, 2.418 mmol, 95% yield) as an off white solid. $^1$H NMR (500 MHz, MeOD): δ: 7.85 (2H, d, J=8.24 Hz), 7.51 (2H, d, J=8.24 Hz), 7.44 (2H, dd, J=7.93, 5.49 Hz), 7.09 (2H, t, J=8.70 Hz), 4.62 (2H, br. s.), 4.01 (2H, s), 3.94 (2H, s), 2.71 (3H, s), 2.49 (3H, s), 2.11-2.29 (4H, m), 1.66-1.86 (4H, m). LCMS (M+H) calcd for C$_{28}$H$_{32}$FN$_4$O$_6$S: 571.20. found: 571.45.

Intermediate 21

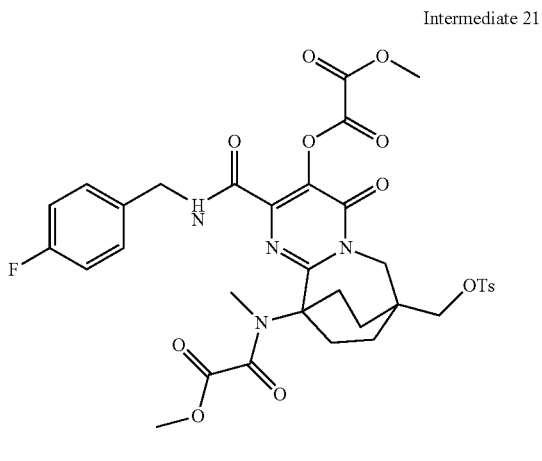 [SMILES: COC(=O)C(=O)Oc1c(C(=O)NCc2ccc(F)cc2)nc2n(c1=O)CC1(COS(=O)(=O)c3ccc(C)cc3)CCC2(N(C)C(=O)C(=O)OC)CC1]

Ethanedioic acid, 2-[[[(4-fluorophenyl)methyl]amino]carbonyl]-4,6,7,8,9,10-hexahydro-10-[(2-methoxy-1,2-dioxoethyl)methylamino]-7-[[[(4-methylphenyl)sulfonyl]oxy]methyl]-4-oxo-7,10-ethanopyrimido[1,2-a]azepin-3-yl methyl ester To a suspension of 7,10-ethanopyrimido[1,2-a]azepine-2-carboxamide, N-[(4-fluorophenyl)methyl]-4,6,7,8,9,10-hexahydro-10-(methylamino)-7-[[[(4-methylphenyl)sulfonyl]oxy]methyl]-4-oxo-. Intermediate 20, (1.38 g, 2.418 mmol) in dichloromethane (50 ml) at 0° C. was added diisopropylethylamine (3.38 ml, 19.34 mmol) followed by methyl 2-chloro-2-oxoacetate (0.892 ml, 9.68 mmol) and the resulting solution was stirred at room temperature for 20 h. The reaction mixture was washed with 1N HCl, dried (Na$_2$SO$_4$), filtered and concentrated to give the title compound as a brown residue. LCMS (M+H) calcd for C$_{34}$H$_{36}$FN$_4$O$_{12}$S: 743.20. found: 743.3.

Intermediate 22

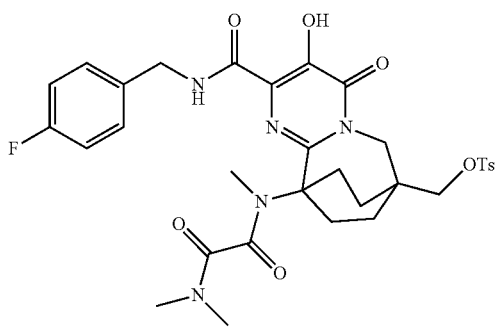

Ethanediamide, N$^1$-[2-[[[(4-fluorophenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N$^1$,N$^2$,N$^2$-trimethyl- A solution of ethanedioic acid, 2-[[[(4-fluorophenyl)methyl]amino]carbonyl]-4,6,7,8,9,10-hexahydro-10-[(2-methoxy-1,2-dioxoethyl)methylamino]-7-[[[(4-methylphenyl)sulfonyl]oxy]methyl]-4-oxo-7,10-ethanopyrimido[1,2-a]azepin-3-yl methyl ester, Intermediate 21, (1.783 g, 2.4 mmol) and dimethylamine/MeOH (24.00 ml, 48.0 mmol, 20 eq) was stirred at 50° C. in a sealed pressure tube. After 18 h, the solution was cooled to room temperature and concentrated. The residue was purified by Prep HPLC to give the title compound (0.5043 g, 0.753 mmol, 31.4% yield) as an off white solid. LCMS (M+H) calcd for C$_{32}$H$_{37}$FN$_5$O$_8$S: 670.23. found: 670.4.

Intermediate 23

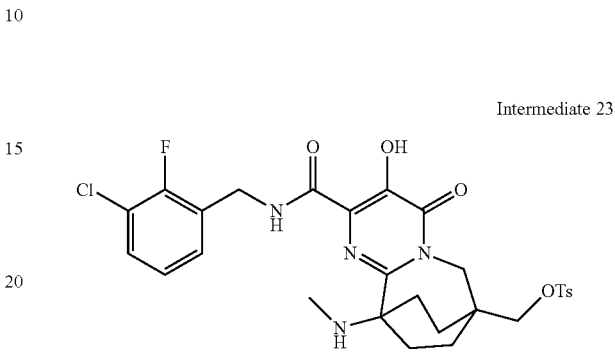

7,10-Ethanopyrimido[1,2-a]azepine-2-carboxamide, N-[(3-chloro-2-fluorophenyl)methyl]-4,6,7,8,9,10-hexahydro-3-hydroxy-10-(methylamino)-7-[[[(4-methylphenyl)sulfonyl]oxy]methyl]-4-oxo- Off-white solid. $^1$H NMR (500 MHz, DMSO-d$_6$): δ: 12.03-12.18 (1H, m), 9.68-9.96 (1H, m), 9.55 (1H, d, J=2.44 Hz), 7.82 (2H, d, J=8.24 Hz), 7.47-7.60 (3H, m), 7.35-7.44 (1H, m), 7.23 (1H, t, J=7.93 Hz), 4.50-4.68 (2H, m), 3.93 (2H, s), 3.83 (2H, s), 2.48-2.49 (3H, m), 2.44 (3H, s), 2.00-2.18 (4H, m), 1.51-1.68 (4H, m). LCMS (M+H) calcd for C$_{28}$H$_{31}$FClN$_4$O$_6$S: 606.15. found: 605.4.

Intermediate 24

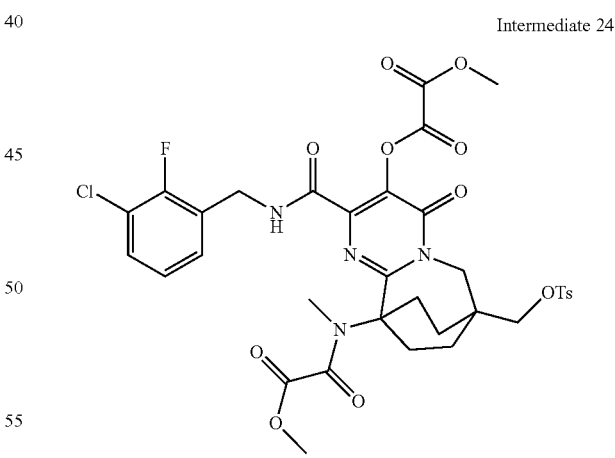

Ethanedioic acid, 2-[[[(3-chloro-2-fluorophenyl)methyl]amino]carbonyl]-4,6,7,8,9,10-hexahydro-10-[(2-methoxy-1,2-dioxoethyl)methylamino]-7-[[[(4-methylphenyl)sulfonyl]oxy]methyl]-4-oxo-7,10-ethanopyrimido[1,2-a]azepin-3-yl methyl ester Yellow foam. LCMS (M+H) calcd for C$_{34}$H$_{35}$FClN$_4$O$_{12}$S: 777.17. found: 777.3.

Intermediate 25

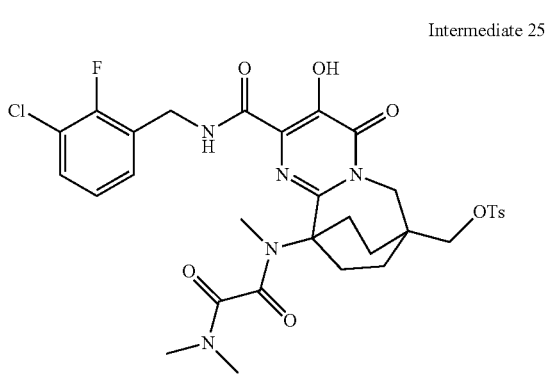 [SMILES: Cc1ccc(S(=O)(=O)OCC23CCC(N(C)C(=O)C(=O)N(C)C)(CC2)c2nc(C(=O)NCc4cccc(Cl)c4F)c(O)c(=O)n2C3)cc1]

Ethanediamide, N¹-[2-[[[(3-chloro-2-fluorophenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N¹,N²,N²-trimethyl- A solution of ethanedioic acid, 2-[[[(3-chloro-2-fluorophenyl)methyl]amino]carbonyl]-4,6,7,8,9,10-hexahydro-10-[(2-methoxy-1,2-dioxoethyl)methylamino]-7-[[[(4-methylphenyl)sulfonyl]oxy]methyl]-4-oxo-7,10-ethanopyrimido[1,2-a]azepin-3-yl methyl ester, Intermediate 24, (1.38 g, 1.77 mmol) in 1,2-dichloroethane (20 mL) and dimethylamine/MeOH (160.00 ml, 320 mmol, 180 eq) was stirred at 55° C. in a sealed pressure tube. After 56 h, the solution was cooled to room temperature and concentrated. The residue was purified by Prep HPLC to give the title compound (0.1939 g, 0.275 mmol, 16% yield) as a pale brown solid. LCMS (M+H) calcd for $C_{32}H_{36}FClN_5O_8S$: 705.18. found: 704.3.

Intermediate 26

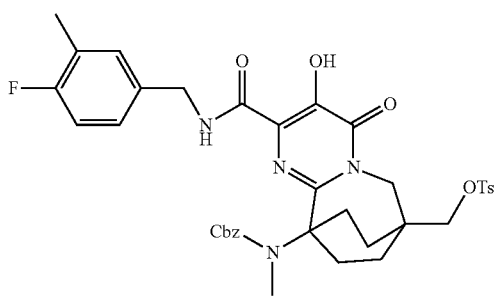

Carbamic acid, N-[2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N-methyl-, phenylmethyl ester To a mixture of 7,10-ethanopyrimido[1,2-a]azepine-2-carboxylic acid, 4,6,7,8,9,10-hexahydro-3-hydroxy-10-[methyl[(phenylmethoxy)carbonyl]amino]-7-[[[(4-methylphenyl)sulfonyl]oxy]methyl]-4-oxo-, ethyl ester, Intermediate 18, (300 mg, 0.479 mmol) in ethanol (5 mL) was added (4-fluoro-3-methylphenyl)methanamine (0.121 mL, 0.959 mmol) followed by triethylamine (0.200 mL, 1.438 mmol) and the mixture was heated at 90° C. for 18 h. At this point LCMS indicates completion of reaction. The reaction mixture was cooled, concentrated, diluted with ethyl acetate and washed with 1N HCl (10 mL), dried ($Na_2SO_4$), filtered and concentrated to afford crude product which was purified by preparative HPLC to afford the title compound (180 mg, 0.250 mmol, 52.2% yield) as an off-white solid. ¹H NMR (500 MHz, CDCl₃) δ: 11.77 (1H, br. s.), 7.83 (3H, d, J=8.24 Hz), 7.54-7.63 (1H, m), 7.42 (3H, d, J=7.93 Hz), 7.10-7.25 (3H, m), 6.80-7.05 (3H, m), 5.05-5.17 (1H, m), 4.67-4.78 (1H, m), 4.32-4.51 (3H, m), 3.79 (2H, br. s.), 3.32-3.47 (1H, m), 3.00 (3H, s), 2.49 (3H, s), 2.29 (3H, s), 1.93-2.04 (3H, m), 1.59-1.78 (3H, m). LCMS (M+H)=719.4.

Intermediate 27

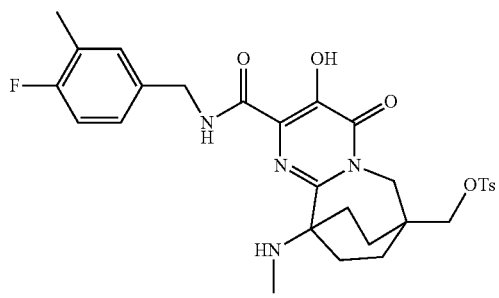

7,10-Ethanopyrimido[1,2-a]azepine-2-carboxamide, N-[(4-fluoro-3-methylphenyl)methyl]-4,6,7,8,9,10-hexahydro-3-hydroxy-10-(methylamino)-7-[[[(4-methylphenyl)sulfonyl]oxy]methyl]-4-oxo- To a solution of carbamic acid, N-[2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N-methyl-, phenylmethyl ester, Intermediate 26, (180 mg, 0.250 mmol) in MeOH (4 mL) and CH₂Cl₂ (2.0 mL) was added 1M HCl (0.275 mL, 0.275 mmol) followed by Pd/C (53.3 mg, 0.050 mmol) and the resulting mixture was stirred under H₂ for 16 h. Catalyst was removed by filtration over Celite washing with methanol and dichloromethane. The filtrate was concentrated and dried in vacuuo to afford the title compound (HCl salt, 140 mg, 0.225 mmol, 90% yield) as an off-white solid. ¹H NMR (500 MHz, DMSO-d₆) δ: 12.27 (1H, br. s.), 9.95 (1H, s), 7.82 (2H, d, J=8.24 Hz), 7.52 (2H, d, J=8.24 Hz), 7.27 (1H, d, J=7.02 Hz), 7.18-7.24 (1H, m), 7.11 (1H, t, J=9.00 Hz), 4.45 (2H, d, J=6.10 Hz), 3.92 (2H, s), 3.83 (2H, s), 2.44 (6H, s), 2.22 (3H, s), 1.94-2.15 (4H, m), 1.52-1.63 (4H, m). LCMS (M+H)=585.3

Intermediate 28

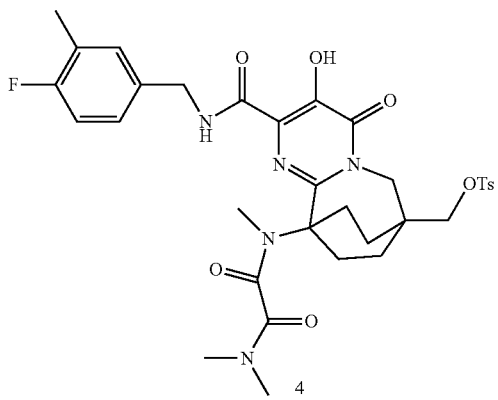

N-[2-[[[(4-Fluoro-3-methylphenyl)methyl]amino]
carbonyl]-6,7,8,9-tetrahydro-3-hydroxy-7-[[[(4-methylphenyl) sulfonyl]oxy]methyl]-4-oxo-7,10-ethanopyrimido[1,2-a]azepin-10(4H)-yl]-N,N',N'-
trimethyl-ethanediamide To a solution of 7,10-ethanopyrimido[1,2-a]azepine-2-carboxamide, N-[(4-fluoro-3-methylphenyl)methyl]-4,6,7,8,9,10-hexahydro-3-hydroxy-10-(methylamino)-7-[[[(4-methylphenyl)sulfonyl]oxy]methyl]-4-oxo-, Intermediate 27, (140 mg, 0.225 mmol) in $CH_2Cl_2$ (4 mL) at 0° C. was added diisopropylethylamine (0.118 mL, 0.676 mmol) followed by methyl 2-chloro-2-oxoacetate (0.042 mL, 0.451 mmol) and the resulting mixture stirred at room temp for 2 h. The reaction was washed with 1N HCl (25 mL), brine (50 mL), then dried ($Na_2SO_4$), filtered, concentrated and dried in vacuuo for 2 hr. The crude product was treated with 2 M $(CH_3)_2NH$/MeOH (2.254 mL, 4.51 mmol) and stirred at 55° C. for 16 h. The mixture was cooled, concentrated and purified by preparative HPLC to afford the title compound (90 mg, 0.125 mmol, 55.5% yield) as white solid. $^1$H NMR (500 MHz, $CDCl_3$) δ: 11.50 (1H, s), 9.57 (1H, t, J=6.10 Hz), 7.83 (2H, d, J=8.24 Hz), 7.42 (2H, d, J=7.93 Hz), 7.16-7.25 (2H, m), 6.93 (1H, t, J=9.00 Hz), 4.53-4.63 (2H, m), 4.41-4.48 (1H, m), 3.77-3.87 (2H, m), 3.33-3.45 (2H, m), 3.04 (3H, s), 3.01 (3H, s), 3.00 (3H, s), 2.49 (3H, s), 2.26 (3H, s), 2.04-2.15 (3H, m), 1.73-1.88 (2H, m), 1.60-1.71 (1H, m), 1.36-1.49 (1H, m). LCMS (M+H)=684.3.

Intermediate 29

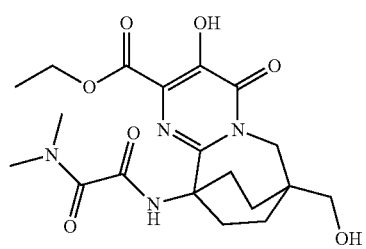

7,10-Ethanopyrimido[1,2-a]azepine-2-carboxylic
acid, 10-[[2-(dimethylamino)-1,2-dioxoethyl]
amino]-4, (hydroxymethyl)-4-oxo-, ethyl ester White solid. $^1$H NMR (500 MHz, $CDCl_3$) δ: 10.45 (1H, br. s.), 9.51 (1H, s), 4.50 (2H, q, J=7.0 Hz), 4.11 (2H, s), 3.53 (2H, s), 3.40 (3H, s), 3.07 (3H, s), 2.98-3.04 (2H, m), 1.80-1.93 (4H, m), 1.63-1.71 (2H, m), 1.51 (3H, t, J=7.2 Hz). LCMS (M+H) calcd for $C_{19}H_{27}N_4O_7$: 423.19. found: 423.3.

Intermediate 30

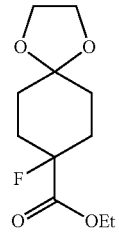

Ethyl
8-fluoro-1,4-dioxaspiro[4.5]decane-8-carboxylate

To a solution of ethyl 1,4-dioxaspiro[4.5]decane-8-carboxylate (15 g, 70.0 mmol, 1 equiv) in THF (200 mL) at 0° C. (ice water bath), was added LiHMDS (98 mL of a 1 M solution in THF, 98 mmol, 1.4 equiv) in 4 portions over ~2 min. After stirring 1 h, N-fluoro-di(benzenesulfonyl)-amine (26.5 g, 84 mmol, 1.2 equiv) was added. The reaction was stirred 20 min then poured into a saturated aqueous solution of $NaHCO_3$. The aqueous solution was extracted with ether (×3). The combined ether layers were dried ($MgSO_4$) and concentrated in vacuo. Crude residue was stirred with hexane (~600 mL) and filtered. The filtrate was concentrated in vacuo to give 16.68 g of the crude product as a yellow oil. ~4:1 product:sm. Taken on as is to the ester reduction. $^1$H NMR (400 MHz, $CDCl_3$) δ ppm 4.25 (q, J=7.11 Hz, 2H), 3.94-4.00 (m, 4H), 2.02-2.26 (m, 4H), 1.92 (td, J=13.30, 4.77 Hz, 2H), 1.66-1.77 (m, 2H), 1.31 (t, J=7.03 Hz, 3H); $^{19}$F NMR (376 MHz, $CDCl_3$) δ ppm −168.50 (br. s., 1F).

Intermediate 31

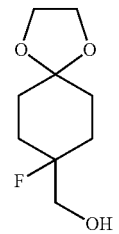

(8-Fluoro-1,4-dioxaspiro[4.5]decan-8-yl)methanol

To a solution of crude ethyl 8-fluoro-1,4-dioxaspiro[4.5]decane-8-carboxylate, Intermediate 30, (16.26 g, 70 mmol calculated based on previous reaction, 1 equiv) in THF (100 mL) was added $LiBH_4$ (45.5 mL of a 2 M solution in THF, 91 mmol, 1.3 equiv) followed by MeOH (3.68 mL, 91 mmol, 1.3 equiv). Significant warming was observed following MeOH addition. The reaction was stirred 30 min at which time TLC showed no ester remaining. The reaction was poured into a saturated aqueous solution of $NaHCO_3$ and the aqueous solution was extracted with ether (×3). The combined ether layers were dried ($MgSO_4$) and concentrated in vacuo. The crude product was purified by silica gel chromatography (30-90% ethyl acetate/hexane) to provide the title compound (7.50 g, 56% yield for 2 steps) as a pale yellow oil. $^1$H NMR (400

MHz, CDCl₃) δ ppm 3.90-4.03 (m, 4H), 3.64 (d, J=6.78 Hz, 1H), 3.59 (d, J=6.78 Hz, 1H), 1.97-2.09 (m, 2H), 1.84-1.95 (m, 2H), 1.62-1.80 (m, 4H); ¹⁹F NMR (376 MHz, CDCl₃) δ ppm −171.25 (br. s., 1F).

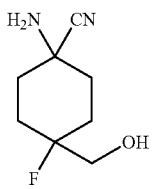

Intermediate 32

1-Amino-4-fluoro-4-(hydroxymethyl)cyclohexanecarbonitrile

A flask was charged with 4-fluoro-4-(hydroxymethyl)cyclohexanone, derived from Intermediate 31, (12.1 g, 83 mmol), methanol (200 mL), aqueous ammonium hydroxide (32.2 mL, 828 mmol) and then NH₄Cl (8.86 g, 166 mmol). After the ammonium chloride had dissolved, NaCN (8.11 g, 166 mmol) was added. The reaction was stirred under nitrogen overnight. The mixture was then concentrated. Brine (100 mL) was added to the resulting residue. The slurry was extracted with chloroform/isopropanol (200 mL, 10%, 7 times) and the combined organic fractions dried (MgSO₄) and evaporated giving the title compound (12.2 g, 70.8 mmol, 86% yield)] as a creamy white solid.

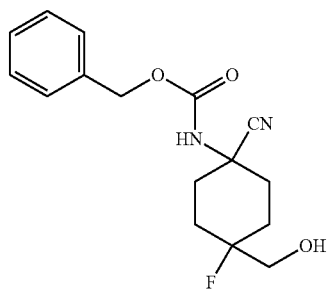

Intermediate 33

Benzyl 1-cyano-4-fluoro-4-(hydroxymethyl)cyclohexylcarbamate

A flask was charged with 1-amino-4-fluoro-4-(hydroxymethyl)cyclohexanecarbonitrile, Intermediate 32, (12.2 g, 70.8 mmol), CH₂Cl₂ (200 mL), water (80 mL) and benzyl chlorocarbonate (12.14 mL, 85 mmol) and the mixture stirred under nitrogen overnight. The CH₂Cl₂ portion of the reaction mixture was separated, washed with water then brine, dried (MgSO₄) and concentrated to give a yellow oil. The oil was purified by column chromatography on silica gel, eluted with hexane/ethyl acetate (0 to 100%). The appropriate fractions were combined and the solvent evaporated to provide the title compound (13.1 g, 42.8 mmol, 60.4% yield)] as a colorless oil that crystallized upon standing.

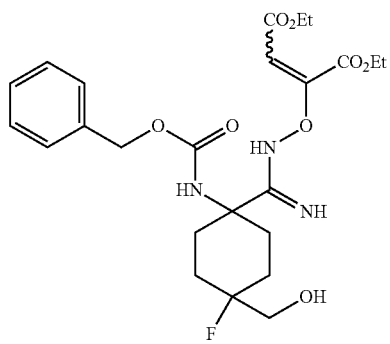

Intermediate 34

Diethyl 2-(1-(benzyloxycarbonylamino)-4-fluoro-4-(hydroxymethyl)cyclohexanecarboximidamidooxy)but-2-enedioate A flask was charged with benzyl 1-cyano-4-fluoro-4-(hydroxymethyl)cyclohexylcarbamate, Intermediate 33, (13.0 g, 42.4 mmol), EtOH (100 mL) and aqueous hydroxylamine (26.0 mL, 424 mmol). The reaction was stirred at 80° C. under nitrogen for 2 hours. The mixture was concentrated and the resulting residue diluted with CH₂Cl₂, washed with brine, dried (MgSO₄) and the solvent evaporated to provide a colorless oil. The oil was dissolved in EtOH (100 mL) to which diethyl acetylenedicarboxylate (13.54 mL, 85 mmol) was added. The reaction was stirred under nitrogen for one hour. The solution was concentrated and the residue was dissolved in CH₂Cl₂ then purified by silica gel column chromatography eluting with hexane/ethyl acetate (0 to 100%). The appropriate fractions were combined and evaporated to give the title compound (13.01 g, 25.5 mmol, 60.2% yield)] as a light yellow syrup.

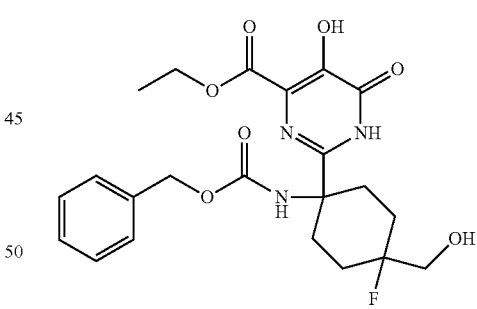

Intermediate 35

Ethyl 2-(1-(benzyloxycarbonylamino)-4-fluoro-4-(hydroxymethyl)cyclohexyl)-5-hydroxy-6-oxo-1,6-dihydropyrimidine-4-carboxylate A flask was charged with diethyl 2-(1-(benzyloxycarbonylamino)-4-fluoro-4-(hydroxymethyl)cyclohexane-carboximidamidooxy)but-2-enedioate, Intermediate 34, (10.1 g, 19.82 mmol) and xylene (200 mL) and the and the resulting mixture stirred at 125° C. under nitrogen overnight. The mixture was allowed to cool room temperature, diluted with ether and extracted with 0.2 N NaOH (300 mL). The aqueous fraction was washed with ethyl acetate (3×200 mL), acidified to pH 2 with 1N HCl and extracted with CH₂Cl₂ (2×200 mL).

The combined CH$_2$Cl$_2$ fractions were washed with brine, dried (MgSO$_4$) and concentrated to provide the title compound (4.10 g, 8.85 mmol, 44.6% yield)] as a creamy yellow powder.

Intermediate 36

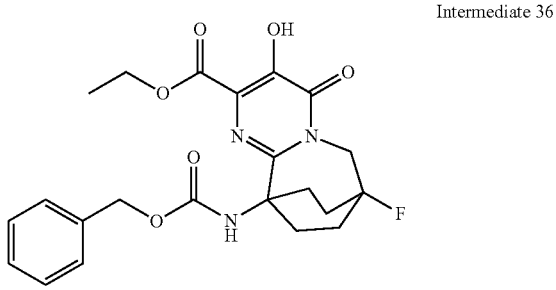 [SMILES: CCOC(=O)c1nc2n(c(=O)c1O)CC1(F)CCC2(NC(=O)OCc2ccccc2)CC1]

7,10-Ethanopyrimido[1,2-a]azepine-2-carboxylic acid, 7-fluoro-4,6,7,8,9,10-hexahydro-3-hydroxy-4-oxo-10-[[(phenylmethoxy)carbonyl]amino]-, ethyl ester A flask was charged with ethyl 2-(1-(benzyloxycarbonylamino)-4-fluoro-4-(hydroxymethyl)cyclohexyl)-5-hydroxy-6-oxo-1,6-dihydropyrimidine-4-carboxylate, Intermediate 35, (1.00 g, 2.16 mmol), polystyrene-bound triphenylphosphine (CAS number: 39319-11-4) 3 mmol/g (1.44 g, 4.32 mmol) and THF (20 mL). Diethyl-diazo-dicarboxylate (0.68 mL, 4.32 mmol) was added dropwise. After stirring at room temperature for 60 minutes, the reaction was stirred at 60° C. under nitrogen overnight. The reaction mixture was diluted with ethyl acetate and filtered. The filtrate was washed with 1N HCl, then brine, dried (MgSO$_4$) and concentrated to provide a golden yellow solid. The solid was dissolved in methanol to form a precipitate which was isolated by filtration and washed with minimal amount of methanol to yield the title compound (0.485 g, 1.089 mmol, 50.5% yield) as creamy white needles, 406 mg.

Intermediate 37

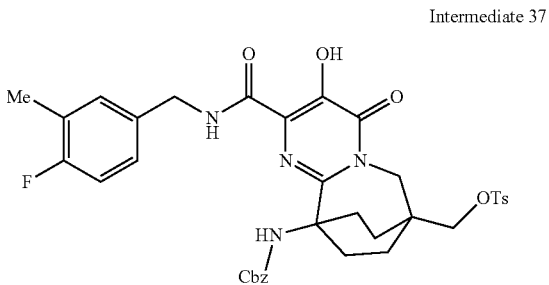 [SMILES: Cc1ccc(S(=O)(=O)OCC23CCC(NC(=O)OCc4ccccc4)(CC2)c2nc(C(=O)NCc4ccc(F)c(C)c4)c(O)c(=O)n2C3)cc1]

Carbamic acid, [2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl], phenylmethyl ester A solution of 4,6,7,8,9,10-hexahydro-3-hydroxy-7-[[[(4-methylphenyl)sulfonyl]oxy]methyl]-4-oxo-10-[[(phenylmethoxy)carbonyl]amino]-, 7,10-ethanopyrimido[1,2-a]azepine-2-carboxylic acid ethyl ester, Intermediate 15, (10.0 g, 16.35 mmol, 1 equiv) and 4-fluoro-3-methylbenzylamine (5.92 g, 42.5 mmol, 2.6 equiv) in EtOH (163 mL) was refluxed for 16 h. Upon completion, the reaction was removed from heat, concentrated in vacuo to remove EtOH, and residue was taken up in EtOAc (200 mL). The EtOAc layer was washed with 1 N HCl (2×200 mL), brine (200 mL), and dried (Na$_2$SO$_4$). CH$_2$Cl$_2$ (250 mL) was added to EtOAc solution as product had begun to precipitate. Combined organics were then concentrated in vacuo to give the product as a yellow solid (10.56 g, 92%). $^1$H NMR (400 MHz, CDCl$_3$) δ ppm 12.01 (1H, br. s.), 7.82 (2H, d, J=8.3 Hz), 7.54-7.60 (1H, m), 7.41 (2H, d, J=8.0 Hz), 7.30-7.39 (4H, m), 6.86-7.14 (3H, m), 5.69 (1H, br. s.), 4.91 (2H, s), 4.40 (2H, d, J=6.0 Hz), 3.94 (2H, br. s.), 3.80 (2H, s), 2.48 (3H, s), 2.24 (3H, s), 1.95-2.10 (2H, m), 1.76 (2H, br. s.), 1.52-1.62 (4H, m); $^{19}$F NMR (376 MHz, CDCl$_3$) δ ppm −118.55 (1F, br. s.); LCMS (ES+, (M+H+water)$^+$) m/z 705.5.

Intermediate 38

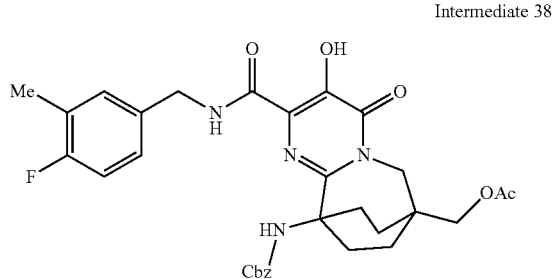

Carbamic acid, N-[7-[(acetyloxy)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-, phenylmethyl ester A solution of carbamic acid, [2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-, phenylmethyl ester, Intermediate 37, (6.24 g, 8.85 mmol, 1 equiv) and tetrabutylammonium acetate (21.4 g, 70.8 mmol, 8 equiv) in DMSO (89 mL) was heated to 80° C. (oil bath) for 3 d. Upon completion, the reaction was added to 1 N HCl and extract with EtOAc (×2). The combined EtOAc layers were washed with brine, dried (Na$_2$SO$_4$), and concentrated in vacuo to give the title compound as a brown solid (5.82 g, ~100%). $^1$H NMR (400 MHz, CDCl$_3$) δ ppm 12.01 (1H, br. s.), 7.60 (1H, br. s.), 7.31-7.42 (5H, m), 7.01 (3H, br. s.), 4.93 (2H, s), 4.41 (2H, d, J=6.3 Hz), 4.09 (2H, br. s.), 3.93 (2H, s), 2.52 (2H, br. s.), 2.24 (3H, s), 2.10-2.11 (3H, m), 2.04-2.14 (4H, m), 1.50-1.76 (2H, m); LCMS (ES+, (M+H+ water)$^+$) m/z 593.5.

Intermediate 39

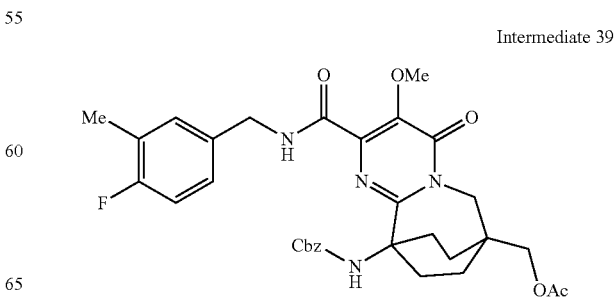

Carbamic acid, N-[7-[(acetyloxy)methyl]-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-, phenylmethyl ester A flask was charged with carbamic acid, N-[7-[(acetyloxy)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-, phenylmethyl ester, Intermediate 38, (2.87 g, 4.85 mmol), benzene (25 mL), MeOH (25 mL), and trimethylsilyldiazomethane (2 M in hexane 7.28 mL, 14.55 mmol). The reaction was stirred for 1 h. The reaction was concentrated in vacuo. The residue was dissolved in CH$_2$Cl$_2$, washed with water then brine, dried (MgSO$_4$) and concentrated in vacuo giving a yellow syrup. The crude product was purified via silica gel chromatography (30-100% EtOAc/hexane) giving the target compound (2.20 g, 3.63 mmol, 75% yield) as a white foam. LCMS (ES+, (M+H)$^+$) m/z: 607.4. $^1$H NMR (400 MHz, CDCl$_3$) δ ppm 7.56 (1H, br. s.), 7.34 (5H, br. s.), 7.03-7.16 (2H, m), 6.92 (1H, t, J=8.91 Hz), 6.57 (1H, br. s.), 5.00 (2H, s), 4.49 (2H, d, J=6.02 Hz), 4.01-4.06 (5H, m), 3.93 (2H, s), 2.74 (2H, br. s.), 2.24 (3H, d, J=1.76 Hz), 2.10 (3H, s), 2.00 (2H, dt, J=13.61, 6.87 Hz), 1.73-1.83 (2H, m), 1.65 (2H, dt, J=13.80, 6.90 Hz), 1.59 (2H, s).

Intermediate 40

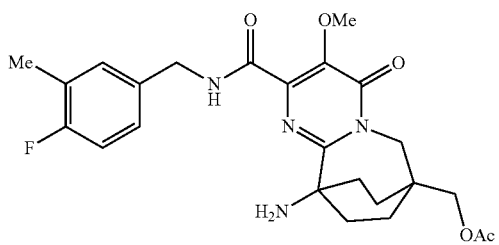

7,10-Ethanopyrimido[1,2-a]azepine-2-carboxamide, 7-[(acetyloxy)methyl]-10-amino-N-[(4-fluoro-3-methylphenyl)methyl]-4,6,7,8,9,10-hexahydro-3-methoxy-4-oxo- A flask was charged with 10% Pd/C (0.22 g, 0.207 mmol), carbamic acid, N-[7-[(acetyloxy)methyl]-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-, phenylmethyl ester, Intermediate 39, (2.19 g, 3.61 mmol), MeOH (25 mL), and a hydrogen balloon. The reaction was stirred overnight. The reaction was mixed with celite, filtered on celite, the solids washed with methanol and the filtrate evaporated to provide an off-white solid. The solid was triturated in methanol and filtered giving the target compound (1.66 g, 3.51 mmol, 97% yield) as an off-white solid. LCMS (ES+, (M+H)$^+$) m/z: 473.3.

Intermediate 41

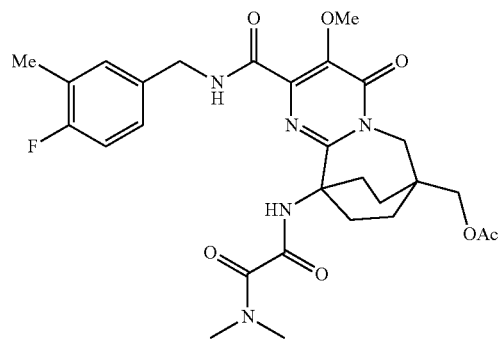

Ethanediamide, N$^2$-[7-[(acetyloxy)methyl]-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-N$^1$,N$^1$-dimethyl- A flask was charged with 7,10-ethanopyrimido[1,2-a]azepine-2-carboxamide, 7-[(acetyloxy)methyl]-10-amino-N-[(4-fluoro-3-methylphenyl)methyl]-4,6,7,8,9,10-hexahydro-3-methoxy-4-oxo-, Intermediate 40, (1.66 g, 3.51 mmol), N-methylmorpholine (0.927 mL, 8.43 mmol), N,N-dimethyloxamic acid (0.494 g, 4.22 mmol) and HATU (1.603 g, 4.22 mmol). The reaction was stirred for 1 hour. The reaction was diluted with water and extracted with CH$_2$Cl$_2$/ethyl acetate. The combined extracts were washed with brine, dried (MgSO$_4$) and concentrated in vacuo giving a yellow syrup. The crude product was purified by silica gel chromatography (0-10% MeOH/DCM) providing the target compound (1.94 g, 3.39 mmol, 97% yield) as an off white foam. LCMS (ES+, (M+H)$^+$) m/z: 572.4. $^1$H NMR (500 MHz, CDCl$_3$) δ ppm 8.37 (1H, t, J=6.26 Hz), 8.33 (1H, s), 7.79 (1H, s), 6.98-7.05 (2H, m), 6.74 (1H, t, J=8.85 Hz), 5.15 (1H, s), 4.30-4.35 (2H, m), 4.32 (2H, d, J=6.10 Hz), 3.87 (2H, s), 3.82 (3H, s), 3.75 (2H, s), 3.08 (3H, s), 3.07-3.11 (3H, m), 2.73-2.78 (4H, m), 2.67 (1H, s), 2.61 (3H, s), 2.42 (2H, ddd, J=14.19, 8.85, 5.95 Hz), 2.06 (4H, s), 1.98-2.05 (2H, m), 1.92 (3H, s), 1.57-1.65 (2H, m), 1.47-1.55 (2H, m). $^{19}$F NMR (376 MHz, CDCl$_3$) δ ppm −120.85 (s, 1F).

Intermediate 42

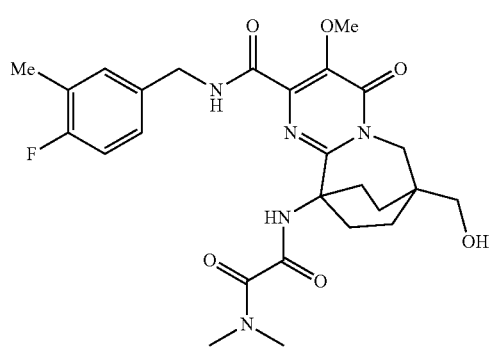

Ethanediamide, $N^2$-[2-[[[(4-fluoro-3-methylphenyl)methyl]amino]carbonyl]-6,7,8,9-tetrahydro-7-(hydroxymethyl)-3-methoxy-4-oxo-7,10-ethanopyrimido[1,2-a]azepin-10(4H)-yl]-$N^1$,$N^1$-dimethyl- A flask was charged with ethanediamide, $N^2$-[7-[(acetyloxy)methyl]-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-$N^1$,$N^1$-dimethyl-, Intermediate 41, (1.92 g, 3.36 mmol) and MeCN (15 mL). After dissolving, the flask was charged with MeOH (15 mL) and $Na_2CO_3$ (10% in water 17.80 mL, 16.80 mmol). The reaction was stirred for 1 h. The reaction was diluted with $CH_2Cl_2$, washed with 1 N HCl then brine, dried ($MgSO_4$) and concentrated in vacuo giving the target compound (1.72 g, 3.25 mmol, 97% yield) as a white foam. LCMS (ES+, $(M+H)^+$) m/z: 530.4. $^1$H NMR (400 MHz, $CDCl_3$) δ ppm 8.61 (1H, s), 8.25 (1H, t, J=5.77 Hz), 7.17-7.24 (2H, m), 6.90-6.97 (1H, m), 4.53 (2H, d, J=6.27 Hz), 4.04 (6H, s), 3.50 (2H, s), 3.32 (3H, s), 2.95 (3H, s), 2.81 (2H, s), 2.68 (2H, ddd, J=14.49, 9.22, 5.65 Hz), 2.26 (3H, d, J=1.76 Hz), 2.06-2.14 (3H, m), 2.05 (1H, s), 1.74-1.84 (3H, m), 1.59-1.69 (3H, m). $^{19}$F NMR (376 MHz, $CDCl_3$) δ ppm −120.54 (s, 1F).

Intermediate 43

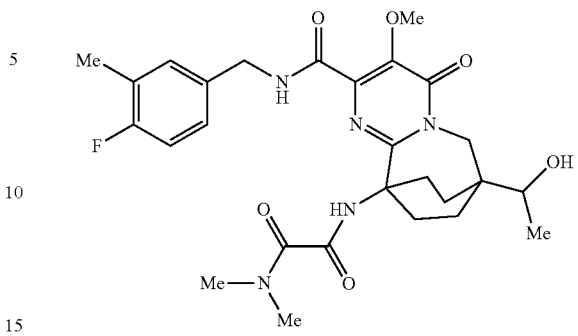

Ethanediamide, $N^2$-[2-[[[(4-fluoro-3-methylphenyl)methyl]amino]carbonyl]-7-formyl-6,7,8,9-tetrahydro-3-methoxy-4-oxo-7,10-ethanopyrimido[1,2-a]azepin-10(4H)-yl]-$N^1$,$N^1$-dimethyl- A flask was charged with ethanediamide, $N^2$-[2-[[[(4-fluoro-3-methylphenyl)methyl]amino]carbonyl]-6,7,8,9-tetrahydro-7-(hydroxymethyl)-3-methoxy-4-oxo-7,10-ethanopyrimido[1,2-a]azepin-10(4H)-yl]-$N^1$,$N^1$-dimethyl-, Intermediate 42, (1.62 g, 3.06 mmol, 1 equiv), $CH_2Cl_2$ (25 mL) and Dess-Martin Periodinane (1.817 g, 4.28 mmol, 1.4 equiv). The reaction was stirred over night. The reaction was diluted with $CH_2Cl_2$, washed with saturated aqueous $NaHCO_3$, then brine, dried ($MgSO_4$) and evaporated giving the crude product (1.60 g, 3.03 mmol, 99% yield) as a white powder. $^1$H NMR (400 MHz, $CDCl_3$) δ ppm 9.51 (1H, s), 8.76 (1H, s), 8.18 (1H, t, J=5.90 Hz), 7.16-7.24 (2H, m), 6.91-6.97 (1H, m), 4.53 (2H, d, J=6.02 Hz), 4.27 (2H, s), 4.06 (3H, s), 3.50 (1H, s), 3.33 (3H, s), 2.96 (3H, s), 2.74-2.84 (3H, m), 2.26 (4H, d, J=1.76 Hz), 2.06-2.19 (5H, m), 1.67-1.78 (3H, m); LCMS (ES+, $(M+H)^+$) m/z: 528.4.

Intermediate 44

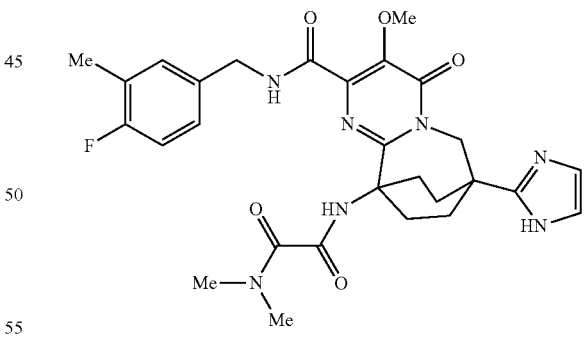

Ethanediamide, $N^2$-[2-[[[(4-fluoro-3-methylphenyl)methyl]amino]carbonyl]-6,7,8,9-tetrahydro-7-(1-hydroxyethyl)-3-methoxy-4-oxo-7,10-ethanopyrimido[1,2-a]azepin-10(4H)-yl]-$N^1$,$N^1$-dimethyl- To a solution of ethanediamide, $N^2$-[2-[[[(4-fluoro-3-methylphenyl)methyl]amino]carbonyl]-7-formyl-6,7,8,9-tetrahydro-3-methoxy-4-oxo-7,10-ethanopyrimido[1,2-a]azepin-10(4H)-yl]-$N^1$,$N^1$-dimethyl-, Intermediate 43 (41 mg, 0.078 mmol, 1 equiv) in THF (1.33 mL) was added methylmagnesium bromide (0.083 mL of a 1.4 M solution in 3:1 toluene:THF, 0.117 mmol, 1.5 equiv). White precipitate observed. After stirring 2 h, more methylmagnesium bromide (0.30 mL of a 1.4 M solution in 3:1 toluene:THF, 5 equiv) was added. After stirring 10 min, LCMS of the reaction showed consumption of the starting aldehyde. The reaction was poured into 1 N HCl and extracted with $CH_2Cl_2$ (×3). Combined organic layers were dried ($Na_2SO_4$) and concentrated in vacuo to provide the crude product (52 mg) as a yellow viscous oil. The crude product was carried on as is. LCMS (ES+, $(M+H)^+$) m/z 544.5.

Intermediate 45

Ethanediamide, $N^2$-[2-[[[(4-fluoro-3-methylphenyl)methyl]amino]carbonyl]-6,7,8,9-tetrahydro-7-(1H-imidazol-2-yl)-3-methoxy-4-oxo-7,10-ethanopyrimido[1,2-a]azepin-10(4H)-yl]-$N^1$,$N^1$-dimethyl- To a slurry of ethanediamide, $N^2$-[2-[[[(4-fluoro-3-methylphenyl)methyl]amino]carbonyl]-7-formyl-6,7,8,9-tetrahydro-3-methoxy-4-oxo-7,10-ethanopyrimido[1,2-a]azepin-10(4H)-yl]-$N^1$,$N^1$-dimethyl-, Intermediate 43 (106 mg, 0.201 mmol, 1 equiv) in MeOH (0.40 mL) was added glyoxal (0.158 g of a 40% aqueous solution, 0.301 mmol, 1.5 equiv) followed by NH₄OH (0.279 mL, 2.01 mmol, 10 equiv). Solution became homogenous upon addition of NH₄OH. The reaction was then stirred 20 h at which time LCMS showed ~85% conversion to product. The dark brown solution was then poured into water and extracted with CH₂Cl₂ (×3).). The combined CH₂Cl₂ layers were dried (Na₂SO₄) and concentrated in vacuo to provide the crude product as a brown solid (38 mg). LCMS (ES+, (M+H)⁺) m/z 566.1.

Intermediate 46

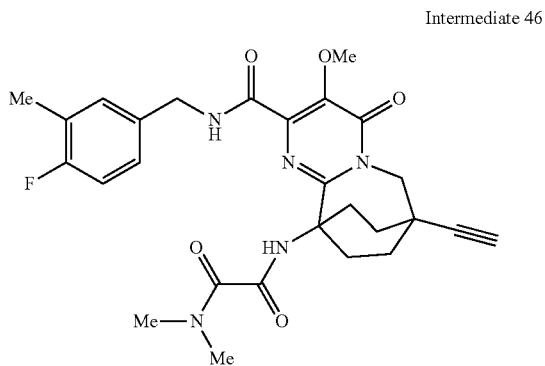 [SMILES: COc1c(C(=O)NCc2ccc(F)c(C)c2)nc2n(c1=O)CC1(C#N)CCC2(NC(=O)C(=O)N(C)C)CC1]

Ethanediamide, $N^2$-[7-ethynyl-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-$N^1$,$N^1$-dimethyl- To a slurry of ethanediamide, $N^2$-[2-[[[(4-fluoro-3-methylphenyl)methyl]amino]carbonyl]-7-formyl-6,7,8,9-tetrahydro-3-methoxy-4-oxo-7,10-ethanopyrimido[1,2-a]azepin-10(4H)-yl]-$N^1$,$N^1$-dimethyl-, Intermediate 43 (120 mg, 0.227 mmol, 1 equiv) in MeOH (1.2 mL) and THF (0.5 mL) was added dimethyl 1-diazo-2-oxopropylphosphonate (0.131, 0.682 mmol, 3 equiv) followed by K₂CO₃ (0.095 mg, 0.682 mmol, 3 equiv). The reaction was stirred 5 h. The solution was then poured into water and extracted with CH₂Cl₂ (×3). The combined CH₂Cl₂ layers were dried (Na₂SO₄) and concentrated in vacuo to provide the crude product. The crude product was purified by preparatory HPLC to provide the product as a white solid (32 mg, 27%). ¹H NMR (400 MHz, CDCl₃) δ ppm 8.67 (1H, s), 8.19 (1H, br. s.), 7.15-7.24 (2H, m), 6.94 (1H, t, J=8.9 Hz), 4.53 (2H, d, J=6.3 Hz), 4.27 (2H, s), 4.06 (3H, s), 3.32 (3H, s), 2.96 (3H, s), 2.67-2.77 (2H, m), 2.34 (1H, s), 2.26 (3H, d, J=1.8 Hz), 2.18-2.25 (2H, m), 1.94-2.13 (4H, m); ¹⁹F NMR (376 MHz, CDCl₃) δ ppm −120.00 (1F, br. s.); LCMS (ES+, (M+H)⁺) m/z 524.2.

Intermediate 47

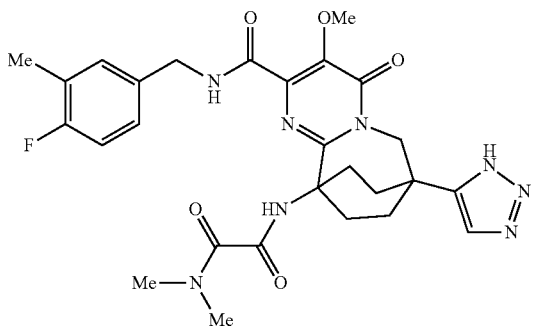

Ethanediamide, $N^2$-[2-[[[(4-fluoro-3-methylphenyl)methyl]amino]carbonyl]-6,7,8,9-tetrahydro-3-methoxy-4-oxo-7-(1H-1,2,3-triazol-5-yl)-7,10-ethanopyrimido[1,2-a]azepin-10(4H)-yl]-$N^1$,$N^1$-dimethyl- Procedure adapted from Eur. J. Org. Chem. 2004, 3789-3791. A solution of ethanediamide, $N^2$-[7-ethynyl-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-$N^1$,$N^1$-dimethyl-, Intermediate 46, (30 mg, 0.057 mmol, 1 equiv), CuI (1.1 mg, 0.006 mmol, 0.1 equiv), and trimethylsilylazide (0.030 mL, 0.229 mmol, 4 equiv) in DMF (0.21 mL) and MeOH (0.02 mL) was heated to 100° C. (oil bath) for 1.5 h. The reaction was removed from the heating bath and poured into a saturated aqueous solution of NaHCO₃. The aqueous solution was extracted with CH₂Cl₂ (×3). The combined CH₂Cl₂ layers were dried (Na₂SO₄) and concentrated in vacuo to provide the crude product as a green blue film (34 mg) which was carried on directly to demethylation reaction. LCMS (ES+, (M+H)⁺) m/z 567.1.

Intermediate 48

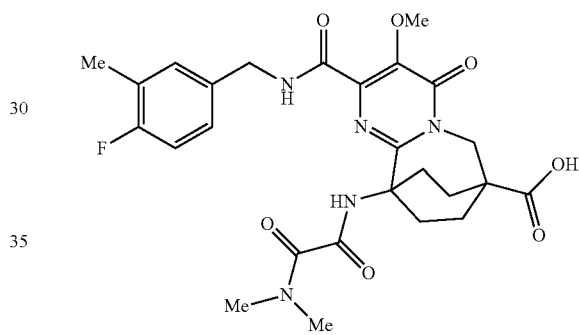

Ethanediamide, $N^2$-[2-[[[(4-fluoro-3-methylphenyl)methyl]amino]carbonyl]-7-formyl-6,7,8,9-tetrahydro-3-methoxy-4-oxo-7,10-ethanopyrimido[1,2-a]azepin-10(4H)-yl]-$N^1$,$N^1$-dimethyl- A flask was charged with ethanediamide, $N^2$-[2-[[[(4-fluoro-3-methylphenyl)methyl]amino]carbonyl]-7-formyl-6,7,8,9-tetrahydro-3-methoxy-4-oxo-7,10-ethanopyrimido[1,2-a]azepin-10(4H)-yl]-$N^1$,$N^1$-dimethyl-, Intermediate 43, (1.50 g, 2.84 mmol, 1 equiv), t-butanol (16 mL), Water 4 mL), NaH₂PO₄ (0.682 g, 5.69 mmol, 2 equiv) and a solution of NaClO₂ (0.360 g, 3.98 mmol, 1.4 equiv) in water (1.5 mL). The reaction was stirred for 45 min. The reaction was diluted with CH₂Cl₂, washed with saturated aqueous NaHCO₃, 10% NaS₂O₃ (to remove yellow color) then brine, dried (MgSO₄) and concentrated in vacuo giving the title compound (1.48 g, 2.72 mmol, 96% yield) as a white crystalline solid. The crude product was used without purification. ¹H NMR (400 MHz, CDCl₃) δ ppm 8.54 (1H, s), 8.27 (1H, t, J=6.15 Hz), 7.15-7.22 (3H, m), 6.91-6.96 (1H, m), 4.52 (2H, d, J=6.02 Hz), 4.38 (2H, s), 4.04 (3H, s), 3.30 (3H, s), 2.69 (2H, ddd, J=14.37, 8.97, 5.77 Hz), 2.26-2.35 (2H, m), 2.25 (3H, d, J=1.51 z), 2.16 (2H, dt, J=14.12, 7.12 Hz), 1.93 (2H, dt, J=13.61, 6.87 Hz). ¹⁹F NMR (376 MHz, CDCl₃) δ ppm −120.07 (s, 1F); LCMS (ES+, (M+H)⁺) m/z: 544.4.

Intermediate 49

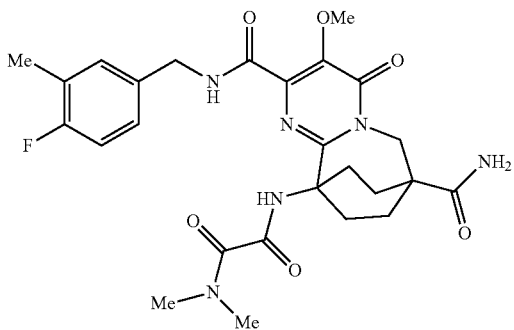

7,10-Ethanopyrimido[1,2-a]azepine-2,7(6H)-dicarboxamide, 10-[[2-(dimethylamino)-1,2-dioxoethyl]amino]-N²-[(4-fluoro-3-methylphenyl)methyl]-4,8,9,10-tetrahydro-3-methoxy-4-oxo- Ethanediamide, N²-[2-[[[(4-fluoro-3-methylphenyl)methyl]amino]carbonyl]-7-formyl-6,7,8,9-tetrahydro-3-methoxy-4-oxo-7,10-ethanopyrimido[1,2-a]azepin-10(4H)-yl]-N¹,N¹-dimethyl-, Intermediate 48 (120 mg, 0.221 mmol, 1 equiv) in dioxane (2.2 mL) was added pyridine (0.018 mL, 0.221 mmol, 1 equiv), di-tert-butyl dicarbonate (0.077 mL, 0.331 mmol, 1.5 equiv), and ammonium bicarbonate (35 mg, 0.442 mmol, 2.0 equiv). After stirring 18 h, LCMS shows completion. The reaction was poured into 1 N HCl and the aqueous solution was extracted with CH₂Cl₂ (×3). The combined CH₂Cl₂ layers were dried (Na₂SO₄) and concentrated in vacuo to provide the title compound as a white solid (112 mg, 94%). ¹H NMR (400 MHz, CDCl₃) δ ppm 8.62 (1H, s), 8.20 (1H, br. s.), 7.16-7.24 (2H, m), 6.90-6.98 (1H, m), 5.73 (1H, br. s.), 5.41 (1H, br. s.), 4.53 (2H, d, J=6.0 Hz), 4.37 (2H, s), 4.04 (3H, s), 3.32 (3H, s), 2.96 (3H, s), 2.70-2.79 (2H, m), 2.26 (3H, d, J=1.8 Hz), 2.09-2.23 (4H, m), 1.97-2.06 (2H, m); ¹⁹F NMR (376 MHz, CDCl₃) δ ppm –120.01 (1F, s); LCMS (ES+, (M+H)⁺) m/z 543.1.

Intermediate 50

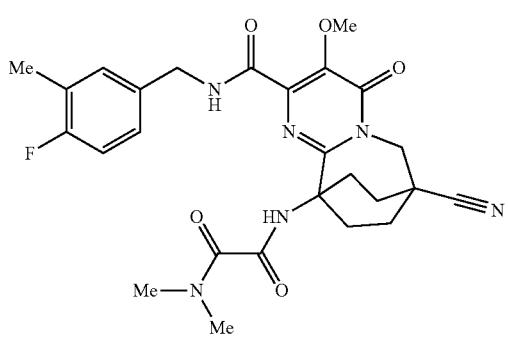

7,10-Ethanopyrimido[1,2-a]azepine-2,7(6H)-dicarboxamide, 10-[[2-(dimethylamino)-1,2-dioxoethyl]amino]-N²-[(4-fluoro-3-methylphenyl)methyl]-4,8,9,10-tetrahydro-3-methoxy-4-oxo- Ethanediamide, N²-[7-cyano-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-N¹,N¹-dimethyl- To a solution of 7,10-ethanopyrimido[1,2-a]azepine-2,7(6H)-dicarboxamide, 10-[[2-(dimethylamino)-1,2-dioxoethyl]amino]-N²-[(4-fluoro-3-methylphenyl)methyl]-4,8,9,10-tetrahydro-3-methoxy-4-oxo-, Intermediate 49, (53 mg, 0.098 mmol, 1 equiv) in pyridine (0.98 mL) at 0° C. (ice water bath) was added trifluoroacetic anhydride (TFAA) (0.021 m, 0.147 mmol, 1.5 equiv). After 2 h, more trifluoroacetic anhydride was added (0.030 mL). The reaction was removed from the cooling bath and more TFAA added (0.10 mL). The reaction was poured into 1 N HCl and the aqueous solution was extracted with CH₂Cl₂ (×3). The combined CH₂Cl₂ layers were dried (Na₂SO₄) and concentrated in vacuo to provide the crude product. The crude product was purified by preparatory HPLC to provide the title compound as a yellow solid (16 mg, 31%). ¹H NMR (400 MHz, CDCl₃) δ ppm 8.79 (1H, br. s.), 8.16 (1H, br. s.), 7.14-7.23 (2H, m), 6.95 (1H, t, J=8.9 Hz), 4.53 (2H, d, J=6.0 Hz), 4.42 (2H, s), 4.07 (3H, s), 3.31 (3H, s), 2.97 (3H, s), 2.71-2.82 (2H, m), 2.33-2.43 (2H, m), 2.26 (3H, d, J=1.5 Hz), 2.09-2.30 (4H, m); ¹⁹F NMR (376 MHz, CDCl₃) δ ppm –119.64 (1F, s); LCMS (ES+, (M+H)⁺) m/z 525.1.

Intermediate 51

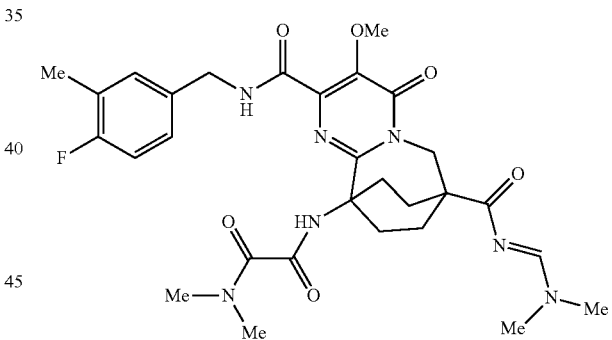

7,10-Ethanopyrimido[1,2-a]azepine-2,7(6H)-dicarboxamide, 10-[[2-(dimethylamino)-1,2-dioxoethyl]amino]-N⁷-[(1E)-(dimethylamino)methylene]-N²-[(4-fluoro-3-methylphenyl)methyl]-4,8,9,10-tetrahydro-3-methoxy-4-oxo- To a slurry of 7,10-ethanopyrimido[1,2-a]azepine-2,7(6H)-dicarboxamide, 10-[[2-(dimethylamino)-1,2-dioxoethyl]amino]-N²-[(4-fluoro-3-methylphenyl)methyl]-4,8,9,10-tetrahydro-3-methoxy-4-oxo-, Intermediate 49, (60 mg, 0.111 mmol, 1 equiv) in 1,1-dimethoxy-N,N-dimethylmethanamine 0.659 mg, 5.53 mmol, 50 equiv) was heated to 120° C. (oil bath) for 2 h. The solution was then removed from the oil bath and concentrated in vacuo to provide the crude product as a yellow solid (66 mg). LCMS (ES+, (M+H)⁺) m/z 598.4.

Intermediate 52

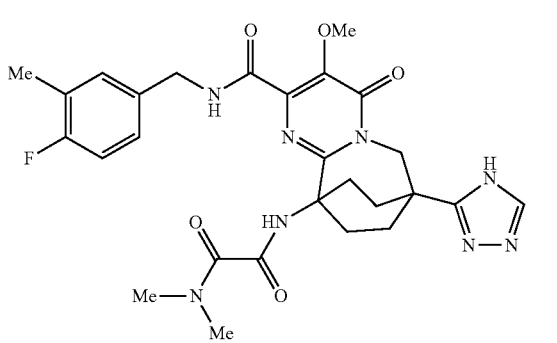

Ethanediamide, $N^2$-[2-[[[(4-fluoro-3-methylphenyl)methyl]amino]carbonyl]-6,7,8,9-tetrahydro-3-methoxy-4-oxo-7-(4H-1,2,4-triazol-3-yl)-7,10-ethanopyrimido[1,2-a]azepin-10(4H)-yl]-$N^1,N^1$-dimethyl- To a solution of 7,10-ethanopyrimido[1,2-a]azepine-2,7(6H)-dicarboxamide, 10-[[2-(dimethylamino)-1,2-dioxoethyl]amino]-$N^7$-[(1E)-(dimethylamino)methylene]-$N^2$-[(4-fluoro-3-methylphenyl)methyl]-4,8,9,10-tetrahydro-3-methoxy-4-oxo-, Intermediate 51, (66 mg) in AcOH (1.1 mL) was added hydrazine acetate salt (102 mg, 1.11 mmol, 10 equiv). The reaction was heated to 80° C. (oil bath) for 2 h. The reaction was removed from the heating bath and poured into a saturated aqueous solution of NaHCO$_3$. The aqueous solution was extracted with CH$_2$Cl$_2$ (×3). The combined CH$_2$Cl$_2$ layers were dried (Na$_2$SO$_4$) and concentrated in vacuo to provide the crude product (51 mg) as a yellow solid. LCMS (ES+, (M+H)$^+$) m/z 567.1.

Intermediate 53

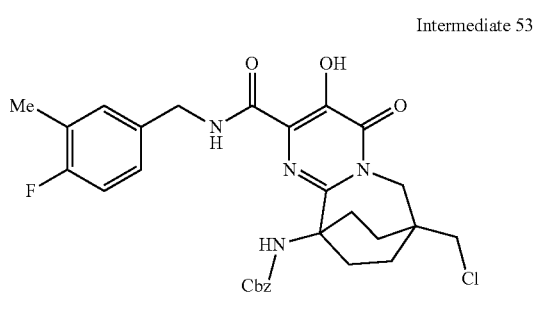 [SMILES: Cc1cc(CNC(=O)c2nc3n(c(=O)c2O)CC2(CCl)CCC3(NC(=O)OCc3ccccc3)CC2)ccc1F]

Carbamic acid, N-[7-(chloromethyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-, phenylmethyl ester To a solution of carbamic acid, [2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-, phenylmethyl ester, Intermediate 37, (94 mg, 0.133 mmol, 1 equiv) in DMSO (1.33 mL) was added tetramethylammonium chloride (292 mg, 2.67 mmol, 20 equiv). The reaction was then heated to 80° C. (oil bath). After 4 d, LCMS of the reaction showed ~85% conversion to the chloride product. The reaction was removed from the heating bath and diluted with EtOAc. The organic layer was washed with 1 N HCl and brine (×2). The organic layer was dried (Na$_2$SO$_4$) and concentrated in vacuo to provide the crude product (82 mg) as a yellow viscous oil. The crude product was carried on as is. LCMS (ES+, (M+H)$^+$) m/z 569.4.

Intermediate 54

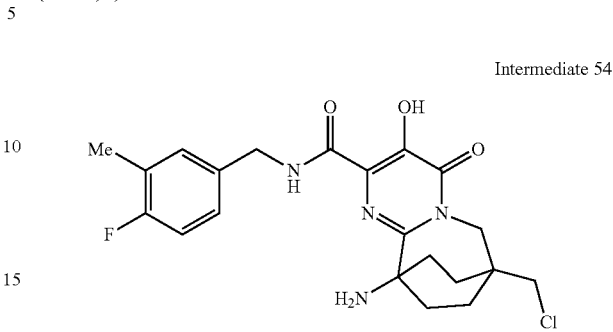

7,10-Ethanopyrimido[1,2-a]azepine-2-carboxamide, 10-amino-7-(chloromethyl)-N-[(4-fluoro-3-methylphenyl)methyl]-4,6,7,8,9,10-hexahydro-3-hydroxy-4-oxo- To a solution of carbamic acid, N-[7-(chloromethyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-, phenylmethyl ester, Intermediate 53, (82 mg, 0.144 mmol, 1 equiv) in EtOH (2.88 mL) was added 10% Pd/C (31 mg, 0.029 mmol, 0.2 equiv). The reaction was then put under a balloon of hydrogen. After stirring 20 h, the reaction was filtered through celite eluting with MeOH. The filtrate was concentrated in vacuo to provide the crude product (62 mg) as a pale yellow solid. The crude product was carried on as is. LCMS (ES+, (M+H)$^+$) m/z 435.3.

Intermediate 55

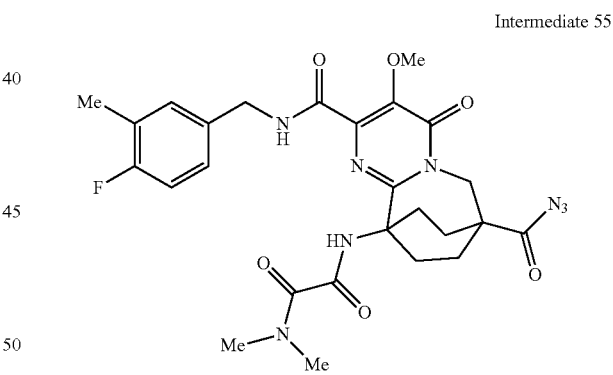

7,10-Ethanopyrimido[1,2-a]azepine-7(6H)-carbonyl azide, 10-[[2-(dimethylamino)-1,2-dioxoethyl]amino]-2-[[[(4-fluoro-3-methylphenyl)methyl]amino]carbonyl]-4,8,9,10-tetrahydro-3-methoxy-4-oxo- A flask was charged with ethanediamide, $N^2$-[2-[[[(4-fluoro-3-methylphenyl)methyl]amino]carbonyl]-7-formyl-6,7,8,9-tetrahydro-3-methoxy-4-oxo-7,10-ethanopyrimido[1,2-a]azepin-10(4H)-yl]-$N^1,N^1$-dimethyl-, Intermediate 48, (300 mg, 0.552 mmol, 1 equiv), TEA (0.231 mL, 1.656 mmol, 3 equiv), CH$_2$Cl$_2$ (6 mL) and diphenylphosphoryl azide (167 mL, 0.773 mmol, 1.4 equiv). The reaction was stirred under nitrogen for 1 hour. The reaction was diluted with CH$_2$Cl$_2$, washed with water, a saturated aqueous solution of NaHCO₃, then brine, dried (MgSO₄) and concentrated in vacuo giving the title compound as a near colorless film. LCMS (ES+, (M+H)⁺) m/z 569.3.

Intermediate 56

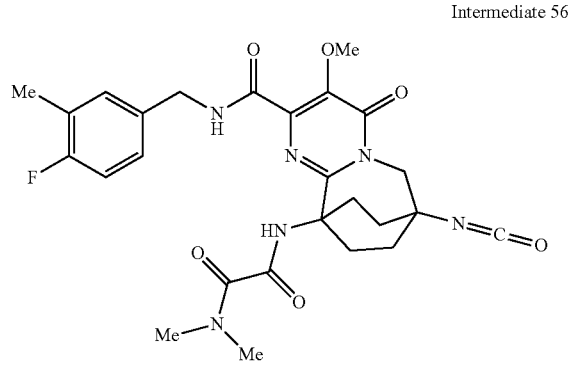 [SMILES: COc1c(C(=O)NCc2ccc(F)c(C)c2)nc2n(c1=O)CC1(N=C=O)CCC2(NC(=O)C(=O)N(C)C)CC1]

Ethanediamide, N²-[2-[[[(4-fluoro-3-methylphenyl)methyl]amino]carbonyl]-6,7,8,9-tetrahydro-7-isocyanato-3-methoxy-4-oxo-7,10-ethanopyrimido[1,2-a]azepin-10(4H)-yl]-N¹,N¹-dimethyl- A flask was charged with 7,10-ethanopyrimido[1,2-a]azepine-7(6H)-carbonyl azide, 10-[[2-(dimethylamino)-1,2-dioxoethyl]amino]-2-[[[(4-fluoro-3-methylphenyl)methyl]amino]carbonyl]-4,8,9,10-tetrahydro-3-methoxy-4-oxo-, Intermediate 55 (314 mg, 0.552 mmol, 1 equiv) and CH₂Cl₂ (6 mL). The reaction was refluxed under nitrogen for 1 hour. The reaction was concentrated in vacuo giving the title compound as a thick yellow syrup. LCMS (ES+, (M+H)⁺) m/z 541.4.

Intermediate 57

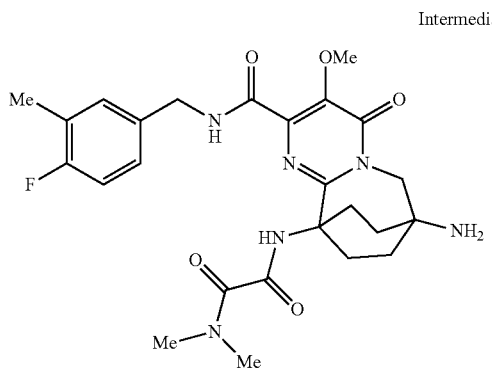

Ethanediamide, N²-[7-amino-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-N¹,N¹-dimethyl- A flask was charged with ethanediamide, N²-[2-[[[(4-fluoro-3-methylphenyl)methyl]amino]carbonyl]-6,7,8,9-tetrahydro-7-isocyanato-3-methoxy-4-oxo-7,10-ethanopyrimido[1,2-a]azepin-10(4H)-yl]-N¹,N¹-dimethyl-, Intermediate 56, (314 mg, 0.552 mmol, 1 equiv), THF (2 mL) and 1 N HCl (5.52 mL, 5.52 mmol). The reaction was stirred overnight. The reaction was concentrated in vacuo giving a thick yellow syrup. The syrup was dissolved in CH₂Cl₂, ether was added and the mixture was filtered giving the title compound as an HCl salt (153 mg, 0.297 mmol, 54% yield for three steps) as a creamy white powder. LCMS (ES+, (M+H)⁺) m/z 515.4.

Intermediate 58

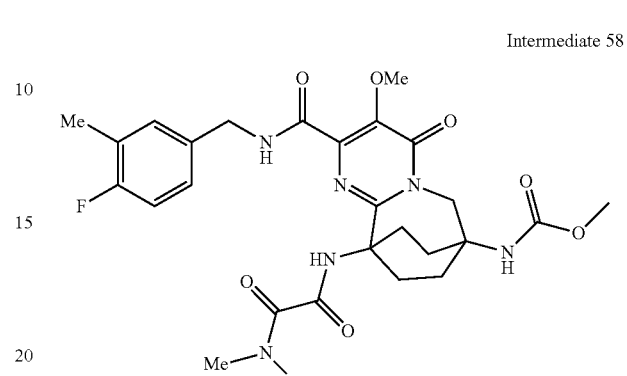

Carbamic acid, N-[10-[[2-(dimethylamino)-1,2-dioxoethyl]amino]-2-[[[(4-fluoro-3-methylphenyl)methyl]amino]carbonyl]-4,8,9,10-tetrahydro-3-methoxy-4-oxo-7,10-ethanopyrimido[1,2-a]azepin-7(6H)-yl]-, methyl ester A flask was charged with the ethanediamide, N²-[2-[[[(4-fluoro-3-methylphenyl)methyl]amino]carbonyl]-6,7,8,9-tetrahydro-7-isocyanato-3-methoxy-4-oxo-7,10-ethanopyrimido[1,2-a]azepin-10(4H)-yl]-N¹,N¹-dimethyl-. Intermediate 56, (10 mg, 0.0175 mmol), methanol (0.5 mL) and silica gel (4 g). The reaction was concentrated in vacuo. The crude product was purified by silica gel chromatography (0-20% MeOH/CH₂Cl₂) to provide the target compound as a colorless film (2.7 mg, 4.72 μmol, 27% yield). ¹H NMR (400 MHz, CDCl₃) δ ppm 8.71 (1H, s), 8.15 (1H, t, J=6.02 Hz), 7.16-7.23 (2H, m), 6.90-6.97 (1H, m), 4.92 (1H, s), 4.52 (2H, d, J=6.27 Hz), 4.36 (2H, s), 4.02-4.07 (3H, m), 3.66 (2H, s), 3.29-3.33 (3H, m), 2.93-2.97 (3H, m), 2.73-2.83 (2H, m), 2.25 (3H, d, J=1.76 Hz), 2.16-2.23 (2H, m), 2.01-2.12 (4H, m); ¹⁹F NMR (376 MHz, CDCl₃) δ ppm −120.05 (s, 1F); LCMS (ES+, (M+H)⁺) m/z: 573.4.

Intermediate 59

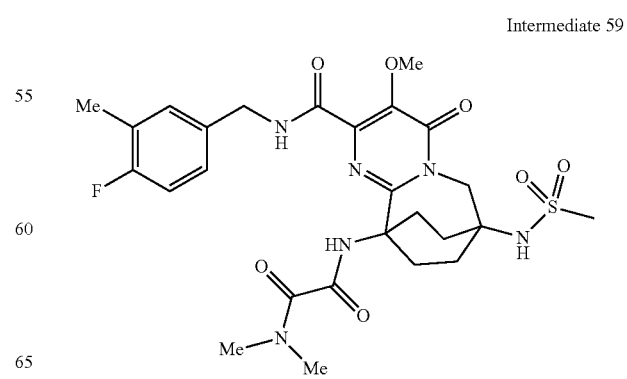

Ethanediamide, $N^2$-[2-[[[(4-fluoro-3-methylphenyl)methyl]amino]carbonyl]-6,7,8,9-tetrahydro-3-methoxy-7-[(methylsulfonyl)amino]-4-oxo-7,10-ethanopyrimido[1,2-a]azepin-10(4H)-yl]-$N^1,N^1$-dimethyl- A flask was charged with ethanediamide, $N^2$-[7-amino-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-$N^1,N^1$-dimethyl-, Intermediate 57 (30 mg, 0.058 mmol), TEA (0.024 mL, 0.175 mmol), CH$_2$Cl$_2$ (1 mL) and Ms$_2$O (20.31 mg, 0.117 mmol). The reaction was stirred for 1 h. The reaction was diluted with CH$_2$Cl$_2$, washed with 1 N HCl, a saturated aqueous solution of NaHCO$_3$, and brine, dried (MgSO$_4$) and evaporated giving a light yellow film. The crude product was purified by silica gel chromatography (0-20% MeOH/CH$_2$Cl$_2$) to provide the target compound as a colorless film. LCMS (ES+, (M+H)$^+$) m/z: 593.2.

Ethanediamide, $N^2$-[7-(acetylamino)-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-$N^1,N^1$-dimethyl- A flask was charged with ethanediamide, $N^2$-[7-amino-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-$N^1,N^1$-dimethyl-, Intermediate 57 (0.030 g, 0.058 mmol, 1 equiv), TEA (0.081 mL, 0.583 mmol, 10 equiv), CH$_2$Cl$_2$ (1 mL) and Ac$_2$O (0.055 mL, 0.583 mmol, 10 equiv). The reaction was stirred for 1 h. The reaction was diluted with CH$_2$Cl$_2$, washed with 1 N HCl, a saturated aqueous solution of NaHCO$_3$, and brine, dried (MgSO$_4$) and concentrated in vacuo giving the title compound. The crude product was used without purification. LCMS (ES+, (M+H)$^+$) m/z: 557.4.

Intermediate 60

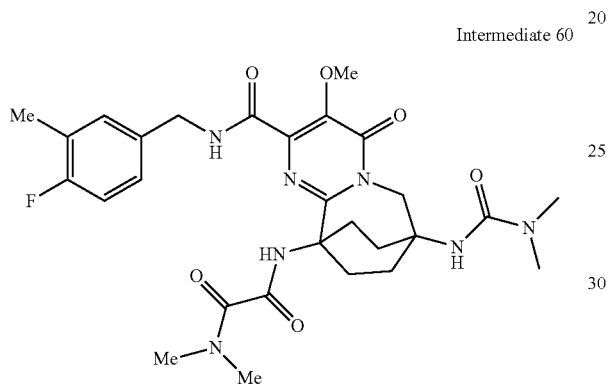

Ethanediamide, $N^2$-[7-[[(dimethylamino)carbonyl]amino]-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-$N^1,N^1$-dimethyl A flask was charged with ethanediamide, $N^2$-[2-[[[(4-fluoro-3-methylphenyl)methyl]amino]carbonyl]-6,7,8,9-tetrahydro-7-isocyanato-3-methoxy-4-oxo-7,10-ethanopyrimido[1,2-a]azepin-10(4H)-yl]-$N^1,N^1$-dimethyl-, Intermediate 56, (50 mg, 0.092 mmol, 1 equiv), DCE (1 mL), and dimethylamine (0.231 mL of a 2 M solution in THF, 0.462 mmol, 5 equiv). The reaction was stirred for 1 h. The reaction was concentrated in vacuo giving the target compound. The crude product was used without purification. LCMS (ES+, (M+H)$^+$) m/z: 586.4.

Intermediate 62

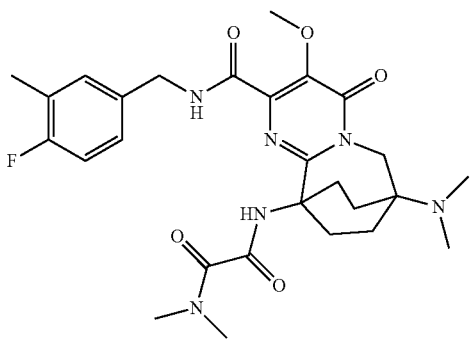

Ethanediamide, N2-[7-(dimethylamino)-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-N1,N1-dimethyl- A flask was charged with Intermediate 57 HCl (100 mg, 0.181 mmol), CH$_2$Cl$_2$ (3 mL), paraformaldehyde (109 mg, 3.63 mmol) and sodium triacetoxyborohydride (385 mg, 1.815 mmol). The reaction was stirred under nitrogen overnight. AcOH (54.5 mg, 0.907 mmol) was added to the reaction. 0.2-Equivalents of additional reagent was added. Upon completion the reaction was dissolved in CH$_2$Cl$_2$, washed with saturated NaHCO$_3$ then brine, dried and evaporated giving a light yellow syrup which was used without purification.

Intermediate 61

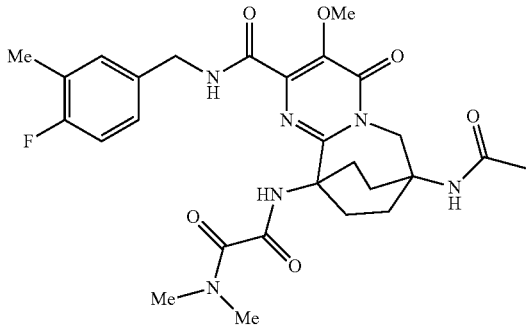

Intermediate 63

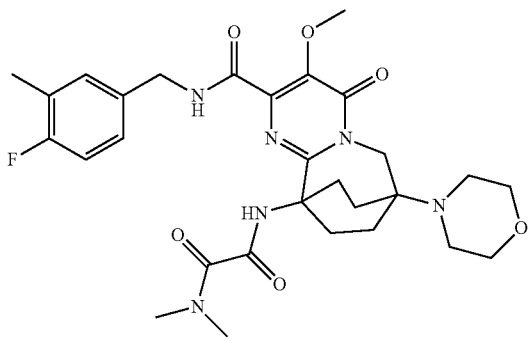

Ethanediamide, N2-[2-[[[(4-fluoro-3-methylphenyl)methyl]amino]carbonyl]-6,7,8,9-tetrahydro-3-methoxy-7-(4-morpholinyl)-4-oxo-7,10-ethanopyrimido[1,2-a]azepin-10(4H)-yl]-N1, N1-dimethyl- A flask was charged with Intermediate 57, HCl (200 mg, 0.363 mmol), DMF (3.5 mL), 2-bromoethyl ether (0.050 mL, 0.399 mmol), potassium iodide (133 mg, 0.799 mmol) and $K_2CO_3$ (75 mg, 0.544 mmol). The reaction was stirred under nitrogen overnight. The reaction then was heated at 60° C. After 6 hours 5 equivalents of Hunig's base was added. Additional 2-bromoethyl ether (0.050 mL, 0.399 mmol) was added and stirring continued overnight. Additional 2-bromoethyl ether (0.050 mL, 0.399 mmol) and Hunig's base were added. The reaction was dissolved in $CH_2Cl_2$, washed with saturated $NaHCO_3$ then brine, dried and the solvent evaporated giving a light yellow syrup which was used without purification.

Intermediate 63

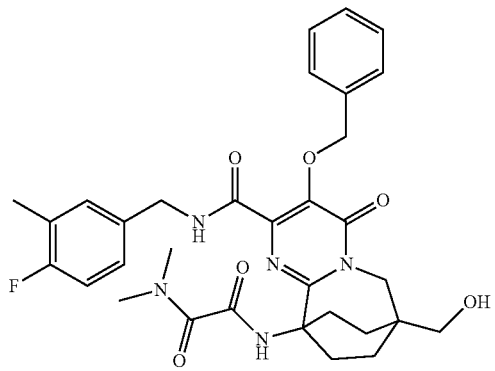

Ethanediamide, N'-[2-[[[(4-fluoro-3-methylphenyl)methyl]amino]carbonyl]-6,7,8,9-tetrahydro-7-(hydroxymethyl)-4-oxo-3-(phenylmethoxy)-7,10-ethanopyrimido[1,2-a]azepin-10(4H)-yl]-N,N-dimethyl- A mixture of ethanediamide, N'-[2-[[[(4-fluoro-3-methylphenyl)methyl]amino]carbonyl]-6,7,8,9-tetrahydro-3-hydroxy-7-(hydroxymethyl)-4-oxo-7,10-ethanopyrimido[1,2-a]azepin-10(4H)-yl]-N,N-dimethyl-, Example 2, (80 mg, 0.155 mmol), $K_2CO_3$ (44 mg, 0.318 mmol), and benzyl bromide (0.024 mL, 0.202 mmol) in DMF (1 mL) was stirred under N2 at room temp overnight. The mixture was concentrated and the residue suspended in water (10 mL) and then extracted with EtOAc (15 mL). The EtOAc extract was washed with brine, dried ($Na_2SO_4$) and concentrated to yield the title compound (90 mg, 0.149 mmol, 96% yield) as an off-white powder: HPLC: 2.32 min (AP 91% at 254 nm) LCMS: m/z 606 (M+H). $^1$H NMR (500 MHz, $CDCl_3$) δ ppm 1.54-1.66 (2H, m, 9a, 13a-$CH_2$), 1.68-1.79 (2H, m, 9b, 13b-$CH_2$), 1.99-2.10 (2H, m, 10a,12a-$CH_2$), 2.24 (3H, d, J=1.2 Hz, 27-$CH_3$), 2.68 (2H, m, 10b, 12b-$CH_2$), 2.84 (1H, br.s, 14-OH), 2.94, 3.28 (2×3H, 2s, 17-, 18-$NCH_3$), 3.43 (2H, s, 14-$OCH_2$), 4.03 (2H, s, 7-$NCH_2$), 4.49 (2H, d, J=6.1 Hz, 20-$NCH_2$), 5.26 (2H, s, 28-$OCH_2$), 6.92 (1H, t, J=8.9 Hz, 25-CH), 7.12 (1H, td, J=5.3, 2.4 Hz, 26-CH), 7.16 (1H, d, J=7.3 Hz, 22-CH), 7.29-7.37 (3H, m, 31,32,33-CH), 7.51 (2H, d, J=6.1 Hz, 30,34-CH), 8.19 (1H, t, J=6.1 Hz, 19-CONH), 8.66 (1H, s, 15-CONH).

Intermediate 64

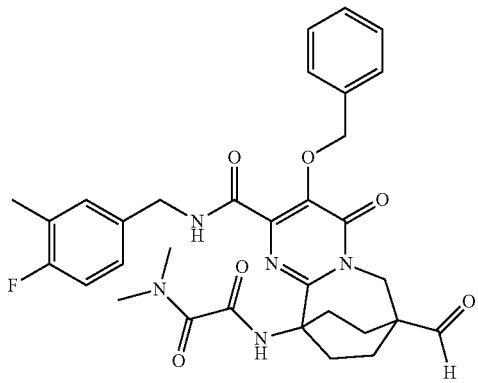

Ethanediamide, N2-[2-[[[(4-fluoro-3-methylphenyl)methyl]amino]carbonyl]-7-formyl-6,7,8,9-tetrahydro-4-oxo-3-(phenylmethoxy)-7,10-ethanopyrimido[1,2-a]azepin-10(4H)-yl]-N1,N1-dimethyl- Dess-MartinPeriodinane (336 mg, 0.793 mmol) was added to a solution of ethanediamide, N'-[2-[[[(4-fluoro-3-methylphenyl)methyl]amino]carbonyl]-6,7,8,9-tetrahydro-7-(hydroxymethyl)-4-oxo-3-(phenylmethoxy)-7,10-ethanopyrimido[1,2-a]azepin-10(4H)-yl]-N,N-dimethyl-, Intermediate 63 (400 mg, 0.660 mmol) in $CH_2Cl_2$ (20 mL) at r and the reaction stirred for 1.5 hr. The crude product was purified by column chromatography (40 g, $SiO_2$). 60% EtOAc/Hexane to 100% EtOAc/Hexane.

Intemediate 65

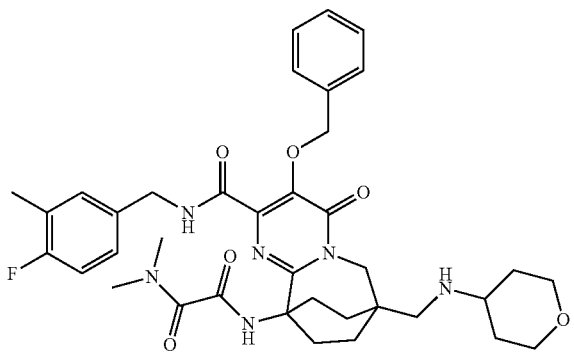

Ethanediamide, N2-[2-[[[(4-fluoro-3-methylphenyl)methyl]amino]carbonyl]-6,7,8,9-tetrahydro-4-oxo-3-(phenylmethoxy)-7-[[(tetrahydro-2H-pyran-4-yl)amino]methyl]-7,10-ethanopyrimido[1,2-a]azepin-10(4H)-yl]-N1, N1-dimethyl- Sodium cyanoborohydride (41.6 mg, 0.663 mmol) was added to a solution of Intermediate 64 (100 mg, 0.166 mmol) and tetrahydro-2H-pyran-4-amine (50.3 mg, 0.497 mmol) in MeOH (2 mL) and acetic acid (0.400 mL). The resulting solution was stirred at RT overnight. The reaction was concentrated and purified by HPLC (Xbridge C18 10u (30×100 mm); flow=42 ml/min; solvent gradient=95:5 to 5:95 water/acetonitrile (with 0.1% TFA)). The product fractions were concentrated to give the title compound as white solid. LCMS: Start % B=0 Final % B=100 Gradient Time=2 min Flow Rate=1 ml/min, Wavelength=220, Solvent Pair=Water:Methanol:0.1% TFA, Solvent A=90% Water:10% Methanol:0.1% TFA, Solvent B=10% Water:90% Methanol:0.1% TFA, Column; PHENOMENEX-LUNA 2.0×30 mm 3 um. Observed mass; 689.3 (M+1); retention time, 1.91 min.

Example 1

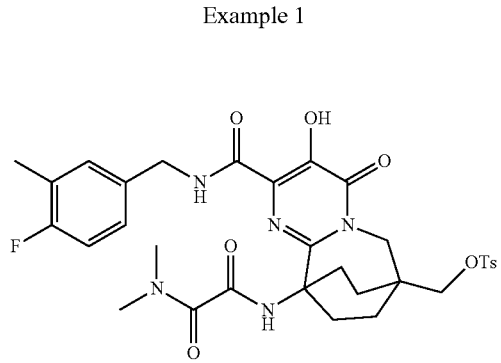

N'-[2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N,N-dimethyl-ethanediamide A mixture of 7,10-amino-N-[(4-fluoro-3-methylphenyl)methyl]-4,6,7,8,9,10-hexahydro-3-hydroxy-7-[[[(4-methylphenyl)sulfonyl]oxy]methyl]-4-oxo-, 10-ethanopyrimido[1,2-a]azepine-2-carboxamide hydrochloride, intermediate 17, (9.45 g, 15.6 mmol) and N,N-diisopropylethylamine (0.33 ml, 1.87 mmol) in DMF (60 mL) was stirred for 10 minutes, then treated with a solution of N,N,N',N'-tetramethyl-O-(7-azabenzotriazol-1-yl)uronium hexafluorophosphate (7.69 g, 20.2 mmol), 2-(dimethylamino)-2-oxoacetic acid (2.37 g, 20.2 mmol) and DMAP (0.095 g, 0.78 mmol) in DMF (40 mL). The mixture was stirred at room temp, under a nitrogen atmosphere, for 16 hrs. The reaction was then concentrated under reduced pressure. The resulting residue was taken up in $CH_2Cl_2$ (75 mL) and washed with 1.0 N HCl (2×75 mL). The organic layer was then dried ($Na_2SO_4$), filtered, and concentrated under reduced pressure, to afford a purple oil (~19 g). Absolute EtOH (~30 mL), was added to the oil. After stirring for 5 min the resulting solids were collected by filtration. The filter cake was washed with small portions of absolute EtOH, and the solid was dried under vacuum for 20 min to afford 8.10 g (11.18 mmol, 71.8% yield) of the title compound as a pale purple powder. HPLC (System A): 92% AP, rt=2.94 min. LC/MS (81476-083-04): 670.3 (M+H). $^1$H NMR (500 MHz, $CDCl_3$) δ ppm 1.61 (2H, m), 1.74-1.84 (2H, m), 2.06-2.17 (2H, m), 2.27 (3H, s), 2.49 (3H, s), 2.50-2.57 (2H, m), 2.93 (3H, s), 3.28 (3H, s), 3.81 (2H, s), 3.95 (2H, s), 4.52 (2H, d, J=6.1 Hz), 6.96 (1H, t, J=8.9 Hz), 7.16-7.23 (2H, m), 7.42 (2H, d, J=7.9 Hz), 7.58 (1H, br), 7.83 (1H, d, J=7.9 Hz), 7.99 (1H, s), 8.62 (1H, t, J=5.8 Hz), 12.11 (1H, br.s). $^{13}$C NMR (126 MHz, $CDCl_3$) δ ppm 14.7, 21.8, 26.0, 29.2, 35.9, 36.4, 38.2, 42.5, 53.6, 57.7, 75.3, 115.1, 125.0, 127.1, 128.1, 130.3, 131.4, 132.2, 133.2, 145.5, 146.9, 150.9, 159.4, 160.9, 162.1, 163.3, 168.0. Anal. Calc'd. for $C_{32}H_{36}FN_5O_8S$: C57.38, H5.41, N10.45. found: C57.17, H5.54, N10.36.

Example 2

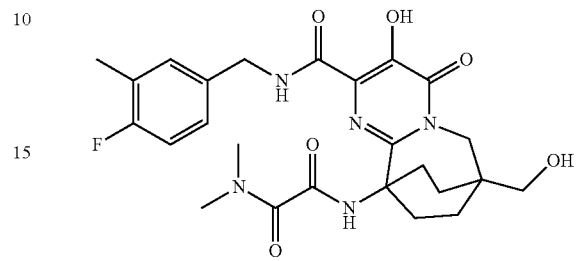

N'-[2-[[[(4-fluoro-3-methylphenyl)methyl]amino]carbonyl]-6,7,8,9-tetrahydro-3-hydroxy-7-(hydroxymethyl)-4-oxo-7,10-ethanopyrimido[1,2-a]azepin-10(4H)-yl]-N,N-dimethyl-ethanediamide A 25 mL round bottom flask was charged with a mixture of N'-[2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N,N-dimethyl-ethanediamide, Example 1 (0.91 g, 1.4 mmol), potassium acetate (0.400 g, 4.08 mmol), $K_2CO_3$ (0.188 g, 1.4 mmol), EtOH (1 ml, 17.13 mmol), N,N-dimethylacetamide (9 mL) and stirred in a pre-heated oil bath (145° C.) for 5 h. The reaction mixture was cooled and then quenched with 1 N HCl (3 mL). It was then diluted with ethyl acetate (100 mL) and the resulting solution washed with water (3×25 mL). The combined aqueous layers were extracted with ethyl acetate (2×50 mL). The organic fractions were combined then washed with brine (50 mL), dried ($Na_2SO_4$), filtered and concentrated to afford a brown solid which was crystallized from MeOH/$H_2O$ (30 mL) to give the title compound (0.387 g, 0.75 mmol, 55.2% yield) as white crystals. The filtrate was concentrated and the resulting solid was recrystallized to afford an additional lot of product (0.129 g, 18.36% yield) as a white solid. $^1$H NMR (500 MHz, $CDCl_3$) δ ppm 1.59-1.71 (2H, m, 9a, 13a-$CH_2$), 1.72-1.83 (2H, m, 9b, 13b-$CH_2$), 2.08-2.19 (2H, m, 10a, 12a-$CH_2$), 2.28 (3H, d, J=1.8 Hz, 27-$CH_3$), 2.55 (2H, m, 10b, 12b-$CH_2$), 2.94 (3H, s, 18-$NCH_3$), 3.30 (3H, s, 17-$NCH_3$), 3.51 (2H, s, 14-$OCH_2$), 4.10 (2H, s, 7-$NCH_2$), 4.54 (2H, d, J=6.1 Hz, 20-$NCH_2$), 6.97 (1H, t, J=8.7 Hz, 25-CH), 7.17-7.26 (2H, m, 22,26-CH), 8.05 (1H, s, 15-CONH), 8.64 (1H, t, J=6.3 Hz, 19-CONH), 12.07 (1H, br.s, 5-OH). $^{13}$C NMR (126 MHz, $CDCl_3$) δ ppm 14.7 (d, J=3.8 Hz, 27-$CH_3$), 26.1 (9,13-$CH_2$), 29.7 (10,12-$CH_2$), 36.4 (17- or 18-$NCH_3$), 37.0 (8-C), 38.2 (17- or 18-$NCH_3$), 42.5 (20-$NCH_2$), 55.0 (7-$NCH_2$), 58.1 (11-C), 70.4 (14-$OCH_2$), 115.1 (d, J=22.1 Hz, 25-CH), 124.6 (4-C), 125.0 (d, 18.2 Hz, 23-C), 127.1 (d, J=7.7 Hz, 26-CH), 131.4 (d, J=5.8 Hz, 22-CH), 133.3 (d, J=3.8 Hz, 21-C), 146.8 (5-OC=), 151.5 (2-C), 159.8 (6-C=O), 160.8 (d, J=245 Hz, 24-FC), 162.0, 163.4 (2s, 15,16-NC=O), 168.1 (19-NC=O). HPLC: 1.99 min (AP 100% at 254 nm, 5 min-run). HPLC: 6.32 min (AP 100% at 254 nm, 25 min-run). LCMS:

Example 3

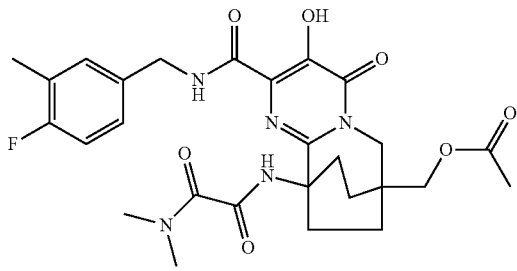 [SMILES: CC(=O)OCC12CCC(NC(=O)C(=O)N(C)C)(CC1)c1nc(C(=O)NCc3ccc(F)c(C)c3)c(O)c(=O)n1C2]

N'-[7-[(Acetyloxy)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (500 MHz, CDCl$_3$) δ ppm 1.64-1.73 (2H, m, 9a, 13a-CH$_2$), 1.73-1.83 (2H, m, 9b, 13b-CH$_2$), 2.06-2.17 (2H, m, 10a, 12a-CH$_2$), 2.12 (3H, s, 16-CH$_3$), 2.12-2.19 (2H, m, 10a, 12a-CH$_2$), 2.28 (3H, s, 29-CH$_3$), 2.53-2.63 (2H, m, 10b, 12b-CH$_2$), 2.94 (3H, s, 20-NCH$_3$), 3.31 (3H, s, 19-NCH$_3$), 3.94 (2H, s, 14-OCH$_2$), 4.12 (2H, s, 7-NCH$_2$), 4.54 (2H, d, J=6.1 Hz, 22-NCH$_2$), 6.98 (1H, t, J=8.7 Hz, 27-CH), 7.17-7.26 (2H, m, 24,28-CH), 8.17 (1H, s, 17-CONH), 8.59 (1H, t, J=5.7 Hz, 21-CONH), 12.11 (1H, br.s, 5-OH). $^{13}$C NMR (126 MHz, CDCl$_3$) δ ppm 14.7 (d, J=3.8 Hz, 29-CH$_3$), 20.9 (16-CH$_3$), 26.5 (9,13-CH$_2$), 29.3 (10,12-CH$_2$), 35.4 (8-C), 36.6, 38.3 (2s, 19,20-NCH$_3$), 42.6 (22-NCH$_2$), 54.5 (7-NCH$_2$), 57.8 (11-C), 71.0 (14-OCH$_2$), 115.1 (d, J=23.0 Hz, 27-CH), 124.5 (4-C), 125.1 (d, J=17.3 Hz, 25-C), 127.1 (d, J=7.7 Hz, 28-CH), 131.4 (d, J=5.8 Hz, 24-CH), 133.2 (d, J=2.9 Hz, 23-C), 146.9 (5-OC=), 151.2 (2-C), 159.6 (6-C=O), 160.9 (d, J=245 Hz, 26-FC), 161.9, 163.2 (2s, 17,18-NC=O), 168.0 (21-NC=O), 171.0 (15-OC=O). HPLC: 2.37 min (AP 96% at 254 nm, 5 min-run). HPLC: 8.14 min (AP 97% at 254 nm, 25 min-run). LCMS: m/z 558 (M+H).

Example 4

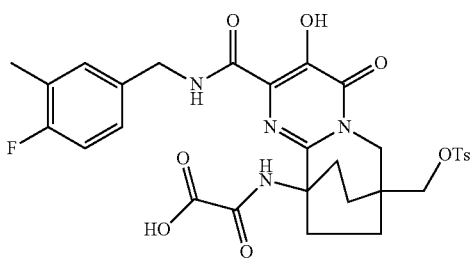 [SMILES: Cc1ccc(S(=O)(=O)OCC23CCC(NC(=O)C(=O)O)(CC2)c2nc(C(=O)NCc4ccc(F)c(C)c4)c(O)c(=O)n2C3)cc1]

[[2-[[[(4-Fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]amino]oxo-acetic acid $^1$H NMR (500 MHz, CDCl$_3$) δ ppm 1.60-1.72 (2H, m, 9a, 13a-CH$_2$), 1.80-1.91 (4H, m, 9b, 13b, 10a, 12a-CH$_2$), 2.30 (3H, s, 32-CH$_3$), 2.49 (3H, s, 21-CH$_3$), 2.80-2.95 (2H, m, 10b, 12b-CH$_2$), 3.83 (2H, s, 14-OCH$_2$), 3.98 (2H, s, 7-NCH$_2$), 4.58 (2H, d, J=6.1 Hz, 25-NCH$_2$), 7.01 (1H, t, J=9.0 Hz, 30-CH), 7.16-7.22 (2H, m, 31-CH), 7.25 (1H, d, J=7.0 Hz, 27-CH), 7.43 (2H, d, J=7.9 Hz, 17,19-CH), 7.62 (1H, t, J=6.0 Hz, 24-CONH), 7.83 (1H, d, J=8.2 Hz, 16,20-CH), 7.58 (1H, s, 22-CONH), 12.25 (1H, br.s, 5-OH). $^{13}$C NMR (126 MHz, CDCl$_3$) δ ppm 14.6 (d, J=3.8 Hz, 32-CH$_3$), 21.8 (21-CH$_3$), 26.2 (9,13-CH$_2$), 27.3 (10,12-CH$_2$), 35.6 (8-C), 43.0 (27-NCH$_2$), 54.5 (7-NCH$_2$), 57.0 (11-C), 75.1 (14-OCH$_2$), 115.5 (d, J=23.0 Hz, 30-CH), 123.5 (4-C), 125.7 (d, J=16.3 Hz, 28-C), 127.2 (d, J=7.7 Hz, 31-CH), 128.1 (16,20-CH), 130.3 (s, 17,19-CH), 131.5 (d, J=5.8 Hz, 27-CH), 132.2 (15-C), 132.3 (d, J=3.8 Hz, 26-C), 145.6 (18-C), 147.5 (5-OC=), 150.8 (2-C), 155.4 (23- or 22-NC=O), 159.0 (6-C=O), 160.3 (d, J=245 Hz, 29-FC), 160.3 (22- or 23-NC=O), 167.3 (24-NC=O). HPLC: 2.81 min (AP 98% at 254 nm, 5 min-run) 10.8 min (AP 99% at 254 nm, 25 min-run). LCMS: m/z 643 (M+H) Anal. Calcd for C$_{30}$H$_{31}$FN$_4$O$_9$S.0.3CH$_2$Cl$_2$: C54.47, H4.47, N8.39. found: C54.42, H4.61, N8.29.

Example 5

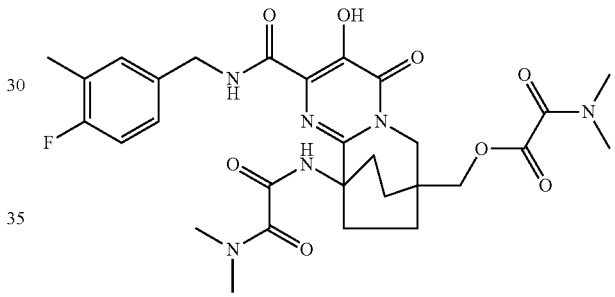

[10-[[2-(Dimethylamino)-1,2-dioxoethyl]amino]-2-[[[(4-fluoro-3-methylphenyl)methyl]amino]carbonyl]-4,8,9,10-tetrahydro-3-hydroxy-4-oxo-7,10-ethanopyrimido[1,2-a]azepin-7(6H)-yl]methyl ester (dimethylamino)oxo-acetic acid $^1$H NMR (500 MHz, CDCl$_3$) δ ppm 1.68-1.78 (2H, m, 9a, 13a-CH$_2$), 1.79-1.90 (2H, m, 9b, 13b-CH$_2$), 2.17 (2H, m, 10a, 12a-CH$_2$), 2.28 (3H, s, 31-CH$_3$), 2.57 (2H, m, 10b, 12b-CH$_2$), 2.94 (3H, s, 21- or 22-NCH$_3$), 3.03, 3.09 (2×3H, 2s, 17,18-NCH$_3$), 3.30 (3H, s, 22- or 21-NCH$_3$), 4.12 (2H, s, 14-OCH$_2$, or 7-NCH$_2$), 4.16 (2H, s, 7-NCH$_2$, or 14-OCH$_2$), 4.54 (2H, d, J=6.1 Hz, 24-NCH$_2$), 6.98 (1H, t, J=8.9 Hz, 29-CH), 7.15-7.25 (2H, m, 26,30-CH), 8.02 (1H, s, 19-CONH), 8.62 (1H, t, J=5.8 Hz, 23-CONH), 12.14 (1H, br, 5-OH). $^{13}$C NMR (126 MHz, CDCl$_3$) δ ppm 14.7 (d, J=3.8 Hz, 31-CH$_3$), 26.4 (9,13-CH$_2$), 29.3 (10,12-CH$_2$), 34.3 (17- or 18-NCH$_3$), 35.7 (17- or 18-NCH$_3$), 36.5 (21- or 22-NCH$_3$), 37.4 (8-C), 38.2 (21- or 22-NCH$_3$), 42.6 (24-NCH$_2$), 54.0 (7-NCH$_2$), 57.8 (11-C), 71.7 (14-OCH$_2$), 115.1 (d, J=22.1 Hz, 29-CH), 124.7 (4-C), 125.1 (d, 17.3 Hz, 27-C), 127.1 (d, J=7.7 Hz, 30-CH), 131.4 (d, J=4.8 Hz, 26-CH), 133.2 (d, J=3.8 Hz, 25-C), 146.9 (5-OC=), 151.0 (2-C), 159.6 (6-C=O), 160.9 (d, J=245 Hz, 28-FC), 161.2, 162.0, 162.7, 163.3 (4s, 15,16,19,20-NC=O), 167.9 (23-NC=O). HPLC: 2.25 min (AP 96% at 254 nm, 5 min-run). HPLC: 7.67 min (AP 95% at 254 nm, 25 min-run). LCMS: m/z 615 (M+H).

Example 6

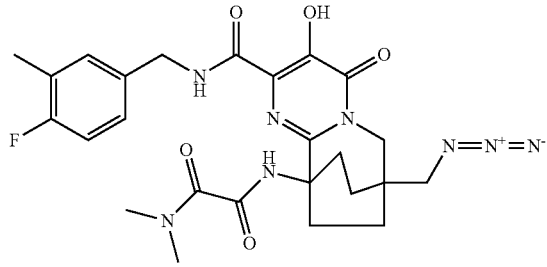 [SMILES: Cc1cc(CNC(=O)c2nc3n(c(=O)c2O)CC2(CN=[N+]=[N-])CCC3(NC(=O)C(=O)N(C)C)CC2)ccc1F]

N'-[7-(Azidomethyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (500 MHz, CDCl$_3$) δ ppm 1.64 (2H, m, 9a, 13a-CH$_2$), 1.77-1.88 (2H, m, 9b, 13b-CH$_2$), 2.08-2.17 (2H, m, 10a, 12a-CH$_2$), 2.29 (3H, d, J=1.8 Hz, 27-CH$_3$), 2.57 (2H, m, 10b, 12b-CH$_2$), 2.94 (3H, s, 18-NCH$_3$), 3.31 (3H, s, 17-NCH$_3$), 3.35 (2H, s, 14-OCH$_2$), 4.04 (2H, s, 7-NCH$_2$), 4.54 (2H, d, J=6.4 Hz, 20-NCH$_2$), 6.94 (1H, t, J=9 Hz, 25-CH), 7.18-7.25 (2H, m, 22,26-CH), 8.12 (1H, s, 15-CONH), 8.59 (1H, t, J=6.6 Hz, 19-CONH), 12.11 (1H, s, 5-OH). $^{13}$C NMR (126 MHz, CDCl$_3$) δ ppm 14.7 (d, J=2.8 Hz, 27-CH$_3$), 27.1 (9,13-CH$_2$), 29.5 (10,12-CH$_2$), 36.4 (17-, 18-NCH$_3$, or 8-C), 36.5 (8-C or 17-, 18-NCH$_3$), 38.2 (17- or 18-NCH$_3$), 42.6 (20-NCH$_2$), 54.9 (7-NCH$_2$), 57.8 (11-C), 60.8 (14-NCH$_2$), 115.1 (d, J=22.1 Hz, 25-CH), 124.5 (4-C), 125.1 (d, J=17.3 Hz, 23-C), 127.1 (d, J=7.7 Hz, 26-CH), 131.4 (d, J=4.8 Hz, 22-CH), 133.2 (d, J=3.8 Hz, 21-C), 146.9 (5-OC=), 151.2 (2-C), 159.5 (6-C=O), 160.9 (d, J=245 Hz, 24-FC), 161.9, 163.3 (2s, 15,16-NC=O), 168.0 (19-NC=O). HPLC: 2.59 min (AP 91% at 254 nm, 5 min-run) HPLC: 9.29 min (AP 89% at 254 nm, 25 min-run). LCMS: m/z 541 (M+H).

Example 7

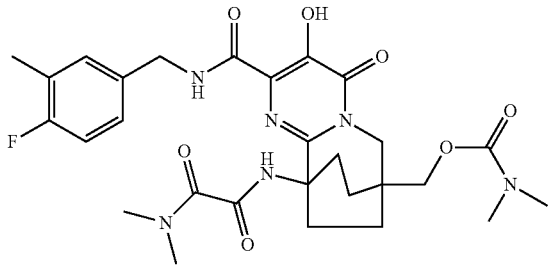

[10-[[2-(Dimethylamino)-1,2-dioxoethyl]amino]-2-[[[(4-fluoro-3-methylphenyl)methyl]amino]carbonyl]-4,8,9,10-tetrahydro-3-hydroxy-4-oxo-7,10-ethanopyrimido[1,2-a]azepin-7(6H)-yl]methyl ester dimethyl-carbamic acid $^1$H NMR (500 MHz, CDCl$_3$) δ ppm 1.66 (2H, m, 9a, 13a-CH$_2$), 1.75-1.85 (2H, m, 9b, 13b-CH$_2$), 2.03 (2H, s, H$_2$O), 2.08-2.19 (2H, m, 10a, 12a-CH$_2$), 2.28 (3H, d, J=1.5 Hz, 30-CH$_3$), 2.57 (2H, m, 10b, 12b-CH$_2$), 2.91, 2.94 (2×3H, 2s, 16,17-NCH$_3$), 2.94, 3.20 (2×3H, 2s, 20,21-NCH$_3$), 3.95 (2H, s, 14-OCH$_2$), 4.14 (2H, s, 7-NCH$_2$), 4.53 (2H, d, J=6.4 Hz, 23-NCH$_2$), 6.97 (1H, t, J=9 Hz, 28-CH), 7.16-7.24 (2H, m, 25,29-CH), 8.10 (1H, s, 18-CONH), 8.62 (1H, t, J=6.1 Hz, 22-CONH), 12.10 (1H, s, 5-OH). $^{13}$C NMR (126 MHz, CDCl$_3$) δ ppm 14.7 (d, J=3.8 Hz, 30-CH$_3$), 26.5 (9,13-CH$_2$), 29.4 (10,12-CH$_2$), 35.8 (8-C), 35.9 (16- or 17-NCH$_3$), 36.5 (20- or 21-NCH$_3$), 36.7 (16- or 17-NCH$_3$), 38.2 (21- or 20-NCH$_3$), 42.6 (23-NCH$_2$), 54.4 (7-NCH$_2$), 57.9 (11-C), 71.8 (14-OCH$_2$), 115.1 (d, J=22.1 Hz, 28-CH), 124.5 (4-C), 125.1 (d, J=18.2 Hz, 26-C), 127.1 (d, J=8.6 Hz, 29-CH), 131.4 (d, J=5.8 Hz, 25-CH), 133.2 (d, J=3.8 Hz, 24-C), 146.9 (5-OC=), 151.3 (2-C), 156.1 (15-NC=O), 159.6 (6-C=O), 160.8 (d, J=245 Hz, 27-FC), 161.9, 163.3 (2s, 18,19-NC=O), 168.0 (22-NC=O). HPLC: 2.29 min (AP 98% at 254 nm, 5 min-run). HPLC: 7.86 min (AP 99% at 254 nm, 25 min-run). LCMS: m/z 587 (M+H). Anal. Calcd for C$_{28}$H$_{35}$FN$_6$O$_7$.H$_2$O: C55.62, H6.17, N13.90. found: C55.65, H5.86, N13.61.

Example 8

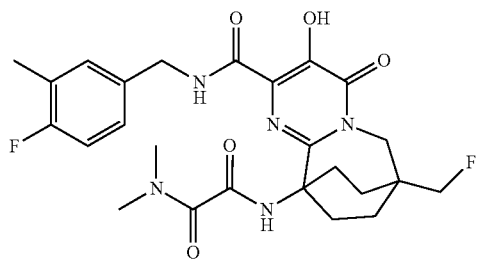 [SMILES: Cc1cc(CNC(=O)c2nc3n(c(=O)c2O)CC2(CF)CCC3(NC(=O)C(=O)N(C)C)CC2)ccc1F]

N'-[7-(Fluoromethyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (500 MHz, CDCl$_3$) δ ppm 12.08 (1H, br. s.), 8.59 (1H, br. s.), 8.12 (1H, br. s.), 7.14-7.22 (2H, m), 6.92-6.99 (1H, m), 4.51 (2H, d, J=6.41 Hz), 4.25 (1H, s), 4.16 (1H, s), 4.08 (2H, s), 3.28 (3H, s), 2.91 (3H, s), 2.56 (2H, ddd, J=14.50, 9.16, 5.65 Hz), 2.25 (3H, d, J=1.83 Hz), 2.06-2.16 (2H, m), 1.73-1.83 (2H, m), 1.62-1.68 (2H, m). HPLC: 2.40 min (AP 98.8% at 254 nm, 5 min-run). LCMS: m/z 518.3 (M+H).

Example 9

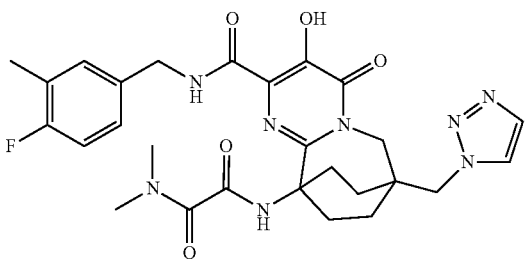 [SMILES: Cc1cc(CNC(=O)c2nc3n(c(=O)c2O)CC2(Cn4ccnn4)CCC3(NC(=O)C(=O)N(C)C)CC2)ccc1F]

N'-[2-[[[(4-Fluoro-3-methylphenyl)methyl]amino]carbonyl]-6,7,8,9-tetrahydro-3-hydroxy-4-oxo-7-(1H-1,2,3-triazol-1-ylmethyl)-7,10-ethanopyrimido[1,2-a]azepin-10(4H)-yl]-N,N-dimethyl-ethanediamide $^1$H NMR (500 MHz, CDCl$_3$) δ ppm 12.11 (1H, br. s.), 8.59 (1H, t, J=6.26 Hz), 7.95 (1H, s), 7.73 (1H, s), 7.66 (1H, s), 7.13-7.21 (2H, m), 6.89-6.98 (1H, m), 4.49 (2H, d, J=6.10 Hz), 4.35 (2H, s), 4.08 (2H, s), 3.24 (3H, s), 2.90 (3H, s), 2.48 (2H, ddd, J=14.57, 9.23, 5.80 Hz), 2.24 (3H, d, J=1.83 Hz), 2.07-2.15 (2H, m), 1.84-1.93 (2 H, m), 1.64-1.68 (2H, m). $^{13}$C NMR (126 MHz, CDCl$_3$) δ ppm 167.91, 163.24, 162.10, 161.84, 159.89, 159.48, 150.86, 146.86, 134.01, 133.20, 133.17, 131.38, 131.35, 127.15, 127.08, 125.17, 124.99, 124.62, 115.22, 115.04, 58.49, 57.59, 54.63, 42.57, 38.18, 36.71, 36.42, 29.37, 27.10, 14.66, 14.63. HPLC: 2.08 min (AP 97% at 254 nm, 5 min-run). LCMS: m/z 567.4 (M+H).

Example 10

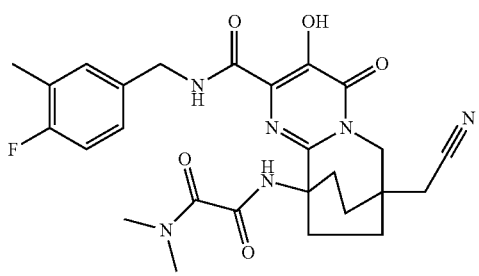 [SMILES: Cc1cc(CNC(=O)c2nc3n(c(=O)c2O)CC2(CC#N)CCC3(NC(=O)C(=O)N(C)C)CC2)ccc1F]

N'-[7-(Cyanomethyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (500 MHz, CDCl$_3$) δ ppm 1.77 (2H, m, 9a, 13a-CH$_2$), 1.98-2.07 (2H, m, 9b, 13b-CH$_2$), 2.19 (2H, m, 10a, 12a-CH$_2$), 2.29 (3H, d, J=1.5 Hz, 28-CH$_3$), 2.49 (2H, s, 14-CH$_2$), 2.63 (2H, m, 10b, 12b-CH$_2$), 2.95, 3.30 (2×3H, 2s, 18,19-NCH$_3$), 4.09 (2H, s, 7-NCH$_2$), 4.54 (2H, d, J=6.4 Hz, 21-NCH$_2$), 6.98 (1H, t, J=8.9 Hz, 26-CH), 7.16-7.25 (2H, m, 23,27-CH), 8.06 (1H, s, 16-CONH), 8.60 (1H, t, J=5.8 Hz, 20-CONH), 12.17 (1H, s, 5-OH). $^{13}$C NMR (101 MHz, CDCl$_3$) δ ppm 14.1 (d, J=3.1 Hz, 28-CH$_3$), 28.4 (9,13-CH$_2$), 29.0 (10,12-CH$_2$), 30.1 (14-CH$_2$), 34.0 (8-C), 36.1 (18- or 19-NCH$_3$), 37.7 (18- or 19-NCH$_3$), 42.1 (21-NCH$_2$), 55.5 (7-NCH$_2$), 56.8 (11-C), 114.7 (d, J=23.1 Hz, 26-CH), 124.0 (4-C), 124.6 (d, J=17.7 Hz, 24-C), 126.7 (d, J=8.5 Hz, 27-CH), 130.9 (d, J=5.4 Hz, 23-CH), 132.7 (d, J=3.1 Hz, 22-C), 146.5 (5-OC=), 150.3 (2-C), 158.8 (6-C=O), 160.4 (d, J=244 Hz, 25-FC), 161.4 (16-NC=O), 162.6 (17-NC=O), 167.4 (20-NC=O). HPLC: 2.28 min (AP 96% at 254 nm, 5 min-run). HPLC: 7.59 min (AP 97% at 254 nm, 25 min-run). LCMS: m/z 525 (M+H). Anal. Calcd for C$_{26}$H$_{29}$FN$_6$O$_5$.0.5 CH$_2$Cl$_2$: C59.17, H5.55, N15.89. found: C58.98, H5.33, N15.77.

Example 11

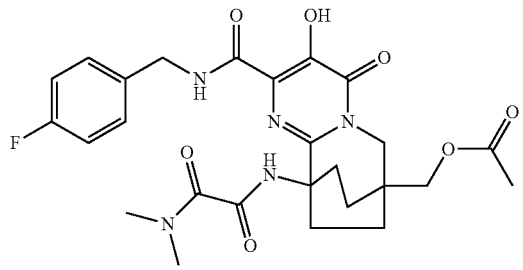 [SMILES: CC(=O)OCC12CCC(NC(=O)C(=O)N(C)C)(CC1)c1nc(C(=O)NCc3ccc(F)cc3)c(O)c(=O)n1C2]

N'-[7-[(Acetyloxy)methyl]-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (500 MHz, CDCl$_3$) δ ppm 1.63-1.73 (2H, m, 9a, 13a-CH$_2$), 1.73-1.84 (2H, m, 9b, 13b-CH$_2$), 2.10-2.19 (2H, m, 10a, 12a-CH$_2$), 2.12 (3H, s, 16-CH$_3$), 2.57 (2H, m, 10b, 12b-CH$_2$), 2.94, 3.30 (2×3H, 2s, 19, 20-NCH$_3$), 3.94 (2H, s, 14-OCH$_2$), 4.12 (2H, s, 7-NCH$_2$), 4.58 (2H, d, J=6.1 Hz, 22-NCH$_2$), 7.04 (1H, t, J=8.6 Hz, 25,27-CH), 7.40 (2H, dd, J=7.9, 5.8 Hz, 24,28-CH), 8.10 (1H, s, 17-CONH), 8.63 (1H, t, J=5.6 Hz, 21-CONH), 12.08 (1H, br, 5-OH). $^{13}$C NMR (126 MHz, CDCl$_3$) δ ppm 20.9 (16-CH$_3$), 26.4 (9,13-CH$_2$), 29.4 (10,12-CH$_2$), 35.5 (8-C), 36.5, 38.2 (2s, 19,20-NCH$_3$), 42.6 (22-NCH$_2$), 54.6 (7-NCH$_2$), 57.9 (11-C), 71.0 (14-OCH$_2$), 115.5 (d, J=21.1 Hz, 25,27-CH), 124.6 (4-C), 130.0 (d, J=8.6 Hz, 24,28-CH), 133.5 (d, J=2.9 Hz, 23-C), 146.8 (5-OC=), 151.2 (2-C), 159.8 (6-C=O), 162.0 (17-NC=O), 162.3 (d, J=246 Hz, 26-FC), 163.4 (18-NC=O), 168.0 (21-NC=O), 171.0 (15-OC=O). HPLC: 2.20 min (AP 99% at 254 nm, 5 min-run). HPLC: 7.27 min (AP 99% at 254 nm, 25 min-run). LCMS: m/z 545 (M+H).

Example 12

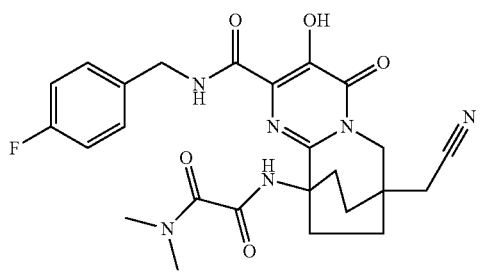 [SMILES: CN(C)C(=O)C(=O)NC12CCC(CC#N)(CC1)Cn1c2nc(C(=O)NCc2ccc(F)cc2)c(O)c1=O]

N'-[7-(Cyanomethyl)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (500 MHz, CDCl$_3$) δ ppm 1.71-1.82 (2H, m, 9a, 13a-CH$_2$), 1.98-2.08 (2H, m, 9b, 13b-CH$_2$), 2.113-2.26 (2H, m, 10a, 12a-CH$_2$), 2.49 (2H, s, 14-CH$_2$), 2.62 (2H, m, 10b, 12b-CH$_2$), 2.95, 3.30 (2×3H, 2s, 18,19-NCH$_3$), 4.09 (2H, s, 7-NCH$_2$), 4.58 (2H, d, J=6.4 Hz, 21-NCH$_2$), 7.05 (1H, t, J=8.7 Hz, 24,26-CH), 7.39 (2H, dd, J=8.4, 5.3 Hz, 23,27-CH), 8.03 (1H, s, 16-CONH), 8.63 (1H, t, J=5.5 Hz, 21-CONH), 12.13 (1H, s, 5-OH). $^{13}$C NMR (101 MHz, CDCl$_3$) δ ppm 28.8 (9,13-CH$_2$), 29.6 (10,12-CH$_2$), 30.6 (14-CH$_2$), 34.6 (8-C), 36.5 (18- or 19-NCH$_3$), 38.2 (18- or 19-NCH$_3$), 42.6 (21-NCH$_2$), 56.0 (7-NCH$_2$), 57.4 (11-C), 115.5 (d, J=22.1 Hz, 24,26-CH), 124.5 (4-C), 130.0 (d, J=8.6 Hz, 23,27-CH), 133.5 (d, J=3.8 Hz, 22-C), 146.9 (5-OC=), 150.7 (2-C), 159.4 (6-C=O), 162.0 (16-NC=O), 163.2 (17-NC=O), 167.9 (20-NC=O). HPLC: 2.11 min (AP 95% at 254 nm, 5 min-run). HPLC: 6.66 min (AP 95% at 254 nm, 25 min-run). LCMS: m/z 511 (M+H).

Example 13

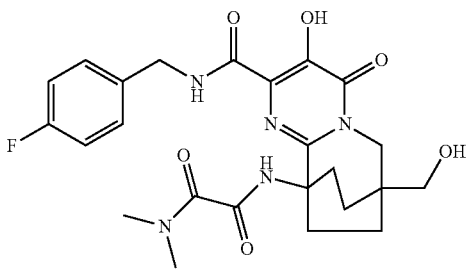 [SMILES: CN(C)C(=O)C(=O)NC12CCC(CO)(CC1)Cn1c2nc(C(=O)NCc2ccc(F)cc2)c(O)c1=O]

N'-[2-[[[(4-Fluorophenyl)methyl]amino]carbonyl]-6, 7,8,9-tetrahydro-3-hydroxy-7-(hydroxymethyl)-4-oxo-7,10-ethanopyrimido[1,2-a]azepin-10(4H)-yl]-N,N-dimethyl-ethanediamide $^1$H NMR (500 MHz, CDCl$_3$) δ ppm 1.65 (2H, m, 9a, 13a-CH$_2$), 1.75-1.83 (3H, m, 9b, 13b-CH$_2$, 14-OH), 2.08-2.20 (2H, m, 10a, 12a-CH$_2$), 2.56 (2H, m, 10b, 12b-CH$_2$), 2.94, 3.30 (2×3H, 2s, 17,18-NCH$_3$), 3.52 (2H, d, J=5.2 Hz, 14-OCH$_2$), 4.10 (2H, s, 7-NCH$_2$), 4.58 (2H, d, J=6.4 Hz, 20-NCH$_2$), 7.05 (1H, t, J=8.7 Hz, 23,25-CH), 7.40 (2H, dd, J=8.7, 5.3 Hz, 22,26-CH), 8.06 (1H, s, 15-CONH), 8.63 (1H, t, J=6.1 Hz, 19-CONH), 12.05 (1H, br, 5-OH). $^{13}$C NMR (100.6 MHz, CDCl$_3$) δ ppm 25.7 (9,13-CH$_2$), 29.1 (10,12-CH$_2$), 36.1 (8-C), 36.5, 37.7 (2s, 19,20-NCH$_3$), 42.1 (22-NCH$_2$), 54.4 (7-NCH$_2$), 57.6 (11-C), 69.9 (14-OCH$_2$), 115.0 (d, J=21.6 Hz, 23,25-CH), 124.0 (4-C), 129.5 (d, J=8.5 Hz, 22,26-CH), 133.1 (d, J=3.1 Hz, 21-C), 146.4 (5-OC=), 151.1 (2-C), 159.2 (6-C=O), 161.3 (15-NC=O), 162.9 (16-NC=O), 167.7 (19-NC=O). HPLC: 1.88 min (AP 97% at 254 nm, 5 min-run). HPLC: 5.57 min (AP 98% at 254 nm, 25 min-run). LCMS: m/z 502 (M+H). Anal. Calc'd. for C$_{24}$H$_{28}$FN$_5$O$_6$: C57.48, H5.63, N13.97. found: C57.47, H5.47, N13.77.

Example 14

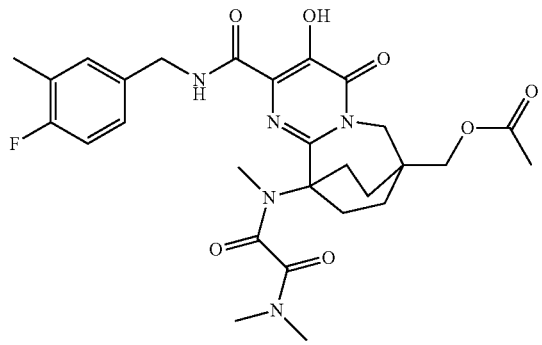 [SMILES: CC(=O)OCC12CCC(N(C)C(=O)C(=O)N(C)C)(CC1)c1nc(C(=O)NCc3ccc(F)c(C)c3)c(O)c(=O)n1C2]

N-[7-[(acetyloxy)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-ethanediamide White solid. $^1$H NMR (500 MHz, CDCl$_3$) δ ppm 9.57 (1H, t, J=6.26 Hz), 7.24 (1H, d, J=7.32 Hz), 7.17-7.22 (1H, m), 6.94 (1H, t, J=9.00 Hz), 4.81 (1H, d, J=14.95 Hz), 4.57-4.64 (1H, m), 4.42-4.49 (1H, m), 4.01 (1H, s), 3.90-3.99 (2H, m), 3.55-3.61 (1H, m), 3.36-3.48 (1H, m), 3.05 (3H, s), 3.04 (3H, s), 3.01 (3H, s), 2.26 (3H, s), 2.13 (3H, s), 2.09-2.13 (2H, m), 1.68-1.79 (3H, m), 1.47-1.59 (1H, m). LCMS (M+H)=572.3.

Example 15

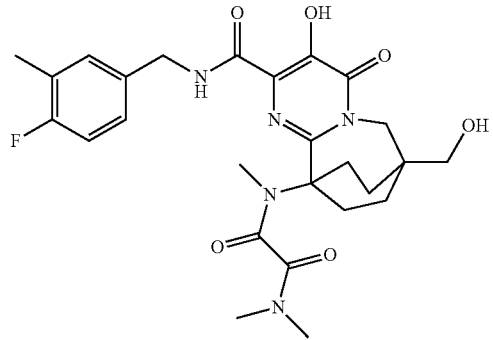 [SMILES: Cc1cc(CNC(=O)c2nc3n(c(=O)c2O)CC2(CO)CCC3(N(C)C(=O)C(=O)N(C)C)CC2)ccc1F]

N-[2-[[[(4-Fluoro-3-methylphenyl)methyl]amino]carbonyl]-6,7,8,9-tetrahydro-3-hydroxy-7-(hydroxymethyl)-4-oxo-7,10-ethanopyrimido[1,2-a]azepin-10(4H)-yl]-N,N',N'-trimethyl-ethanediamide A 25 mL round bottom flask charged with a mixture of N-[2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N,N',N'-trimethyl-ethanediamide, Intermediate 28, (900 mg, 1.316 mmol), potassium acetate (388 mg, 3.95 mmol), K$_2$CO$_3$ (182 mg, 1.316 mmol), EtOH (1 ml, 17.13 mmol), N,N-dimethylacetamide (6 mL) and stirred in a pre-heated oil bath (145° C.) for 3 h. After cooling the reaction was quenched with 1 N HCl (3 mL), diluted with EtOAc (100 mL) and washed with water (3×25 mL). The combined aqueous layers were extracted with EtOAc (2×50 mL). The combined organic layers were washed with brine (50 mL), dried (Na$_2$SO$_4$), filtered and concentrated to afford a brown solid which was crystallized from ethanol (~30 mL) to give the title compound (250 mg, 0.448 mmol, 34.1% yield) as white crystals. $^1$H NMR (500 MHz, CDCl$_3$) δ: 9.59 (1H, t, J=5.95 Hz), 7.24 (1H, d, J=7.63 Hz), 7.16-7.22 (1H, m), 6.94 (1H, t, J=9.00 Hz), 4.76 (1H, d, J=15.26 Hz), 4.58-4.65 (1H, m), 4.42-4.49 (1H, m), 3.48-3.57 (3H, m), 3.37-3.47 (1H, m), 3.05 (3H, s), 3.04 (3H, s), 3.01 (3H, s), 2.26 (3H, d, J=1.53 Hz), 2.08-2.16 (3H, m), 1.77-1.85 (1H, m), 1.67-1.74 (2H, m), 1.41-1.51 (1H, m). LCMS (M+H)=530.3.

Example 16

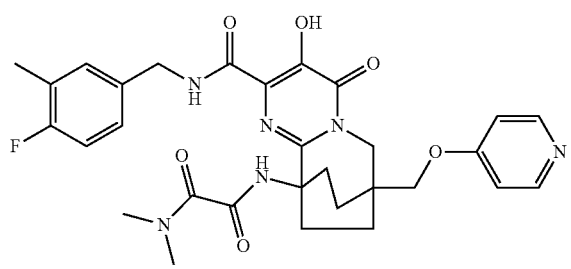 [SMILES: Cc1cc(CNC(=O)c2nc3n(c(=O)c2O)CC2(COc4ccncc4)CCC3(NC(=O)C(=O)N(C)C)CC2)ccc1F]

N'-[2-[[[(4-Fluoro-3-methylphenyl)methyl]amino]carbonyl]-6,7,8,9-tetrahydro-3-hydroxy-4-oxo-7-[(4-pyridinyloxy)methyl]-7,10-ethanopyrimido[1,2-a]azepin-10(4H)-yl]-N,N-dimethyl-ethanediamide $^1$H NMR (500 MHz, CDCl$_3$) δ ppm 1.84 (2H, br. m, 9a, 13a-CH$_2$), 1.91 (2H, br. m, 9b, 13b-CH$_2$), 2.28 (2H, m, 10a, 12a-CH$_2$), 2.28 (3H, s, 32-CH$_3$), 2.60 (2H, br. m, 10b, 12b-CH$_2$), 2.95, 3.28 (2×3H, 2s, 22,23-NCH$_3$), 4.13 (2H, s, 14-OCH$_2$), 4.23 (2H, s, 7-NCH$_2$), 4.53 (2H, d, J=5.8 Hz, 25-NCH$_2$), 6.97 (1H, t, J=8.9 Hz, 30-CH), 7.21 (2H, m, 27,31-CH), 7.36 (2H, br.s, 16,19-CH), 8.03 (1H, s, 20-CONH), 8.73 (3H, m, 24-CONH, 17,18-CH). $^{13}$C NMR (126 MHz, CDCl$_3$) δ ppm 14.6 (d, J=3.8 Hz, 32-CH$_3$), 26.3 (9,13-CH$_2$), 29.3 (10,12-CH$_2$), 36.1 (8-C), 36.3, 38.2 (2s, 22,23-NCH$_3$), 42.6 (25-NCH$_2$), 53.8 (7-NCH$_2$), 57.9 (11-C), 77.7 (14-OCH$_2$), 112.9 (16,19-CH), 115.1 (d, J=22.1 Hz, 30-CH), 125.0 (4-C), 125.1 (d, J=17.3 Hz, 28-C), 127.1 (d, J=7.7 Hz, 31-CH), 131.4 (d, J=4.8 Hz, 27-CH), 133.1 (d, J=2.9 Hz, 26-C), 143.7 (17,18-CH), 146.7 (5-OC=), 151.0 (2-C), 159.9 (6-C=O), 160.9 (d, J=246 Hz, 26-FC), 161.9 (20-NC=O), 162.4 (21-NC=O), 167.9 (24-NC=O), 170.6 (15-OC). HPLC: 1.77 min (AP 96% at 254 nm, 5 min-run). HPLC: 8.17 and 8.29 min (AP 26% and 71% at 254 nm, 25 min-run); a mixture of amide-rotational isomers. LCMS: m/z 593 (M+H).

Example 17

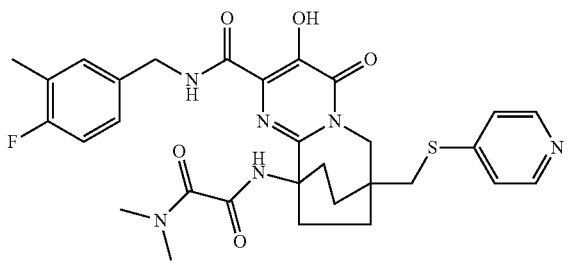

N'-[2-[[[(4-Fluoro-3-methylphenyl)methyl]amino]carbonyl]-6,7,8,9-tetrahydro-3-hydroxy-4-oxo-7-[(4-pyridinylthio)methyl]-7,10-ethanopyrimido[1,2-a]azepin-10(4H)-yl]-N,N-dimethyl-ethanediamide $^1$H NMR (400 MHz, CDCl$_3$) δ ppm 1.74-1.88 (2H, m, 9a, 13a-CH$_2$), 1.92-2.05 (2H, m, 9b, 13b-CH$_2$), 2.14-2.24 (2H, m, 10a, 12a-CH$_2$), 2.26 (3H, d, J=1.8 Hz, 32-CH$_3$), 2.60 (2H, m, 10b, 12b-CH$_2$), 2.94 (2H, s, 14-SCH$_2$), 2.94, 3.28 (2×3H, 2s, 22,23-NCH$_3$), 4.18 (2H, s, 7-NCH$_2$), 4.52 (2H, d, J=6.3 Hz, 25-NCH$_2$), 6.95 (1H, t, J=8.8 Hz, 30-CH), 7.14-7.24 (2H, m, 27,31-CH), 7.61 (2H, d, J=6.0 Hz, 16,19-CH), 8.13 (1H, s, 20-CONH), 8.58 (2H, d, J=6.0 Hz, 17,18-CH), 8.70 (1H, t, J=6.3 Hz, 24-CONH), ~10.5 (br). $^{13}$C NMR (101 MHz, CDCl$_3$) δ ppm 14.1 (d, J=3.9 Hz, 32-CH$_3$), 28.4 (9,13-CH$_2$), 29.2 (10,12-CH$_2$), 35.7 (8-C), 35.8, 37.6 (2s, 22,23-NCH$_3$), 42.1 (25-NCH$_2$), 42.3 (14-SCH$_2$), 55.1 (7-NCH$_2$), 57.0 (11-C), 114.6 (d, J=22.4 Hz, 30-CH), 121.7 (16,19-CH), 124.3 (4-C), 124.6 (d, J=17.7 Hz, 28-C), 126.7 (d, J=7.7 Hz, 31-CH), 130.9 (d, J=5.4 Hz, 27-CH), 132.7 (d, J=3.9 Hz, 26-C), 140.3 (17,18-CH), 146.3 (5-OC=), 150.5 (2-C), 159.0 (6-C=O), 161.0 (15-SC=), 160.4 (d, J=244 Hz, 29-FC), 161.8 (20-NC=O), 162.9 (21-NC=O), 167.5 (24-NC=O). $^{19}$F NMR (470 MHz, CDCl$_3$) δ ppm –119.8 (Ar—F), –76.2 (TFA). HPLC: 1.83 min (AP 97% at 254 nm, 5 min-run). HPLC: 8.65 min (AP 93% at 254 nm, 25 min-run). LCMS: m/z 609 (M+H). Anal. Calcd. for C$_{30}$H$_{33}$FN$_6$O$_5$.CF$_3$CO$_2$H.H$_2$O: C51.89, H4.90, N11.35. found: C52.00, H5.02, N11.16.

Example 18

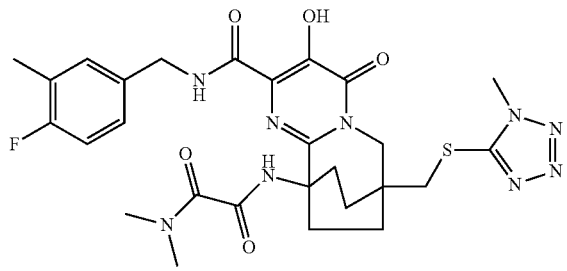 [SMILES: Cc1cc(CNC(=O)c2nc3n(c(=O)c2O)CC2(CSc4nnnn4C)CCC3(NC(=O)C(=O)N(C)C)CC2)ccc1F]

N'-[2-[[[(4-Fluoro-3-methylphenyl)methyl]amino]carbonyl]-6,7,8,9-tetrahydro-3-hydroxy-7-[[(1-methyl-1H-tetrazol-5-yl)thio]methyl]-4-oxo-7,10-ethanopyrimido[1,2-a]azepin-10(4H)-yl]-N,N-dimethyl-ethanediamide $^1$H NMR (500 MHz, CDCl$_3$) δ ppm 1.74 (2H, m, 9a, 13a-CH$_2$), 1.91-2.03 (2H, m, 9b, 13b-CH$_2$), 2.10-2.21 (2H, m, 10a, 12a-CH$_2$), 2.28 (3H, d, J=1.8 Hz, 29-CH$_3$), 2.58 (2H, m, 10b, 12b-CH$_2$), 2.94, 3.29 (2×3H, 2s, 19,20-NCH$_3$), 3.61 (2H, s, 14-SCH$_2$), 3.96 (3H, s, 16-NCH$_3$), 4.16 (2H, s, 7-NCH$_2$), 4.53 (2H, d, J=6.1 Hz, 22-NCH$_2$), 6.97 (1H, t, J=8.9 Hz, 27-CH), 7.16-7.24 (2H, m, 24,28-CH), 8.01 (1H, s, 17-CONH), 8.62 (1H, t, J=6.3 Hz, 21-CONH), 12.13 (1H, s, 5-OH). $^{13}$C NMR (126 MHz, CDCl$_3$) δ ppm 14.7 (d, J=3.8 Hz, 29-CH$_3$), 28.6 (9,13-CH$_2$), 29.7 (10,12-CH$_2$), 33.6 (16-NCH$_3$), 36.4 (8-C), 36.5, 38.2 (2s, 19,20-NCH$_3$), 42.6 (22-NCH$_2$), 44.7 (14-SCH$_2$), 55.4 (7-NCH$_2$), 57.6 (11-C), 115.1 (d, J=23.0 Hz, 27-CH), 124.6 (4-C), 125.1 (d, J=17.3 Hz, 25-C), 127.1 (d, J=7.7 Hz, 28-CH), 131.4 (d, J=4.8 Hz, 24-CH), 133.2 (d, J=2.8 Hz, 23-C), 146.9 (5-OC=), 151.0 (2-C), 154.0 (15-SC=), 159.5 (6-C=O), 160.9 (d, J=245 Hz, 26-FC), 162.1 (17-NC=O), 163.3 (18-NC=O), 168.0 (21-NC=O). HPLC: 2.33 min (AP 99% at 254 nm, 5 min-run). HPLC: 11.7 min (AP 99% at 254 nm, 25 min-run). LCMS: m/z 614 (M+H).

Example 19

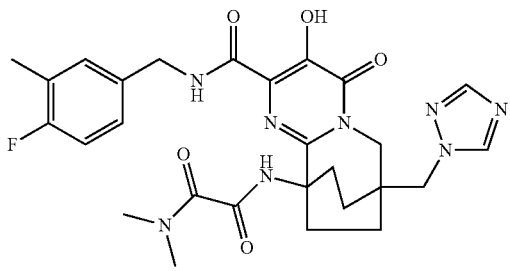 [SMILES: Cc1cc(CNC(=O)c2nc3n(c(=O)c2O)CC2(Cn4cncn4)CCC3(NC(=O)C(=O)N(C)C)CC2)ccc1F]

N'-[2-[[[(4-Fluoro-3-methylphenyl)methyl]amino]carbonyl]-6,7,8,9-tetrahydro-3-hydroxy-4-oxo-7-(1H-1,2,4-triazol-1-ylmethyl)-7,10-ethanopyrimido[1,2-a]azepin-10(4H)-yl]-N,N-dimethyl-ethanediamide $^1$H NMR (500 MHz, CDCl$_3$) δ ppm 1.66 (2H, m, 9a, 13a-CH$_2$), 1.84-1.95 (2H, m, 9b, 13b-CH$_2$), 2.07-2.19 (2H, m, 10a, 12a-CH$_2$), 2.28 (3H, d, J=1.5 Hz, 29-CH$_3$), 2.53 (2H, m, 10b, 12b-CH$_2$), 2.93, 3.28 (2×3H, 2s, 19,20-NCH$_3$), 4.15 (2H, s, 7-NCH$_2$), 4.17 (2H, s, 14-NCH$_2$), 4.53 (2H, d, J=6.4 Hz, 22-NCH$_2$), 6.97 (1H, t, J=8.9 Hz, 27-CH), 7.15-7.24 (2H, m, 24,28-CH), 7.99 (1H, s, 17-CONH), 8.07 (1H, s, 16-CH), 8.15 (1H, s, 15-CH), 8.59 (1H, t, J=6.3 Hz, 21-CONH), 12.12 (1H, s, 5-OH). $^{13}$C NMR (126 MHz, CDCl$_3$) δ ppm 14.6 (d, J=3.8 Hz, 29-CH$_3$), 27.1 (9,13-CH$_2$), 29.3 (10,12-CH$_2$), 36.5 (8-C), 36.6, 38.2 (2s, 19,20-NCH$_3$), 42.6 (22-NCH$_2$), 54.7 (7-NCH$_2$), 57.5 (11-C), 57.9 (14-NCH$_2$), 115.1 (d, J=23.0 Hz, 27-CH), 124.5 (4-C), 125.1 (d, J=17.3 Hz, 25-C), 127.1 (d, J=8.6 Hz, 28-CH), 131.4 (d, J=4.8 Hz, 24-CH), 133.2 (d, J=3.8 Hz, 23-C), 144.4 (15-CH), 146.9 (5-OC=), 150.9 (16-CH), 152.4 (2-C), 159.4 (6-C=O), 160.9 (d, J=245 Hz, 26-FC), 162.0 (17-NC=O), 163.2 (18-NC=O), 167.9 (21-NC=O). $^{19}$F NMR (470 MHz, CDCl$_3$) δ ppm −119.8 (Ar—F). HPLC: 1.97 min (AP 95% at 254 nm, 5 min-run). HPLC: 9.37 min (AP 96% at 254 nm, 25 min-run). LCMS: m/z 567 (M+H).

Example 20

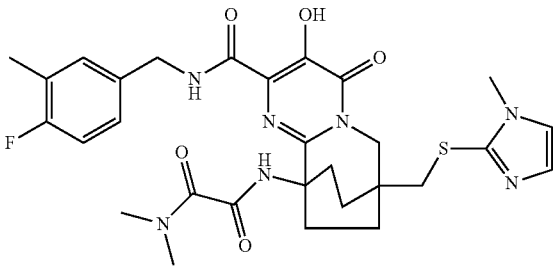 [SMILES: Cc1cc(CNC(=O)c2nc3n(c(=O)c2O)CC2(CSc4nccn4C)CCC3(NC(=O)C(=O)N(C)C)CC2)ccc1F]

N'-[2-[[[(4-Fluoro-3-methylphenyl)methyl]amino]carbonyl]-6,7,8,9-tetrahydro-3-hydroxy-7-[[(1-methyl-1H-imidazol-2-yl)thio]methyl]-4-oxo-7,10-ethanopyrimido[1,2-a]azepin-10(4H)-yl]-N,N-dimethyl-ethanediamide $^1$H NMR (500 MHz, CDCl$_3$) δ ppm 1.70 (2H, m, 9a, 13a-CH$_2$), 1.87-1.96 (2H, m, 9b, 13b-CH$_2$), 2.12 (2H, m, 10a, 12a-CH$_2$), 2.28 (3H, s, 31-CH$_3$), 2.55 (2H, m, 10b, 12b-CH$_2$), 2.93, 3.29 (2×3H, 2s, 19,20-NCH$_3$), 3.33 (2H, s, 14-SCH$_2$), 3.64 (3H, s, 18-NCH$_3$), 4.11 (2H, s, 7-NCH$_2$), 4.53 (2H, d, J=6.1 Hz, 24-NCH$_2$), 6.95 (1H, d, J=0.9 Hz, 16-CH), 6.97 (1H, t, J=8.9 Hz, 29-CH), 7.19 (1H, d, J=1.2 Hz, 17-CH), 7.16-7.25 (2H, m, 26,30-CH), 8.02 (1H, s, 19-CONH), 8.61 (1H, t, J=6.1 Hz, 23-CONH), 12.07 (1H, s, 5-OH). $^{13}$C NMR (126 MHz, CDCl$_3$) δ ppm 14.7 (d, J=2.9 Hz, 31-CH$_3$), 28.6 (9,13-CH$_2$), 29.8 (10,12-CH$_2$), 33.5 (18-NCH$_3$), 36.3 (8-C), 36.5, 38.2 (2s, 21,22-NCH$_3$), 42.6 (24-NCH$_2$), 45.8 (14-SCH$_2$), 55.9 (7-NCH$_2$), 57.7 (11-C), 115.1 (d, J=23.0 Hz, 29-CH), 122.5 (16-CH), 124.5 (4-C), 125.1 (d, J=17.3 Hz, 27-C), 127.1 (d, J=7.7 Hz, 30-CH), 129.3 (17-CH), 131.4 (d, J=4.8 Hz, 26-CH), 133.3 (d, J=2.9 Hz, 25-C), 141.4 (15-SC=), 146.8 (5-OC=), 151.3 (2-C), 159.7 (6-C=O), 160.8 (d, J=244 Hz, 28-FC), 162.0 (19-NC=O), 163.3 (20-NC=O), 168.0 (23-NC=O). $^{19}$F NMR (470 MHz, CDCl$_3$) δ ppm −120.0 (Ar—F); HPLC: 1.77 min (AP 97% at 254 nm, 5 min-run). HPLC: 8.23 min (AP 99% at 254 nm, 25 min-run). LCMS: m/z 612 (M+H). Anal. Calcd for C$_{24}$H$_{28}$FN$_5$O$_6$: C56.94, H5.60, N16.02. found: C56.69, H5.48, N15.88.

Example 21

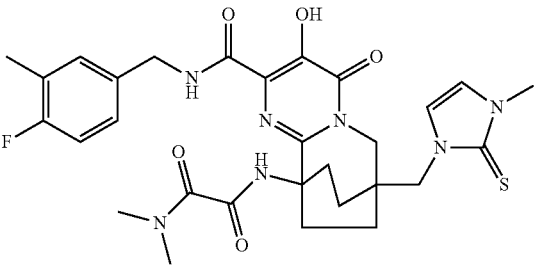

N'-[7-[(2,3-Dihydro-3-methyl-2-thioxo-1H-imidazol-1-yl)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (500 MHz, CDCl$_3$) δ ppm 1.59-1.73 (2H, m, 9a, 13a-CH$_2$), 2.02-2.20 (4H, m, 9b, 13b, 10a, 12a-CH$_2$), 2.28 (3H, s, 31-CH$_3$), 2.44-2.60 (2H, m, 10b, 12b-CH$_2$), 2.93, 3.28 (2×3H, 2s, 19,20-NCH$_3$), 3.65 (3H, s, 18-NCH$_3$), 4.18 (2H, s, 14-NCH$_2$), 4.18 (2H, s, 7-NCH$_2$), 4.53 (2H, d, J=6.1 Hz, 24-NCH$_2$), 6.76 (1H, d, J=2.4 Hz, 17-CH), 6.87 (1H, d, J=2.4 Hz, 16-CH), 6.97 (1H, t, J=8.9 Hz, 29-CH), 7.15-7.24 (2H, m, 26,30-CH), 7.90 (1H, s, 19-CONH), 8.64 (1H, t, J=6.1 Hz, 23-CONH), 12.11 (1H, br.s, 5-OH). $^{13}$C NMR (126 MHz, CDCl$_3$) δ ppm 14.7 (d, s, 31-CH$_3$), 27.4 (9,13-CH$_2$), 29.6 (10,12-CH$_2$), 35.7 (18-NCH$_3$), 36.4, 38.1 (2s, 21,22-NCH$_3$), 38.2 (8-C), 42.5 (24-NCH$_2$), 55.4 (14-NCH$_2$ or 7-NCH$_2$), 55.9 (7-NCH$_2$ or 14-NCH$_2$), 57.7 (11-C), 115.1 (d, J=23.0 Hz, 29-CH), 117.7 (16-CH), 118.4 (17-CH), 124.6 (4-C), 125.1 (d, J=17.3 Hz, 27-C), 127.1 (d, J=7.7 Hz, 30-CH), 131.4 (d, J=4.8 Hz, 26-CH), 133.2 (d, J=3.8 Hz, 25-C), 146.8 (5-OC=), 151.1 (2-C), 159.6 (6-C=O), 160.9 (d, J=250 Hz, 28-FC), 162.1 (19-NC=O), 163.4 (20-NC=O), 165.1 (15-NNC=S), 168.0 (23-NC=O). $^{19}$F NMR (470 MHz, CDCl$_3$) δ ppm −119.9 (Ar—F). HPLC: 2.19 min (AP 87% at 254 nm, 5 min-run). HPLC: 10.8 min (AP 89% at 254 nm, 25 min-run). LCMS: m/z 612 (M+H).

Example 22

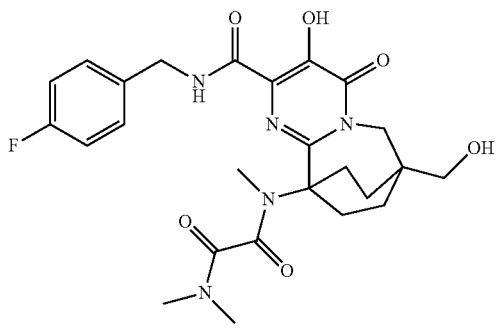 [SMILES: CN(C)C(=O)C(=O)N(C)C12CCC(CO)(CC1)Cn1c2nc(C(=O)NCc2ccc(F)cc2)c(O)c1=O]

N-[2-[[[(4-Fluorophenyl)methyl]amino]carbonyl]-6,7,8,9-tetrahydro-3-hydroxy-7-(hydroxymethyl)-4-oxo-7,10-ethanopyrimido[1,2-a]azepin-10(4H)-yl]-N,N',N'-trimethyl-ethanediamide A mixture of ethanediamide, N$^1$-[2-[[[(4-fluorophenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N$^1$,N$^2$,N$^2$-trimethyl-, Intermediate 22 (0.10 g, 0.149 mmol), potassium acetate (0.044 g, 0.448 mmol), potassium carbonate (0.021 g, 0.149 mmol), n-hexanol (0.150 mL, 1.195 mmol) and dimethyl acetamide (1.5 mL) was placed into a hot oil bath at 140° C. and stirred for 4.5 h. The mixture was cooled to room temperature, filtered and purified by preparative HPLC and triturated with hot ethanol to give the title compound (28.7 mg, 0.055 mmol, 36.9% yield) as a white solid (99% pure). $^1$H NMR (500 MHz, CDCl$_3$) δ: 9.64 (1H, t, J=6.10 Hz), 7.34-7.46 (2H, m), 6.95-7.05 (2H, m), 4.74 (1H, d, J=15.26 Hz), 4.59-4.70 (1H, m), 4.43-4.56 (1H, m), 3.34-3.61 (4H, m), 3.05 (3H, s), 3.02 (3H, s), 3.00 (3H, s), 2.07-2.20 (4H, m), 1.80 (1H, dd, J=13.43, 6.10 Hz), 1.70 (2H, dd, J=9.31, 3.81 Hz), 1.35-1.53 (1H, m). LCMS (M+H) calcd for C$_{25}$H$_{31}$FN$_5$O$_6$S: 516.22. found: 516.3.

Example 23

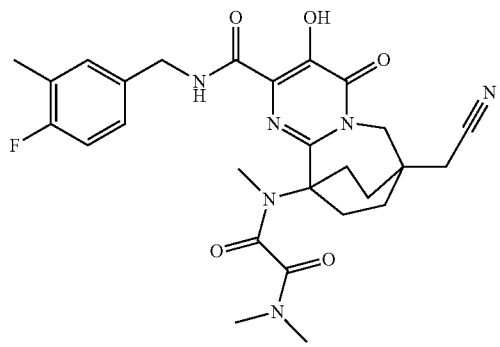 [SMILES: Cc1cc(CNC(=O)c2nc3n(c(=O)c2O)CC2(CC#N)CCC3(N(C)C(=O)C(=O)N(C)C)CC2)ccc1F]

N-[7-(Cyanomethyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-ethanediamide A mixture of N-[2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N,N',N'-trimethyl-ethanediamide, Intermediate 28, (50 mg, 0.073 mmol) and KCN (47.6 mg, 0.731 mmol) in DMA (1.5 mL) was heated at 160° C. in a sealed tube for 3 h. The mixture was then cooled and the product purified by preparative HPLC to afford the title compound (8 mg, 0.014 mmol, 19.30% yield) as off-white solid. $^1$HNMR (500 MHz, CDCl$_3$) δ: 11.97 (1H, br. s.), 9.61 (1H, br. s.), 7.18-7.26 (2H, m), 6.94 (1H, t, J=9.00 Hz), 4.56-4.68 (2H, m), 4.41-4.50 (1H, m), 3.61 (1H, d, J=15.87 Hz), 3.41-3.52 (1H, m), 3.05 (3H, s), 3.03 (3H, s), 3.01 (3H, s), 2.50 (2H, d, J=2.75 Hz), 2.27 (3H, d, J=1.83 Hz), 2.15-2.21 (3H, m), 1.96-2.05 (2H, m), 1.72-1.81 (1H, m), 1.57-1.69 (1H, m). LCMS (M+H)=539.4.

Example 24

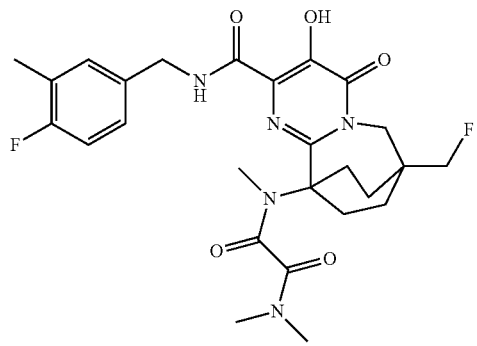 [SMILES: Cc1cc(CNC(=O)c2nc3n(c(=O)c2O)CC2(CF)CCC3(N(C)C(=O)C(=O)N(C)C)CC2)ccc1F]

N-[7-(Fluoromethyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-ethanediamide A mixture of N-[2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N,N',N'-trimethyl-ethanediamide, Intermediate 28, (50 mg, 0.073 mmol) was treated with TBAF, 1M in THF (1.5 mL, 1.500 mmol) and 4 Å molecular sieves. The mixture was then stirred for 30 min at room temp and heated at 80° C. for 18 h. After cooling the reaction mixture was concentrated and purified by preparative HPLC to afford the title compound (14 mg, 0.025 mmol, 34.2% yield) as an off-white solid. $^1$H NMR (500 MHz, CDCl$_3$) δ: 12.18 (1H, br. s.), 9.60 (1H, br. s.), 7.17-7.26 (2H, m), 6.94 (1H, t, J=8.85 Hz), 4.75 (1H, d, J=14.95 Hz), 4.56-4.65 (1H, m), 4.39-4.50 (1H, m), 4.28 (1H, d, J=2.75 Hz), 4.19 (1H, d, J=2.75 Hz), 3.42-3.57 (2H, m), 3.05 (3H, s), 3.03 (3H, s), 3.01 (3H, s), 2.27 (3H, s), 2.07-2.18 (3H, m), 1.80-1.88 (1H, m), 1.70-1.78 (2H, m), 1.42-1.52 (1H, m). LCMS (M+H)=532.4.

and trimethyloxonium tetrafluoroborate were added and the mixture was stirred at room temp for 5 h. The reaction was quenched by addition of 1N KHSO$_4$ (30 mL) and stirred for 10 min and extracted with CH$_2$Cl$_2$ (25 mL×2). The combined extracts were dried, filtered and concentrated. The crude material was then dissolved in CH$_2$Cl$_2$ (1 mL) and treated with TFA (1 mL, 12.98 mmol) at room temp for 16 h. The mixture was concentrated in vacuuo and purified by preparative HPLC to afford the title compound (3.5 mg, 6.12 mmol, 3.79% yield) as a thick film. $^1$H NMR (500 MHz, CDCl$_3$) δ: 12.15 (1H, br. s.), 9.59 (1H, br. s.), 7.24-7.27 (1H, m), 7.17-7.23 (1H, m), 6.90-6.97 (1H, m), 4.71 (1H, d, J=15.6 Hz), 4.58-4.65 (1H, m), 4.43-4.48 (1H, m), 3.51 (1H, d, J=15.6 Hz), 3.39-3.45 (1H, m), 3.20 (2H, d, J=5.8 Hz), 3.05 (3H, s), 3.02 (3H, s), 3.00 (3H, s), 2.27 (3H, d, J=1.8 Hz), 2.08-2.12 (3H, m), 1.76-1.83 (1H, m), 1.66-1.74 (2H, m), 1.38-1.49 (1H, m). LCMS (M+H)=544.5.

Example 25

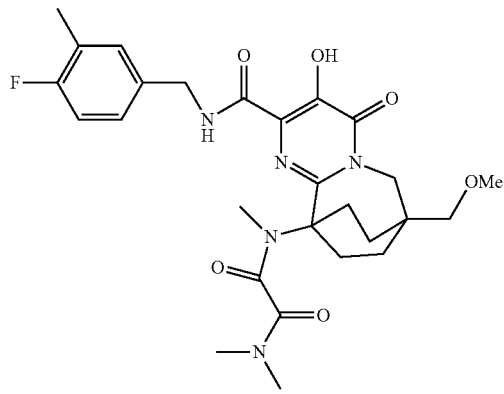 [SMILES: COCC12CCC(N(C)C(=O)C(=O)N(C)C)(CC1)c1nc(C(=O)NCc3ccc(F)c(C)c3)c(O)c(=O)n1C2]

N-[2-[[[(4-Fluoro-3-methylphenyl)methyl]amino]carbonyl]-6,7,8,9-tetrahydro-3-hydroxy-7-(methoxymethyl)-4-oxo-7,10-ethanopyrimido[1,2-a]azepin-10(4H)-yl]-N,N',N'-trimethyl-ethanediamide To a solution of N-[2-[[[(4-fluoro-3-methylphenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N,N',N'-trimethyl-ethanediamide, Intermediate 28, (100 mg, 0.161 mmol) in CH$_2$Cl$_2$ (10 mL) was added 2,6-di-tert-butyl-4-methylpyridine (166 mg, 0.807 mmol) and trimethyloxonium tetrafluoroborate (48.5 mg, 0.807 mmol) and the mixture was stirred at room temp for 16 h. Another 5 equiv each of methylpyridine

Example 26

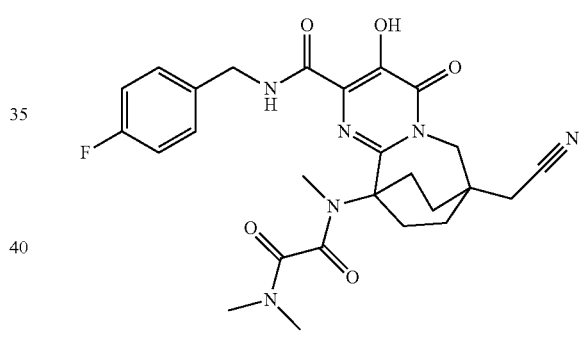

N-[7-(Cyanomethyl)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-ethanediamide A mixture of ethanediamide, N$^1$-[2-[[[(4-fluorophenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-N$^1$,N$^2$,N$^2$-trimethyl-, Intermediate 22, (0.10 g, 0.149 mmol) and KCN (0.097 g, 1.493 mmol) in dimethylacetamide (4 mL) was stirred at 140° C. for 8 h. After cooling to room temperature, the reaction mixture was filtered and purified by preparative HPLC to give the title compound (5.9 mg, 0.011 mmol, 7.48% yield) as an off-white solid (99.3% pure). $^1$H NMR (500 MHz, CDCl$_3$) δ: 9.65 (1H, t, J=6.10 Hz), 7.40 (2H, dd, J=8.55, 5.49 Hz), 7.00 (2H, t, J=8.70 Hz), 4.57-4.70 (2H, m), 4.45-4.55 (1H, m), 3.60 (1H, d, J=15.26 Hz), 3.46 (1H, ddd, J=14.65, 10.53, 10.22 Hz), 3.05 (3H, s), 3.02 (3H, s), 3.00 (3H, s), 2.50 (2H, d, J=2.44 Hz), 2.07-2.24 (4H, m), 1.87-2.07 (2H, m), 1.69-

1.83 (1H, m), 1.54-1.69 (1H, m). LCMS (M+H) calcd for $C_{26}H_{30}FN_6O_5$: 525.22. found: 525.3.

Example 27

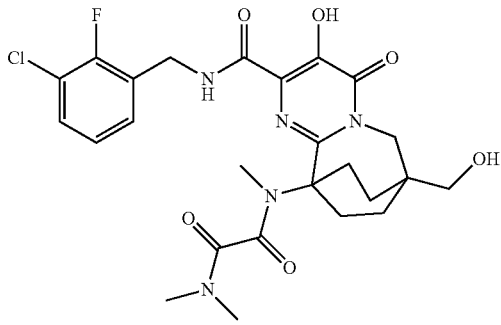 [SMILES: CN(C)C(=O)C(=O)N(C)C12CCC(CO)(CC1)Cn1c2nc(C(=O)NCc2cccc(Cl)c2F)c(O)c1=O]

N-[2-[[[(3-Chloro-2-fluorophenyl)methyl]amino]carbonyl]-6,7,8,9-tetrahydro-3-hydroxy-7-(hydroxymethyl)-4-oxo-7,10-ethanopyrimido[1,2-a]azepin-10(4H)-yl]-N,N',N'-trimethyl-ethanediamide White solid. $^1$H NMR (500 MHz, CDCl$_3$) δ: 12.02 (1H, br. s.), 9.67 (1H, t, J=5.95 Hz), 7.28-7.40 (2H, m), 7.03 (1H, t, J=7.78 Hz), 4.54-4.86 (3H, m), 3.23-3.60 (4H, m), 3.02 (6H, d, J=1.53 Hz), 2.95 (3H, s), 2.03-2.20 (3H, m), 1.57-1.84 (3H, m), 1.37-1.52 (1H, m), 1.27-1.36 (1H, m). LCMS (M+H) calcd for $C_{25}H_{30}FClN_5O_6$: 550.18. found: 550.4.

Example 28

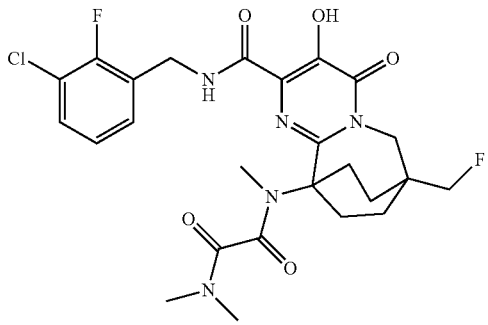 [SMILES: CN(C)C(=O)C(=O)N(C)C12CCC(CF)(CC1)Cn1c2nc(C(=O)NCc2cccc(Cl)c2F)c(O)c1=O]

N-[2-[[[(3-chloro-2-flaorophenyl)methyl]amino]carbonyl]-7-(fluoromethyl)-6,7,8,9-tetrahydro-3-hydroxy-4-oxo-7,10-ethanopyrimido[1,2-a]azepin-10(4H)-yl]-N,N',N'-trimethyl-ethanediamide White solid. $^1$H NMR (500 MHz, CHLOROFORM-d) δ: 11.69 (1H, br. s.), 9.66 (1H, t, J=5.95 Hz), 7.28-7.36 (2H, m), 7.04 (1H, t, J=7.93 Hz), 4.59-4.87 (3H, m), 4.13-4.35 (2H, m), 3.36-3.62 (2H, m), 3.04 (6H, d, J=4.27 Hz), 2.97 (3H, s), 2.14 (3H, d, J=8.55 Hz), 1.84 (1H, dd, J=13.28, 8.39 Hz), 1.74 (2H, d, J=8.55 Hz), 1.42-1.58 (1H, m). LCMS (M+H) calcd for $C_{25}H_{29}F_2ClN_5O_5$: 552.18. found: 552.4.

Example 29

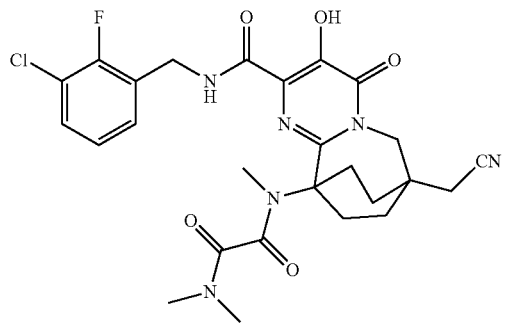 [SMILES: CN(C)C(=O)C(=O)N(C)C12CCC(CC#N)(CC1)Cn1c2nc(C(=O)NCc2cccc(Cl)c2F)c(O)c1=O]

N-[2-[[[(3-chloro-2-fluorophenyl)methyl]amino]carbonyl]-7-(cyanomethyl)-6,7,8,9-tetrahydro-3-hydroxy-4-oxo-7,10-ethanopyrimido[1,2-a]azepin-10(4H)-yl]-N,N',N'-trimethyl-ethanediamide White solid (97% pure). $^1$H NMR (500 MHz, CHLOROFORM-d) δ: 11.69 (1H, br. s.), 9.66 (1H, t, J=5.95 Hz), 7.28-7.36 (2H, m), 7.04 (1H, t, J=7.93 Hz), 4.59-4.87 (3H, m), 4.13-4.35 (2H, m), 3.36-3.62 (2H, m), 3.04 (6H, d, J=4.27 Hz), 2.97 (3H, s), 2.14 (3H, d, J=8.55 Hz), 1.84 (1 H, dd, J=13.28, 8.39 Hz), 1.74 (2H, d, J=8.55 Hz), 1.42-1.58 (1H, m). LCMS (M+H) calcd for $C_{26}H_{29}FClN_6O_5$: 559.18. found: 559.4.

Example 30

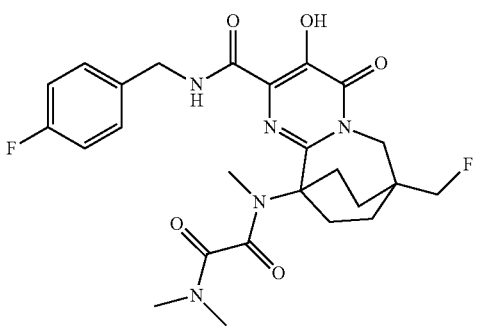 [SMILES: CN(C)C(=O)C(=O)N(C)C12CCC(CF)(CC1)Cn1c2nc(C(=O)NCc2ccc(F)cc2)c(O)c1=O]

N-[7-(fluoromethyl)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-ethanediamide A mixture of ethanediamide, $N^1$-[2-[[[(4-fluorophenyl)methyl]amino]carbonyl]-6,7,8,9-tetrahydro-3-hydroxy-7-[[[(4-methylphenyl)sulfonyl]oxy]methyl]-4-oxo-7,10-ethanopyrimido[1,2-a]azepin-10(4H)-yl]-$N^1$,$N^2$,$N^2$-trimethyl-, Intermediate 22, (0.10 g, 0.149 mmol) and TBAF/THF (5.97 ml, 5.97 mmol) with a small spatula full of molecular sieves was stirred at 80° C. for 32 h. After cooling to room temperature, the reaction was concentrated and taken up in DMF then filtered and purified by preparative HPLC to give the title compound (8.4 mg, 0.016 mmol, 10.44% yield) as a white solid (96% pure). $^1$H NMR (500 MHz, CDCl$_3$) δ: 12.18 (1H, s), 9.64 (1H, t, J=5.80 Hz), 7.40 (2H, dd, J=8.39, 5.65 Hz), 7.00 (2H, t, J=8.70 Hz), 4.75 (1H, d, J=15.26 Hz), 4.59-4.71 (1H, m), 4.44-4.55 (1H, m), 4.28 (1H, d, J=3.05 Hz), 4.18 (1H, d, J=2.75 Hz), 3.05 (3H, s), 3.03 (3H, s), 3.00 (3H, s), 2.04-2.19 (3H, m), 1.84 (1H, dd, J=14.19, 8.09 Hz), 1.73 (2H, d, J=8.55 Hz), 1.40-1.53 (2H, m). LCMS (M+H) calcd for C$_{14}$H$_{20}$FN$_3$O$_4$S: 518.22. found: 518.3.

Example 31

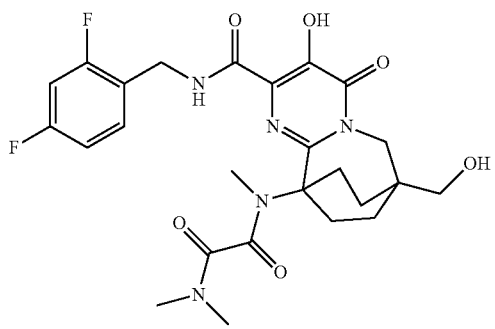 [SMILES: CN(C)C(=O)C(=O)N(C)C12CCC(CO)(CC1)Cn1c2nc(C(=O)NCc2ccc(F)cc2F)c(O)c1=O]

N-[2-[[[(2,4-difluorophenyl)methyl]amino]carbonyl]-6,7,8,9-tetrahydro-3-hydroxy-7-(hydroxymethyl)-4-oxo-7,10-ethanopyrimido[1,2-a]azepin-10(4H)-yl]-N,N',N'-trimethyl-ethanediamide $^1$H NMR (500 MHz, CDCl$_3$) δ: 11.93 (1H, br. s.), 9.60 (1H, t, J=5.8 Hz), 7.38-7.44 (1H, m), 6.77-6.86 (2H, m), 4.56-4.77 (3H, m), 3.47-3.57 (3H, m), 3.04 (3H, s), 3.03 (3H, s), 2.97 (3H, s), 1.95-2.04 (2H, m), 1.79-1.83 (1H, m), 1.68-1.74 (2H, m), 1.41-1.51 (1H, m), 1.25-1.34 (1H, m). LCMS (M+H)= 534.4.

Example 32

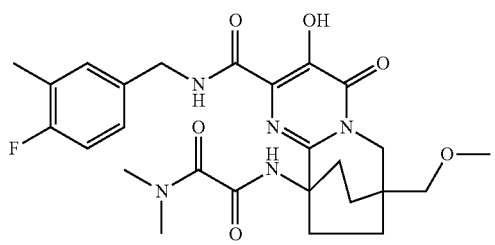 [SMILES: COCC12CCC(NC(=O)C(=O)N(C)C)(CC1)c1nc(C(=O)NCc3ccc(F)c(C)c3)c(O)c(=O)n1C2]

N'-[2-[[[(4-fluoro-3-methylphenyl)methyl]amino]carbonyl]-6,7,8,9-tetrahydro-3-hydroxy-7-(methoxymethyl)-4-oxo-7,10-ethanopyrimido[1,2-a]azepin-10(4H)-yl]-N,N-dimethyl-ethanediamide $^1$H NMR (500 MHz, CDCl$_3$) δ ppm 1.61-1.69 (2H, m, 9a, 13a-CH$_2$), 1.72-1.82 (2H, m, 9b, 13b-CH$_2$), 2.11 (2H, m, 10a, 12a-CH$_2$), 2.28 (3H, d, J=1.8 Hz, 28-CH$_3$), 2.53 (2H, m, 10b, 12b-CH$_2$), 2.93 (3H, s, 18- or 19-NCH$_3$), 3.20 (2H, s, 14-OCH$_2$), 3.30 (3H, s, 18- or 19-NCH$_3$), 3.37 (3H, s, 15-OCH$_3$), 4.08 (2H, s, 7-NCH$_2$), 4.54 (2H, d, J=6.4 Hz, 21-NCH$_2$), 6.97 (1H, t, J=8.9 Hz, 26-CH), 7.17-7.24 (2H, m, 23,27-CH), 8.08 (1H, s, 16-CONH), 8.62 (1H, t, J=6.1 Hz, 20-CONH), 12.05 (1H, br.s, 5-OH). $^{13}$C NMR (126 MHz, CDCl$_3$) δ ppm 14.7 (d, J=2.9 Hz, 28-CH$_3$), 26.5 (9,13-CH$_2$), 29.6 (10,12-CH$_2$), 36.3 (8-C), 36.5, 38.2 (18, 19-NCH$_3$), 42.5 (21-NCH$_2$), 55.1 (7-NCH$_2$), 58.1 (11-C), 59.5 (15-OCH$_3$), 80.4 (14-OCH$_2$), 115.1 (d, J=23.0 Hz, 26-CH), 124.4 (4-C), 125.0 (d, J=17.3 Hz, 25-C), 127.1 (d, J=7.7 Hz, 27-CH), 131.4 (d, J=4.8 Hz, 23-CH), 133.3 (d, J=2.9 Hz, 22-C), 146.8 (5-OC=), 151.6 (2-C), 159.7 (6-C=O), 160.8 (d, J=245 Hz, 25-FC), 161.9 (17-NC=O), 163.4 (16-NC=O), 168.1 (20-NC=O). $^{19}$F NMR (470 MHz, CDCl$_3$) δ ppm −120.0 (Ar—F). HPLC: 2.45 min (AP 98% at 254 nm, 5 min-run) HPLC: 12.2 min (AP 98% at 254 nm, 25 min-run). LCMS: m/z 530 (M+H). Anal. Calcd for C$_{26}$H$_{32}$FN$_5$O$_6$.0.1CF$_3$CO$_2$H: C58.17, H5.98, N12.95. found: C57.94, H5.71, N12.88.

Example 33

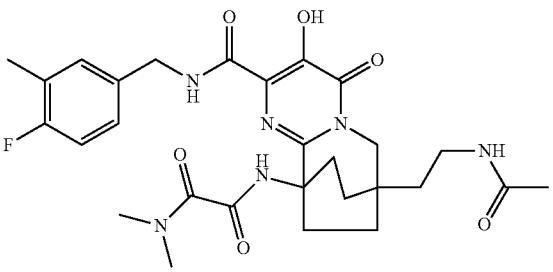 [SMILES: CC(=O)NCCC12CCC(NC(=O)C(=O)N(C)C)(CC1)c1nc(C(=O)NCc3ccc(F)c(C)c3)c(O)c(=O)n1C2]

N'-[7-[2-(Acetylamino)ethyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (500 MHz, CDCl$_3$) δ ppm 1.56-1.71 (4H, m, 9a, 13a, 14-CH$_2$), 1.78-1.91 (2H, m, 9b, 13b-CH$_2$), 2.01 (3H, s, 17-CH$_3$), 2.13 (2H, m, 10a, 12a-CH$_2$), 2.28 (3H, s, 30-CH$_3$), 2.46-2.61 (2H, m, 10b, 12b-CH$_2$), 2.93, 3.28 (2×3H, 2s, 20,21-NCH$_3$), 3.31-3.42 (2H, m, 15-NCH$_2$), 4.01 (2H, s, 7-NCH$_2$), 4.53 (2H, d, J=6.1 Hz, 23-NCH$_2$), 5.71 (1H, br.s, 16-CONH), 6.97 (1H, t, J=8.7 Hz, 28-CH), 7.15-7.26 (2H, m, 25,29-CH), 7.92 (1H, s, 18-CONH), 8.67 (1H, t, J=6.1 Hz, 22-CONH), 12.10 (1H, s, 5-OH). $^{13}$C NMR (101 MHz, CDCl$_3$) δ ppm 14.7 (d, J=2.9 Hz, 30-CH$_3$), 23.4 (17-CH$_3$), 28.7 (9,13-CH$_2$), 30.0 (10,12-CH$_2$), 34.2 (8-C), 35.0 (14-CH$_2$), 36.3, 38.2 (20,21-NCH$_3$), 41.4 (15-NCH$_2$), 42.5 (23-NCH$_2$), 56.5 (7-NCH$_2$), 57.8 (11-C), 115.1 (d, J=23.0 Hz, 28-CH), 124.6 (4-C), 125.0 (d, J=17.3 Hz, 26-C), 127.1 (d, J=8.6 Hz, 29-CH), 131.4 (d, J=5.8 Hz, 25-CH), 133.3 (d, J=3.1 Hz, 24-C), 146.8 (5-OC=), 151.4 (2-C), 159.7 (6-C=O), 160.9 (d, J=244 Hz, 27-FC), 162.2 (18-NC=O), 163.5 (19-NC=O), 168.1 (22-NC=O), 170.3 (16-NC=O).

HPLC: 2.02 min (AP 93% at 254 nm, min-run). HPLC: 6.66 min (AP 93% at 254 nm, 25 min-run). LCMS: m/z 571 (M+H).

Example 34

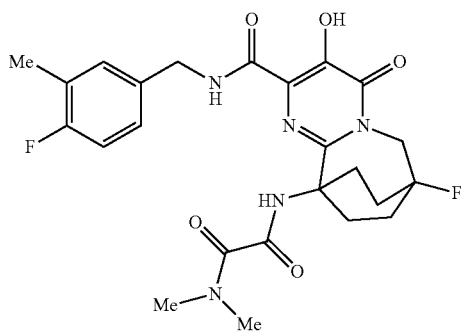 [SMILES: Cc1cc(CNC(=O)c2nc3n(c(=O)c2O)CC2(F)CCC3(NC(=O)C(=O)N(C)C)CC2)ccc1F]

N'-[7-Fluoro-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (400 MHz, CHLOROFORM-d) δ ppm 12.19 (1H, br. s.), 8.56 (1H, br. s.), 8.11 (1H, s), 7.19 (2H, t, J=7.5 Hz), 6.97 (1H, t, J=8.8 Hz), 4.52 (2H, d, J=6.0 Hz), 4.31 (2H, d, J=8.8 Hz), 3.29 (3H, s), 2.93 (3H, s), 2.64-2.75 (2H, m), 2.27 (3H, s), 1.98-2.26 (6H, m). $^{19}$F NMR (376 MHz, CHLOROFORM-d) δ ppm −119.40 (1F, s), −136.06 (1F, br. s.). LCMS ($^+$ESI, M+H$^+$) m/z 504.5.

Example 35

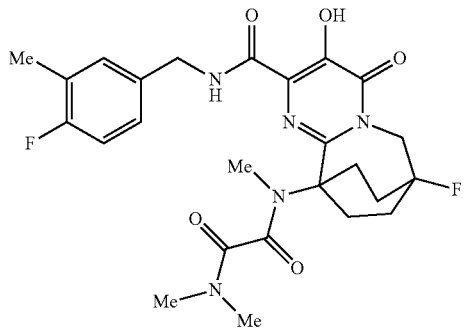 [SMILES: Cc1cc(CNC(=O)c2nc3n(c(=O)c2O)CC2(F)CCC3(N(C)C(=O)C(=O)N(C)C)CC2)ccc1F]

N-[7-Fluoro-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-ethanediamide $^1$H NMR (400 MHz, CHLOROFORM-d) δ ppm 12.30 (1H, s), 9.49-9.65 (1H, m), 7.15-7.26 (2H, m), 6.89-6.96 (1H, m), 4.94 (1H, br. s.), 4.59 (1H, br. s.), 4.40-4.48 (1H, m), 3.84 (1H, d, J=13.3 Hz), 3.35-3.47 (1H, m), 3.03 (3H, s), 3.00 (3H, s), 2.99 (3H, s), 2.25 (3H, d, J=1.8 Hz), 1.89-2.30 (7H, m). $^{19}$F NMR (376 MHz, CHLOROFORM-d) δ ppm −120.24 (1F, s), −135.07 (1F, s). LCMS ($^+$ESI, M+H$^+$) m/z 518.1.

Example 36

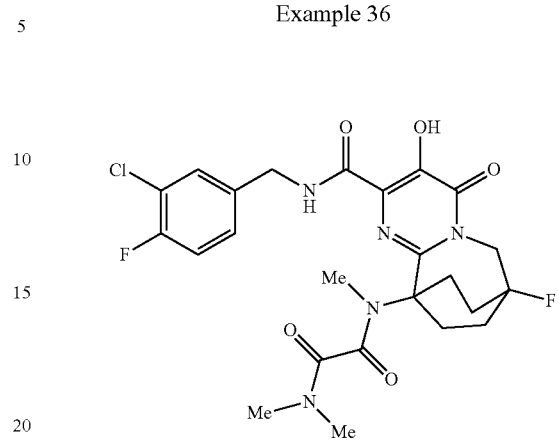

N-[2-[[[(3-Chloro-4-fluorophenyl)methyl]amino]carbonyl]-7-fluoro-6,7,8,9-tetrahydro-3-hydroxy-4-oxo-7,10-ethanopyrimido[1,2-a]azepin-10(4H)-yl]-N,N',N'-trimethyl-ethanediamide $^1$H NMR (400 MHz, CHLOROFORM-d) δ ppm 7.49 (1H, d, J=6.5 Hz), 7.31 (1H, br. s.), 7.16 (1H, t, J=8.8 Hz), 4.53 (2H, s), 3.11 (3H, br. s.), 3.07 (3H, s), 2.97 (3H, s), 1.83-2.43 (8H, m). $^{19}$F NMR (376 MHz, CHLOROFORM-d) δ ppm −120.76 (1F, br. s.), −135.42 (1F, br. s.). LCMS ($^+$ESI, M+H$^+$) m/z 538.0.

Example 37

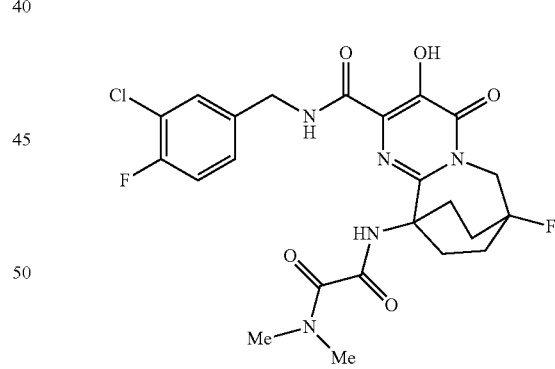

N'-[2-[[[(3-Chloro-4-fluorophenyl)methyl]amino]carbonyl]-7-fluoro-6,7,8,9-tetrahydro-3-hydroxy-4-oxo-7,10-ethanopyrimido[1,2-a]azepin-10(4H)-yl]-N,N-dimethyl-ethanediamide $^1$H NMR (400 MHz, CHLOROFORM-d) δ ppm 12.02 (1H, s), 8.69 (1H, br. s.), 7.99 (1H, br. s.), 7.46 (1H, d, J=6.3 Hz), 7.29-7.36 (1H, m), 7.11 (1H, t, J=8.3 Hz), 4.54 (2H, d, J=5.8 Hz), 4.32 (2H, d, J=9.0 Hz), 3.30 (3H, s), 2.96 (3H, s), 2.68 (2H, br. s.), 2.11-2.33 (4H, m), 2.06 (2H, d, J=11.0 Hz).

¹⁹F NMR (376 MHz, CHLOROFORM-d) δ ppm −117.21 (1F, br. s.), −136.02 (0F, br. s.). LCMS (+ESI, M+H⁺) m/z 524.0.

Example 38

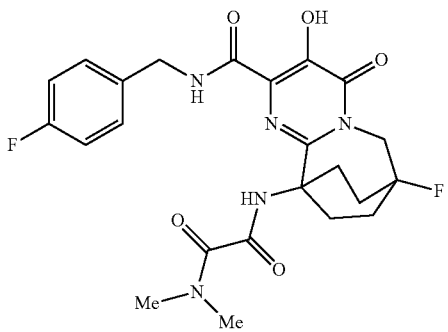

N'-[7-Fluoro-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide ¹H NMR (400 MHz, CHLOROFORM-d) δ ppm 12.14 (1H, s), 8.55 (1H, t, J=4.4 Hz), 8.17 (1H, s), 7.38 (2H, dd, J=8.5, 5.3 Hz), 7.03 (2H, t, J=8.7 Hz), 4.57 (2H, d, J=6.3 Hz), 4.31 (2H, d, J=9.0 Hz), 3.30 (3H, s), 2.94 (3H, s), 2.64-2.77 (2H, m), 2.18-2.31 (2H, m), 1.99-2.17 (4H, m). ¹⁹F NMR (376 MHz, CHLOROFORM-d) δ ppm −115.00 (1F, s), −136.10 (1F, s). LCMS (⁺ESI, M+H⁺) m/z 490.0.

Example 39

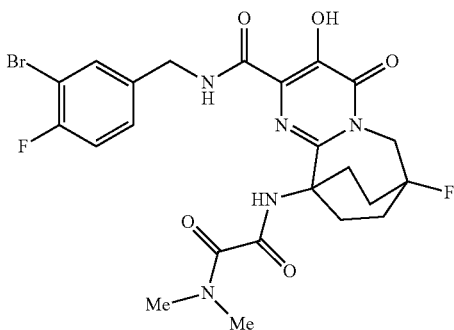 [SMILES: CN(C)C(=O)C(=O)NC12CCC(F)(CC1)Cn1c2nc(C(=O)NCc2ccc(F)c(Cl)c2)c(O)c1=O]

N'-[2-[[[(3-Bromo-4-fluorophenyl)methyl]amino]carbonyl]-7-fluoro-6,7,8,9-tetrahydro-3-hydroxy-4-oxo-7,10-ethanopyrimido[1,2-a]azepin-10(4H)-yl]-N,N-dimethyl-ethanediamide ¹H NMR (400 MHz, CHLOROFORM-d) δ ppm 11.99 (1H, s), 8.69 (1H, br. s.), 7.97 (1H, br. s.), 7.56-7.62 (1H, m), 7.30-7.35 (1H, m), 7.05-7.13 (1H, m), 4.54 (2H, d, J=6.5 Hz), 4.32 (2H, d, J=9.3 Hz), 3.30 (3H, s), 2.96 (3H, s), 2.67 (2H, br. s.), 2.11-2.30 (4H, m), 2.00-2.10 (2H, m). ¹⁹F NMR (376

MHz, CHLOROFORM-d) δ ppm −109.13 (1F, s), −136.01 (1F, s). LCMS (⁺ESI, M+H⁺) m/z 569.9.

Example 40

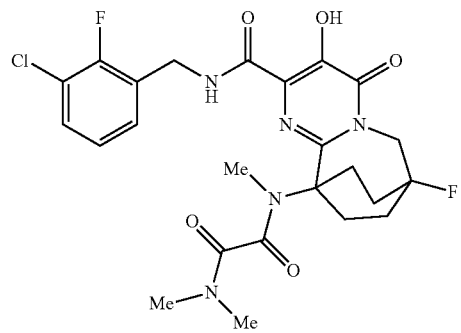 [SMILES: CN(C)C(=O)C(=O)N(C)C12CCC(F)(CC1)Cn1c2nc(C(=O)NCc2cccc(Cl)c2F)c(O)c1=O]

N-[2-[[[(3-Chloro-2-fluorophenyl)methyl]amino]carbonyl]-7-fluoro-6,7,8,9-tetrahydro-3-hydroxy-4-oxo-7,10-ethanopyrimido[1,2-a]azepin-10(4H)-yl]-N,N',N'-trimethyl-ethanediamide ¹H NMR (400 MHz, CHLOROFORM-d) δ ppm 12.16 (1H, s), 9.63 (1H, br. s.), 7.27-7.34 (2H, m), 7.03 (1H, t, J=7.8 Hz), 4.86-5.00 (1H, m), 4.62-4.74 (2H, m), 3.85 (1H, d, J=15.1 Hz), 3.36-3.49 (1H, m), 3.01 (6H, s), 2.96 (3H, s), 1.88-2.35 (7H, m). ¹⁹F NMR (376 MHz, CHLOROFORM-d) δ ppm −120.30 (1F, br. s.), −135.04 (1F, br. s.). LCMS (⁺ESI, M+H⁺) m/z 538.3.

Example 41

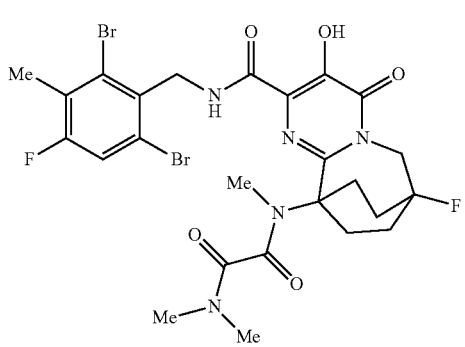 [SMILES: Cc1c(F)cc(Br)c(CNC(=O)c2nc3n(c(=O)c2O)CC2(F)CCC3(N(C)C(=O)C(=O)N(C)C)CC2)c1Br]

N-[2-[[[(2,6-Dibromo-4-fluoro-3-methylphenyl)methyl]amino]carbonyl]-7-fluoro-6,7,8,9-tetrahydro-3-hydroxy-4-oxo-7,10-ethanopyrimido[1,2-a]azepin-10(4H)-yl]-N,N',N'-trimethyl-ethanediamide ¹H NMR (400 MHz, CHLOROFORM-d) δ ppm 12.32 (1H, br. s.), 9.05 (1H, br. s.), 7.31 (1H, d, J=8.8 Hz), 4.85-5.03 (3H, m), 3.78-3.93 (1H, m), 3.32-3.47 (1H, m), 2.92 (6H, s), 2.75 (3H, s), 2.33 (3H, d, J=2.3 Hz), 1.83-2.28 (7H, m). ¹⁹F NMR (376 MHz, CHLOROFORM-d) δ ppm −111.07 (1F, s), −134.96 (1F, s). LCMS (+ESI, M+H+) m/z 675.9.

Example 42

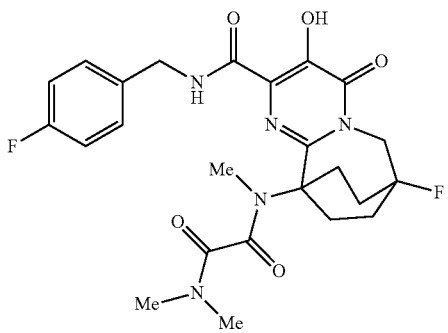 [SMILES: CN(C)C(=O)C(=O)N(C)C12CCC(F)(CC1)Cn1c2nc(C(=O)NCc2ccc(F)cc2)c(O)c1=O]

N-[7-Fluoro-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-ethanediamide $^1$H NMR (400 MHz, CHLOROFORM-d) δ ppm 12.27 (1H, br. s.), 9.60 (1H, t, J=6.0 Hz), 7.36 (2H, dd, J=8.1, 5.6 Hz), 6.97 (2H, t, J=8.5 Hz), 4.86-4.98 (1H, m), 4.61 (1H, dd, J=14.3, 6.4 Hz), 4.42-4.49 (1H, m), 3.82 (1H, d, J=15.0 Hz), 3.33-3.44 (1H, m), 3.01 (3H, s), 2.98 (3H, s), 2.97 (3H, s), 2.02-2.30 (6H, m), 1.86-1.95 (1H, m). $^{19}$F NMR (376 MHz, CHLOROFORM-d) δ ppm −116.24 (1F, br. s.), −135.51 (1F, br. s.). LCMS (+ESI, M+H+) m/z 504.1.

Example 43

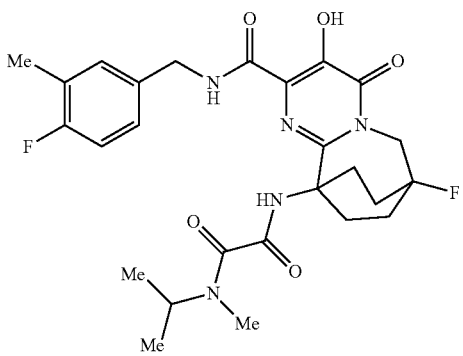 [SMILES: Cc1cc(CNC(=O)c2nc3n(c(=O)c2O)CC2(F)CCC3(NC(=O)C(=O)N(C)C(C)C)CC2)ccc1F]

N'-[7-Fluoro-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N-methyl-N-(1-methylethyl)-ethanediamide $^1$H NMR (400 MHz, CHLOROFORM-d) δ ppm 12.18 (1H, br. s.), 8.86 (1H, br. s.), 7.51 (1H, br. s.), 7.13-7.23 (2H, m), 6.90-7.00 (1H, m), 4.59 (1H, dt, J=18.8, 6.7 Hz), 4.52 (2H, d, J=6.0 Hz), 4.32 (2H, d, J=9.0 Hz), 2.75 (3H, s), 2.52-2.73 (2H, m), 2.27 (3H, br. s.), 1.99-2.29 (6H, m), 1.23 (6H, d, J=6.5 Hz). $^{19}$F NMR (376 MHz, CHLOROFORM-d) δ ppm −119.64 (1F, br. s.), −135.87 (1F, s). LCMS (+ESI, M+H+) m/z 532.1.

Example 44

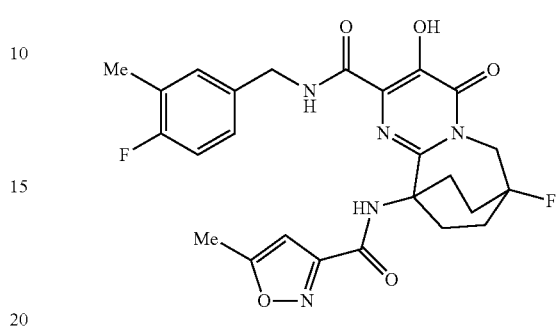

7-Fluoro-N-[(4-fluoro-3-methylphenyl)methyl]-4,6,7,8,9,10-hexahydro-3-hydroxy-10-[[(5-methyl-3-isoxazolyl)carbonyl]amino]-4-oxo-7,10-ethanopyrimido[1,2-a]azepine-2-carboxamide $^1$H NMR (400 MHz, CHLOROFORM-d) δ ppm 12.20 (1H, br. s.), 8.95 (1H, s), 7.90 (1H, br. s.), 7.18-7.27 (2H, m), 6.95-7.02 (1H, m), 6.40 (1H, s), 4.58 (2H, d, J=6.3 Hz), 4.32 (2H, d, J=8.3 Hz), 3.11-3.24 (2H, m), 2.48 (3H, s), 2.29-2.41 (2H, m), 2.28 (3H, d, J=1.8 Hz), 2.01-2.12 (2H, m), 1.87-1.99 (2H, m). $^{19}$F NMR (376 MHz, CHLOROFORM-d) δ ppm −118.94 (1F, s), −136.80 (1F, s). LCMS (+ESI, M+H+) m/z 514.0.

Example 45

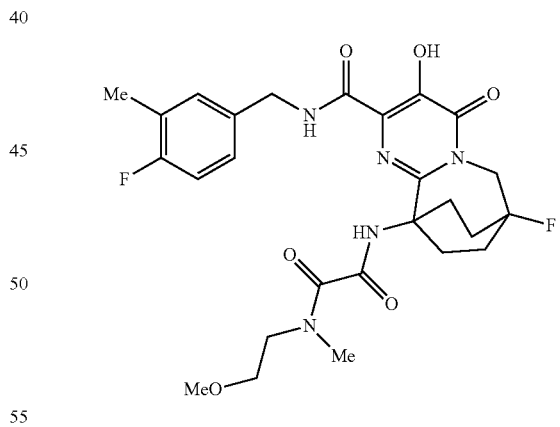

N'-[7-Fluoro-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N-(2-methoxyethyl)-N-methyl-ethanediamide $^1$H NMR (400 MHz, CHLOROFORM-d) δ ppm 12.13 (1H, br. s.), 8.54 (1H, br. s.), 8.16 (1H, br. s.), 7.12-7.25 (2H, m), 6.96 (1H, t, J=8.8 Hz), 4.53 (2H, d, J=5.8 Hz), 4.31 (2H, d, J=7.0 Hz), 3.85 (2H, t, J=5.0 Hz), 3.57 (2H, t, J=4.9 Hz), 3.35 (3H, s), 2.97 (3H, s), 2.62-2.78 (2H, m), 2.27 (3H, s), 1.96-2.31 (6H, m). ¹⁹F NMR (376 MHz, CHLOROFORM-d) δ ppm −119.42 (1F, s), −136.08 (0F, s). LCMS (⁺ESI, M+H⁺) m/z 548.0.

Example 46

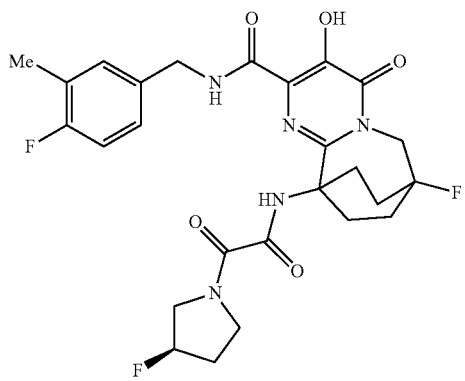 [SMILES: Cc1cc(CNC(=O)c2nc3n(c(=O)c2O)CC2(F)CCC3(NC(=O)C(=O)N3CC[C@@H](F)C3)CC2)ccc1F]

7-Fluoro-N-[(4-fluoro-3-methylphenyl)methyl]-10-[[2-[(3R)-3-fluoro-1-pyrrolidinyl]-1,2-dioxoethyl]amino]-4,6,7,8,9,10-hexahydro-3-hydroxy-4-oxo-7,10-ethanopyrimido[1,2-a]azepine-2-carboxamide ¹H NMR (400 MHz, CHLOROFORM-d) δ ppm 12.15 (1H, br. s.), 9.43 (1H, br. s.), 8.06 (1H, br. s.), 7.17-7.25 (2H, m), 6.98 (1H, t, J=8.9 Hz), 5.18-5.27 (1H, m), 4.23-4.65 (5H, m), 3.45-4.06 (3H, m), 2.92-3.07 (2H, m), 2.28 (3H, d, J=1.5 Hz), 2.23-2.46 (2H, m), 1.82-2.11 (6H, m). ¹⁹F NMR (376 MHz, CHLOROFORM-d) δ ppm −119.12 (1F, s), −136.63 (1F, s), −178.38 (1F, s). LCMS (⁺ESI, M+H⁺) m/z 548.0.

Example 47

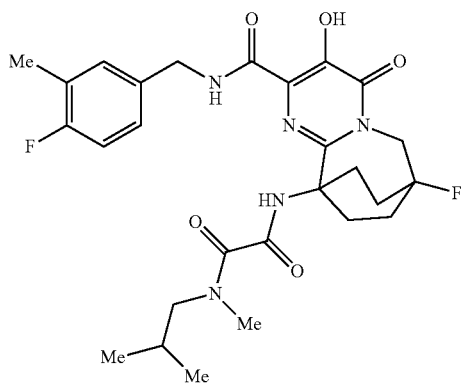 [SMILES: Cc1cc(CNC(=O)c2nc3n(c(=O)c2O)CC2(F)CCC3(NC(=O)C(=O)N(C)CC(C)C)CC2)ccc1F]

N'-[7-Fluoro-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N-methyl-N-(2-methylpropyl)-ethanediamide ¹H NMR (400 MHz, CHLOROFORM-d) δ ppm 12.25 (1H, br. s.), 8.60 (1H, br. s.), 8.04 (1H, br. s.), 7.13-7.22 (2H, m), 6.96 (1H, t, J=8.9 Hz), 4.52 (2H, t, J=5.3 Hz), 4.32 (2H, d, J=8.8 Hz), 3.54 (2H, d, J=7.5 Hz), 2.89 (3H, s), 2.58-2.76 (2H, m), 2.27 (3H, s), 1.91-2.27 (7H, m), 0.91 (6H, dd, J=6.7, 4.4 Hz). ¹⁹F NMR (376 MHz, CHLOROFORM-d) δ ppm −119.47 (1F, s), −136.01 (1F, s). LCMS (⁺ESI, M+H⁺) m/z 546.1.

Example 48

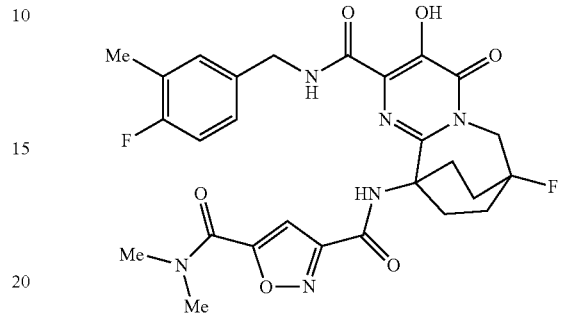

N~3~-[7-Fluoro-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N~5~,N~5~-dimethyl-3,5-isoxazoledicarboxamide ¹H NMR (400 MHz, CHLOROFORM-d) δ ppm 12.22 (1H, br. s.), 9.09 (1H, br. s.), 7.80 (1H, br. s.), 7.18-7.26 (2H, m), 7.04 (1H, s), 6.98 (1H, t, J=8.8 Hz), 4.59 (2H, d, J=6.0 Hz), 4.33 (2H, d, J=8.5 Hz), 3.17 (3H, s), 3.15 (3H, s), 3.12-3.27 (2H, m), 2.29-2.43 (2H, m), 2.26 (3H, s), 2.01-2.12 (2H, m), 1.89-1.99 (2H, m). ¹⁹F NMR (376 MHz, CHLOROFORM-d) δ ppm −118.79 (1F, s), −137.00 (1F, s). LCMS (⁺ESI, M+H⁺) m/z 571.1.

Example 49

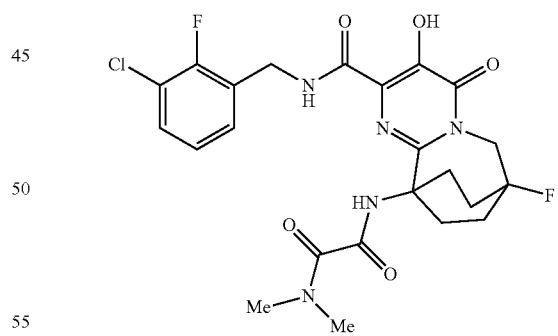

N'-[2-[[[(3-Chloro-2-fluorophenyl)methyl]amino]carbonyl]-7-fluoro-6,7,8,9-tetrahydro-3-hydroxy-4-oxo-7,10-ethanopyrimido[1,2-a]azepin-10(4H)-yl]-N,N-dimethyl-ethanediamide ¹H NMR (400 MHz, CHLOROFORM-d) δ ppm 8.62 (1H, br. s.), 8.04 (1H, br. s.), 7.33 (2H, br. s.), 7.07 (1H, t, J=7.7 Hz), 4.66 (2H, d, J=5.5 Hz), 4.31 (2H, d, J=8.3 Hz), 3.29 (3H, s), 2.95 (3H, s), 2.67 (2H, br. s.), 2.13-2.34 (4H, m), 1.98-2.11

(2H, m). ¹⁹F NMR (376 MHz, CHLOROFORM-d) δ ppm −120.26 (1F, br. s.), −135.98 (1F, br. s.). LCMS (⁺ESI, M+H⁺) m/z 524.0.

Example 50

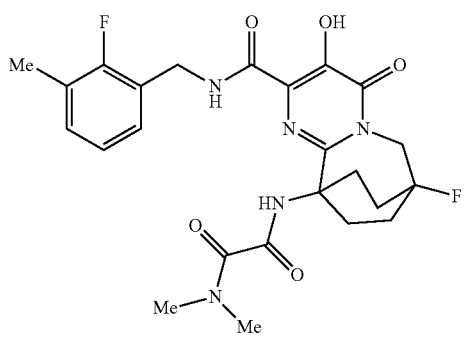 [SMILES: Cc1cccc(CNC(=O)c2nc3n(c(=O)c2O)CC2(F)CCC3(NC(=O)C(=O)N(C)C)CC2)c1F]

N'-[7-Fluoro-2-[[[(2-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide ¹H NMR (400 MHz, CHLOROFORM-d) δ ppm 11.98 (1H, br. s.), 8.46 (1H, br. s.), 8.24 (1H, br. s.), 7.23 (1H, br. s.), 7.12 (1H, br. s.), 6.97-7.05 (1H, m), 4.65 (2H, d, J=5.3 Hz), 4.31 (2H, d, J=8.3 Hz), 3.30 (3H, br. s.), 2.94 (3H, br. s.), 2.72 (2H, br. s.), 2.29 (3H, br. s.), 1.95-2.38 (6H, m). ¹⁹F NMR (376 MHz, CHLOROFORM-d) δ ppm −122.92 (1F, br. s.), −136.08 (1F, br. s.). LCMS (⁺ESI, M+H⁺) m/z 504.0.

Example 51

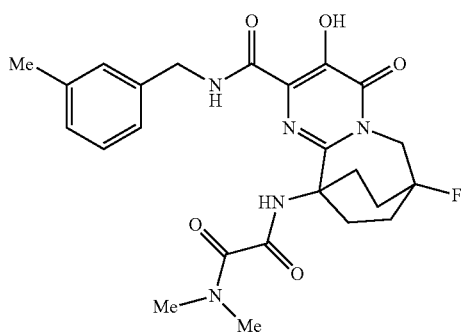 [SMILES: Cc1cccc(CNC(=O)c2nc3n(c(=O)c2O)CC2(F)CCC3(NC(=O)C(=O)N(C)C)CC2)c1]

N'-[7-Fluoro-6,7,8,9-tetrahydro-3-hydroxy-2-[[[(3-methylphenyl)methyl]amino]carbonyl]-4-oxo-7,10-ethanopyrimido[1,2-a]azepin-10(4H)-yl]-N,N-dimethyl-ethanediamide ¹H NMR (400 MHz, CHLOROFORM-d) δ ppm 8.48 (1H, br. s.), 8.25 (1H, br. s.), 7.17-7.26 (3H, m), 7.10 (1H, d, J=7.0 Hz), 4.57 (2H, d, J=6.3 Hz), 4.32 (2H, d, J=8.8 Hz), 3.30 (3H, s), 2.92 (3H, s), 2.66-2.77 (2H, m), 2.36 (3H, s), 2.19-2.31 (2H, m), 2.00-2.17 (4H, m). ¹⁹F NMR (376 MHz, CHLOROFORM-d) δ ppm −136.13 (1F, s). LCMS (⁺ESI, M+H⁺) m/z 486.0.

Example 52

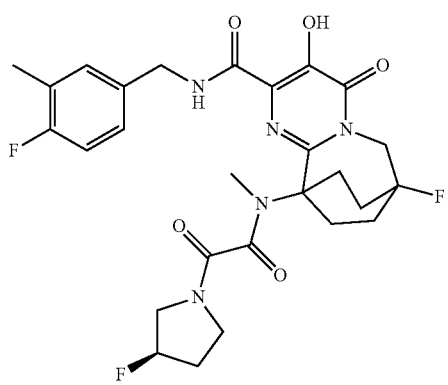 [SMILES: Cc1cc(CNC(=O)c2nc3n(c(=O)c2O)CC2(F)CCC3(N(C)C(=O)C(=O)N3CC[C@@H](F)C3)CC2)ccc1F]

7-Fluoro-N-[(4-fluoro-3-methylphenyl)methyl]-10-[[2-[(3R)-3-fluoro-1-pyrrolidinyl]-1,2-dioxoethyl]methylamino]-4,6,7,8,9,10-hexahydro-3-hydroxy-4-oxo-7,10-ethanopyrimido[1,2-a]azepine-2-carboxamide ¹H NMR (400 MHz, CHLOROFORM-d) δ ppm 9.16 (1H, br. s.), 7.70-7.79 (1H, m), 7.09-7.23 (4H, m), 6.87-6.95 (2H, m), 5.37 (1H, d, J=12.80 Hz), 5.24 (1H, d, J=12.05 Hz), 4.87 (1H, s), 4.68-4.85 (1H, m), 4.57 (1H, br. s.), 4.41 (1H, br. s.), 3.46-4.02 (5H, m), 3.38 (1H, br. s.), 3.01-3.11 (3H, m). ¹⁹F NMR (376 MHz, CHLOROFORM-d) δ ppm −120.15 (1F, s), −135.09 (1F, s.). LCMS (⁺ESI, M+H⁺) m/z: 582.13.

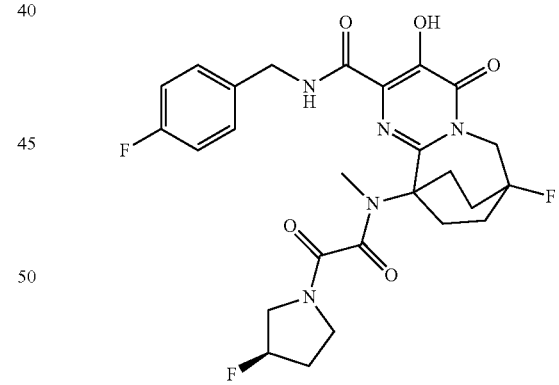

7-Fluoro-N-[(4-fluorophenyl)methyl]-10-[[2-[(3R)-3-fluoro-1-pyrrolidinyl]-1,2-dioxoethyl]methylamino]-4,6,7,8,9,10-hexahydro-3-hydroxy-4-oxo-7,10-ethanopyrimido[1,2-a]azepine-2-carboxamide ¹H NMR (400 MHz, CHLOROFORM-d) δ ppm 12.26 (1H, br. s.), 9.46 (1H, br. s.), 7.38 (3H, ddd, J=8.47, 5.46, 2.64 Hz), 7.05 (1H, d, J=9.04 Hz), 6.96-7.03 (2H, br. s.), 5.22-5.43 (1H, m), 4.84-4.98 (1H, m), 4.58-4.68 (1H, m), 4.43-4.53 (1H, m), 3.76-4.01 (3H, m), 3.45-3.75 (3H, m), 3.31-3.45 (1H, m), 3.01-3.06 (3H, m), 2.70 (1H, br. s.), 1.99-

2.44 (10H, m), 1.87-1.98 (2H, m). ¹⁹F NMR (376 MHz, CHLOROFORM-d) δ ppm −115.75 (1F, s), −135.01 (1F, s.). LCMS (⁺ESI, M+H⁺) m/z: 655.34.

Example 54

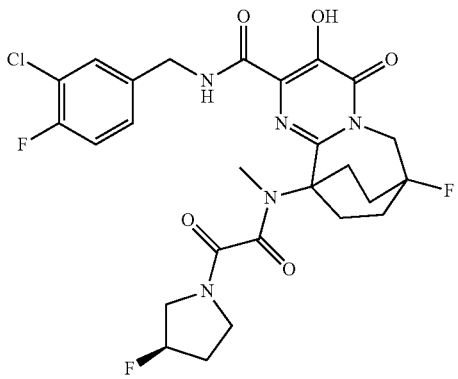 [SMILES: CN(C(=O)C(=O)N1CC[C@@H](F)C1)C12CCC(F)(CC1)Cn1c2nc(C(=O)NCc2ccc(F)c(Cl)c2)c(O)c1=O]

N-[(3-Chloro-4-fluorophenyl)methyl]-7-fluoro-10-[[2-[(3R)-3-fluoro-1-pyrrolidinyl]-1,2-dioxoethyl]methylamino]-4,6,7,8,9,10-hexahydro-3-hydroxy-4-oxo-7,10-ethanopyrimido[1,2-a]azepine-2-carboxamide ¹H NMR (400 MHz, CHLOROFORM-d) δ ppm 12.14 (1H, br. s.), 9.49 (1H, br. s.), 7.28-7.34 (3H, m), 7.03 (1H, t, J=7.91 Hz), 5.21-5.42 (1H, m), 4.85-4.98 (1H, m), 4.59-4.75 (2H, m), 3.76-3.97 (2H, m), 3.46-3.73 (3H, m), 3.32-3.45 (1H, m), 3.05 (3H, d, J=2.76 Hz), 2.34-2.42 (1H, m), 2.23-2.34 (2H, m), 2.11-2.23 (5H, m), 1.99-2.11 (2H, m), 1.90-1.99 (1H, m). ¹⁹F NMR (376 MHz, CHLOROFORM-d) δ ppm −120.15 (1F, s), −135.06 (1F, s.). LCMS (⁺ESI, M+H⁺) m/z: 582.13.

Example 55

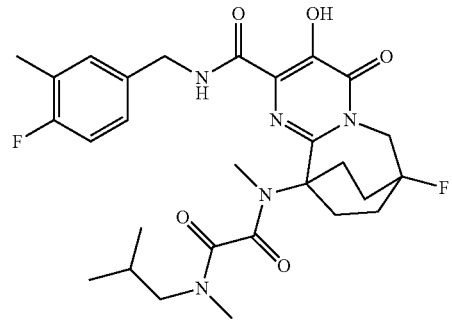 [SMILES: Cc1cc(CNC(=O)c2nc3n(c(=O)c2O)CC2(F)CCC3(N(C)C(=O)C(=O)N(C)CC(C)C)CC2)ccc1F]

N-[7-Fluoro-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N'-dimethyl-N'-(2-methylpropyl)-ethanediamide ¹H NMR (500 MHz, CHLOROFORM-d) δ ppm 12.25-12.29 (1H, m), 9.56-9.64 (1H, m), 7.15-7.23 (2H, m), 6.86-6.95 (1H, m), 4.85-4.97 (1H, m), 4.52-4.61 (1H, m), 4.38-4.46 (1H, m), 3.82 (1H, d, J=15.26 Hz), 3.34-3.44 (1H, m), 3.17-3.23 (1H, m), 3.00 (2H, s), 2.99 (1H, s), 2.98 (2H, s), 2.24-2.30 (1H, m), 2.23 (3H, d, J=1.83 Hz), 2.11-2.19 (3H, m), 2.03-2.10 (2H, m), 1.95-2.03 (1H, m), 1.86-1.95 (1H, m), 0.88-0.94 (6H, m). ¹⁹F NMR (376 MHz, CHLOROFORM-d) δ ppm −120.65 (1F, s), −135.49 (1F, s.). LCMS (⁺ESI, M+H⁺) m/z: 560.20.

Example 56

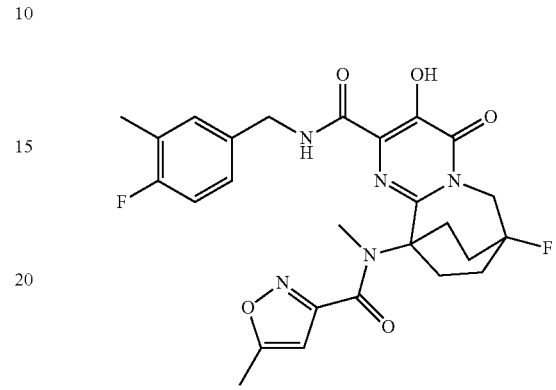

7-Fluoro-N-[(4-fluoro-3-methylphenyl)methyl]-4,6,7,8,9,10-hexahydro-3-hydroxy-10-[methyl[(5-methyl-3-isoxazolyl)carbonyl]amino-]-4-oxo-7,10-ethanopyrimido[1,2-a]azepine-2-carboxamide ¹H NMR (500 MHz, CHLOROFORM-d) δ ppm 12.20 (1H, s), 8.66 (1H, t, J=6.71 Hz), 7.10-7.16 (2H, m), 6.91 (1H, t, J=8.85 Hz), 6.09 (1H, s), 4.85-4.95 (1H, m), 4.58 (1H, dd, J=14.65, 7.32 Hz), 4.39 (1H, dd), 3.89 (1H, d, J=14.65 Hz), 3.33-3.43 (1H, m), 3.13 (3H, s), 2.42 (3H, s), 2.29-2.37 (1H, m), 2.23 (3H, s), 2.12-2.21 (2H, m), 2.02-2.12 (1H, m), 1.88 (1H, tq). ¹⁹F NMR (376 MHz, CHLOROFORM-d) δ ppm −120.20 (1F, s), −135.36 (1F, s.). LCMS (⁺ESI, M+H⁺) m/z: 528.14.

Example 57

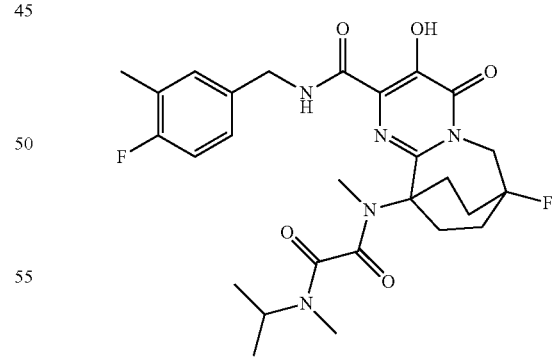

N-[7-Fluoro-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N'-dimethyl-N'-(1-methylethyl)-ethanediamide ¹H NMR (500 MHz, CHLOROFORM-d) δ ppm 9.65 (1H, d, J=19.84 Hz), 7.15-7.23 (2H, m), 6.90 (1H, td, J=8.85, 3.97

Hz), 4.85-4.97 (1H, m), 4.66 (1H, ddd, J=13.58, 7.02, 6.87 Hz), 4.52-4.63 (1H, m), 4.36-4.47 (1H, m), 3.88 (1H, ddd, J=12.97, 6.71, 6.56 Hz), 3.82 (1H, ddd, J=14.11, 3.74, 1.98 Hz), 3.33-3.44 (1H, m), 2.98 (2H, d, J=14.04 Hz), 2.83 (2H, d, J=6.41 Hz), 2.25-2.31 (1H, m), 2.23 (3H, s), 2.09-2.17 (3H, m), 2.01-2.09 (2H, m), 1.87-1.94 (2H, m), 1.22-1.27 (5H, m), 1.14-1.20 (3H, m), 0.82-0.90 (1H, m). $^{19}$F NMR (376 MHz, CHLOROFORM-d) δ ppm −120.65−−120.70 (1F, d), −135.48 (1F, s.). LCMS ($^{+}$ESI, M+H$^{+}$) m/z: 528.14.

Example 58

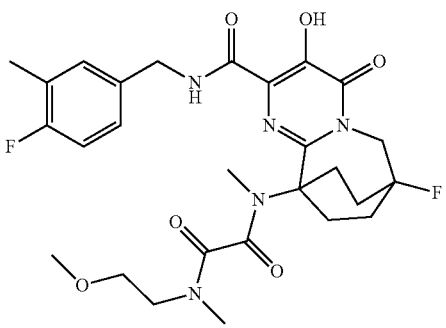 [SMILES: COCCN(C)C(=O)C(=O)N(C)C12CCC(F)(CC1)Cn1c2nc(C(=O)NCc2ccc(F)c(C)c2)c(O)c1=O]

N-[7-Fluoro-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N'-(2-methoxyethyl)-N,N'-dimethyl-ethanediamide $^{1}$H NMR (500 MHz, CHLOROFORM-d) δ ppm 12.26 (1H, br. s.), 9.55-9.62 (1H, m), 7.13-7.23 (2H, m), 6.90 (1H, td, J=8.93, 5.95 Hz), 4.86-4.96 (1H, m), 4.57 (1H, ddd, J=14.42, 7.10, 6.87 Hz), 4.37-4.45 (1H, m), 3.77-3.86 (2H, m), 3.61-3.73 (1H, m), 3.52-3.60 (2H, m), 3.42-3.49 (1H, m), 3.36-3.41 (1H, m), 3.35 (2H, s), 3.32 (3H, s), 3.06 (2H, s), 2.99 (3H, s), 2.97 (1H, s), 2.24-2.30 (1H, m), 2.23 (3H, s), 2.10-2.20 (4H, m), 2.01-2.08 (1H, m), 1.87-1.94 (1H, m), 1.43 (1H, d, J=6.71 Hz), 1.39 (1H, d, J=6.71 Hz). $^{19}$F NMR (376 MHz, CHLOROFORM-d) δ ppm −120.64 (1F, s), −135.50 (1F, s.). LCMS ($^{+}$ESI, M+H$^{+}$) m/z: 562.15.

Example 59

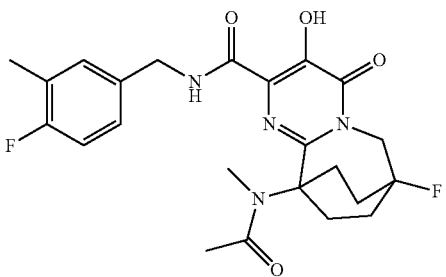 [SMILES: CC(=O)N(C)C12CCC(F)(CC1)Cn1c2nc(C(=O)NCc2ccc(F)c(C)c2)c(O)c1=O]

10-(Acetylmethylamino)-7-fluoro-N-[(4-fluoro-3-methylphenyl)methyl]-4,6,7,8,9,10-hexahydro-3-hydroxy-4-oxo-7,10-ethanopyrimido[1,2-a]azepine-2-carboxamide $^{1}$H NMR (500 MHz, CHLOROFORM-d) δ ppm 11.70 (1H, s), 7.30 (1H, br. s.), 7.13 (1H, dd, J=7.02, 0.92 Hz), 7.09 (1H, dd, J=8.09, 4.73 Hz), 6.99 (1H, t, J=8.85 Hz), 4.66-4.92 (1H, m), 4.31-4.63 (2H, m), 3.91 (1H, br. s.), 3.30 (1H, br. s.), 2.96-3.01 (3H, m), 2.26-2.30 (3H, m), 2.11 (3H, dd, J=12.51, 8.24 Hz), 1.96 (2H, d, J=8.85 Hz), 1.80-1.83 (3H, m), 1.55 (1H, br. s.). $^{19}$F NMR (376 MHz, CHLOROFORM-d) δ ppm −118.48 (1F, s), −135.32 (1F, s.). LCMS ($^{+}$ESI, M+H$^{+}$) m/z: 461.10.

Example 60

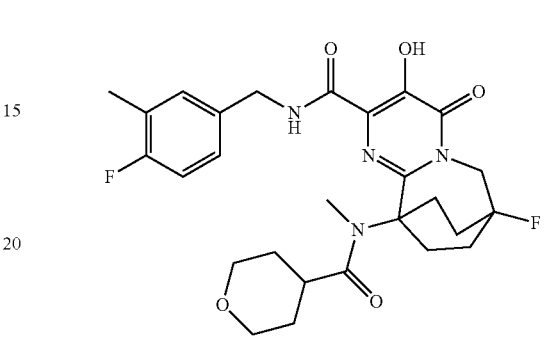

7-Fluoro-N-[(4-fluoro-3-methylphenyl)methyl]-4,6,7,8,9,10-hexahydro-3-hydroxy-10-[methyl[(tetrahydro-2H-pyran-4-yl)carbonyl]amino]-4-oxo-7,10-ethanopyrimido[1,2-a]azepine-2-carboxamide $^{1}$H NMR (400 MHz, CHLOROFORM-d) δ ppm 11.79 (1H, br. s.), 7.09-7.14 (1H, m), 7.03-7.08 (1H, m), 6.96-7.03 (1H, m), 4.42 (1H, br. s.), 4.01-4.08 (1H, m), 3.91 (1H, br. s.), 3.44-3.59 (1H, m), 3.32 (1H, br. s.), 3.06 (3H, d, J=18.32 Hz), 2.34-2.56 (1H, m), 2.29 (3H, br. s.), 2.09-2.21 (2H, m), 1.95-2.09 (3H, m), 1.89 (2H, br. s.), 1.59 (5H, ddd, J=4.89, 2.38, 2.26 Hz), 1.22 (1H, t, J=7.03 Hz). $^{19}$F NMR (376 MHz, CHLOROFORM-d) δ ppm −117.82−−118.13 (1F, d), −134.96−−135.52 (1F, d.). LCMS ($^{+}$ESI, M+H$^{+}$) m/z: 531.2

Example 61

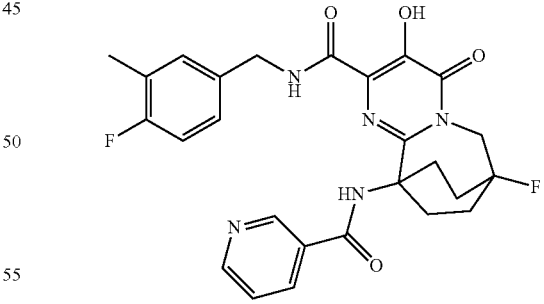

7-Fluoro-N-[(4-fluoro-3-methylphenyl)methyl]-4,6,7,8,9,10-hexahydro-3-hydroxy-4-oxo-10-[(3-pyridinylcarbonyl)amino]-, 10-ethanopyrimido[1,2-a]azepine-2-carboxamide $^{1}$H NMR (400 MHz, CHLOROFORM-d) δ ppm 12.12 (1H, br. s.), 8.93 (1H, d, J=1.76 Hz), 8.75 (1H, dd, J=4.77, 1.76 Hz), 7.97 (1H, ddd, J=8.16, 2.01, 1.88 Hz), 7.60 (1H, s), 7.21-7.26 (2H, m), 7.16-7.21 (1H, m), 7.08 (1H, d, J=7.03

Hz), 7.01-7.05 (1H, m), 6.95 (1H, t, J=8.78 Hz), 4.47 (2H, d, J=6.02 Hz), 4.35 (2H, d, J=8.78 Hz), 3.04-3.12 (2H, m), 2.29-2.39 (2H, m), 2.07 (4H, dd, J=8.41, 2.64 Hz). LCMS (⁺ESI, M+H⁺) m/z: 510.51.

Example 62

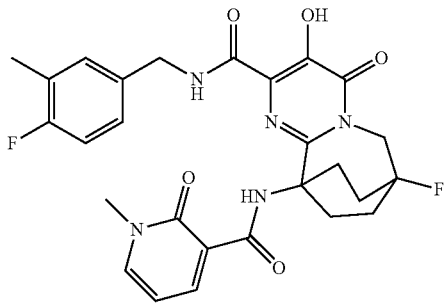 [SMILES: Cc1cc(CNC(=O)c2nc3n(c(=O)c2O)CC2(F)CCC3(NC(=O)c3cccn(C)c3=O)CC2)ccc1F]

10-[[(1,2-Dihydro-1-methyl-2-oxo-3-pyridinyl)carbonyl]amino]-7-fluoro-N-[(4-fluoro-3-methylphenyl)methyl]-4,6,7,8,9,10-hexahydro-3-hydroxy-4-oxo-7,10-ethanopyrimido[1,2-a]azepine-2-carboxamide ¹H NMR (400 MHz, CHLOROFORM-d) δ ppm 11.58 (1H, s), 9.77 (1H, t, J=6.27 Hz), 8.56 (1H, dd, J=7.40, 2.13 Hz), 7.53 (1H, dd, J=6.53, 2.01 Hz), 7.15-7.22 (2H, m), 6.96 (1H, t, J=8.91 Hz), 6.49 (1H, t, J=6.90 Hz), 4.69 (2H, d, J=6.53 Hz), 4.35 (2H, d, J=8.53 Hz), 3.44-3.53 (3H, m), 3.38 (3H, s), 2.32-2.43 (2H, m), 2.27 (3H, d, J=1.51 Hz), 2.01-2.10 (2H, m), 1.82 (2H, ddd, J=14.31, 8.41, 6.40 Hz). ¹⁹F NMR (376 MHz, CHLOROFORM-d) δ ppm −119.63 (1F, s), −136.89 (1F, s.). LCMS (⁺ESI, M+H⁺) m/z: 540.51.

Example 63

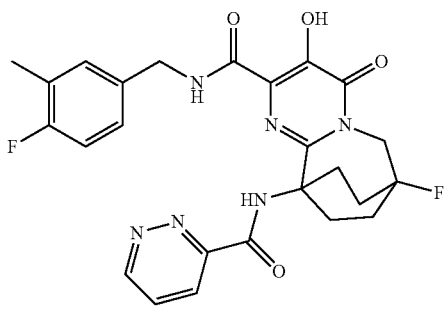 [SMILES: Cc1cc(CNC(=O)c2nc3n(c(=O)c2O)CC2(F)CCC3(NC(=O)c3cccnn3)CC2)ccc1F]

7-Fluoro-N-[(4-fluoro-3-methylphenyl)methyl]-4,6,7,8,9,10-hexahydro-3-hydroxy-4-oxo-10-[(3-pyridazinylcarbonyl)amino]-7,10-ethanopyrimido[1,2-a]azepine-2-carboxamide ¹H NMR (400 MHz, CHLOROFORM-d) δ ppm 12.17 (1H, s), 10.75 (1H, s), 9.32 (1H, dd, J=5.02, 1.76 Hz), 8.41 (1H, t, J=6.78 Hz), 8.30 (1H, dd, J=8.28, 1.76 Hz), 7.70 (1H, dd, J=8.53, 5.02 Hz), 7.34 (1H, dd, J=7.15, 1.88 Hz), 7.28-7.32 (1H, m), 6.89-6.95 (1H, m), 4.68 (2H, d, J=6.53 Hz), 4.35 (2H, d, J=8.53 Hz), 3.24-3.33 (2H, m), 2.33-2.46 (2H, m, J=11.98, 11.70, 11.70, 5.52 Hz), 2.06-2.16 (2H, m), 1.92-2.02 (2H, m). ¹⁹F NMR (376 MHz, CHLOROFORM-d) δ ppm −119.21 (1F, s), −136.74 (1F, s.). LCMS (⁺ESI, M+H⁺) m/z: 511.51.

Example 64

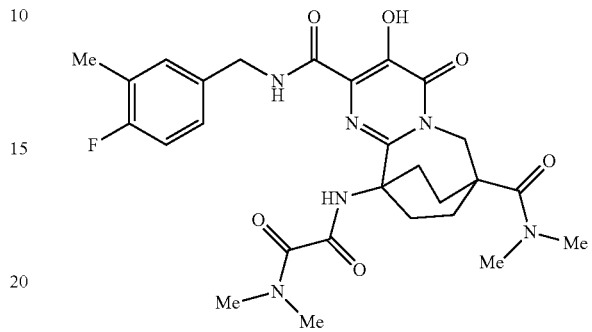

10-[[2-(Dimethylamino)-1,2-dioxoethy]amino]-N~2~-[(4-fluoro-3-methylphenyl)methyl]-4,8,9,10-tetrahydro-3-hydroxy-N~7~,N~7~-dimethyl-4-oxo-7,10-ethanopyrimido[1,2-a]azepine-2,7(6H)-dicarboxamide ¹H NMR (400 MHz, CHLOROFORM-d) δ ppm 12.17 (1H, br. s.), 8.72 (1H, br. s.), 7.69 (1H, br. s.), 7.14-7.23 (2H, m), 6.96 (1H, t, J=8.5 Hz), 4.55 (2H, br. s.), 4.52 (2H, d, J=6.3 Hz), 3.26 (3H, s), 3.03 (6H, br. s.), 2.92 (3H, s), 2.48 (2H, br. s.), 2.27 (3H, s), 2.06-2.23 (6H, m). ¹⁹F NMR (376 MHz, CHLOROFORM-d) δ ppm −119.52 (1F, br. s.). LCMS (⁺ESI, M+H⁺) m/z 557.4.

Example 65

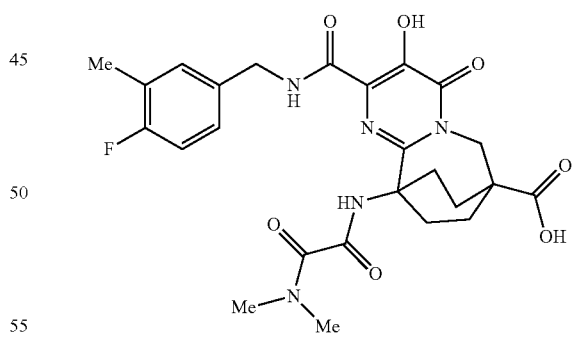

10-[[2-(Dimethylamino)-1,2-dioxoethyl]amino]-2-[[[(4-fluoro-3-methylphenyl)methyl]amino]carbonyl]-4,8,9,10-tetrahydro-3-hydroxy-4-oxo-7,10-ethanopyrimido[1,2-a]azepine-7(6H)-carboxylic acid ¹H NMR (400 MHz, CHLOROFORM-d) δ ppm 12.13 (1H, br. s.), 8.59 (1H, br. s.), 8.06 (1H, br. s.), 7.10-7.24 (2H, m), 6.87-7.02 (1H, m), 4.52 (2H, d, J=5.5 Hz), 4.43 (2H, br. s.), 3.29 (3H, s), 2.93 (3H, s), 2.51-2.66 (2H, m), 2.27 (3H, br.

s.), 2.11-2.32 (4H, m), 1.85-1.99 (2H, m). $^{19}$F NMR (376 MHz, CHLOROFORM-d) δ ppm −119.51 (1F, s). LCMS ($^+$ESI, M+H$^+$) m/z 530.1.

Example 66

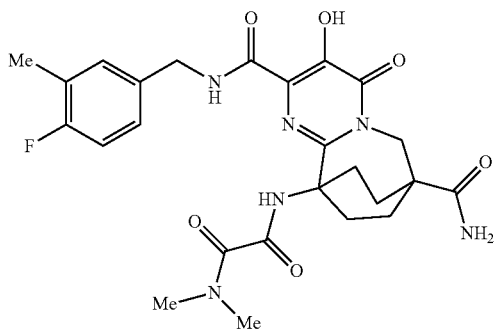 [SMILES: Cc1cc(CNC(=O)c2nc3n(c(=O)c2O)CC2(C(N)=O)CCC3(NC(=O)C(=O)N(C)C)CC2)ccc1F]

10-[[2-(Dimethylamino)-1,2-dioxoethyl]amino]-N~2~-[(4-fluoro-3-methylphenyl)methyl]-4,8,9,10-tetrahydro-3-hydroxy-4-oxo-7,10-ethanopyrimido[1,2-a]azepine-2,7(6H)-dicarboxamide $^1$H NMR (400 MHz, CHLOROFORM-d) δ ppm 12.12 (1H, br. s.), 8.58 (1H, br. s.), 8.06 (1H, br. s.), 7.15-7.24 (2H, m), 6.92-7.01 (1H, m), 5.83 (1H, br. s.), 5.61 (1H, br. s.), 4.52 (2H, d, J=5.8 Hz), 4.40 (2H, br. s.), 3.29 (3H, br. s.), 2.93 (3H, br. s.), 2.52-2.67 (2 H, m), 2.27 (3H, br. s.), 2.11-2.23 (4H, m), 1.92-2.05 (2H, m). $^{19}$F NMR (376 MHz, CHLOROFORM-d) δ ppm −119.47 (1F, br. s.). LCMS ($^+$ESI, M+H$^+$) m/z 529.1.

Example 67

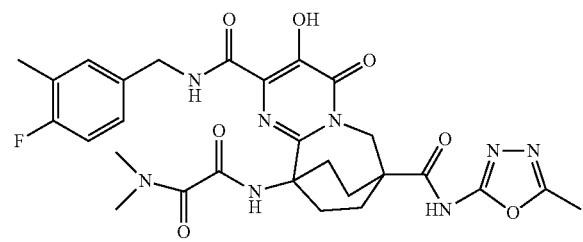 [SMILES: Cc1nnc(NC(=O)C23CCC(NC(=O)C(=O)N(C)C)(CC2)c2nc(C(=O)NCc4ccc(F)c(C)c4)c(O)c(=O)n2C3)o1]

10-[[2-(Dimethylamino)-1,2-dioxoethyl]amino]-N~2~-[(4-fluoro-3-methylphenyl)methyl]-4,8,9,10-tetrahydro-3-hydroxy-N~7~-(5-methyl-1,3,4-oxadiazol-2-yl)-4-oxo-7,10-ethanopyrimido[1,2-a]azepine-2,7(6H)-dicarboxamide $^1$H NMR (500 MHz, DMSO-d$_6$) δ ppm 12.02 (br. s., 1H) 11.45 (br. s., 1H) 9.77 (t, J=6.56 Hz, 1H) 8.89 (s, 1H) 7.27 (d, J=7.63 Hz, 1H) 7.18-7.23 (m, 1H) 7.10 (t, J=9.16 Hz, 1H) 4.46 (d, J=6.41 Hz, 2H) 4.39 (s, 2H) 2.97 (s, 3H) 2.89 (s, 3H) 2.48 (s, 3H) 2.31-2.39 (m, 2H) 2.22 (s, 3H) 2.07-2.19 (m, 4H) 1.89 (br. s., 2H). LCMS (M+H)$^+$=611.20.

Example 68

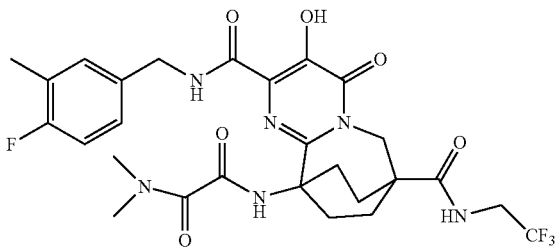 [SMILES: Cc1cc(CNC(=O)c2nc3n(c(=O)c2O)CC2(C(=O)NCC(F)(F)F)CCC3(NC(=O)C(=O)N(C)C)CC2)ccc1F]

10-[[2-(Dimethylamino)-1,2-dioxoethyl]amino]-N~2~-[(4-fluoro-3-methylphenyl)methyl]-4,8,9,10-tetrahydro-3-hydroxy-4-oxo-N~7~-(2,2,2-trifluoroethyl)-7,10-ethanopyrimido[1,2-a]azepine-2,7(6H)-dicarboxamide $^1$H NMR (500 MHz, DMSO-d$_6$) δ ppm 12.00 (br. s., 1H) 9.78 (t, J=6.56 Hz, 1H) 8.86 (s, 1H) 8.52 (t, J=6.26 Hz, 1H) 7.27 (dd, J=7.32, 1.83 Hz, 1H) 7.20 (ddd, J=8.01, 5.42, 2.14 Hz, 1H) 7.07-7.13 (m, 1H) 4.45 (d, J=6.41 Hz, 2H) 4.30 (s, 2H) 3.91-4.01 (m, 2H) 2.97 (s, 3H) 2.89 (s, 3H) 2.27-2.36 (m, 2H) 2.22 (s, 3H) 2.08-2.17 (m, 2H) 1.96-2.06 (m, 2H) 1.76-1.85 (m, 2H). LCMS (M+H)$^+$=611.15

Example 69

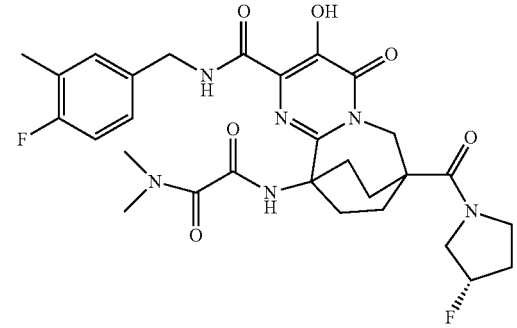 [SMILES: Cc1cc(CNC(=O)c2nc3n(c(=O)c2O)CC2(C(=O)N4CC[C@H](F)C4)CCC3(NC(=O)C(=O)N(C)C)CC2)ccc1F]

N'-[2-[[[(4-Fluoro-3-methylphenyl)methyl]amino]carbonyl]-7-[[(3S)-3-fluoro-1-pyrrolidinyl]carbonyl]-6,7,8,9-tetrahydro-3-hydroxy-4-oxo-7,10-ethanopyrimido[1,2-a]azepin-10(4H)-yl]-N,N-dimethylethanediamide $^1$H NMR (500 MHz, DMSO-d$_6$) δ ppm 12.02 (br. s., 1H) 9.78 (t, J=6.56 Hz, 1H) 8.87 (s, 1H) 7.27 (dd, J=7.32, 1.83 Hz, 1H) 7.18-7.23 (m, 1H) 7.06-7.15 (m, 1H) 5.20-5.45 (m, 1H) 4.51-4.61 (m, 1H) 4.39-4.51 (m, 2H) 4.21 (d, J=15.56 Hz, 1H) 3.53-3.61 (m, 2H) 3.43-3.53 (m, 2H) 2.98 (s, 3H) 2.90 (s, 3H) 2.41-2.50 (m, 2H) 2.22 (s, 3H) 2.16-2.21 (m, 2H) 2.08-2.15 (m, 2H) 2.00-2.07 (m, 2H) 1.96 (m, 2H). LCMS (M+H)⁺=601.22.

2.07-2.16 (m, 2H) 1.98-2.06 (m, 2H) 1.80-1.89 (m, 2H) 1.09-1.15 (m, 4H). LCMS (M+H)⁺=633.1.

Example 70

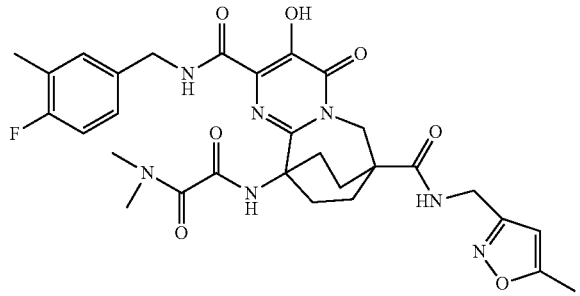 [SMILES: Cc1cc(CNC(=O)C23CCC(NC(=O)C(=O)N(C)C)(CC2)c2nc(C(=O)NCc4ccc(F)c(C)c4)c(O)c(=O)n2C3)no1]

10-[[2-(Dimethylamino)-1,2-dioxoethyl]amino]-N~2~-[(4-fluoro-3-methylphenyl)methyl]-4,8,9,10-tetrahydro-3-hydroxy-N~7~-[(5-methyl-3-isoxazolyl)methyl]-4-oxo-7,10-ethanopyrimido[1,2-a]azepine-2,7(6H)-dicarboxamide ¹H NMR (500 MHz, CDCl₃) δ ppm 8.63 (t, J=6.26 Hz, 1H) 7.97 (s, 1H) 7.17-7.24 (m, 2H) 6.97 (t, J=8.85 Hz, 1H) 6.63 (br. s., 1H) 5.99 (s, 1H) 4.47-4.57 (m, 4H) 4.41 (s, 2H) 3.29 (s, 3H) 2.94 (s, 3H) 2.53-2.63 (m, 2H) 2.43 (s, 3H) 2.28 (s, 3H) 1.97-2.25 (m, 6H). LCMS (M+H)⁺=624.1.

Example 71

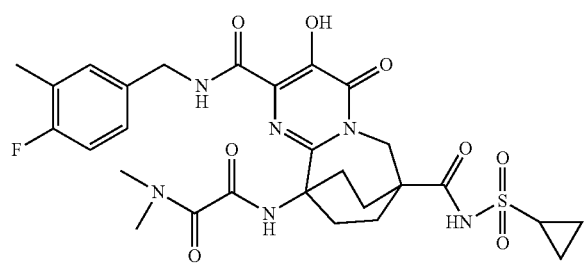 [SMILES: Cc1cc(CNC(=O)c2nc3n(c(=O)c2O)CC2(C(=O)NS(=O)(=O)C4CC4)CCC3(NC(=O)C(=O)N(C)C)CC2)ccc1F]

N~7~-(Cyclopropylsulfonyl)-10-[[2-(dimethylamino)-1,2-dioxoethyl]amino]-N~2~-[(4-fluoro-3-methylphenyl)methyl]-4,8,9,10-tetrahydro-3-hydroxy-4-oxo-7,10-ethanopyrimido[1,2-a]azepine-2,7(6H)-dicarboxamide ¹H NMR (500 MHz, DMSO-d₆) δ ppm 12.02 (br. s., 1H) 11.77 (br. s., 1H) 9.77 (t, J=6.56 Hz, 1H) 8.88 (s, 1H) 7.27 (d, J=7.63 Hz, 1H) 7.18-7.23 (m, 1H) 7.07-7.13 (m, 1H) 4.45 (d, J=6.71 Hz, 2H) 4.34 (s, 2H) 3.00-3.08 (m, 1H) 2.97 (s, 3H) 2.89 (s, 3H) 2.26-2.35 (m, 2H) 2.22 (d, J=1.53 Hz, 4H)

Example 72

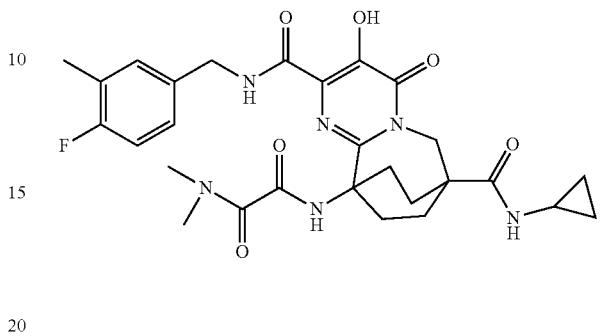

N~7~-Cyclopropyl-10-[[2-(dimethylamino)-1,2-dioxoethyl]amino]-N~2~-[(4-fluoro-3-methylphenyl)methyl]-4,8,9,10-tetrahydro-3-hydroxy-4-oxo-7,10-ethanopyrimido[1,2-a]azepine-2,7(6H)-dicarboxamide ¹H NMR (500 MHz, CHLOROFORM-d) δ ppm 8.67 (t, J=6.26 Hz, 1H) 7.81 (s, 1H) 7.15-7.24 (m, 2H) 6.94-7.02 (m, 1H) 6.34 (br. s., 1H) 4.51 (d, J=6.41 Hz, 2H) 4.34 (s, 2H) 3.27 (s, 3H) 2.94 (s, 3H) 2.77 (tt, J=7.02, 3.51 Hz, 1H) 2.48-2.56 (m, 2H) 2.28 (d, J=1.53 Hz, 3H) 2.17-2.24 (m, 2H) 2.09-2.17 (m, 2H) 1.95-2.03 (m, 2H) 0.80-0.85 (m, 2H) 0.53-0.59 (m, 2H). LCMS (M+H)⁺=569.17.

Example 73

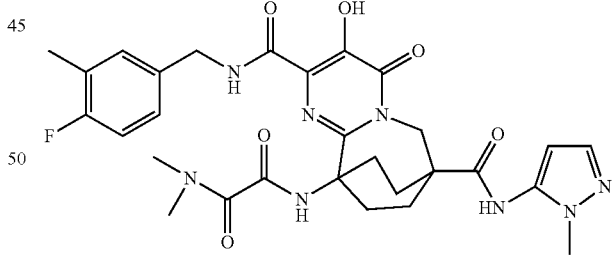

10-[[2-(Dimethylamino)-1,2-dioxoethyl]amino]-N~2~-[(4-fluoro-3-methylphenyl)methyl]-4,8,9,10-tetrahydro-3-hydroxy-N~7~-(1-methyl-1H-pyrazol-5-yl)-4-oxo-7,10-ethanopyrimido[1,2-a]azepine-2,7(6H)-dicarboxamide ¹H NMR (500 MHz, CDCl₃) δ ppm 8.96 (s, 1H) 8.86 (t, J=6.41 Hz, 1H) 7.53 (s, 1H) 7.51 (d, J=2.14 Hz, 1H) 7.14-7.21 (m, 2H) 6.94-7.00 (m, 1H) 6.30 (d, J=1.83 Hz, 1H) 4.46-4.52

(m, 4H) 3.77 (s, 3H) 3.24 (s, 3H) 2.92 (s, 3H) 2.47-2.54 (m, 2H) 2.20-2.33 (m, 9H). LCMS (M+H)⁺=609.3.

Example 74

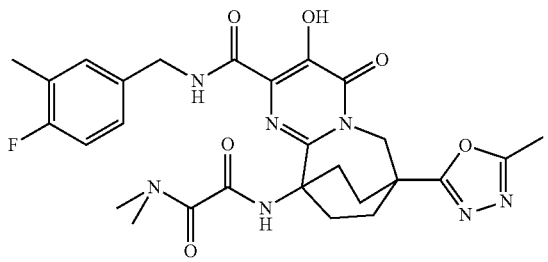 [SMILES: Cc1nnc(C23CCC(NC(=O)C(=O)N(C)C)(CC2)c2nc(C(=O)NCc4ccc(F)c(C)c4)c(O)c(=O)n2C3)o1]

N'-[2-[[[(4-Fluoro-3-methylphenyl)methyl]amino]carbonyl]-6,7,8,9-tetrahydro-3-hydroxy-7-(5-methyl-1,3,4-oxadiazol-2-yl)-4-oxo-7,10-ethanopyrimido[1,2-a]azepin-10(4H)-yl]-N,N-dimethyl-ethanediamide 1H NMR (500 MHz, CHLOROFORM-d) δ ppm 8.64 (t, J=6.10 Hz, 1H) 8.05 (s, 1H) 7.18-7.25 (m, 2H) 6.95-7.02 (m, 1H) 4.55 (d, J=6.41 Hz, 2H) 4.46 (s, 2H) 3.31 (s, 3H) 2.95 (s, 3H) 2.67 (ddd, J=14.11, 9.08, 5.49 Hz, 2H) 2.59 (s, 3H) 2.35-2.42 (m, 2H) 2.24-2.32 (m, 5H) 2.16-2.24 (m, 2H). LCMS (M+H)⁺=568.3.

Example 75

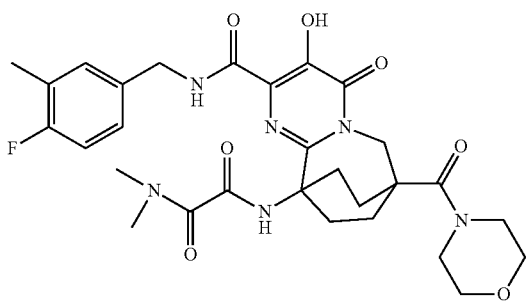 [SMILES: Cc1cc(CNC(=O)c2nc3n(c(=O)c2O)CC2(C(=O)N4CCOCC4)CCC3(NC(=O)C(=O)N(C)C)CC2)ccc1F]

N'-[2-[[[(4-Fluoro-3-methylphenyl)methyl]amino]carbonyl]-6,7,8,9-tetrahydro-3-hydroxy-7-(4-morpholinylcarbonyl)-4-oxo-7,10-ethanopyrimido[1,2-a]azepin-10(4H)-yl]-N,N-dimethyl-ethanediamide ¹H NMR (500 MHz, DMSO-d₆) δ ppm 12.02 (br. s., 1H) 9.78 (t, J=6.41 Hz, 1H) 8.88 (s, 1H) 7.27 (dd, J=7.48, 1.98 Hz, 1H) 7.17-7.22 (m, 1H) 7.08-7.14 (m, 1H) 4.46 (d, J=6.71 Hz, 2H) 4.40 (s, 2H) 3.55-3.59 (m, 4H) 3.51 (d, J=4.27 Hz, 4H)

2.96 (s, 3H) 2.89 (s, 3H) 2.26-2.35 (m, 2H) 2.22 (d, J=1.53 Hz, 3H) 2.10 (ddd, J=14.11, 8.47, 6.10 Hz, 2H) 1.89-2.03 (m, 4H). LCMS (M+H)⁺=599.4.

Example 76

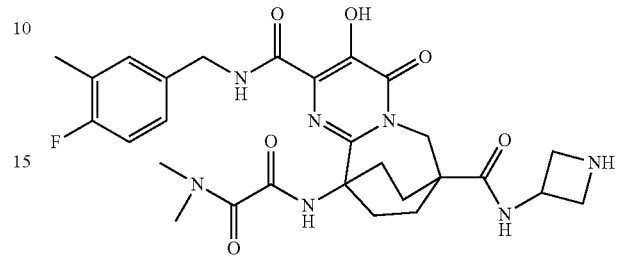

N~7~-3-Azetidinyl-10-[[2-(dimethylamino)-1,2-dioxoethyl]amino]-N~2~-[(4-fluoro-3-methylphenyl)methyl]-4,8,9,10-tetrahydro-3-hydroxy-4-oxo-7,10-ethanopyrimido[1,2-a]azepine-2,7(6H)-dicarboxamide ¹H NMR (500 MHz, MeOD) δ ppm 9.67-9.73 (m, 1H) 8.90 (s, 1H) 8.45 (br. s., 1H) 7.26-7.30 (m, 1H) 7.21-7.25 (m, 1H) 6.93-6.99 (m, 1H) 4.60-4.68 (m, 1H) 4.54 (d, J=6.41 Hz, 2H) 4.44 (br. s., 2H) 4.23-4.36 (m, 4H) 3.09 (s, 3H) 2.99 (s, 3H) 2.40-2.47 (m, 2H) 2.30-2.38 (m, 2H) 2.25 (d, J=1.83 Hz, 3H) 2.12-2.19 (m, 2H) 1.95 (d, 2H). LCMS (M+H)⁺=584.2.

Example 77

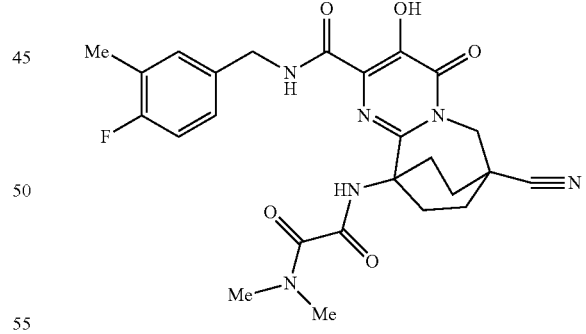

N'-[7-Cyano-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide ¹H NMR (400 MHz, CHLOROFORM-d) δ ppm 12.22 (1H, br. s.), 8.48 (1H, br. s.), 8.20 (1H, br. s.), 7.15-7.24 (2H, m), 6.97 (1H, t, J=8.4 Hz), 4.53 (2H, d, J=6.0 Hz), 4.47 (2H, br. s.), 3.30 (3H, s), 2.94 (3H, s), 2.61-2.71 (2H, m), 2.32-2.43

(2H, m), 2.27 (3H, br. s.), 2.08-2.22 (4H, m). $^{19}$F NMR (376 MHz, CHLOROFORM-d) δ ppm −119.31 (1F, br. s.). LCMS ($^{+}$ESI, M+H$^{+}$) m/z 511.1.

Example 78

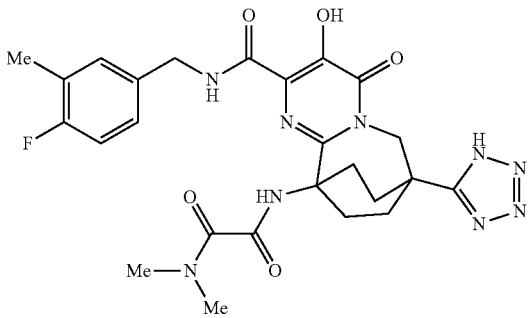 [SMILES: Cc1cc(CNC(=O)c2nc3n(c(=O)c2O)CC2(c4nnn[nH]4)CCC3(NC(=O)C(=O)N(C)C)CC2)ccc1F]

N'-[2-[[[(4-Fluoro-3-methylphenyl)methyl]amino] carbonyl]-6,7,8,9-tetrahydro-3-hydroxy-4-oxo-7- (1H-tetrazol-5-yl)-7,10-ethanopyrimido[1,2-a] azepin-10(4H)-yl]-N,N-dimethyl-ethanediamide To a solution of ethanediamide, N$^2$-[7-cyano-2-[[[(4-fluoro-3-methylphenyl)methyl]amino]carbonyl]-6,7,8,9-tetrahydro-3-methoxy-4-oxo-7,10-ethanopyrimido[1,2-a]azepin-10(4H)-yl]-N$^1$,N$^1$-dimethyl-, Intermediate 50 (24 mg, 0.046 mmol, 1 equiv) in dioxane (0.92 mL) was added tributyltin azide (0.125 m, 0.458 mmol, 10 equiv). The reaction was heated to 90° C. (oil bath) for 20 h. The reaction was then removed from heat and HCl (1 mL of a 4 M solution in dioxane) was added. After stirring 20 min, the reaction mixture was added dropwise into hexane (25 mL). The solids were then filtered to provide the crude product. The crude material was purified by preparatory HPLC to provide the title compound as a pale pink solid (3.6 mg, 14%). $^1$H NMR (400 MHz, CDCl$_3$) δ ppm 12.34 (1H, br. s.), 8.89 (1H, br. s.), 7.53 (1H, br. s.), 7.11-7.23 (2H, m), 6.89-7.00 (1H, m), 4.60 (1H, br. s.), 4.51 (2H, br. s.), 3.23 (3H, br. s.), 2.92 (3H, br. s.), 2.26 (3H, br. s.), 1.91-2.66 (10H, m); $^{19}$F NMR (376 MHz, CDCl$_3$) δ ppm −119.41 (1F, br. s.); LCMS (ES+, (M+H)$^+$) m/z 554.1.

Example 79

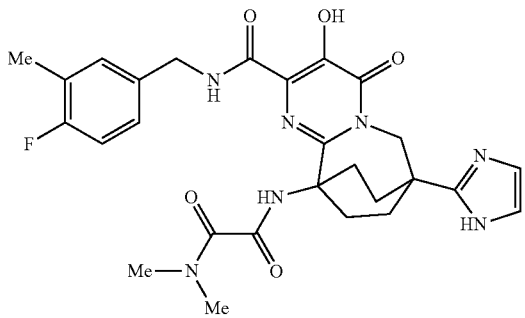 [SMILES: Cc1cc(CNC(=O)c2nc3n(c(=O)c2O)CC2(c4ncc[nH]4)CCC3(NC(=O)C(=O)N(C)C)CC2)ccc1F]

N'-[2-[[[(4-Fluoro-3-methylphenyl)methyl]amino] carbonyl]-6,7,8,9-tetrahydro-3-hydroxy-7-(1H-imidazol-2-yl)-4-oxo-7,10-ethanopyrimido[1,2-a] azepin-10(4H)-yl]-N,N-dimethyl-ethanediamide To a solution of ethanediamide, N$^2$-[2-[[[(4-fluoro-3-methylphenyl)methyl]amino]carbonyl]-6,7,8,9-tetrahydro-7-(1H-imidazol-2-yl)-3-methoxy-4-oxo-7,10-ethanopyrimido[1,2-a]azepin-10(4H)-yl]-N$^1$,N$^1$-dimethyl- Intermediate 45 (38 mg, 1 equiv) in DMF (0.67 mL) was added lithium chloride (43 mg, 1.008 mmol, 15 equiv). The reaction was then heated to 120° C. (oil bath). After 1 h, the reaction was removed from the heating bath and purified by preparative HPLC to provide the TFA salt of the product as an off white solid (28 mg, 20% over two steps). $^1$H NMR (400 MHz, CDCl$_3$) δ ppm 9.68 (1H, br. s.), 8.93 (1H, s), 7.57 (2H, s), 7.26 (1H, d, J=7.3 Hz), 7.18-7.24 (1H, m), 6.90-6.98 (1H, m), 4.53 (2H, d, J=6.0 Hz), 4.48 (2H, s), 3.09 (3H, s), 2.98 (3H, s), 2.51-2.62 (2H, m), 2.39-2.49 (2H, m), 2.28 (4H, br. s.), 2.24 (3H, d, J=1.5 Hz); $^{19}$F NMR (376 MHz, CDCl$_3$) δ ppm −77.24 (3F, br. s.), −122.23 (1F, br. s.); LCMS (ES+, (M+H)$^+$) m/z 552.1.

Example 80

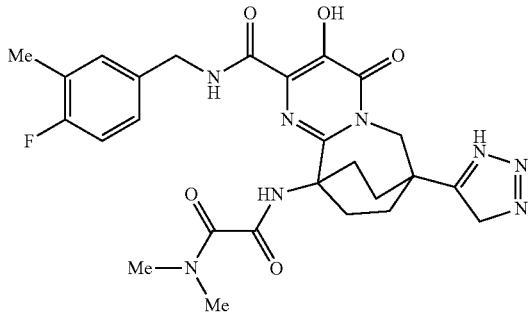

N'-[2-[[[(4-Fluoro-3-methylphenyl)methyl]amino] carbonyl]-6,7,8,9-tetrahydro-3-hydroxy-4-oxo-7- (1H-1,2,3-triazol-4-yl)-7,10-ethanopyrimido[1,2-a] azepin-10(4H)-yl]-N,N-dimethyl-ethanediamide To a solution of ethanediamide, N$^2$-[2-[[[(4-fluoro-3-methylphenyl)methyl]amino]carbonyl]-6,7,8,9-tetrahydro-3-methoxy-4-oxo-7-(1H-1,2,3-triazol-5-yl)-7,10-ethanopyrimido[1,2-a]azepin-10(4H)-yl]-N$^1$,N$^1$-dimethyl-, Intermediate 47 (32 mg, 1 equiv) in DMF (0.77 mL) was added lithium chloride (36 mg, 0.847 mmol, 15 equiv). The reaction was then heated to 120° C. (oil bath). After 2 h, the reaction was removed from the heating bath and purified by preparative HPLC to provide the product as a pale purple solid (5.7 mg, 16% over two steps). $^1$H NMR (400 MHz, CDCl$_3$) δ ppm 12.15 (1H, br. s.), 8.68 (1H, br. s.), 8.13 (1H, br. s.), 7.59 (1H, br. s.), 7.12-7.25 (2H, m), 6.96 (1H, br. s.), 4.53 (2H, br. s.), 4.39 (2H, br. s.), 3.29 (3H, br. s.), 2.93 (3H, br. s.), 2.64 (2H, br. s.), 2.27 (3H, br. s.), 1.99-2.25 (6H, m); $^{19}$F NMR (376 MHz, CDCl$_3$) δ ppm −119.53 (1F, br. s.); LCMS (ES+, (M+H)$^+$) m/z 553.1

Example 81

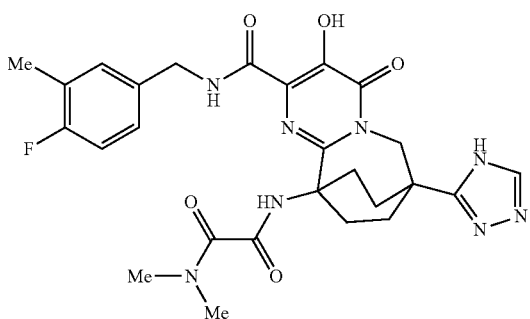 [SMILES: Cc1cc(CNC(=O)c2nc3n(c(=O)c2O)CC2(c4nnc[nH]4)CCC3(NC(=O)C(=O)N(C)C)CC2)ccc1F]

N'-[2-[[[(4-Fluoro-3-methylphenyl)methyl]amino]
carbonyl]-6,7,8,9-tetrahydro-3-hydroxy-4-oxo-7-
(1H-1,2,4-triazol-3-yl)-7,10-ethanopyrimido[1,2-a]
azepin-10(4H)-yl]-N,N-dimethyl-ethanediamide To a solution of ethanediamide, N$^2$-[2-[[[(4-fluoro-3-methylphenyl)methyl]amino]carbonyl]-6,7,8,9-tetrahydro-3-methoxy-4-oxo-7-(4H-1,2,4-triazol-3-yl)-7,10-ethanopyrimido[1,2-a]azepin-10(4H)-yl]-N$^1$,N$^1$-dimethyl- Intermediate 52 (51 mg, 1 equiv) in DMF (1.8 mL) was added lithium chloride (114 mg, 0.270 mmol, 30 equiv). The reaction was then heated to 120° C. (oil bath). After 2 h, the reaction was removed from the heating bath and purified by preparative HPLC to provide the product as an off-white solid (24 mg, 37% over three steps). $^1$H NMR (400 MHz, CDCl$_3$) δ ppm 12.13 (1H, br. s.), 8.76 (1H, br. s.), 8.25 (1H, br. s.), 7.80 (1H, br. s.), 7.11-7.23 (2H, m), 6.95 (1H, br. s.), 4.52 (5H, br. s.), 3.25 (3H, br. s.), 2.91 (3H, br. s.), 2.59 (2H, br. s.), 2.22-2.45 (4H, m), 2.22-2.28 (3H, m), 2.12 (2H, br. s.); $^{19}$F NMR (376 MHz, CDCl$_3$) δ ppm −119.99 (1F, br. s.); LCMS (ES+, (M+H)$^+$) m/z 553.1.

Example 82

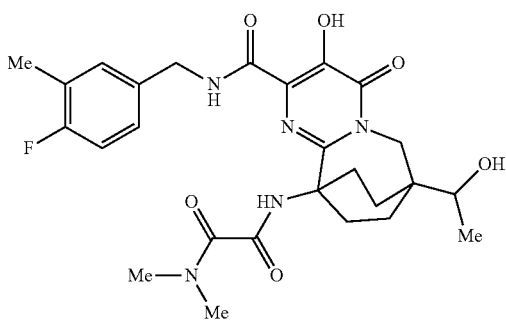 [SMILES: Cc1cc(CNC(=O)c2nc3n(c(=O)c2O)CC2(C(C)O)CCC3(NC(=O)C(=O)N(C)C)CC2)ccc1F]

N'-[2-[[[(4-Fluoro-3-methylphenyl)methyl]amino]
carbonyl]-6,7,8,9-tetrahydro-3-hydroxy-7-(1-hy-
droxyethyl)-4-oxo-7,10-ethanopyrimido[1,2-a]
azepin-10(4H)-yl]-N,N-dimethyl-ethanediamide To a solution of ethanediamide, N$^2$-[2-[[[(4-fluoro-3-methylphenyl)methyl]amino]carbonyl]-6,7,8,9-tetrahydro-7-(1-hydroxyethyl)-3-methoxy-4-oxo-7,10-ethanopyrimido[1,2-a]azepin-10(4H)-yl]-N$^1$,N$^1$-dimethyl-, Intermediate 44 (52 mg, 1 equiv) in DMF (1.0 mL) was added lithium chloride (49 mg, 1.166 mmol, 15 equiv). The reaction was then heated to 120° C. (oil bath). After 1 h, the reaction was removed from the heating bath and purified by preparative HPLC to provide the product as a pale pink solid (5 mg, 12% over two steps). $^1$H NMR (400 MHz, CDCl$_3$) δ ppm 12.04 (1H, br. s.), 8.47-8.62 (1H, m), 8.10 (1H, s), 7.15-7.24 (2H, m), 6.96 (1H, t, J=8.8 Hz), 4.53 (2H, d, J=6.3 Hz), 4.23 (1H, d, J=15.1 Hz), 4.02 (1H, d, J=15.3 Hz), 3.63-3.73 (1H, m), 3.29 (3H, s), 2.93 (3H, s), 2.48-2.60 (2H, m), 2.27 (3H, s), 1.46-2.22 (7H, m), 1.25 (3H, d, J=6.3 Hz); $^{19}$F NMR (376 MHz, CDCl$_3$) δ ppm −119.57 (1F, br. s.); LCMS (ES+, (M+H)$^+$) m/z 530.1.

Example 83

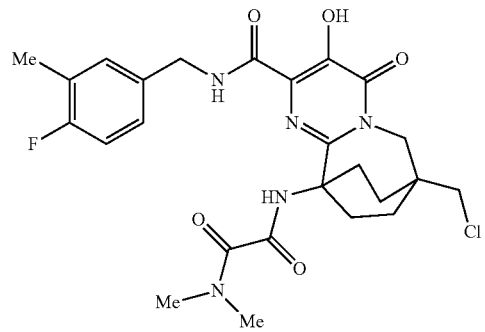 [SMILES: Cc1cc(CNC(=O)c2nc3n(c(=O)c2O)CC2(CCl)CCC3(NC(=O)C(=O)N(C)C)CC2)ccc1F]

N'-[7-(Chloromethyl)-2-[[[(4-fluoro-3-methylphe-
nyl)methyl]amino]carbonyl]-6,7,8,9-tetrahydro-3-
hydroxy-4-oxo-7,10-ethanopyrimido[1,2-a]azepin-
10(4H)-yl]-N,N-dimethyl-ethanediamide To a solution of 7,10-ethanopyrimido[1,2-a]azepine-2-carboxamide, 10-amino-7-(chloromethyl)-N-[(4-fluoro-3-methylphenyl)methyl]-4,6,7,8,9,10-hexahydro-3-hydroxy-4-oxo-, Intermediate 54 (62 mg, 0.143 mmol, 1 equiv), dimethyloxamic acid (27 mg, 0.228 mmol, 1.6 equiv), and DIPEA (0.075 mL, 0.428 mmol, 3 equiv) in DMF (1.46 mL) was added HATU (65 mg, 0.171 mmol, 1.2 equiv). After 1 h, dimethyl amine (2 mL of a 2 M solution in MeOH, 4 mmol, 28 equiv) was added and the mixture was heated at 60° C. (oil bath) for 1 h. Reaction was removed from bath and the MeOH was blown off under a stream of nitrogen. The resulting DMF solution was purified by preparative HPLC to provide the product as a white solid (33 mg, 46% over three steps). $^1$H NMR (400 MHz, CDCl$_3$) δ ppm 12.09 (1H, br. s.), 8.54 (1H, br. s.), 8.19 (1H, s), 7.17-7.24 (2H, m), 6.93-6.99 (1H, m), 4.53 (2H, d, J=6.3 Hz), 4.13 (2H, s), 3.47 (2H, s), 3.30 (3H, s), 2.94 (3H, s), 2.60 (2H, ddd, J=14.4, 9.2, 5.8 Hz), 2.27 (3H, d, J=1.8 Hz), 2.08-2.16 (2H, m), 1.81-1.92 (2H, m), 1.66-1.75

(2H, m); ¹⁹F NMR (376 MHz, CDCl₃) δ ppm −119.50 (1F, s); LCMS (ES+, (M+H)⁺) m/z 534.4.

Example 84

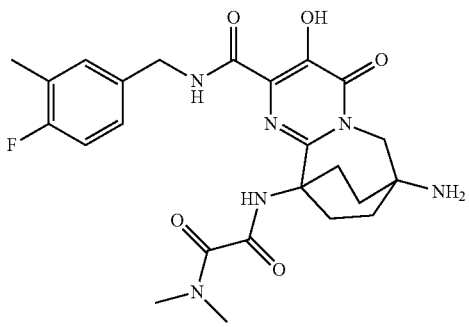 [SMILES: Cc1cc(CNC(=O)c2nc3n(c(=O)c2O)CC2(N)CCC3(NC(=O)C(=O)N(C)C)CC2)ccc1F]

N'-[7-Amino-2-[[[(4-fluoro-3-methylphenyl)methyl] amino]carbonyl]-6,7,8,9-tetrahydro-3-hydroxy-4-oxo-7,10-ethanopyrimido[1,2-a]azepin-10(4H)-yl]-N,N-dimethyl-ethanediamide ¹H NMR (400 MHz, CHLOROFORM-d) δ ppm 12.23 (1H, s), 8.96 (1H, br. s.), 8.75 (1H, t, J=5.77 Hz), 7.10-7.21 (2H, m), 6.90-6.98 (1H, m), 6.89-6.99 (1H, m), 4.50 (2H, d, J=6.02 Hz), 4.20 (2H, br. s.), 3.21 (3H, s), 2.90 (3H, s), 2.32 (2H, br. s.), 2.26 (3H, d, J=1.25 Hz), 1.88-2.13 (4H, m), 1.76 (2H, br. s.). ¹⁹F NMR (376 MHz, CHLOROFORM-d) δ ppm −119.58 (1F, s.). LCMS (⁺ESI, M+H⁺) m/z: 501.3.

Example 85

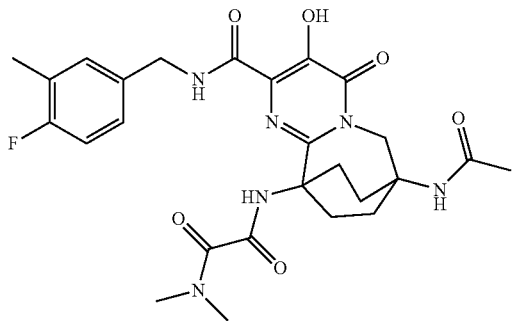 [SMILES: CC(=O)NC12CCC(NC(=O)C(=O)N(C)C)(CC1)c1nc(C(=O)NCc3ccc(F)c(C)c3)c(O)c(=O)n1C2]

N'-[7-(Acetylamino)-2-[[[(4-fluoro-3-methylphenyl) methyl]amino]carbonyl]-6,7,8,9-tetrahydro-3-hydroxy-4-oxo-7,10-ethanopyrimido[1,2-a]azepin-10 (4H)-yl]-N,N-dimethyl-ethanediamide ¹H NMR (400 MHz, CHLOROFORM-d) δ ppm 12.16 (1H, s), 8.51 (1H, t, J=5.90 Hz), 8.18 (1H, s), 7.16-7.23 (2H, m), 6.96 (1H, t, J=8.91 Hz), 5.63 (1H, br. s.), 4.53 (2H, d, J=6.27 Hz), 4.44 (2H, s), 3.30 (3H, s), 2.93 (3H, s), 2.75 (1H, s), 2.59-2.70 (2H, m), 2.27 (3H, d, J=1.51 Hz), 2.17-2.25 (2H, m), 2.07-2.17 (4H, m), 2.00 (3H, s). LCMS (⁺ESI, M+H⁺) m/z: 543.4.

Example 86

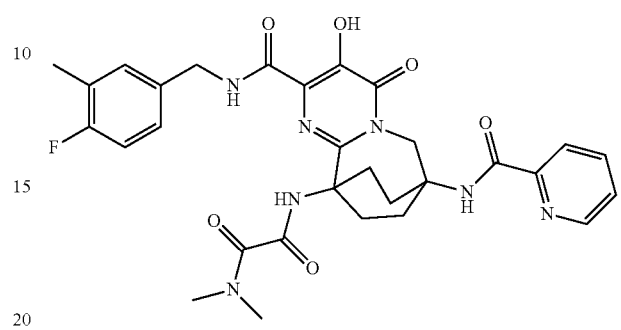

N'-[2-[[[(4-Fluoro-3-methylphenyl)methyl]amino]carbonyl]-6,7,8,9-tetrahydro-3-hydroxy-4-oxo-7-[(2-pyridinylcarbonyl)amino]-7,10-ethanopyrimido[1,2-a]azepin-10 (4H)-yl]-N,N-dimethyl-ethanediamide ¹H NMR (500 MHz, CHLOROFORM-d) δ ppm 12.09 (1H, br. s.), 8.56 (1H, t, J=5.95 Hz), 8.52 (1H, d, J=4.58 Hz), 8.20 (1H, s), 8.15 (1H, d, J=7.63 Hz), 8.11 (1H, br. s.), 7.86 (1H, t, J=7.17 Hz), 7.43-7.47 (1H, m), 7.16-7.22 (2H, m), 6.95 (1H, t, J=8.85 Hz), 4.55 (2H, s), 4.52 (2H, d, J=6.10 Hz), 3.28 (3H, s), 2.92 (3H, s), 2.67 (2H, ddd, J=14.04, 8.85, 5.49 Hz), 2.36-2.42 (2H, m), 2.23-2.30 (5H, m), 2.15-2.22 (2H, m). ¹⁹F NMR (376 MHz, CHLOROFORM-d) δ ppm −119.96 (1F, s). LCMS (⁺ESI, M+H⁺) m/z: 606.4.

Example 87

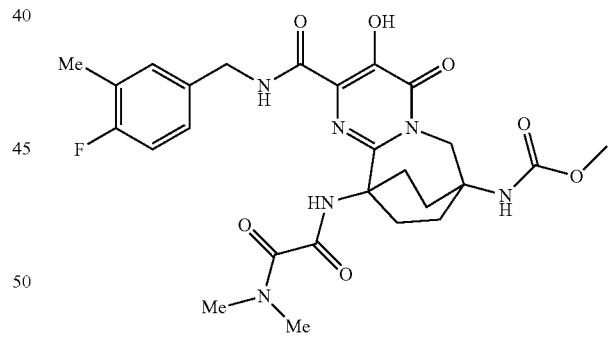

[10-[[2-(Dimethylamino)-1,2-dioxoethyl]amino]-2-[[[(4-fluoro-3-methylphenyl)methyl]amino]carbonyl]-4,8,9,10-tetrahydro-3-hydroxy-4-oxo-7,10-ethanopyrimido[1,2-a]azepin-7(6H)-yl]-carbamic acid, methyl ester To a solution of carbamic acid, N-[10-[[2-(dimethylamino)-1,2-dioxoethyl]amino]-2-[[[(4-fluoro-3-methylphenyl)methyl]amino]carbonyl]-4,8,9,10-tetrahydro-3-methoxy-4-oxo-7,10-ethanopyrimido[1,2-a]azepin-7(6H)-yl]-, methyl ester, Intermediate 58 (24 mg, 0.042 mmol, 1 equiv) in DMF (0.3 mL) was added lithium chloride (1.8 mg, 0.042 mmol, 1 equiv). The reaction was then heated to 120° C. (oil bath). After 1 h, the reaction was removed from the heating bath and purified by preparatory HPLC to provide the product as a white solid (7.6 mg, 31%). ¹H NMR (400 MHz, CDCl₃) δ ppm 12.09 (1H, br. s.), 8.50 (1H, t, J=5.52 Hz), 8.20 (1H, br. s.), 7.19 (2H, t, J=7.78 Hz), 6.96 (1H, t, J=8.78 Hz), 4.89 (1H, br. s.), 4.53 (2H, d, J=6.27 Hz), 4.39 (2H, s), 3.67 (3H, s), 3.30 (3H, s), 2.93 (3H, s), 2.58-2.70 (2H, m), 2.27 (3H, s), 2.01-2.23 (6H, m); LCMS (ES+, (M+H)⁺) m/z 559.3

Example 88

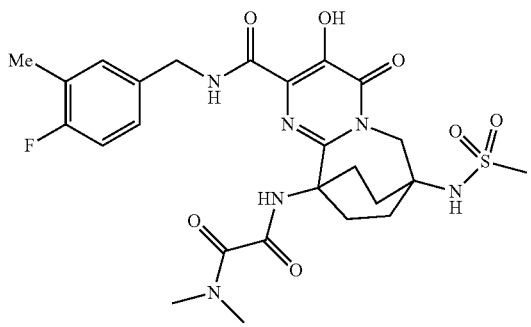 [SMILES: Cc1cc(CNC(=O)c2nc3n(c(=O)c2O)CC2(NS(C)(=O)=O)CCC3(NC(=O)C(=O)N(C)C)CC2)ccc1F]

N'-[2-[[[(4-Fluoro-3-methylphenyl)methyl]amino]carbonyl]-6,7,8,9-tetrahydro-3-hydroxy-7-[(methylsulfonyl)amino]-4-oxo-7,10-ethanopyrimidol[1,2-a]azepin-10(4H)-yl]-N,N-dimethyl-ethanediamide A vial was charged with ethanediamide, N²-[2-[[[(4-fluoro-3-methylphenyl)methyl]amino]carbonyl]-6,7,8,9-tetrahydro-3-methoxy-7-[(methylsulfonyl)amino]-4-oxo-7,10-ethanopyrimido[1,2-a]azepin-10(4H)-yl]-N¹,N¹-dimethyl-, Intermediate 59 (20 mg, 0.034 mmol), LiCl (14 mg, 0.337 mmol), and DMF (0.3 mL). The reaction was stirred at 120° C. for 1 hour. The reaction was purified by preparative HPLC to provide an off white foam. The solid was triturated in ether and filtered giving the target compound (1.8 mg, 8.5% yield) as a creamy white powder. LCMS (ES+, (M+H)⁺) m/z: 579.4.

Example 89

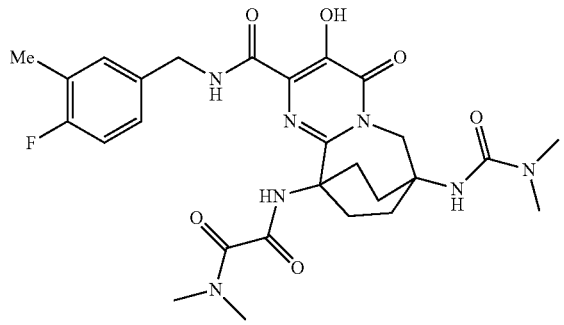 [SMILES: Cc1cc(CNC(=O)c2nc3n(c(=O)c2O)CC2(NC(=O)N(C)C)CCC3(NC(=O)C(=O)N(C)C)CC2)ccc1F]

N'-[7-[[(Dimethylamino)carbonyl]amino]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-ethanediamide A vial was charged with ethanediamide, N²-[7-[[(dimethylamino)carbonyl]amino]-2-[[[(4-fluoro-3-methylphenyl) methyl]amino]carbonyl]-6,7,8,9-tetrahydro-3-methoxy-4-oxo-7,10-ethanopyrimido[1,2-a]azepin-10(4H)-yl]-N¹,N¹-dimethyl, Intermediate 60 (24 mg, 0.041 mmol), DMF (0.3 mL), and LiCl (8.69 mg, 0.205 mmol). The reaction was stirred at 120° C. for 1 hour. The reaction was purified with a prep-HPLC to provide an off white solid. The solid was triturated in ether and filtered giving the target compound (8.2 mg, 0.013 mmol, 33% yield) as a white solid. LCMS (ES+, (M+H)⁺) m/z: 572.4.

Example 90

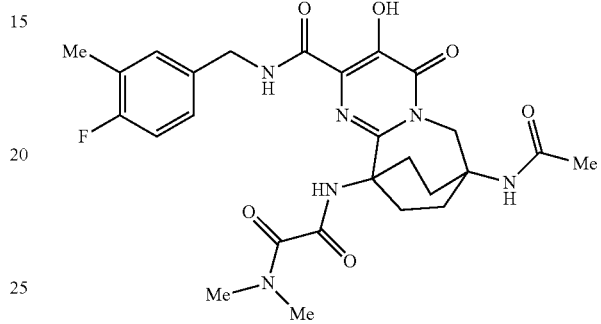

N~1~,N~1'~-[2-[[[(4-Fluoro-3-methylphenyl)methyl]amino]carbonyl]-8,9-dihydro-3-hydroxy-4-oxo-7,10-ethanopyrimido[1,2-a]azepine-7,10(4H, 6H)-diyl]bis[N~2~,N~2~-dimethyl-ethanediamide To a solution of ethanediamide, N²-[7-(acetylamino)-2-[[[(4-fluoro-3-methylphenyl)methyl]amino]carbonyl]-6,7,8,9-tetrahydro-3-methoxy-4-oxo-7,10-ethanopyrimido[1,2-a] azepin-10(4H)-yl]-N¹,N¹-dimethyl-, Intermediate 61 (32 mg, 0.058 mmol, 1 equiv) in DMF (1.0 mL) was added lithium chloride (12 mg, 0.290 mmol, 5 equiv). The reaction was then heated to 120° C. (oil bath). After 1 h, the reaction was removed from the heating bath and purified by preparatory HPLC to provide the product as a white solid (2 mg, 6%). ¹H NMR (400 MHz, CDCl₃) δ ppm 12.16 (1H, s), 8.51 (1H, t, J=5.90 Hz), 8.18 (1H, s), 7.16-7.23 (2H, m), 6.96 (1H, t, J=8.91 Hz), 5.63 (1H, br. s.), 4.53 (2H, d, J=6.27 Hz), 4.44 (2H, s), 3.30 (3H, s), 2.93 (3H, s), 2.75 (1H, s), 2.59-2.70 (2H, m), 2.27 (3H, d, J=1.51 Hz), 2.17-2.25 (2H, m), 2.07-2.17 (4H, m), 2.00 (3H, s); LCMS (ES+, (M+H)⁺) m/z 543.4

Example 91

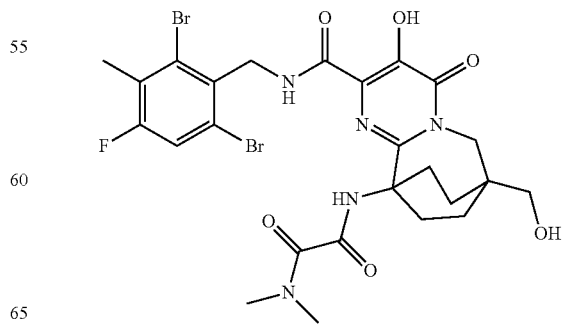

N'-[2-[[[(2,6-Dibromo-4-fluoro-3-methylphenyl)methyl]amino]carbonyl]-6,7,8,9-tetrahydro-3-hydroxy-7-(hydroxymethyl)-4-oxo-7,10-ethanopyrimido[1,2-a]azepin-10(4H)-yl]-N,N-dimethylethanediamide A solution of 7,10-ethanopyrimido[1,2-a]azepine-2-carboxylic acid, 10-[[2-(dimethylamino)-1,2-dioxoethyl]amino]-4,6,7,8,9,10-hexahydro-3-hydroxy-7-(hydroxymethyl)-4-oxo-, ethyl ester (0.02 g, 0.047 mmol), (2,6-dibromo-4-fluoro-3-methylphenyl)methanamine (0.017 g, 0.057 mmol) and Et₃N (0.066 ml, 0.473 mmol) in EtOH (2 mL) was heated at reflux for 40 h. The reaction was cooled and the product purified by preparative HPLC(CH₃CN/H₂O; 10 mmol NH₄OAc) to afford the title compound (0.0127 g, 0.018 mmol, 37.8% yield) as a white solid. $^1$H NMR (400 MHz, CDCl₃) δ: 12.15 (1H, br. s.), 8.70 (1H, s), 8.04 (1H, br. s.), 7.35 (1H, d, J=8.5 Hz), 5.01 (2H, d, J=5.3 Hz), 4.09 (2H, s), 3.51 (2H, s), 3.35 (3H, s), 2.92 (3H, s), 2.70-2.78 (2H, m), 2.35 (3H, d, J=2.0 Hz), 1.93-2.04 (2H, m), 1.74-1.84 (2H, m), 1.52-1.68 (3H, m). LCMS (M+H) calcd for $C_{25}H_{29}Br_2FN_5O_6$: 674.04. found: 674.2.

Example 92

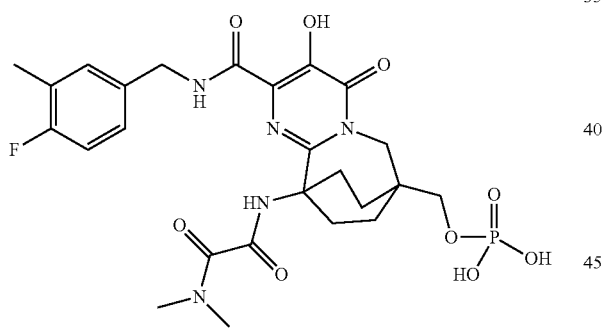

Ethanediamide, N-[2-[[[(4-fluoro-3-methylphenyl)methyl]amino]carbonyl]-6,7,8,9-tetrahydro-3-hydroxy-4-oxo-7-[(phosphonooxy)methy]-7,10-ethanopyrimido[1,2-a]azepin-10(4H)-yl]-N,N',N'-trimethyl- $^1$H NMR (500 MHz, DMSO-d₆) δ ppm 11.98 (1H, br. s.), 9.78 (1H, t, J=6.56 Hz), 8.81 (1H, s), 7.25 (1H, d, J=7.32 Hz), 7.16-7.22 (1H, m), 7.09 (1H, t, J=9.16 Hz), 4.43 (2H, d, J=6.41 Hz), 3.97 (2H, s), 3.64 (2H, d, J=4.27 Hz), 2.95 (3H, s), 2.88 (3H, s), 2.24-2.34 (2H, m), 2.21 (3H, s), 2.02-2.11 (2H, m), 1.50-1.64 (4H, m). $^{31}$P NMR (202 MHz, DMSO-d₆) δ ppm 52.26, 0.01. $^{19}$F NMR (471 MHz, DMSO-d₆) δ ppm −73.89, −120.50. $^{13}$C NMR (126 MHz, DMSO-d₆) δ ppm 168.05, 165.57, 164.28, 160.74, 158.82, 158.73, 151.35, 145.51, 134.21, 134.18, 131.11, 131.06, 127.08, 127.01, 124.30, 123.92, 123.78, 114.77, 114.58, 72.06, 72.02, 57.56, 53.42, 41.45, 36.69, 35.53, 35.46, 32.97, 29.90, 25.04, 14.12, 14.10.

Example 93

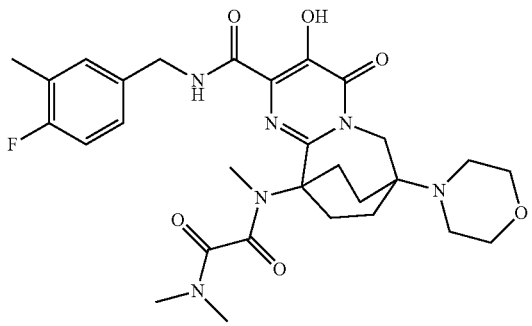 [SMILES: Cc1cc(CNC(=O)c2nc3n(c(=O)c2O)CC2(N4CCOCC4)CCC3(N(C)C(=O)C(=O)N(C)C)CC2)ccc1F]

Ethanediamide, N-[2-[[[(4-fluoro-3-methylphenyl)methyl]amino]carbonyl]-6,7,8,9-tetrahydro-3-hydroxy-7-(4-morpholinyl)-4-oxo-7,10-ethanopyrimido[1,2-a]azepin-10(4H)-yl]-N,N',N'-trimethyl- $^1$H NMR (400 MHz, CHLOROFORM-d) δ ppm 12.15 (1H, br. s.), 9.53 (1H, br. s.), 7.16-7.26 (2H, m), 6.92 (1H, t, J=9.0 Hz), 5.10 (1H, d, J=15.6 Hz), 4.54-4.65 (1H, m), 4.39-4.49 (1H, m), 3.72 (4H, t, J=4.3 Hz), 3.40 (1H, br. s.), 3.03 (3H, s), 2.99 (3H, s), 2.99 (3H, s), 2.70 (2H, br. s.), 2.57 (2H, br. s.), 2.25 (3H, s), 2.08 (4H, br. s.), 1.86 (4H, d, J=1.8 Hz). $^{19}$F NMR (376 MHz, CHLOROFORM-d) δ ppm −120.29 (1F, br. s.).

Example 94

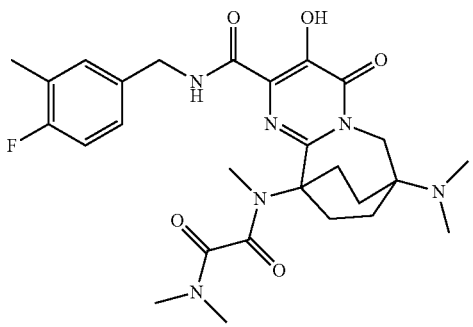 [SMILES: Cc1cc(CNC(=O)c2nc3n(c(=O)c2O)CC2(N(C)C)CCC3(N(C)C(=O)C(=O)N(C)C)CC2)ccc1F]

Ethanediamide, N-[7-(dimethylamino)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- $^1$H NMR (400 MHz, CHLOROFORM-d) δ ppm 12.16 (1H, br. s.), 9.53 (1H, br. s.), 7.14-7.27 (2H, m), 6.92 (1H, t, J=8.9 Hz), 5.07 (1H, d, J=15.1 Hz), 4.52-4.66 (1H, m), 4.38-4.49 (1H, m), 3.31-3.47 (2H, m), 3.03 (3H, s), 2.99 (3H, s), 2.99 (3H, s), 2.33 (6H, s), 2.25 (3H, d, J=1.3 Hz), 1.99-2.17

(5H, m), 1.77-1.91 (2H, m). ¹⁹F NMR (376 MHz, CHLOROFORM-d) δ ppm −120.33 (1F, s).

Example 95

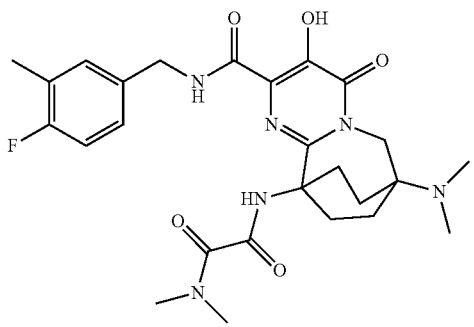 [SMILES: Cc1cc(CNC(=O)c2nc3n(c(=O)c2O)CC2(N(C)C)CCC3(NC(=O)C(=O)N(C)C)CC2)ccc1F]

Ethanediamide, N'-[7-(dimethylamino)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- A flask was charged with Intermediate 62 (98 mg, 0.181 mmol), DMF (1 mL) and LiCl (77 mg, 1.81 mmol). The reaction was stirred at 120° C. for 1 hour. The crude product was purified by preparative-HPLC. The appropriate fractions were combined and evaporated giving 56 mg of a white powder. The powder was triturated in ether. The product was re-purified by preparative-HPLC using acetonitrile. The appropriate fractions were combined and evaporated giving a white powder. The powder was triturated in ether and filtered giving the title compound as a white powder, 34 mg. LCMS, observed mass, 529.3, retention time, 2.18 minutes.

Example 96

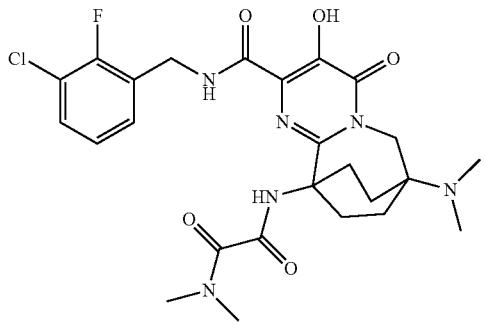 [SMILES: CN(C)C(=O)C(=O)NC12CCC(N(C)C)(CC1)Cn1c2nc(C(=O)NCc2cccc(Cl)c2F)c(O)c1=O]

Ethanediamide, N'-[2-[[[(3-chloro-2-fluorophenyl)methyl]amino]carbonyl]-7-(dimethylamino)-6,7,8,9-tetrahydro-3-hydroxy-4-oxo-7,10-ethanopyrimido[1,2-a]azepin-10(4H)-yl]-N,N-dimethyl- ¹H NMR (400 MHz, CHLOROFORM-d) δ ppm 8.72 (t, J=6.0 Hz, 1H), 7.75 (s, 1H), 7.36-7.30 (m, 2H), 7.10-7.04 (m, 1H), 4.66 (d, J=6.3 Hz, 2H), 4.19 (s, 2H), 3.50 (s, 2H), 3.26 (s, 3H), 2.95 (s, 3H), 2.49 (ddd, J=14.2, 8.8, 5.8 Hz, 2H), 2.34 (s, 6H), 2.15 (dt, J=14.3, 6.9 Hz, 3H), 1.94-1.86 (m, 3H), 1.79 (dt, J=13.6, 6.8 Hz, 3H).

Example 97

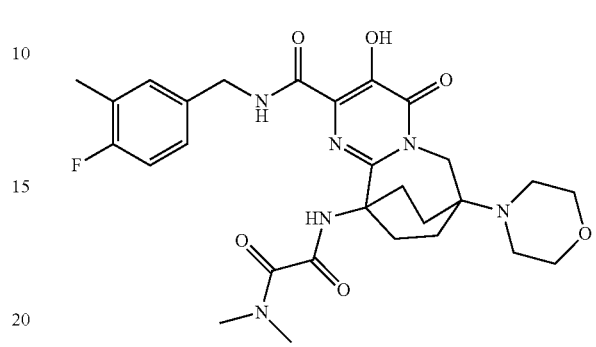

Ethanediamide, N'-[2-[[[(4-fluoro-3-methylphenyl)methyl]amino]carbonyl]-6,7,8,9-tetrahydro-3-hydroxy-7-(4-morpholinyl)-4-oxo-7,10-ethanopyrimido[1,2-a]azepin-10(4H)-yl]-N,N-dimethyl- A flask was charged with N1-(2-((4-fluoro-3-methylbenzyl)carbamoyl)-3-methoxy-7-morpholino-4-oxo-4,6,7,8,9,10-hexahydro-7,10-ethanopyrimido[1,2-a]azepin-10-yl)-N2,N2-dimethyloxalamide, Intermediate 63 (120 mg, 0.205 mmol), DMF (1 mL) and LiCl (87 mg, 2.05 mmol). The reaction was stirred at 120° C. for 1 hour. The crude product was purified by preparative-HPLC. The appropriate fractions were combined and evaporated giving a white solid which was triturated in ether and filtered giving the title compound (78 mg, 0.133 mmol, 64.7% yield)] as a white powder. 1H NMR & 19F NMR were consistent with the product. 1H NMR (400 MHz, CHLOROFORM-d) δ ppm 12.04 (1H, br. s.), 8.60 (1H, t, J=6.15 Hz), 7.91 (1H, s), 7.16-7.22 (2H, m), 6.96 (1H, t, J=8.91 Hz), 4.52 (2H, d, J=6.27 Hz), 4.19 (2H, s), 3.68-3.76 (4H, m), 3.27 (3H, s), 2.92 (3H, s), 2.59-2.67 (4H, m), 2.53 (2H, ddd, J=14.18, 8.91, 5.52 Hz), 2.27 (3H, d, J=1.51 Hz), 2.12 (3H, td, J=14.18, 7.53 Hz), 1.87-1.96 (2H, m), 1.68 (2H, ddd, J=13.18, 6.78, 6.65).

Example 98

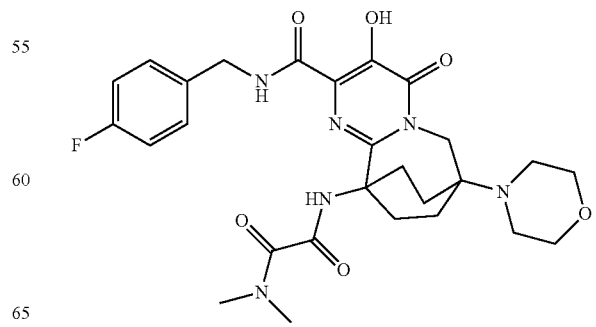

Ethanediamide, N'-[2-[[[(4-fluorophenyl)methyl]amino]carbonyl]-6,7,8,9-tetrahydro-3-hydroxy-7-(4-morpholinyl)-4-oxo-7,10-ethanopyrimido[1,2-a]azepin-10(4H)-yl]-N,N-dimethyl- ¹H NMR (400 MHz, CHLOROFORM-d) δ ppm 8.64 (br. s., 1H), 7.88 (s, 1H), 7.37 (dd, J=8.5, 5.5 Hz, 2H), 7.27 (s, 1H), 7.03 (t, J=8.7 Hz, 2H), 4.56 (d, J=6.3 Hz, 2H), 4.19 (s, 2H), 3.72 (br. s., 3H), 3.27 (s, 2H), 2.93 (s, 3H), 2.63 (br. s., 3H), 2.53 (ddd, J=14.2, 8.8, 5.6 Hz, 2H), 2.29-2.00 (m, 2H), 2.00-1.80 (m, 2H), 1.68 (dt, J=12.7, 6.6 Hz, 2H).

Example 99

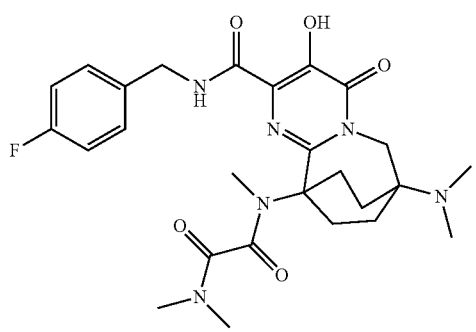 [SMILES: CN(C)C(=O)C(=O)N(C)C12CCC(N(C)C)(CC1)Cn1c2nc(C(=O)NCc2ccc(F)cc2)c(O)c1=O]

Ethanediamide, N-[7-(dimethylamino)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- LC/MS. Start % B=0, Final % B=100, Gradient Time=4 min, Flow Rate=0.8 ml/min, Wavelength=220, Solvent Pair=Water/Acetonitrile/0.1% TFA, Solvent A=90% Water/10% Acetonitrile/0.1% TFA, Solvent B=10% Water/90% Acetonitrile/0.1% TFA Column; Phenomenex LUNA C18, 50×2, 3 u. Observed mass, 529.5 (M+1), retention time. 1.79 min.

Example 100

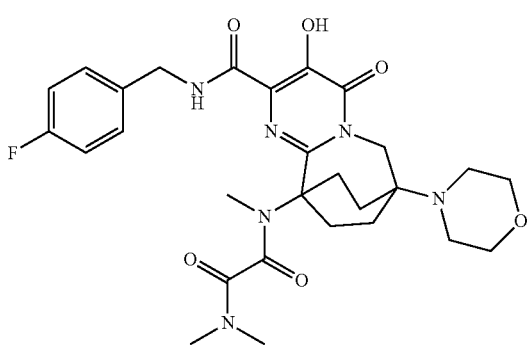 [SMILES: CN(C)C(=O)C(=O)N(C)C12CCC(N3CCOCC3)(CC1)Cn1c2nc(C(=O)NCc2ccc(F)cc2)c(O)c1=O]

Ethanediamide, N-[2-[[[(4-fluorophenyl)methyl]amino]carbonyl]-6,7,8,9-tetrahydro-3-hydroxy-7-(4-morpholinyl)-4-oxo-7,10-ethanopyrimido[1,2-a]azepin-10(4H)-yl]-N,N',N'-trimethyl- ¹H NMR (400 MHz, CHLOROFORM-d) δ ppm 9.67 (t, J=6.3 Hz, 1H), 7.38 (dd, J=7.8, 5.5 Hz, 2H), 7.00 (t, J=8.4 Hz, 2H), 5.47 (d, J=15.6 Hz, 1H), 4.67-4.56 (m, 1H), 4.52-4.44 (m, 1H), 4.07 (br. s., 4H), 3.59 (d, J=15.1 Hz, 1H), 3.51-3.15 (m, 5H), 3.04 (s, 3H), 3.00 (br. s., 3H), 2.99 (br. s., 3H), 2.63 (dd, J=12.8, 9.8 Hz, 1H), 2.49-2.23 (m, 4H), 2.18-2.08 (m, 1H), 1.78-1.64 (m, 1H).

Example 101

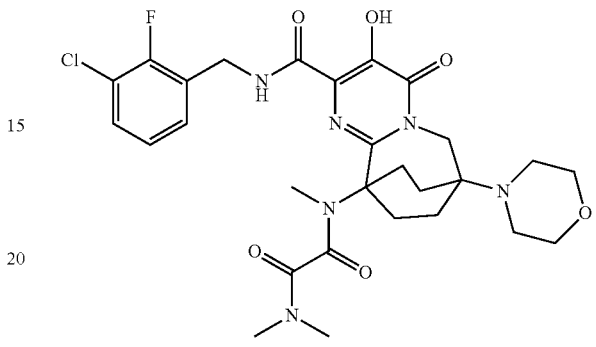

Ethanediamide, N-[2-[[[(3-chloro-2-fluorophenyl)methyl]amino]carbonyl]-6,7,8,9-tetrahydro-3-hydroxy-7-(4-morpholinyl)-4-oxo-7,10-ethanopyrimido[1,2-a]azepin-10(4H)-yl]-N,N',N'-trimethyl- ¹H NMR (400 MHz, CHLOROFORM-d) δ ppm 12.01 (br. s., 1H), 9.60 (t, J=6.1 Hz, 1H), 7.34-7.28 (m, 2H), 7.06-6.99 (m, 1H), 5.10 (d, J=15.3 Hz, 1H), 4.67 (dd, J=9.3, 6.5 Hz, 2H), 3.72 (t, J=4.4 Hz, 4H), 3.46-3.32 (m, 2H), 3.01 (d, J=6.5 Hz, 6H), 2.95 (s, 3H), 2.77-2.65 (m, 2H), 2.61-2.50 (m, 2H), 2.19-2.05 (m, 3H), 1.93-1.77 (m, 3H), 1.49-1.37 (m, 1H)

Example 102

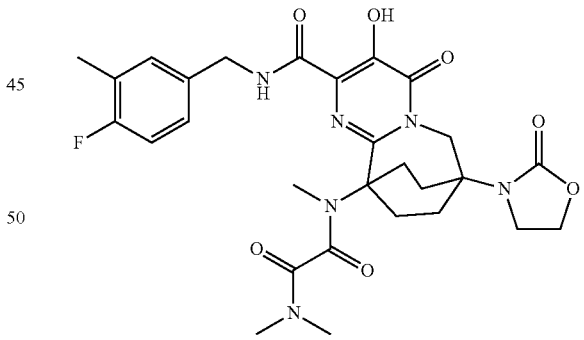

Ethanediamide, N-[2-[[[(4-fluoro-3-methylphenyl)methyl]amino]carbonyl]-6,7,8,9-tetrahydro-3-hydroxy-4-oxo-7-(2-oxo-3-oxazolidinyl)-7,10-ethanopyrimido[1,2-a]azepin-10(4H)-yl]-N,N',N'-trimethyl- ¹H NMR (400 MHz, CHLOROFORM-d) δ ppm 9.53 (1H, br. s.), 7.15-7.26 (2H, m), 6.88-6.96 (1H, m), 5.06 (1H, d, J=14.3 Hz), 4.53-4.65 (1H, m), 4.39-4.49 (1H, m), 4.27-4.36 (2H, m), 3.92 (1H, d, J=15.8 Hz), 3.69 (2H, t, J=7.8 Hz), 3.38-3.48 (1H, m), 3.03 (3H, s), 3.01 (3H, s), 2.99 (3H, s), 2.54 (2H, br. s.), 2.25 (3H, d, J=1.5 Hz), 2.07-2.24 (6H, m).

Example 103

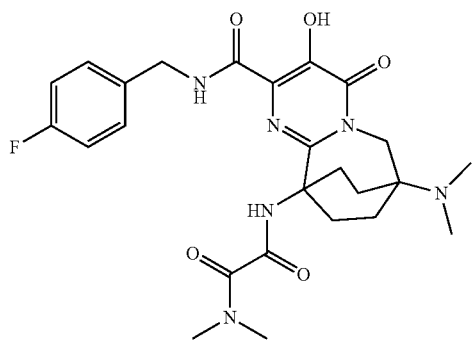 [SMILES: CN(C)C(=O)C(=O)NC12CCC(N(C)C)(CC1)Cn1c2nc(C(=O)NCc2ccc(F)cc2)c(O)c1=O]

Ethanediamide, N'-[7-(dimethylamino)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- $^1$H NMR (400 MHz, CHLOROFORM-d) δ ppm 8.64 (1H, br. s.), 7.88 (1H, br. s.), 7.38 (2H, dd, J=8.5, 5.5 Hz), 7.03 (2H, t, J=8.7 Hz), 4.56 (2H, d, J=6.3 Hz), 4.19 (2H, s), 3.27 (3H, s), 2.93 (3H, s), 2.53 (2H, ddd, J=14.2, 8.7, 5.8 Hz), 2.33 (6H, s), 2.04-2.17 (2H, m), 1.85-1.96 (2H, m), 1.71-1.85 (2H, m).

Example 104

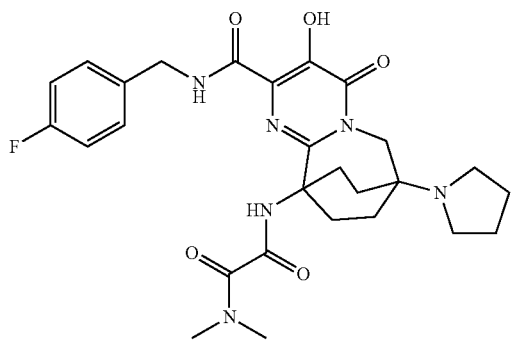 [SMILES: CN(C)C(=O)C(=O)NC12CCC(N3CCCC3)(CC1)Cn1c2nc(C(=O)NCc2ccc(F)cc2)c(O)c1=O]

Ethanediamide, N'-[2-[[[(4-fluorophenyl)methyl]amino]carbonyl]-6,7,8,9-tetrahydro-3-hydroxy-4-oxo-7-(1-pyrrolidinyl)-7,10-ethanopyrimido[1,2-a]azepin-10(4H)-yl]-N,N-dimethyl- $^1$H NMR (400 MHz, CHLOROFORM-d) δ ppm 12.01 (br. s., 1H), 8.66 (t, J=5.9 Hz, 1H), 7.86 (s, 1H), 7.41-7.35 (m, 2H), 7.07-7.00 (m, 2H), 4.56 (d, J=6.3 Hz, 2H), 4.23 (s, 2H), 3.27 (s, 3H), 2.92 (s, 3H), 2.73 (br. s., 4H), 2.53 (ddd, J=14.2, 8.8, 5.8 Hz, 2H), 2.11 (td, J=14.1, 7.0 Hz, 3H), 2.03-1.94 (m, 3H), 1.85-1.76 (m, 6H).

Example 105

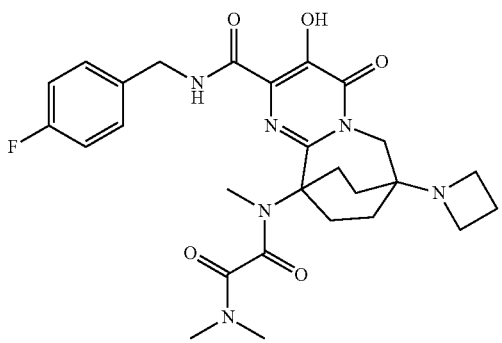 [SMILES: CN(C)C(=O)C(=O)N(C)C12CCC(N3CCC3)(CC1)Cn1c2nc(C(=O)NCc2ccc(F)cc2)c(O)c1=O]

Ethanediamide, N-[7-(1-azetidinyl)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- $^1$H NMR (400 MHz, CHLOROFORM-d) δ ppm 13.61 (br. s., 1H), 9.67 (t, J=6.0 Hz, 1H), 7.38 (dd, J=8.3, 5.5 Hz, 2H), 6.99 (t, J=8.7 Hz, 2H), 5.47 (d, J=14.8 Hz, 1H), 4.66-4.57 (m, 1H), 4.52-4.43 (m, 1H), 4.34-4.02 (m, 5H), 3.69 (d, J=14.8 Hz, 1H), 3.47-3.35 (m, 1H), 3.03 (s, 3H), 3.00 (s, 3H), 2.99 (br. s., 3H), 2.78 (br. s., 1H), 2.46 (br. s., 1H), 2.37-2.19 (m, 3H), 2.10 (t, J=10.2 Hz, 1H), 1.86 (t, J=9.4 Hz, 1H), 1.69 (d, J=10.0 Hz, 1H).

Example 106

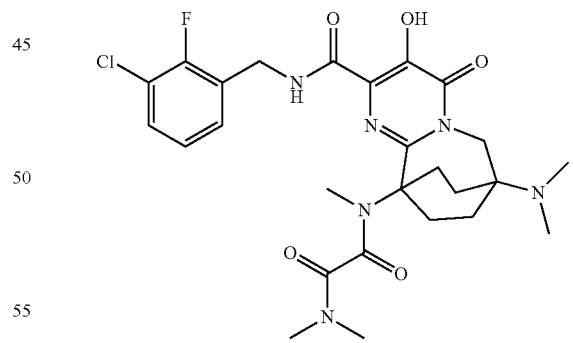

Ethanediamide, N-[2-[[[(3-chloro-2-fluorophenyl)methyl]amino]carbonyl]-7-(dimethylamino)-6,7,8,9-tetrahydro-3-hydroxy-4-oxo-7,10-ethanopyrimido[1,2-a]azepin-10(4H)-yl]-N,N',N'-trimethyl- $^1$H NMR (400 MHz, CHLOROFORM-d) δ ppm 11.99 (br. s., 1H), 9.60 (t, J=6.1 Hz, 1H), 7.35-7.28 (m, 2H), 7.06-6.99 (m, 1H), 5.07 (d, J=15.6 Hz, 1H), 4.75-4.60 (m, 2H), 3.46-

3.30 (m, 2H), 3.01 (d, J=5.8 Hz, 6H), 2.95 (s, 3H), 2.33 (s, 6H), 2.17-2.00 (m, 4H), 1.91-1.75 (m, 2H), 1.55-1.45 (m, 1H).

Example 107

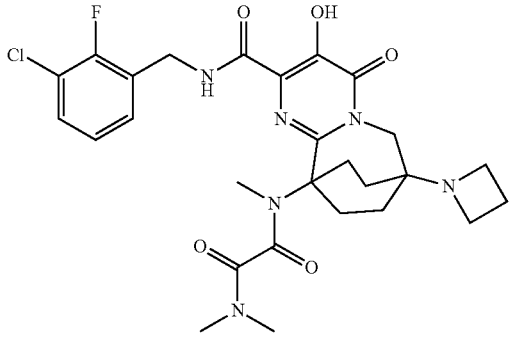 [SMILES: CN(C)C(=O)C(=O)N(C)C12CCC(N3CCC3)(CC1)Cn1c2nc(C(=O)NCc2cccc(Cl)c2F)c(O)c1=O]

Ethanediamide, N-[7-(1-azetidinyl)-2-[[[(3-chloro-2-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- $^1$H NMR (400 MHz, CHLOROFORM-d) δ ppm 9.61 (t, J=6.1 Hz, 1H), 7.33-7.28 (m, 2H), 7.06-6.99 (m, 1H), 4.87 (d, J=14.8 Hz, 1H), 4.67 (dd, J=10.5, 6.3 Hz, 2H), 3.46 (d, J=15.1 Hz, 1H), 3.38-3.28 (m, 4H), 3.00 (d, J=3.0 Hz, 6H), 2.95 (s, 3H), 2.13-2.04 (m, 6H), 1.91 (d, J=12.8 Hz, 1H), 1.82-1.72 (m, 1H), 1.70-1.62 (m, 1H), 1.42-1.31 (m, 1H).

Example 108

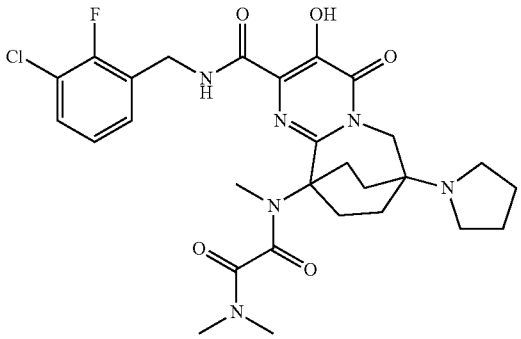 [SMILES: CN(C)C(=O)C(=O)N(C)C12CCC(N3CCCC3)(CC1)Cn1c2nc(C(=O)NCc2cccc(Cl)c2F)c(O)c1=O]

Ethanediamide, N-[2-[[[(3-chloro-2-fluorophenyl)methyl]amino]carbonyl]-6,7,8,9-tetrahydro-3-hydroxy-4-oxo-7-(1-pyrrolidinyl)-7,10-ethanopyrimido[1,2-a]azepin-10(4H)-yl]-N,N',N'-trimethyl- $^1$H NMR (400 MHz, CHLOROFORM-d) δ ppm 9.61 (t, J=6.1 Hz, 1H), 7.34-7.28 (m, 2H), 7.02 (td, J=7.9, 1.0 Hz, 1H), 5.07 (d, J=15.3 Hz, 1H), 4.67 (dd, J=10.2, 6.4 Hz, 2H), 3.54 (d, J=14.1 Hz, 1H), 3.44-3.31 (m, 1H), 3.01 (d, J=5.8 Hz, 6H), 2.95 (s, 3H), 2.80 (d, J=5.8 Hz, 2H), 2.71 (d, J=4.5 Hz, 2H), 2.16-2.08 (m, 3H), 2.04-1.92 (m, 3H), 1.85-1.78 (m, 4H).

Example 109

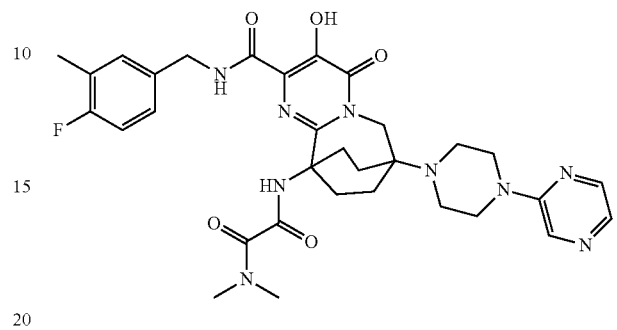

Ethanediamide, N'-[2-[[[(4-fluoro-3-methylphenyl)methyl]amino]carbonyl]-6,7,8,9-tetrahydro-3-hydroxy-4-oxo-7-(4-pyrazinyl-1-piperazinyl)-7,10-ethanopyrimido[1,2-a]azepin-10(4H)-yl]-N,N-dimethyl- $^1$H NMR (400 MHz, CHLOROFORM-d) δ ppm 12.17 (br. s., 1H), 8.64 (t, J=6.3 Hz, 1H), 7.72 (s, 1H), 7.22-7.14 (m, 2H), 6.99-6.92 (m, 1H), 4.51 (d, J=6.3 Hz, 2H), 4.15 (s, 2H), 3.54-3.41 (m, 3H), 3.25 (s, 3H), 3.16-3.03 (m, 2H), 2.92 (s, 7H), 2.50 (ddd, J=14.2, 8.8, 5.5 Hz, 2H), 2.27 (d, J=1.5 Hz, 3H), 2.18 (dt, J=13.7, 7.0 Hz, 3H), 2.05-1.95 (m, 2H), 1.61-1.51 (m, 2H), 1.38 (d, J=6.8 Hz, 6H).

Example 110

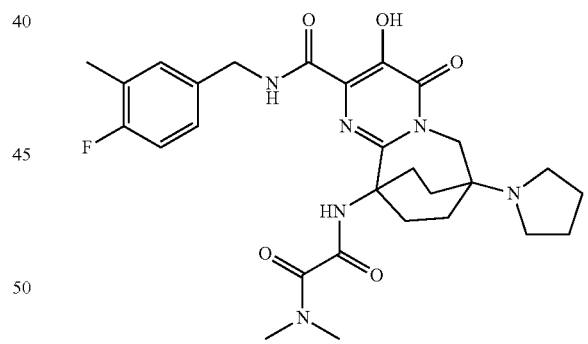

Ethanediamide, N'-[2-[[[(4-fluoro-3-methylphenyl)methyl]amino]carbonyl]-6,7,8,9-tetrahydro-3-hydroxy-4-oxo-7-(1-pyrrolidinyl)-7,10-ethanopyrimido[1,2-a]azepin-10(4H)-yl]-N,N-dimethyl- $^1$H NMR (400 MHz, CHLOROFORM-d) δ ppm 12.05 (br. s., 1H), 8.63 (t, J=6.3 Hz, 1H), 7.90 (s, 1H), 7.33-7.24 (m, 3H), 7.24-7.16 (m, 1H), 7.02-6.93 (m, 1H), 4.52 (d, J=6.3 Hz, 3H), 4.23 (s, 1H), 3.32-3.24 (m, 2H), 2.92 (s, 2H), 2.73 (br. s., 3H), 2.53 (ddd, J=14.3, 8.9, 5.9 Hz, 2H), 2.27 (d, J=1.8 Hz, 2H), 2.20-2.05 (m, 2H), 2.05-1.89 (m, 2H), 1.89-1.73 (m, 5H), 1.65 (br. s., 2H), 1.24 (d, J=17.8 Hz, 1H) LCMS: observed mass 555.4, retention time, 2.03 minutes. Start %

B=0 Final % B=100, Gradient Time=4 min, Flow Rate=0.8 ml/min, Wavelength=220, Solvent Pair=Water/Acetonitrile/0.1% TFA, Solvent A=90% Water/10% Acetonitrile/0.1% TFA, Solvent B=10% Water/90% Acetonitrile/0.1% TFA, Column, Phenomenex LUNA C18, 50×2, 3 u.

Example 111

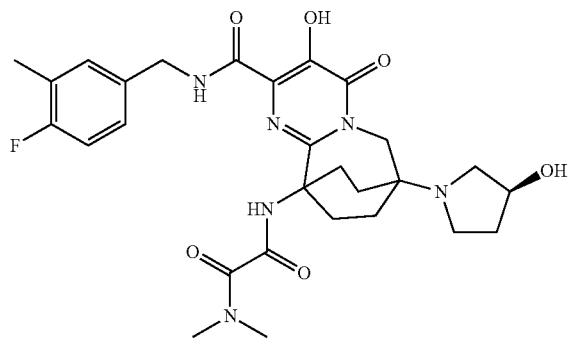 [SMILES: Cc1cc(CNC(=O)c2nc3n(c(=O)c2O)CC2(N4CC[C@H](O)C4)CCC3(NC(=O)C(=O)N(C)C)CC2)ccc1F]

Ethanediamide, N'-[2-[[[(4-fluoro-3-methylphenyl)methyl]amino]carbonyl]-6,7,8,9-tetrahydro-3-hydroxy-7-[(3S)-3-hydroxy-1-pyrrolidinyl]-4-oxo-7,10-ethanopyrimido[1,2-a]azepin-10(4H)-yl]-N,N-dimethyl- LCMS: observed mass 571.4, retention time 1.92 minutes. Start % B=0, Final % B=100, Gradient Time=4 min, Flow Rate=0.8 ml/min, Wavelength=220, Solvent Pair=Water/Acetonitrile/0.1% TFA, Solvent A=90% Water/10% Acetonitrile/0.1% TFA, Solvent B=10% Water/90% Acetonitrile/0.1% TFA, Column, Phenomenex LUNA C18, 50×2, 3 u.

Example 112

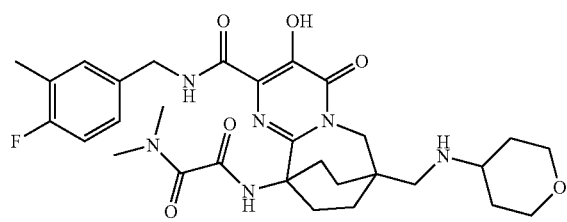 [SMILES: Cc1cc(CNC(=O)c2nc3n(c(=O)c2O)CC2(CNC4CCOCC4)CCC3(NC(=O)C(=O)N(C)C)CC2)ccc1F]

Ethanediamide, N'-[2-[[[(4-fluoro-3-methylphenyl)methyl]amino]carbonyl]-6,7,8,9-tetrahydro-3-hydroxy-4-oxo-7-[[(tetrahydro-2H-pyran-4-yl)amino]methyl]-7,10-ethanopyrimido[1,2-a]azepin-10(4H)-yl]-N,N-dimethyl- Intermediate 65 (62.0 mg, 0.09 mmol) in CH$_2$Cl$_2$ (1 mL) and TFA (1.0 mL) was stirred at rt for 1 h. The crude product was purified by preparative-HPLC. $^1$H NMR (500 MHz, DMSO-d$_6$) δ ppm 1.55-1.67 (m, 4H) 1.68-1.77 (m, 2H) 1.99 (d, J=12.51 Hz, 2H) 2.05-2.14 (m, 2H) 2.21 (d, J=1.53 Hz, 3H) 2.25-2.34 (m, 2H) 2.87 (s, 3H) 2.92-2.97 (m, 3H) 2.97-3.03 (m, 2H) 3.30 (t, J=11.44 Hz, 3H) 3.94 (dd, J=11.29, 3.97 Hz, 2H) 4.02 (s, 2H) 4.43 (d, J=6.41 Hz, 2H) 7.05-7.12 (m, 1H) 7.19 (ddd, J=8.16, 5.42, 2.59 Hz, 1H) 7.22-7.29 (m, 1H) 8.33 (br. s., 2H) 8.84 (s, 1H) 9.77 (t, J=6.56 Hz, 1H) 12.02 (br. s., 1H).

Example 113

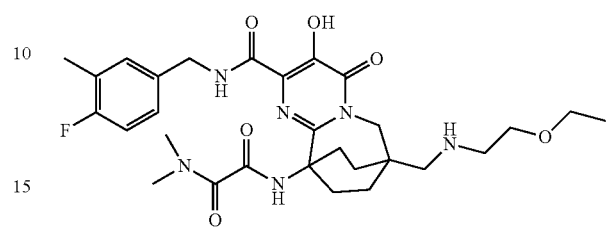

Ethanediamide, N'-[7-[[(2-ethoxyethyl)amino]methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- $^1$H NMR (500 MHz, DMSO-d$_6$) δ ppm 1.12-1.22 (m, 3H) 1.54-1.67 (m, 2H) 1.67-1.78 (m, 2H) 2.08 (ddd, J=14.19, 8.55, 5.95 Hz, 2H) 2.21 (d, J=1.22 Hz, 3H) 2.29 (ddd, J=13.73, 7.32, 7.02 Hz, 2H) 2.81-2.90 (m, 3H) 2.90-2.96 (m, 3H) 2.98 (d, J=7.02 Hz, 2H) 3.12-3.21 (m, 2H) 3.52 (q, J=7.02 Hz, 2H) 3.66 (t, J=5.34 Hz, 2H) 4.02 (s, 2H) 4.43 (d, J=6.41 Hz, 2H) 7.05-7.14 (m, 1H) 7.15-7.23 (m, 1H) 7.23-7.29 (m, 1H) 8.43 (br. s., 2H) 8.84 (s, 1H) 9.77 (t, J=6.56 Hz, 1H) 12.01 (br. s., 1H). LCMS: r.t.=1.87 min., [M+H]$^+$=587.3 Phenomenex Luna 2.0×30 mm 3 um; Solvent A=90% water-10% methanol-0.1% TFA, Solvent B=10% water-90% methanol-0.1% TFA; gradient=0% to 100% solvent B over 2 min. and then hold for 1 min.; Flow rate=1 ml/min; inj. vol.=3 ul; wavelength=220 nm.

Example 114

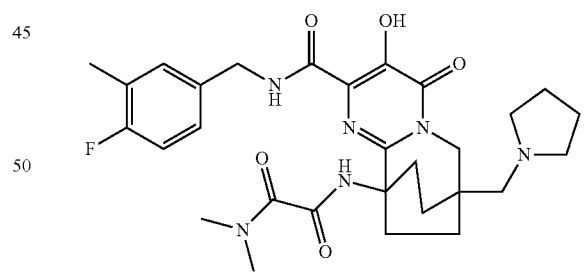

Ethanediamide, N'-[2-[[[(4-fluoro-3-methylphenyl)methyl]amino]carbonyl]-6,7,8,9-tetrahydro-3-hydroxy-4-oxo-7-(1-pyrrolidinylmethyl)-7,10-ethanopyrimido[1,2-a]azepin-10(4H)-yl]-N,N-dimethyl- $^1$H NMR (500 MHz, CD$_3$OD) δ ppm 1.81 (2H, br, 9a, 13a-CH$_2$), 1.96 (2H, br, 9b, 13b-CH$_2$), 2.08 (2H, br, 16a, 17a-CH$_2$), 2.21 (2H, br, 16b, 17b-CH$_2$), 2.24 (3H, d, J=1.5 Hz, 31-CH$_3$), 2.27-2.38 (2H, m, 10a, 12a-CH$_2$), 2.38-2.50 (2H, m, 10b, 12b-CH$_2$), 2.98, 3.08 (2×3H, 2s, 21,22-NCH$_3$), 3.27 (2H, br, 15a, 16a-CH$_2$), 3.41 (2H, s, 14-NCH$_2$), 3.87

(2H, br, 15b, 16b-CH$_2$), 4.18 (2H, s, 7-NCH$_2$), 4.53 (2H, d, J=4.9 Hz, 24-NCH$_2$), 6.95 (1H, t, J=9 Hz, 29-CH), 7.16-7.24 (1H, m, 30-CH), 7.27 (1H, d, J=7.3 Hz, 26-CH), 8.93 (<1H, s, 19-CONH), 9.72 (<1H, t, J=6.3 Hz, 23-CONH). $^{19}$F-NMR: −122.6 ppm (28-F), and −77.68 (qt, TFA).

Example 115

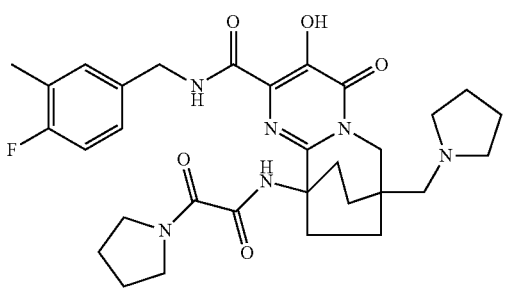 [SMILES: Cc1cc(CNC(=O)c2nc3n(c(=O)c2O)CC2(CN4CCCC4)CCC3(NC(=O)C(=O)N3CCCC3)CC2)ccc1F]

7,10-Ethanopyrimido[1,2-a]azepine-2-carboxamide, 10-[[1,2-dioxo-2-(1-pyrrolidinyl)ethyl]amino]-N-[(4-fluoro-3-methylphenyl)methyl]-4,6,7,8,9,10-hexahydro-3-hydroxy-4-oxo-7-(1-pyrrolidinylmethyl)-

$^1$H NMR (500 MHz, CD$_3$OD) δ ppm 1.81 (2H, br, 9a, 13a-CH$_2$), 1.89-2.00 (5H, m, 22,23-CH$_2$, 9b, 13b-CH$_2$), 2.09 (2H, br, 16a, 17a-CH$_2$), 2.21 (2H, br, 16b, 17b-CH$_2$), 2.25 (3H, d, J=1.8 Hz, 33-CH$_3$), 2.36 (2H, br.s, 10a, 12a-CH$_2$), 2.47 (2H, br.s, 10b, 12b-CH$_2$), 3.28 (2H, br, 15a, 16a-CH$_2$), 3.41 (2H, br.s, 14-NCH$_2$), 3.45, 3.68 (2×2H, 2t, J=6.5 Hz, 21,24-NCH$_2$), 3.86 (2H, br, 15b, 16b-CH$_2$), 4.18 (2H, s, 7-NCH$_2$), 4.50-4.58 (2H, m, 26-NCH$_2$), 6.97 (1H, dd, J=9.5, 8.9 Hz, 31-CH), 7.21 (1H, m, 32-CH), 7.26 (1H, d, J=7.0 Hz, 28-CH), 8.97 (<1H, s, 19-CONH), 9.30 (<1H, t, J=7 Hz, 25-CONH). F-NMR (CD$_3$OD): −122.6 ppm (28-F), and −77.7 (TFA).

Example 116

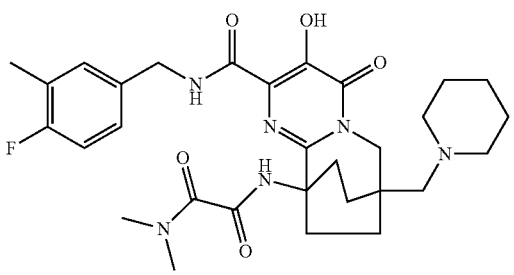 [SMILES: Cc1cc(CNC(=O)c2nc3n(c(=O)c2O)CC2(CN4CCCCC4)CCC3(NC(=O)C(=O)N(C)C)CC2)ccc1F]

Ethanediamide, N'-[2-[[[(4-fluoro-3-methylphenyl)methyl]amino]carbonyl]-6,7,8,9-tetrahydro-3-hydroxy-4-oxo-7-(1-piperidinylmethyl)-7,10-ethanopyrimido[1,2-a]azepin-10(4H)-yl]-N,N-dimethyl- $^1$H NMR (500 MHz, CD$_3$OD) δ ppm 1.62 (2H, br, 9a, 13a-CH$_2$), 1.81 (2H, br, 9b, 13b-CH$_2$), 1.87-2.08 (6H, br, 16,17,18-CH$_2$), 2.24 (3H, d, J=1.5 Hz, 32-CH$_3$), 2.34 (2H, br, 10a, 12a-CH$_2$), 2.43 (2H, br, 10b, 12b-CH$_2$), 2.98, 3.08 (2×3H, 2s, 22,23-NCH$_3$), 3.12-3.26 (2H, br, 15a, 19a-CH$_2$), ~3.3 (2H, s, 14-NCH$_2$; not seen or overlapped with MeOD), 3.50-3.75 (2H, br, 15b, 19b-CH$_2$), 4.19 (2H, s, 7-NCH$_2$), 4.53 (2H, d, J=5.2 Hz, 25-NCH$_2$), 6.95 (1H, t, J=9 Hz, 30-CH), 7.22 (1H, m, 31-CH), 7.27 (1H, d, J=7.3 Hz, 27-CH), 8.93 (<1H, s, 20-CONH), 9.72 (<1H, t, J=5.8 Hz, 24-CONH).

Example 117

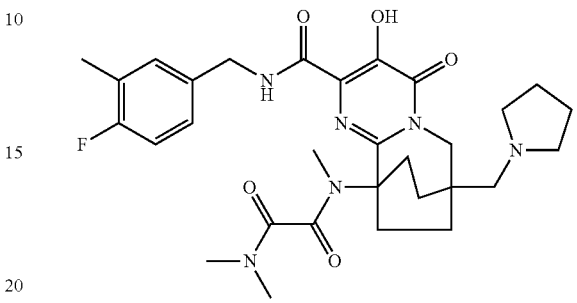

Ethanediamide, N-[2-[[[(4-fluoro-3-methylphenyl)methyl]amino]carbonyl]-6,7,8,9-tetrahydro-3-hydroxy-4-oxo-7-(1-pyrrolidinylmethyl)-7,10-ethanopyrimido[1,2-a]azepin-10(4H)-yl]-N,N',N'-trimethyl- $^1$H NMR (500 MHz, CDCl$_3$) δ ppm 1.57-1.69 (1H, br, 9a- or 13a-CH$_2$), 1.74 (2H, br, 9b- or 13b-CH$_2$), 2.01-2.28 (8H, m, 9b, 13b, 16,17, 10a, 12a-CH$_2$), 2.24 (3H, s, 32-CH$_3$), 3.00 (3H, s, 22 or 23-NCH$_3$), 3.01 (3H, s, 19-NCH$_3$), 3.04 (3H, s, 22 or 23-NCH$_3$), 3.18 (2H, br, 15a, 18a-CH$_2$), 3.29-3.50 (5H, m, 10b, 12b-CH$_2$, 14-NCH$_2$, 7a-NCH$_2$), 3.99 (2H, br, 15b, 18b-CH$_2$), 4.53-4.61 (1H, m, 24a-NCH$_2$), 4.41-4.49 (1H, m, 24b-NCH$_2$), 4.78 (2H, d, J=15.0 Hz, 7b-NCH$_2$), 6.93 (1H, t, J=9 Hz, 30-CH), 7.14-7.19 (1H, m, 31-CH), 7.21 (1H, d, J=7.3 Hz, 27-CH), 9.71 (<1H, t, J=6.3 Hz, 24-CONH), 10.0 (<1H, br, 14-NH$^+$), 11.1 (<1H, br, 5-OH). $^{19}$F-NMR (CDCl$_3$): −119.8 ppm (29-F), and −76.2 (qt, TFA). $^{13}$C NMR (126 MHz, CDCl$_3$) δ ppm 14.6, 23.0, 23.4, 25.2, 28.1, 28.6, 32.4, 33.6, 34.0, 35.6, 37.0, 42.6, 53.1, 57.9, 58.7, 62.8 (11-C), 65.3, 114.9, 124.8, 126.6, 127.0, 131.3, 133.6, 145.9, 149.8, 160.3, 160.6, 160.7, 165.4, 166.8, 168.3

Example 118

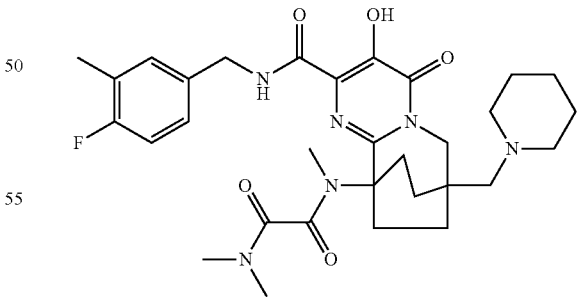

Ethanediamide, N-[2-[[[(4-fluoro-3-methylphenyl)methyl]amino]carbonyl]-6,7,8,9-tetrahydro-3-hydroxy-4-oxo-7-(1-piperidinylmethyl)-7,10-ethanopyrimido[1,2-a]azepin-10(4H)-yl]-N,N',N'-trimethyl- $^1$H NMR (500 MHz, CDCl$_3$) δ ppm 1.35-1.47 (1H, br, 9a- or 13a-CH$_2$), 1.53 (2H, br, 17-CH$_2$?), 1.58-1.68 (1H, br, 9a- or 13a-CH$_2$), 1.87 (4H, br, 16,18-CH$_2$?), 2.02 (1H, m, 9b or 13b-CH$_2$), 2.16-2.24 (2H, m, 9b or 13b, and 10a or 12a-CH$_2$), 2.26 (3H, d, J=1.2 Hz, 33-CH$_3$), 2.38-2.56 (2H, m, 10a or 12a, and 10b or 12b-CH$_2$), 2.99 (3H, s, 20-NCH$_3$), 3.00 3.04 (2×3H, 2s, 23, 24-NCH$_3$), 3.05-3.08-3.18-3.12 (2H, ABq, 14-NCH$_2$), 3.38 (1H, m, 10b or 12b-CH$_2$), 3.49 (1H, d, J=14.3 Hz, 7a-NCH$_2$), 3.66 (xH, br, 15b, 18b-CH$_2$?), 4.38-4.50 (1H, m, 26a-NCH$_2$), 4.53-4.63 (1H, m, 26b-NCH$_2$), 4.70 (1H, d, J=15.0 Hz, 7b-NCH$_2$), 6.94 (1H, t, J=9.0 Hz, 31-CH), 7.20 (1H, m, 32-CH), 7.23 (1H, d, J=7.3 Hz, 28-CH), 9.66 (1H, t, J=6.4 Hz, 25-CONH), 12.3 (1H, br, 5-OH). Note: The piperidine-protons appeared as broadened peaks between ~1.4-3.8 ppm Example 119

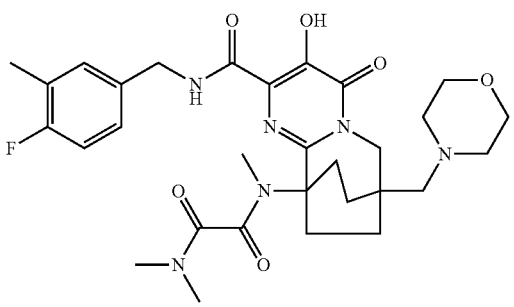 [SMILES: Cc1cc(CNC(=O)c2nc3n(c(=O)c2O)CC2(CN4CCOCC4)CCC3(N(C)C(=O)C(=O)N(C)C)CC2)ccc1F]

Ethanediamide, N-[2-[[[(4-fluoro-3-methylphenyl)methyl]amino]carbonyl]-6,7,8,9-tetrahydro-3-hydroxy-7-(4-morpholinylmethyl)-4-oxo-7,10-ethanopyrimido[1,2-a]azepin-10(4H)-yl]-N,N',N'-trimethyl- $^1$H NMR (500 MHz, CDCl$_3$) δ ppm 1.44-1.57 (1H, bm, 9a- or 13a-CH$_2$), 1.69 (1H, m, 10a or 12a-CH$_2$), 1.97-2.09 (1H, 9a or 13a-CH$_2$), 2.12-2.23 (2H, m, 9b or 13b, and 10a or 12a-CH$_2$), 2.26 (3H, d, J=1.5 Hz, 32-CH$_3$), 2.27-2.38 (2H, m, 9b or 13b, and 10b or 12b-CH$_2$), 2.99 (3H, s, 22 or 23-NCH$_3$), 3.00 (3H, s, 19-NCH$_3$), 3.04 (3H, s, 22 or 23-NCH$_3$), 3.17-3.29 (2H, m, 14-NCH$_2$), 3.29-3.47 (5H, m, 10b or 12b-CH$_2$, 15,18-NCH$_2$), 3.51 (1H, d, J=15.3 Hz, 7a-NCH$_2$), 4.02 (4H, br.s, 16,17-OCH$_2$), 4.45 (1H, dd, J=14.5, 6.0 Hz, 24a-NCH$_2$), 4.58 (1H, dd, J=14.5, 6.6 Hz, 24b-NCH$_2$), 4.77 (2H, d, J=15.0 Hz, 7b-NCH$_2$), 6.93 (1H, t, J=9.0 Hz, 30-CH), 7.15-7.21 (1H, m, 31-CH), 7.23 (1H, d, J=7.3 Hz, 27-CH), 9.66 (1H, t, J=6.4 Hz, 24-CONH). Note: $^{19}$F-NMR (CDCl$_3$): −120.2 ppm (29-F), and −76.1 (TFA).

Example 120

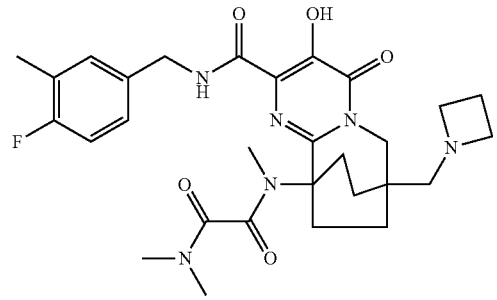 [SMILES: Cc1cc(CNC(=O)c2nc3n(c(=O)c2O)CC2(CN4CCC4)CCC3(N(C)C(=O)C(=O)N(C)C)CC2)ccc1F]

Ethanediamide, N-[7-(1-azetidinylmethyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- $^1$H NMR (500 MHz, CDCl$_3$) δ ppm 1.34-1.47 (1H, br, 9a- or 13a-CH$_2$), 1.54-1.64 (1H, br, 10a- or 12a-CH$_2$), 2.00-2.10 (1H, br, 9a- or 13a-CH$_2$), 2.11-2.24 (4H, m, 9b, 13b, 10a, 12a-CH$_2$), 2.26 (3H, s, 31-CH$_3$), 2.99 (3H, s, 18-NCH$_3$), 3.01 (3H, s, 22 or 23-NCH$_3$), 3.04 (3H, s, 22 or 23-NCH$_3$), 3.14-3.17-3.26-3.28 (2H, ABq, 14-NCH$_2$), 3.31-3.42 (1H, m, 10b, 12b-CH$_2$), 3.50 (2H, d, J=14 Hz, 7a-NCH$_2$), 4.40-4.48 (1H, m, 24a-NCH$_2$), 4.55-4.63 (1H, m, 24b-NCH$_2$), 4.59 (2H, d, J=14 Hz, 7b-NCH$_2$), 6.93 (1H, t, J=9.0 Hz, 29-CH), 7.19 (1H, m, 30-CH), 7.23 (1H, d, J=7.3 Hz, 26-CH), 9.66 (1H, t, J=6.1 Hz, 23-CONH), 12.35 (<1H, br, 5-OH). Note: Azetidine-protons were not observed as distinct peaks, but multiple broad peaks seen, such as peaks at 2.38, 2.79, and 4.07 ppm may belong to them. $^{19}$F-NMR (CDCl$_3$): −120.5 ppm (28-F), and −75.9 (TFA).

Example 121

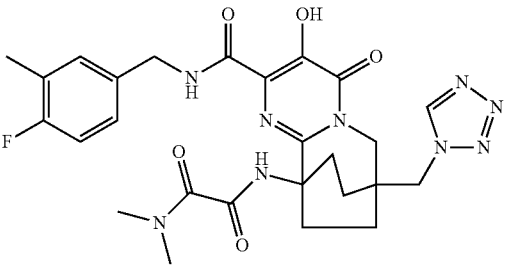 [SMILES: Cc1cc(CNC(=O)c2nc3n(c(=O)c2O)CC2(Cn4cnnn4)CCC3(NC(=O)C(=O)N(C)C)CC2)ccc1F]

Ethanediamide, N'-[2-[[[(4-fluoro-3-methylphenyl)methyl]amino]carbonyl]-6,7,8,9-tetrahydro-3-hydroxy-4-oxo-7-(1H-tetrazol-1-ylmethyl)-7,10-ethanopyrimido[1,2-a]azepin-10(4H)-yl]-N,N-dimethyl- $^1$H NMR (400 MHz, CDCl$_3$) δ ppm 1.52-1.78 (2H, m, 9a, 13a-CH$_2$), 1.78-1.95 (2H, m, 9b, 13b-CH$_2$), 2.16 (2H, m, 10a, 12a-CH$_2$), 2.28 (3H, d, J=1.5 Hz, 28-CH$_3$), 2.54 (2H, m, 10b, 12b-CH$_2$), 2.94, 3.28 (2×3H, 2s, 18,19-NCH$_3$), 4.13 (2H, s, 7-NCH$_2$), 4.44 (2H, s, 14-NCH$_2$), 4.53 (2H, d, J=6.0 Hz, 21-NCH$_2$), 6.97 (1H, t, J=8.8 Hz, 26-CH), 7.15-7.26 (2H, m, 23,27-CH), 8.03 (1H, s, 17-CONH), 8.57 (1H, t, J=6.0 Hz, 20-CONH), 8.75 (1H, s, 15-CH), 12.18 (1H, br, 5-OH). $^{19}$F NMR (470 MHz, CDCl$_3$) δ ppm −119.6 (Ar—F).

Example 122

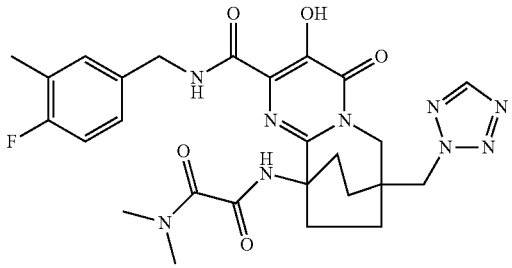 [SMILES: Cc1cc(CNC(=O)c2nc3n(c(=O)c2O)CC2(Cn4ncnn4)CCC3(NC(=O)C(=O)N(C)C)CC2)ccc1F]

Ethanediamide, N'-[2-[[[(4-fluoro-3-methylphenyl)methyl]amino]carbonyl]-6,7,8,9-tetrahydro-3-hydroxy-4-oxo-7-(2H-tetrazol-2-ylmethyl)-7,10-ethanopyrimido[1,2-a]azepin-10(4H)-yl]-N,N-dimethyl- $^1$H NMR (500 MHz, CDCl$_3$) δ ppm 1.66 (2H, m, 9a,13a-CH$_2$), 1.82-1.97 (2H, m, 9b, 13b-CH$_2$), 2.14 (2H, m, 10a, 12a-CH$_2$), 2.27 (3H, d, J=1.5 Hz, 28-CH$_3$), 2.53 (2H, m, 10b, 12b-CH$_2$), 2.93, 3.28 (2×3H, 2s, 18,19-NCH$_3$), 4.24 (2H, s, 7-NCH$_2$), 4.53 (2H, d, J=6.1 Hz, 21-NCH$_2$), 4.66 (2H, s, 14-NCH$_2$), 6.97 (1H, t, J=9 Hz, 26-CH), 7.14-7.24 (2H, m, 23,27-CH), 8.06 (1H, s, 16-CONH), 8.57 (1H, s, 15-CH), 8.58 (1H, t, J=6.4 Hz, 20-CONH), 12.14 (1H, br, 5-OH). $^{19}$F NMR (470 MHz, CDCl$_3$) δ ppm −119.9 (Ar—F).

Example 123

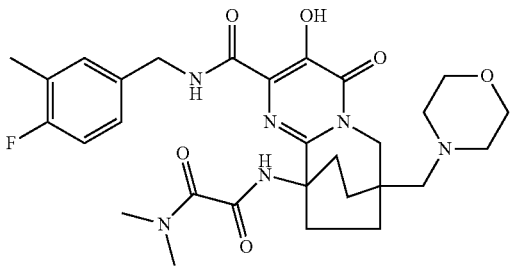 [SMILES: Cc1cc(CNC(=O)c2nc3n(c(=O)c2O)CC2(CN4CCOCC4)CCC3(NC(=O)C(=O)N(C)C)CC2)ccc1F]

Ethanediamide, N'-[2-[[[(4-fluoro-3-methylphenyl)methyl]amino]carbonyl]-6,7,8,9-tetrahydro-3-hydroxy-7-(4-morpholinylmethyl)-4-oxo-7,10-ethanopyrimido[1,2-a]azepin-10(4H)-yl]-N,N-dimethyl- $^1$H NMR (500 MHz, CDCl$_3$) δ ppm 1.53-1.63 (2H, m, 9a, 13a-CH$_2$), 1.78-1.89 (2H, m, 9b, 13b-CH$_2$), 2.03-2.13 (2H, 10a, 12a-CH$_2$), 2.12-2.23 (2H, m, 9b or 13b, and 10a or 12a-CH$_2$), 2.28 (3H, d, J=1.8 Hz, 31-CH$_3$), 2.31 (2H, s, 14-NCH$_2$), 2.53-2.58 (2H, m, 10b, 12b-CH$_2$), 2.60 (4H, t, J=4.5 Hz, 15,18-NCH$_2$), 2.94, 3.32 (2×3H, 2s, 21,22-NCH$_3$), 3.70 (4H, t, J=4.5 Hz, 16,17-OCH$_2$), 4.03 (2H, s, 7-NCH$_2$), 4.54 (2H, d, J=6.1 Hz, 24-NCH$_2$), 6.98 (1H, t, J=9 Hz, 29-CH), 7.18-7.25 (2H, m, 26,30-CH), 8.24 (1H, s, 19-CONH), 8.57 (1H, t, J=6.1 Hz, 23-CONH), 12.04 (1H, s, 5-OH).

Example 124

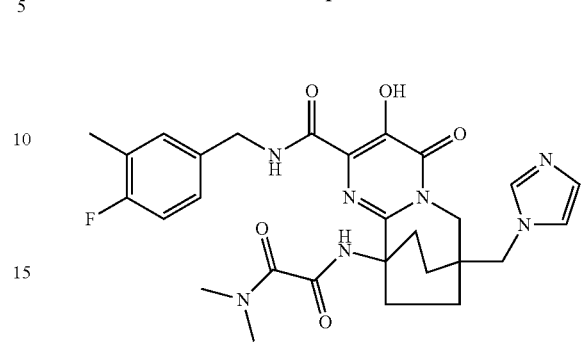

Ethanediamide, N'-[2-[[[(4-fluoro-3-methylphenyl)methyl]amino]carbonyl]-6,7,8,9-tetrahydro-3-hydroxy-7-(1H-imidazol-1-ylmethyl)-4-oxo-7,10-ethanopyrimido[1,2-a]azepin-10(4H)-yl]-N,N-dimethyl- $^1$H NMR (500 MHz, CDCl$_3$) δ ppm 1.64-1.78 (2H, m, 9a, 13a-CH$_2$), 1.80-1.95 (2H, m, 9b, 13b-CH$_2$), 2.18-2.29 (2H, m, 10a, 12a-CH$_2$), 2.25 (3H, d, J=1.8 Hz, 30-CH$_3$), 2.50 (2H, m, 10b, 12b-CH$_2$), 2.92, 3.22 (2×3H, 2s, 20,21-NCH$_3$), 4.13 (2H, s, 7-NCH$_2$), 4.40 (2H, m, 14-NCH$_2$), 4.49 (2H, d, J=6.1 Hz, 23-NCH$_2$), 6.95 (1H, t, J=8.9 Hz, 28-CH), 7.12-7.20 (2H, m, 25,29-CH), 7.42 (1H, s, 17-CH), 7.45 (1H, s, 16-CH), 7.73 (1H, s, 18-CONH), 8.84 (1H, t, J=6.4 Hz, 22-CONH), 9.31 (1H, s, 15-CH). $^{19}$F NMR (470 MHz, CDCl$_3$) δ ppm −119.9 (Ar—F), 76.0 (TFA).

Example 125

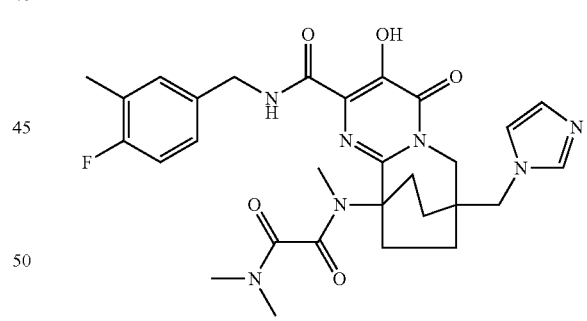

Ethanediamide, N-[2-[[[(4-fluoro-3-methylphenyl)methyl]amino]carbonyl]-6,7,8,9-tetrahydro-3-hydroxy-7-(1H-imidazol-1-ylmethyl)-4-oxo-7,10-ethanopyrimido[1,2-a]azepin-10(4H)-yl]-N,N',N'-trimethyl- $^1$H NMR (500 MHz, CHLOROFORM-d) ppm 12.29 (2H, br. s.), 9.63 (3H, t, J=5.8 Hz), 9.23 (2H, d, J=1.5 Hz), 7.42 (3H, br. s.), 7.37 (2H, br. s.), 7.21 (3H, d, J=7.3 Hz), 7.13-7.19 (2H, m), 6.92 (3H, t, J=8.9 Hz), 4.80 (3H, d, J=14.0 Hz), 4.50-4.62 (3H, m), 4.31-4.50 (7H, m), 3.50 (4H, q, J=7.0 Hz), 3.30-3.45 (3H, m), 3.02 (9H, s), 2.99 (15H, s), 2.24 (8H, s), 2.11 (8H, br. s.), 1.89 (3H, br. s.), 1.75 (5H, br. s.), 1.51 (3H, br. s.). $^{19}$F NMR (470 MHz, CDCl$_3$) δ ppm −120.5 (Ar—F), −75.9 (TFA).

Example 126

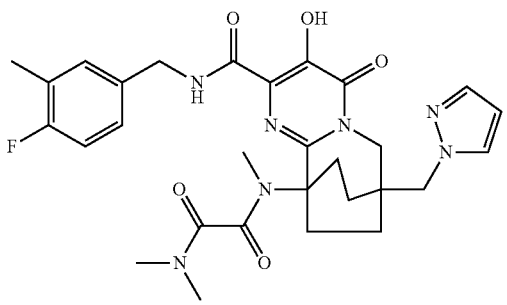 [SMILES: Cc1cc(CNC(=O)c2nc3n(c(=O)c2O)CC2(Cn4cccn4)CCC3(N(C)C(=O)C(=O)N(C)C)CC2)ccc1F]

Ethanediamide, N-[2-[[[(4-fluoro-3-methylphenyl)methyl]amino]carbonyl]-6,7,8,9-tetrahydro-3-hydroxy-4-oxo-7-(1H-pyrazol-1-ylmethyl)-7,10-ethanopyrimido[1,2-a]azepin-10(4H)-yl]-N,N',N'-trimethyl- $^1$H NMR (500 MHz, CHLOROFORM-d) δ ppm 12.19 (3H, s), 9.59 (3H, t, J=6.3 Hz), 7.54 (3H, d, J=1.5 Hz), 7.47 (2H, d, J=2.1 Hz), 7.23 (2H, d, J=7.3 Hz), 7.15-7.22 (3H, m), 6.88-6.98 (3H, m), 6.30 (2H, t, J=2.1 Hz), 4.79 (3H, d, J=15.0 Hz), 4.54-4.65 (3H, m), 4.39-4.49 (3H, m), 4.10 (5H, d, J=1.8 Hz), 3.46-3.51 (3H, m), 3.32-3.44 (3H, m), 3.02 (7H, s), 2.99 (6H, s), 2.99 (8H, s), 2.25 (7H, d, J=1.8 Hz), 2.14-2.24 (3H, m), 1.96-2.13 (8H, m), 1.66-1.82 (6H, m), 1.50-1.63 (3H, m), 1.32-1.45 (3H, m). $^{19}$F NMR (470 MHz, CDCl$_3$) δ ppm −120.6 (Ar—F); no TFA observed.

Example 127

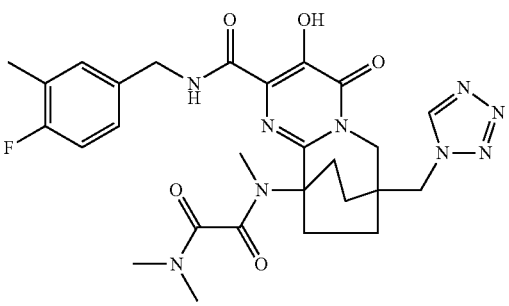 [SMILES: Cc1cc(CNC(=O)c2nc3n(c(=O)c2O)CC2(Cn4cnnn4)CCC3(N(C)C(=O)C(=O)N(C)C)CC2)ccc1F]

Ethanediamide, N-[2-[[[(4-fluoro-3-methylphenyl)methyl]amino]carbonyl]-6,7,8,9-tetrahydro-3-hydroxy-4-oxo-7-(1H-tetrazol-1-ylmethyl)-7,10-ethanopyrimido[1,2-a]azepin-10(4H)-yl]-N,N',N'-trimethyl- $^1$H NMR (500 MHz, CDCl$_3$) δ ppm 1.44-1.59 (2H, m, 9a, 13a-CH$_2$), 1.70-1.83 (1H, m, 9b or 13b-CH$_2$), 1.96-2.06 (2H, m, 9b or 13b, and 10a or 12a-CH$_2$), 2.06-2.18 (2H, m, 10a or 12a, and 10b or 12b-CH$_2$), 2.26 (3H, s, 29-CH$_3$), 2.99, 3.00, 3.03 (3×3H, 3s, 16, 19, 20-NCH$_3$), 3.37-3.48 (1H, m, 10b or 12b-CH$_2$), 3.54 (1H, d, J=15.3 Hz, 7a-NCH$_2$), 4.40-4.48 (1H, m, 22a-NCH$_2$), 4.51 (2H, ABq, 14-NCH$_2$), 4.54-4.65 (1H, m, 23b-NCH$_2$), 4.83 (1H, d, J=15.3 Hz, 7b-NCH$_2$), 6.93 (1H, t, J=8.9 Hz, 27-CH), 7.20 (1H, m, 27-CH), 7.23 (1H, d, J=7.3 Hz, 24-CH), 8.88 (1H, s, 15-CH), 9.62 (1H, t, J=6.4 Hz, 22-CONH), 12.32 (1H, s, 5-OH)

Example 128

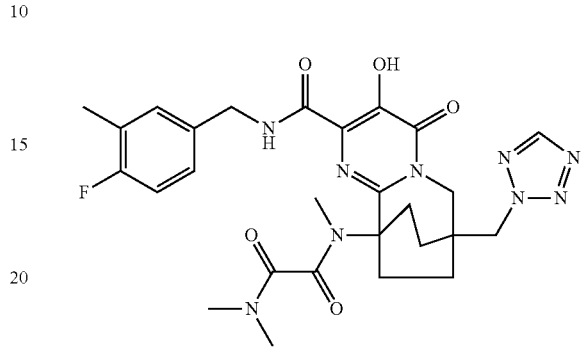

Ethanediamide, N-[2-[[[(4-fluoro-3-methylphenyl)methyl]amino]carbonyl]-6,7,8,9-tetrahydro-3-hydroxy-4-oxo-7-(2H-tetrazol-2-ylmethyl)-7,10-ethanopyrimido[1,2-a]azepin-10(4H)-yl]-N,N',N'-trimethyl- $^1$H NMR (500 MHz, CDCl$_3$) δ ppm 1.35-1.55 (2H, m, 9a, 13a-CH$_2$), 1.73-1.85 (1H, m, 9b or 13b-CH$_2$), 1.95-2.21 (4H, m, 9b or 13b, and 10a, 12a-CH$_2$, and 10b or 12b), 2.25 (3H, d, J=1.8 Hz, 29-CH$_3$), 2.99, 2.99, 3.02 (3×3H, 3s, 16, 19, 20-NCH$_3$), 3.36-3.47 (1H, m, 10b or 12b-CH$_2$), 3.58 (1H, d, J=15.6 Hz, 7a-NCH$_2$), 4.40-4.48 (1H, m, 22a-NCH$_2$), 4.54-4.62 (1H, m, 23b-NCH$_2$), 4.66 (2H, ABq, 14-NCH$_2$), 5.00 (1H, d, J=15.3 Hz, 7b-NCH$_2$), 6.93 (1H, t, J=9 Hz, 27-CH), 7.16-7.21 (1H, m, 27-CH), 7.23 (1H, d, J=7.6 Hz, 24-CH), 8.57 (1H, s, 15-CH), 9.59 (1H, t, J=6.3 Hz, 22-CONH), 12.24 (1H, s, 5-OH). $^{19}$F NMR (470 MHz, CDCl$_3$) δ ppm −120.6 (Ar—F).

Example 129

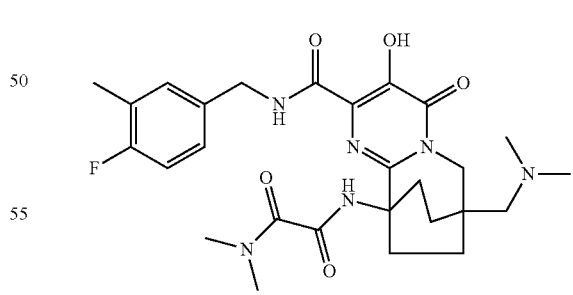

Ethanediamide, N'-[7-[(dimethylamino)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- $^1$H NMR (500 MHz, CHLOROFORM-d) δ 12.23 (br. s., 1H), 8.93 (t, J=6.3 Hz, 1H), 7.25 (s, 1H), 7.19 (d, J=7.0 Hz, 2H), 7.18-7.15 (m, 1H), 6.97 (t, J=8.9 Hz, 1H), 4.51 (d, J=6.4 Hz, 1H), 4.10 (s, 1H), 3.22 (s, 2H), 3.12 (s, 1H), 2.99 (s, 2H), 2.92 (s, 1H), 2.55-2.44 (m, 1H), 2.28 (s, 2H), 2.35-2.22 (m, 1H), 1.74-1.60 (m, 1H). $^{19}$F-NMR (CDCl$_3$): −119.8 ppm (Ar—F), and −75.9 (TFA). Anal. Calc'd. for C$_{27}$H$_{35}$FN$_6$O$_5$/ CF$_3$CO$_2$H/0.5H$_2$O: C52.33, H5.60, N12.63. found: C52.30, H5.56, N12.64.

Example 130

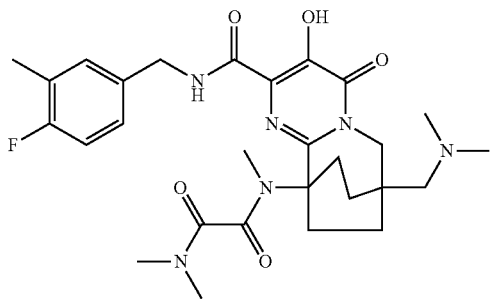

Ethanediamide, N-[7-[(dimethylamino)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- $^1$H NMR (500 MHz, CHLOROFORM-d) δ ppm 12.36 (2H, br. s.), 9.67 (2H, t, J=6.4 Hz), 7.23 (2H, d, J=7.3 Hz), 7.20 (2H, td, J=5.5, 2.4 Hz), 6.94 (2H, t, J=9.0 Hz), 4.73 (2H, d, J=15.3 Hz), 4.53-4.63 (2H, m), 4.40-4.50 (2H, m), 3.50 (3H, d, J=15.3 Hz), 3.33-3.45 (3H, m), 3.23 (5H, s), 3.05 (6H, s), 3.01 (8H, br. s.), 3.00 (8H, br. s.), 3.00 (12H, br. s.), 2.29-2.43 (5H, m), 2.26 (9H, d, J=1.5 Hz), 2.15-2.23 (3H, m), 2.00-2.10 (3H, m), 1.69 (3H, t, J=10.2 Hz), 1.40-1.55 (3H, m). $^{19}$F NMR (470 MHz, CDCl$_3$) δ ppm −120.4 (Ar—F), −75.7 (TFA). Anal. Calc'd. for C$_{28}$H$_{37}$FN$_6$O$_5$.1CF$_3$CO$_2$H.0.6H$_2$O: C52.87, H5.80, N12.33. found: C52.66, H5.68, N12.60.

Example 131

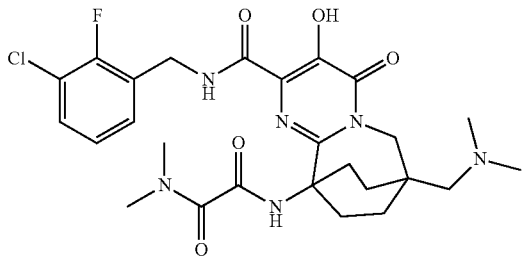 [SMILES: CN(C)CC12CCC(NC(=O)C(=O)N(C)C)(CC1)c1nc(C(=O)NCc3cccc(Cl)c3F)c(O)c(=O)n1C2]

Ethanediamide, N'-2-[[[(3-chloro-2-fluorophenyl)methyl]amino]carbonyl]-7-[(dimethylamino)methyl]-6,7,8,9-tetrahydro-3-hydroxy-4-oxo-7,10-ethanopyrimido[1,2-a]azepin-10(4H)-yl]-N,N-dimethyl- $^1$H NMR (500 MHz, CDCl$_3$) δ ppm 11.85 (1H, br. s.), 8.69 (1H, t, J=6.1 Hz), 7.84 (1H, s), 7.31 (2H, t, J=7.5 Hz), 7.05 (1H, t, J=7.9 Hz), 4.64 (2H, d, J=6.4 Hz), 4.00 (2H, s), 3.25 (3H, s), 2.92 (3H, s), 2.45 (2H, ddd, J=14.3, 9.3, 5.6 Hz), 2.33 (6H, s), 2.24 (2H, s), 2.11 (2H, dq, J=14.0, 7.0 Hz), 1.77-1.86 (1H, m), 1.51-1.59 (2H, m). $^{13}$C NMR (126 MHz, CDCl$_3$-d) δ ppm 168.56, 163.56, 162.29, 159.72, 155.44, 151.76, 146.80, 129.95, 128.78, 128.75, 126.64, 126.52, 124.69, 124.65, 124.35, 69.67, 58.12, 56.19, 48.99, 38.15, 37.57, 36.94, 36.90, 36.37, 30.21, 27.50.

Example 132

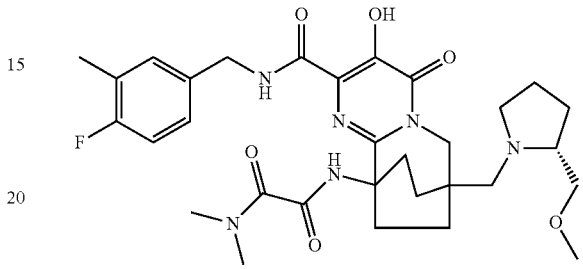

Ethanediamide, N'-[2-[[[(4-fluoro-3-methylphenyl)methyl]amino]carbonyl]-6,7,8,9-tetrahydro-3-hydroxy-7-[[(2R)-2-(methoxymethyl)-1-pyrrolidinyl]methyl]-4-oxo-7,10-ethanopyrimido[1,2-a]azepin-10(4H)-yl]-N,N-dimethyl- $^1$H NMR (500 MHz, CHLOROFORM-d) δ ppm 12.15 (2H, br. s.), 8.96 (2H, t, J=6.3 Hz), 7.14-7.23 (5H, m), 6.91-7.01 (2H, m), 4.51 (4H, d, J=6.4 Hz), 4.32 (3H, d, J=13.7 Hz), 4.11 (2H, br. s.), 3.76 (3H, d, J=14.3 Hz), 3.70 (2H, d, J=9.5 Hz), 3.40 (7H, s), 3.21 (6H, s), 2.91 (7H, s), 2.42-2.55 (4H, m), 2.31-2.40 (4H, m), 2.27 (7H, d, J=1.5 Hz), 2.01-2.18 (5H, m), 1.80-1.96 (4H, m), 1.63-1.74 (2H, m), 1.49-1.61 (2H, m). $^{19}$F-NMR (CDCl$_3$): −120.01 ppm (Ar—F), and −75.92 (TFA).

Example 133

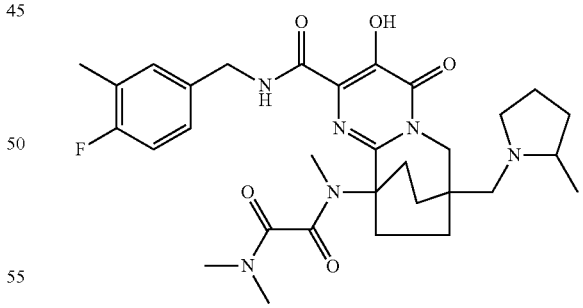

Ethanediamide, N-[2-[[[(4-fluoro-3-methylphenyl)methyl]amino]carbonyl]-6,7,8,9-tetrahydro-3-hydroxy-7-[(2-methyl-1-pyrrolidinyl)methyl]-4-oxo-7,10-ethanopyrimido[1,2-a]azepin-10(4H)-yl]-N,N',N'-trimethyl- $^1$H NMR (500 MHz, CHLOROFORM-d) δ ppm 12.32 (1H, br. s.), 9.68 (2H, t, J=6.3 Hz), 7.24 (2H, d, J=7.3 Hz), 7.21 (2H, td, J=5.2, 2.4 Hz), 6.94 (2H, t, J=9.0 Hz), 4.53-4.64

(3H, m), 4.45 (2H, dd, J=14.6, 6.1 Hz), 4.32-4.41 (1H, m), 3.46-3.54 (2H, m), 3.32-3.42 (2H, m), 3.29 (3H, d, J=13.1 Hz), 3.05 (6H, s), 3.01 (6H, s), 2.99 (6H, s), 2.49-2.60 (2H, m), 2.45 (2H, dd, J=13.7, 9.2 Hz), 2.25-2.27 (7H, m), 2.15-2.32 (14H, m), 2.09 (4H, dd, J=13.6, 7.5 Hz), 1.92-2.04 (6H, m), 1.60 (5H, d, J=5.8 Hz), 1.30-1.44 (3H, m). $^{19}$F-NMR (CDCl$_3$): −120.4 ppm (30-F), and −75.9 (TFA).

Example 134

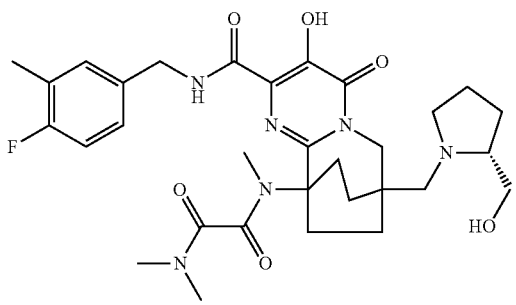 [SMILES: Cc1cc(CNC(=O)c2nc3n(c(=O)c2O)CC2(CN4CCC[C@@H]4CO)CCC3(N(C)C(=O)C(=O)N(C)C)CC2)ccc1F]

Ethanediamide, N-[2-[[[(4-fluoro-3-methylphenyl)methyl]amino]carbonyl]-6,7,8,9-tetrahydro-3-hydroxy-7-[[(2R)-2-(hydroxymethyl)-1-pyrrolidinyl]methyl]-4-oxo-7,10-ethanopyrimido[1,2-a]azepin-10(4H)-yl]-N,N',N'-trimethyl- $^{19}$F-NMR (CDCl$_3$): −120.0 ppm (Ar—F), and −75.3 (TFA). $^1$H NMR (400 MHz, CDCl$_3$) δ ppm 1.39-1.54 (1H, m, 9a- or 13a-CH$_2$), 1.68-1.85 (2H, m, 9a- or 13a and 16a-CH$_2$), 1.99-2.11 (1H, m, 9b- or 13b-CH$_2$), 2.11-2.24 (3H, m, 16b-, 17-CH$_2$), 2.26 (3H, d, J=1.8 Hz, 33-CH$_3$), 2.27-2.37 (1H, m, 9b- or 13b-CH$_2$), 2.44 (10b- or 12b-CH$_2$), 2.99 (3H, s, 23 or 24-NCH$_3$), 3.00 (3H, s, 20-NCH$_3$), 3.05 (3H, s, 23 or 24-NCH$_3$), 3.15-3.25 (1H, m, 18a-NCH$_2$), 3.20 (1H, J=14 Hz, 14a-NCH$_2$), 3.3-3.45 (1H, 10b- or 12b-CH$_2$), 3.66 (1H, d, J=13.3 Hz, 14b-NCH$_2$), 3.51 (d, J=14 Hz, 7a-NCH$_2$), 3.75 (1H, br, 15-NCH), 3.95 (1H, ABq., 19-OCH$_2$), 4.40-4.50 (1H, m, 18b-NCH$_2$), 4.45 (1H, ABq, 26a-NCH$_2$), 4.58 (1H, ABq, 26a-NCH$_2$), 4.59 (1H, d, J=14 Hz, 7b-NCH$_2$), 6.94 (1H, t, J=9.0 Hz, 31-CH), 7.15-7.21 (1H, m, 32-CH), 7.23 (1H, d, J=7.5 Hz, 28-CH), 9.65 (1H, t, J=6.3 Hz, 25-CONH), 12.33 (<1H, br, 5-OH).

Example 135

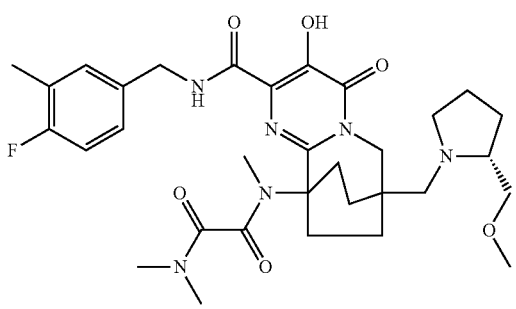

Ethanediamide, N-[2-[[[(4-fluoro-3-methylphenyl)methyl]amino]carbonyl]-6,7,8,9-tetrahydro-3-hydroxy-7-[[(2R)-2-(methoxymethyl)-1-pyrrolidinyl]methyl]-4-oxo-7,10-ethanopyrimido[1,2-a]azepin-10(4H)-yl]-N,N',N'-trimethyl- $^1$H NMR (400 MHz, CHLOROFORM-d) δ ppm 12.26 (1H, br. s.), 9.66 (2H, t, J=5.9 Hz), 7.24 (2H, d, J=7.5 Hz), 7.14-7.22 (2H, m), 6.94 (2H, t, J=8.9 Hz), 4.59 (2H, dd, J=14.6, 6.5 Hz), 4.51 (2H, br. s.), 4.40-4.49 (3H, m), 4.30 (2H, br. s.), 4.12 (2H, t, J=9.7 Hz), 3.85 (2H, d, J=12.8 Hz), 3.71 (2H, d, J=9.0 Hz), 3.60 (2H, br. s.), 3.43 (2H, d, J=7.5 Hz), 3.37 (5H, s), 3.05 (6H, s), 3.00 (10H, s), 2.95 (21H, d, J=14.6 Hz), 2.43-2.61 (4H, m), 2.26 (8H, s), 2.17-2.37 (13H, m), 2.13 (4H, d, J=4.3 Hz), 1.98-2.08 (3H, m), 1.83 (2H, br. s.), 1.60 (2H, t, J=9.8 Hz), 1.26-1.38 (2H, m). $^{19}$F-NMR (CDCl$_3$): −120.4 ppm (Ar—F), and −75.9 (TFA).

Example 136

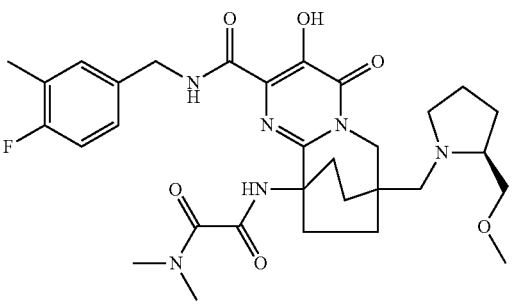

Ethanediamide, N'-[2-[[[(4-fluoro-3-methylphenyl)methyl]amino]carbonyl]-6,7,8,9-tetrahydro-3-hydroxy-7-[[(2S)-2-(methoxymethyl)-1-pyrrolidinyl]methyl]-4-oxo-7,10-ethanopyrimido[1,2-a]azepin-10(4H)-yl]-N,N-dimethyl- $^1$H NMR (500 MHz, CHLOROFORM-d) δ 12.16 (br. s., 1H), 8.96 (t, J=6.3 Hz, 1H), 7.23-7.15 (m, 3H), 7.01-6.92 (m, 1H), 4.51 (d, J=6.4 Hz, 2H), 4.32 (d, J=12.8 Hz, 1H), 4.13 (br. s., 1H), 3.84 (br. s., 1H), 3.77 (br. s., 1H), 3.71 (d, J=8.9 Hz, 1H), 3.57-3.48 (m, 2H), 3.41 (s, 3H), 3.21 (s, 3H), 3.08-2.96 (m, 1H), 2.92 (s, 3H), 2.59 (dd, J=2.7, 1.8 Hz, 1H), 2.55-2.42 (m, 2H), 2.41-2.32 (m, 2H), 2.28 (d, J=1.5 Hz, 3H), 2.19-2.03 (m, 2H), 1.88 (d, J=8.5 Hz, 2H), 1.74-1.63 (m, 1H), 1.61-1.50 (m, 1H). $^{19}$F-NMR (CDCl$_3$): −120.0 ppm (30-F), and −75.9 (TFA).

Example 137

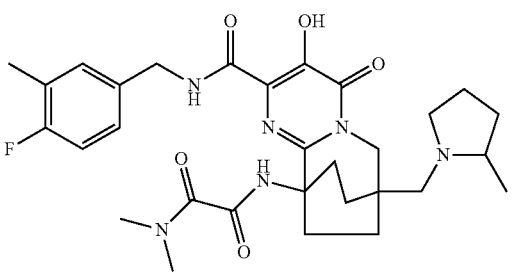

Ethanediamide, N'-[2-[[[(4-fluoro-3-methylphenyl)methyl]amino]carbonyl]-6,7,8,9-tetrahydro-3-hydroxy-7-[(2-methyl-1-pyrrolidinyl)methyl]-4-oxo-7,10-ethanopyrimido[1,2-a]azepin-10(4H)-yl]-N,N-dimethyl- $^1$H NMR (400 MHz, MeOD) δ ppm 7.27 (2H, d, J=7.3 Hz), 7.18-7.25 (2H, m), 6.95 (2H, t, J=9.0 Hz), 4.45-4.61 (4H, m), 4.32 (2H, d, J=14.6 Hz), 4.01 (2H, d, J=14.8 Hz), 3.94 (1H, br. s.), 3.45-3.64 (4H, m), 3.41 (2H, br. s.), 3.27 (2H, d, J=11.5 Hz), 3.08 (6H, s), 2.98 (6H, s), 2.63 (2H, br. s.), 2.32 (7H, br. s.), 2.24 (6H, d, J=1.5 Hz), 2.17 (4H, br. s.), 1.94 (4H, d, J=13.6 Hz), 1.77 (6H, br. s.), 1.55 (6H, d, J=5.0 Hz). $^{19}$F-NMR (CD$_3$OD): −122.7 ppm (Ar—F), and −77.3 (TFA)

Example 138

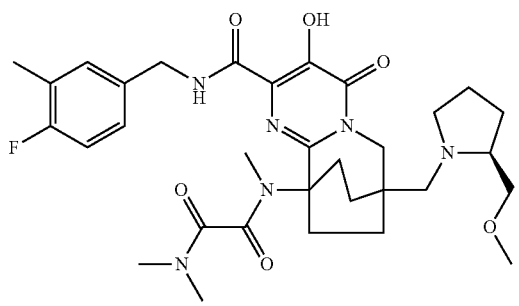

Ethanediamide, N-[2-[[[(4-fluoro-3-methylphenyl)methyl]amino]carbonyl]-6,7,8,9-tetrahydro-3-hydroxy-7-[[(2S)-2-(methoxymethyl)-1-pyrrolidinyl]methyl]-4-oxo-7,10-ethanopyrimido[1,2-a]azepin-10(4H)-yl]-N,N',N'-trimethyl- $^{19}$F-NMR (CDCl$_3$): −120.4 ppm (Ar—F), and −75.9 (TFA). $^1$H NMR (500 MHz, CHLOROFORM-d) δ ppm 12.31 (1H, br. s.), 9.68 (2H, t, J=6.3 Hz), 7.23 (2H, d, J=7.3 Hz), 7.16-7.22 (2H, m), 6.93 (2H, t, J=9.0 Hz), 4.58 (2H, dd, J=14.5, 6.6 Hz), 4.52 (2H, d, J=15.3 Hz), 4.45 (2H, dd, J=14.6, 6.1 Hz), 4.31 (3H, t, J=9.2 Hz), 3.84 (2H, d, J=13.4 Hz), 3.79 (2H, d, J=7.6 Hz), 3.73 (2H, d, J=10.7 Hz), 3.48-3.54 (2H, m), 3.40 (5H, s), 3.28-3.37 (2H, m), 3.22 (3H, d, J=12.8 Hz), 3.05 (7H, s), 3.02 (6H, s), 3.00 (6H, s), 2.59-2.71 (2H, m), 2.40-2.59 (4H, m), 2.25 (7H, s), 2.31 (10H, d, J=7.6 Hz), 2.13-2.23 (5H, m), 2.04 (3H, dd, J=11.7, 8.4 Hz), 1.87 (3H, br. s.), 1.69 (2H, t, J=9.9 Hz), 1.38 (2H, d, J=11.0 Hz).

Example 139

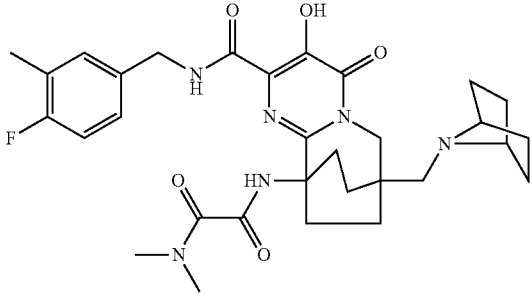 [SMILES: Cc1cc(CNC(=O)c2nc3n(c(=O)c2O)CC2(CN4C5CCC4CC5)CCC3(NC(=O)C(=O)N(C)C)CC2)ccc1F]

Ethanediamide, N'-[7-(7-azabicyclo[2.2.1]hept-7-ylmethyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- $^{13}$C NMR (126 MHz, CHLOROFORM-d) δ ppm 168.03, 164.04, 163.55, 159.66 150.45, 146.65, 133.38, 131.29, 127.06, 125.21, 124.98, 114.07-115.53, 66.91, 57.86, 55.78, 54.41, 42.48, 37.93, 35.63, 35.60, 30.15, 29.70, 27.84, 26.63, 26.45, 14.66.

Example 140

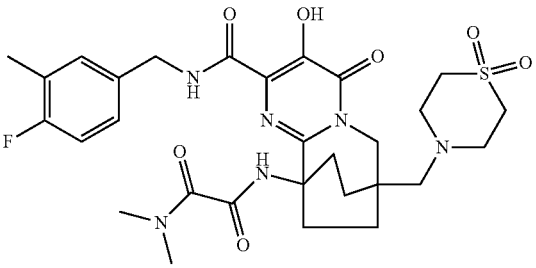 [SMILES: Cc1cc(CNC(=O)c2nc3n(c(=O)c2O)CC2(CN4CCS(=O)(=O)CC4)CCC3(NC(=O)C(=O)N(C)C)CC2)ccc1F]

Ethanediamide, N'-[7-[(1,1-dioxido-4-thiomorpholinyl)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- $^1$H NMR (500 MHz, CHLOROFORM-d) δ 8.57 (t, J=6.3 Hz, 1H), 8.16 (s, 1H), 7.25-7.15 (m, 2H), 7.02-6.94 (m, 1H), 4.54 (d, J=6.1 Hz, 1H), 4.04 (s, 1H), 3.31 (s, 1H), 3.21 (d, J=5.2 Hz, 2H), 3.09 (d, J=4.9 Hz, 2H), 2.95 (s, 2H), 2.62-2.55 (m, 1H), 2.53 (s, 1H), 2.28 (d, J=1.5 Hz, 2H), 2.18-2.08 (m, 2H), 1.87-1.75 (m, 1H), 1.67-1.54 (m, 1H).

Example 141

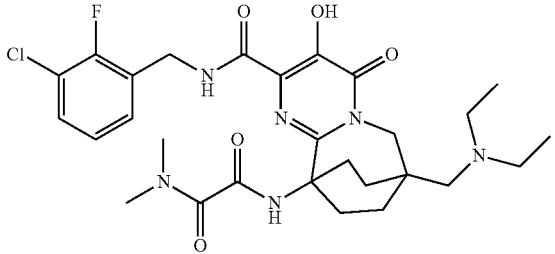 [SMILES: CCN(CC)CC12CCC(NC(=O)C(=O)N(C)C)(CC1)c1nc(C(=O)NCc3cccc(Cl)c3F)c(O)c(=O)n1C2]

Ethanediamide, N'-[2-[[[(3-chloro-2-fluorophenyl)methyl]amino]carbonyl]-7-[(diethylamino)methyl]-6,7,8,9-tetrahydro-3-hydroxy-4-oxo-7,10-ethanopyrimido[1,2-a]azepin-10(4H)-yl]-N,N-dimethyl- LCMS; observed mass, 591.2. Retention time, 2.34 min. Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection.

Compounds in tables 3, 4 and 5 were synthesized according to the methods described above and were analyzed by LC/MS according to the following methods:

Method A:
Start % B=0
Final % B=100
Gradient Time=4 min
Flow Rate=0.8 ml/min
Wavelength=220
Solvent Pair=Water/Acetonitrile/0.1% TFA
Solvent A=90% Water/10% Acetonitrile/0.1% TFA
Solvent B=10% Water/90% Acetonitrile/0.1% TFA
Column; Phenomenex LUNA C18, 50×2, 3 um
Method B
Start % B=0
Final % B=100
Gradient Time=4 min
Flow Rate=0.8 ml/min
Wavelength=220
Solvent Pair=Methanol:Water:0.1% TFA
Solvent A=5% Water:95% Methanol:0.1% TFA
Solvent B=95% Water:5% Methanol:0.1% TFA
Column; PHENOMENEX-LUNA 2.0×50 mm 3 um
Method C
Final % B=100
Gradient Time=4 min
Flow Rate=0.8 ml/min
Wavelength=220
Solvent Pair=Water-Methanol-TFA
Solvent A=90% Water-10% Methanol-0.1% TFA
Solvent B=10% Water-90% Methanol-0.1% TFA
Column; PHENOMENEX-LUNA 2.0×50 mm 3 um
Method D
Start % B=0
Final % B=100
Gradient Time=3 min
Flow Rate=0.8 ml/min
Wavelength=220
Solvent Pair=ACN: Water: Ammonium Actetate
Solvent A=5% ACN: 95% Water:10 mM Ammonium Actetate
Solvent B=95% ACN: 5% Water:10 mM Ammonium Actetate
Column; Phenomenex LUNA C18, 50×2, 3 u
Method E
Start % B=30
Final % B=100
Gradient Time=2 min
Flow Rate=0.8 ml/min
Wavelength=220
Solvent Pair=Water-Methanol-TFA
Solvent A=90% Water-10% Methanol-0.1% TFA
Solvent B=10% Water-90% Methanol-0.1% TFA
Column; PHENOMENEX-LUNA 2.0×50 mm 3 um
Method F
Start % B=0
Final % B=100
Gradient Time=4 min
Flow Rate=0.8 ml/min
Wavelength=220
Solvent Pair=ACN:Water:Ammonium Actetate
Solvent A=5% ACN:95% Water:10 mM Ammonium Actetate
Solvent B=95% ACN:5% Water:10 mM Ammonium Actetate
Column; Phenomenex LUNA C18, 50×2, 3 u
Method G
Start % B=0
Final % B=100
Gradient Time=2 min
Flow Rate=1 ml/min
Wavelength=220
Solvent Pair=Water:Methanol:0.1% TFA
Solvent A=90% Water:10% Methanol:0.1% TFA
Solvent B=10% Water:90% Methanol:0.1% TFA
Column; PHENOMENEX-LUNA 2.0×30 mm 3 um
Method H
Start % B=0
Final % B=100
Gradient Time=2 min
Flow Rate=1 ml/min
Wavelength=254
Solvent Pair=Water/Acetonitrile/0.1% TFA
Solvent A=90% Water/10% Acetonitrile/0.1% TFA
Solvent B=10% Water/90% Acetonitrile/0.1% TFA
Column; Phenomenex LUNA C18, 30×2, 3 u
Method I
Start % B=0
Final % B=100
Gradient Time=2 min
Flow Rate=1 ml/min
Wavelength=220
Solvent Pair=ACN:Water:Ammonium Actetate
Solvent A=5% ACN:95% Water:10 mM Ammonium Actetate
Solvent B=95% ACN:5% Water:10 mM Ammonium Actetate
Column; Phenomenex LUNA C18, 30×2, 3 u

TABLE 3

| Example | | M + 1 observed | RT | Method |
|---|---|---|---|---|
| 142 | 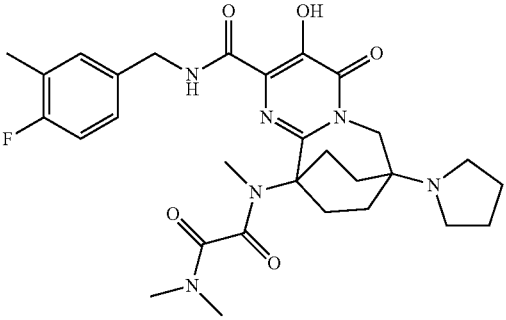 [SMILES: Cc1cc(CNC(=O)c2nc3n(c(=O)c2O)CC2(N4CCCC4)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-4-oxo-7-(1-pyrrolidinyl)-7,10-ethanopyrimido[1,2-a]azepin-10(4H)-yl]-N,N',N'-trimethyl- | 569.4 | 2.12 | A |

TABLE 3-continued

| Example | | M + 1 observed | RT | Method |
|---|---|---|---|---|
| 143 | 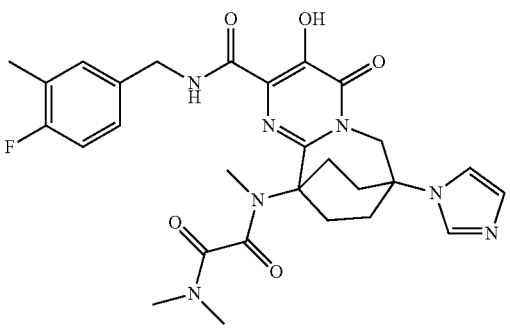 [SMILES: Cc1cc(CNC(=O)c2nc3n(c(=O)c2O)CC2(n4ccnc4)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-7-(1H-imidazol-1-yl)-4-oxo-7,10-ethanopyrimido[1,2-a]azepin-10(4H)-yl]-N,N',N'-trimethyl- | 566.3 | 2.15 | A |
| 144 | 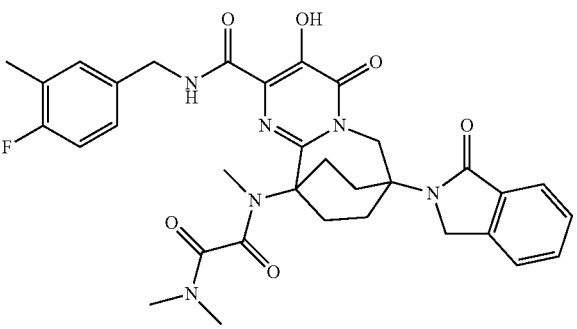 [SMILES: Cc1cc(CNC(=O)c2nc3n(c(=O)c2O)CC2(N4Cc5ccccc5C4=O)CCC3(N(C)C(=O)C(=O)N(C)C)CC2)ccc1F] Ethanediamide, N-[7-(1,3-dihydro-1-oxo-2H-isoindol-2-yl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl | 631.3 | 2.78 | A |
| 145 | 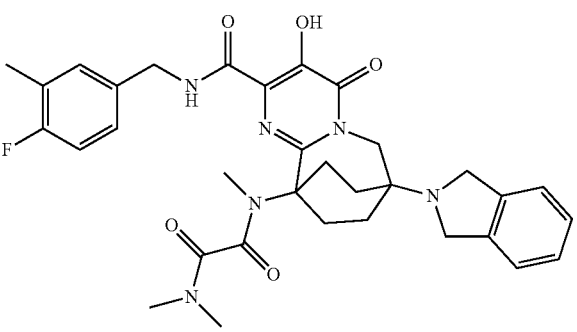 [SMILES: Cc1cc(CNC(=O)c2nc3n(c(=O)c2O)CC2(N4Cc5ccccc5C4)CCC3(N(C)C(=O)C(=O)N(C)C)CC2)ccc1F] Ethanediamide, N-[7-(1,3-dihydro-2H-isoindol-2-yl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 617.4 | 2.18 | A |

TABLE 3-continued

| Example | | M + 1 observed | RT | Method |
|---|---|---|---|---|
| 146 | 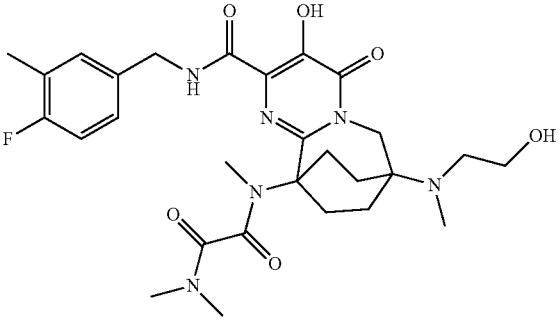 [SMILES: Cc1cc(CNC(=O)c2nc3n(c(=O)c2O)CC2(N(C)CCO)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-7-[(2-hydroxyethyl)methylamino]-4-oxo-7,10-ethanopyrimido[1,2-a]azepin-10(4H)-yl]-N,N',N'-trimethyl- | 573.4 | 1.98 | A |
| 147 | 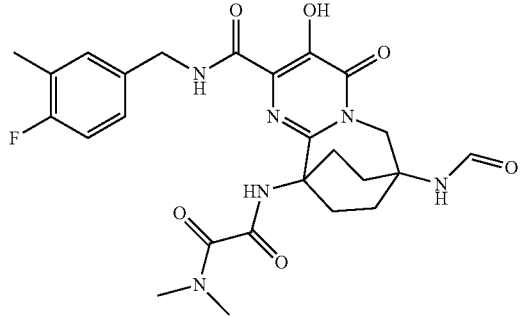 [SMILES: Cc1cc(CNC(=O)c2nc3n(c(=O)c2O)CC2(NC=O)CCC3(NC(=O)C(=O)N(C)C)CC2)ccc1F] Ethanediamide, N'-[2-[[[(4-fluoro-3-methylphenyl)methyl]amino]carbonyl]-7-(formylamino)-6,7,8,9-tetrahydro-3-hydroxy-4-oxo-7,10-ethanopyrimido[1,2-a]azepin-10(4H)-yl]-N,N-dimethyl- | 5.293 | 2.19 | A |
| 148 | 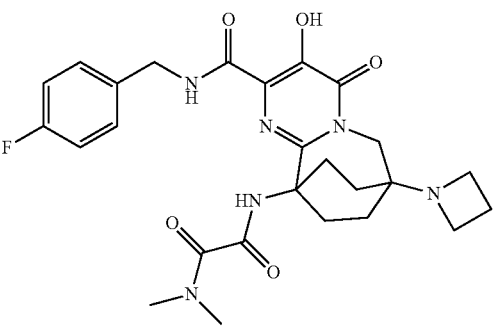 [SMILES: CN(C)C(=O)C(=O)NC12CCC(N3CCC3)(CC1)Cn1c2nc(C(=O)NCc2ccc(F)cc2)c(O)c1=O] Ethanediamide, N'-[7-(1-azetidinyl)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 527.3 | 2.08 | A |

TABLE 3-continued

| Example | | M + 1 observed | RT | Method |
|---|---|---|---|---|
| 149 | 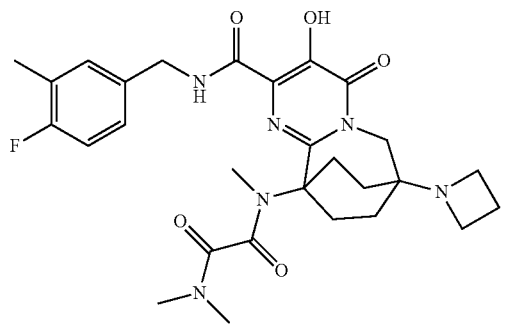 [SMILES: Cc1cc(CNC(=O)c2nc3n(c(=O)c2O)CC2(N4CCC4)CCC3(N(C)C(=O)C(=O)N(C)C)CC2)ccc1F] Ethanediamide, N-[7-(1-azetidinyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 555.4 | 2.05 | A |
| 150 | 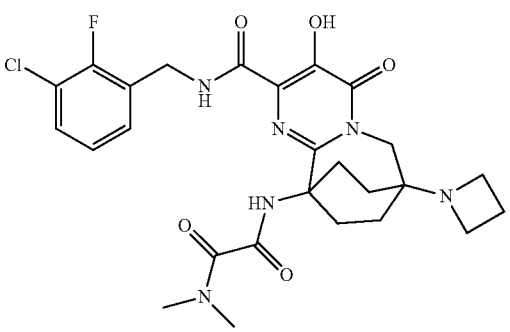 [SMILES: CN(C)C(=O)C(=O)NC12CCC(N3CCC3)(CC1)Cn1c2nc(C(=O)NCc2cccc(Cl)c2F)c(O)c1=O] Ethanediamide, N'-[7-(1-azetidinyl)-2-[[[(3-chloro-2-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 561.3 | 2.01 | A |
| 151 | 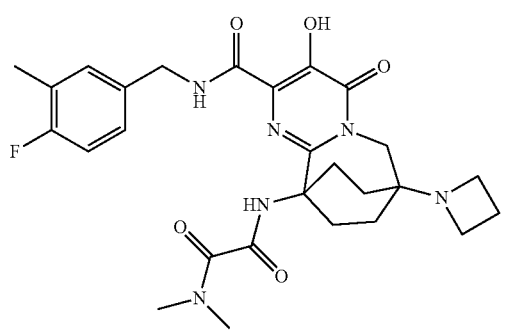 [SMILES: Cc1cc(CNC(=O)c2nc3n(c(=O)c2O)CC2(N4CCC4)CCC3(NC(=O)C(=O)N(C)C)CC2)ccc1F] Ethanediamide, N'-[7-(1-azetidinyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 541.3 | 2.00 | A |

TABLE 3-continued

| Example | | M + 1 observed | RT | Method |
|---|---|---|---|---|
| 152 | 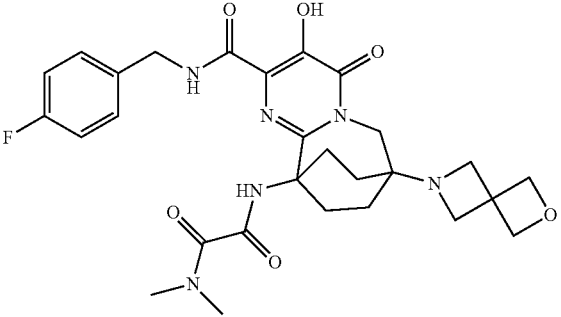 [SMILES: CN(C)C(=O)C(=O)NC12CCC(N3CC4(COC4)C3)(CC1)Cn1c2nc(C(=O)NCc2ccc(F)cc2)c(O)c1=O] Ethanediamide, N'-[2-[[[(4-fluorophenyl)methyl]amino]carbonyl]-6,7,8,9-tetrahydro-3-hydroxy-7-(2-oxa-6-azaspiro[3.3]hept-6-yl)-4-oxo-7,10-ethanopyrimido[1,2-a]azepin-10(4H)-yl]-N,N-dimethyl- | 569.4 | 1.85 | A |
| 153 | 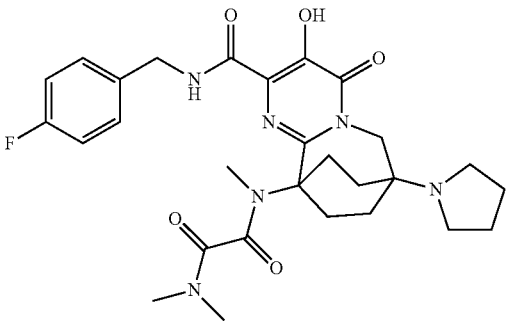 Ethanediamide, N-[2-[[[(4-fluorophenyl)methyl]amino]carbonyl]-6,7,8,9-tetrahydro-3-hydroxy-4-oxo-7-(1-pyrrolidinyl)-7,10-ethanopyrimido[1,2-a]azepin-10(4H)-yl]-N,N',N'-trimethyl- | 555.5 | 1.95 | A |
| 154 | 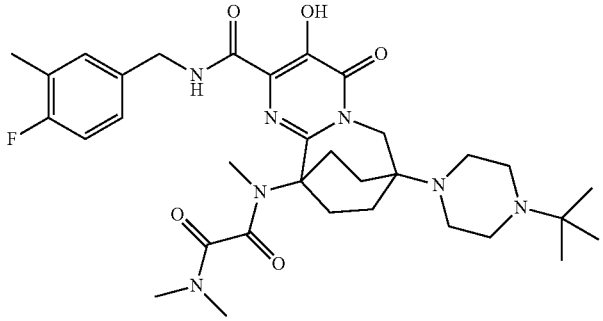 [SMILES: Cc1cc(CNC(=O)c2nc3n(c(=O)c2O)CC2(N4CCN(C(C)(C)C)CC4)CCC3(N(C)C(=O)C(=O)N(C)C)CC2)ccc1F] Ethanediamide, N-[7-[4-(1,1-dimethylethyl)-1-piperazinyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 641.0 | 3.02 | B |

TABLE 3-continued

| Example | | M + 1 observed | RT | Method |
|---|---|---|---|---|
| 155 | Ethanediamide, N-[2-[[[(4-fluoro-3-methylphenyl)methyl]amino]carbonyl]-6,7,8,9-tetrahydro-3-hydroxy-7-[4-[(4-methylphenyl)sulfonyl]-1-piperazinyl]-4-oxo-7,10-ethanopyrimido[1,2-a]azepin-10(4H)-yl]-N,N',N',-trimethyl- | 739.0 | 3.46 | B |
| 156 | Ethanediamide, N-[7-(dimethyl-d_3_-amino)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 549.5 | 2.05 | A |
| 157 | Ethanediamide, N1-[7-[(cyclopropylmethyl)amino]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N1, N2, N2-trimethyl- | 569.5 | 2.12 | A |

TABLE 3-continued

| Example | | M + 1 observed | RT | Method |
|---|---|---|---|---|
| 158 | 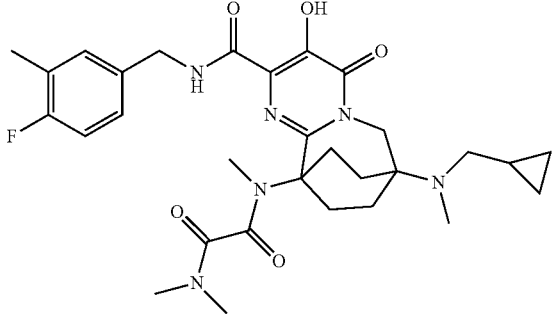 [SMILES: Cc1cc(CNC(=O)c2nc3n(c(=O)c2O)CC2(N(C)CC4CC4)CCC3(N(C)C(=O)C(=O)N(C)C)CC2)ccc1F] Ethanediamide, N1-[7-[(cyclopropylmethyl)methylamino]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N1, N2, N2-trimethyl- | 583.5 | 2.18 | A |
| 159 | 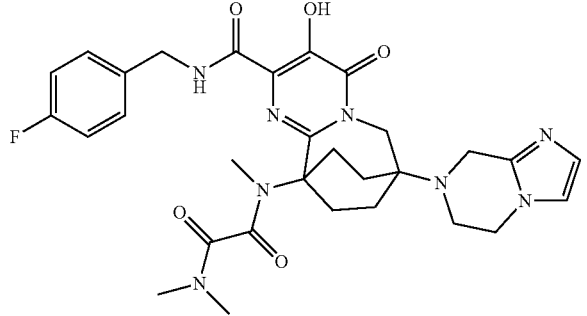 [SMILES: CN(C)C(=O)C(=O)N(C)C12CCC(N3CCn4ccnc4C3)(CC1)Cn1c2nc(C(=O)NCc2ccc(F)cc2)c(O)c1=O] Ethanediamide, N-[7-(5,6-dihydroimidazo[1,2-a]pyrazin-7(8H)-yl)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 607.5 | 1.98 | A |
| 160 | 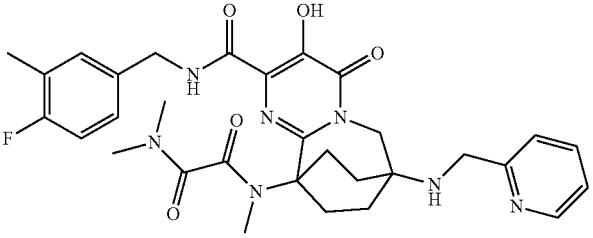 [SMILES: Cc1cc(CNC(=O)c2nc3n(c(=O)c2O)CC2(NCc4ccccn4)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-4-oxo-7-[(2-pyridinylmethyl)amino]-7,10-ethanopyrimido[1,2-a]azepin-10(4H)-yl]-N,N',N'-trimethyl- | 606.3 | 3.62 | C |

TABLE 3-continued

| Example | | M + 1 observed | RT | Method |
|---|---|---|---|---|
| 161 | 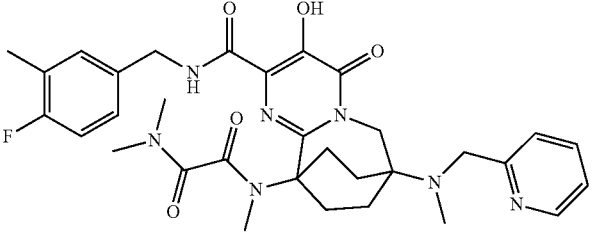 [SMILES: Cc1cc(CNC(=O)c2nc3n(c(=O)c2O)CC2(N(C)Cc4ccccn4)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-7-[methyl(2-pyridinylmethyl)amino]-4-oxo-7,10-ethanopyrimido[1,2-a]azepin-10(4H)-yl]-N,N',N'-trimethyl- | 618.6 | 2.43 | D |
| 162 | 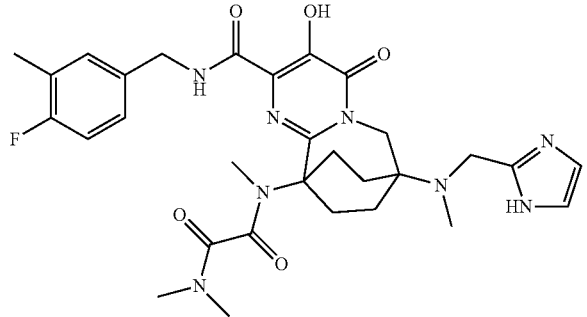 [SMILES: Cc1cc(CNC(=O)c2nc3n(c(=O)c2O)CC2(N(C)Cc4ncc[nH]4)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-7-[(1H-imidazol-2-ylmethyl)methylamino]-4-oxo-7,10-ethanopyrimido[1,2-a]azepin-10(4H)-yl]-N,N',N'-trimethyl- | 609.2 | 2.06 | A |
| 163 | 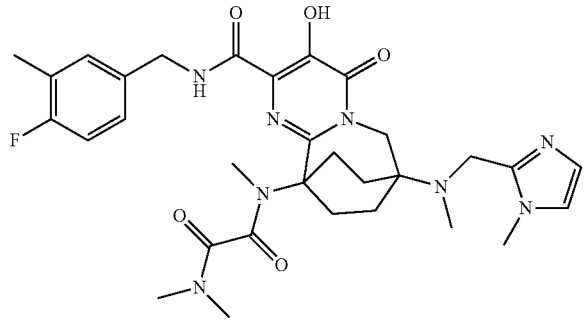 [SMILES: Cc1cc(CNC(=O)c2nc3n(c(=O)c2O)CC2(N(C)Cc4nccn4C)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-7-[methyl[(1-methyl-1H-imidazol-2-yl)methyl]amino]-4-oxo-7,10-ethanopyrimido[1,2-a]azepin-10(4H)-yl]-N,N',N'-trimethyl- | 623.2 | 2.12 | A |

TABLE 3-continued

| Example | | M + 1 observed | RT | Method |
|---|---|---|---|---|
| 164 | 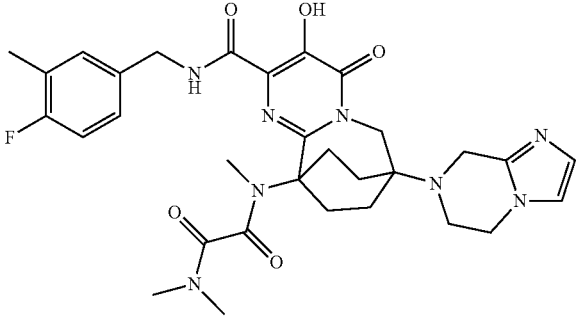 [SMILES: Cc1cc(CNC(=O)c2nc3n(c(=O)c2O)CC2(N4CCn5ccnc5C4)CCC3(N(C)C(=O)C(=O)N(C)C)CC2)ccc1F]<br>Ethanediamide, N-[7-(5,6-dihydroimidazo[1,2-a]pyrazin-7(8H)-yl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 621.4 | 2.20 | A |
| 165 | 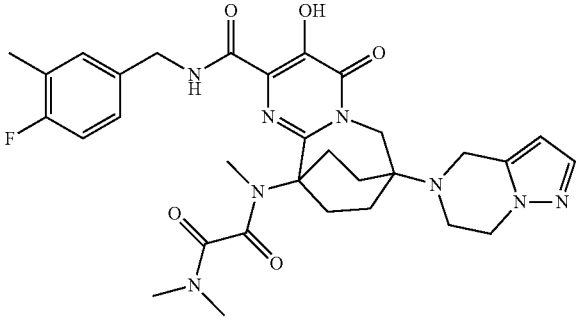 [SMILES: Cc1cc(CNC(=O)c2nc3n(c(=O)c2O)CC2(N4CCn5nccc5C4)CCC3(N(C)C(=O)C(=O)N(C)C)CC2)ccc1F]<br>Ethanediamide, N-[7-(6,7-dihydropyrazolo[1,5-a]pyrazin-5(4H)-yl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 621.4 | 2.43 | A |
| 166 | 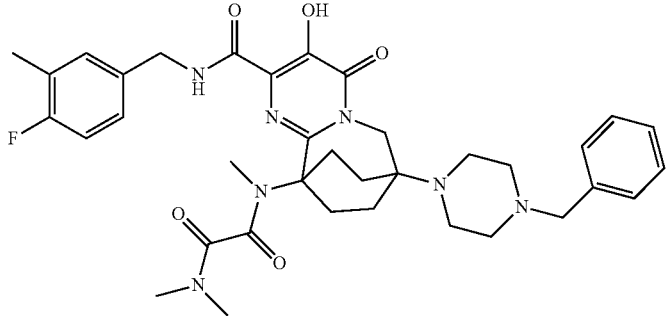 [SMILES: Cc1cc(CNC(=O)c2nc3n(c(=O)c2O)CC2(N4CCN(Cc5ccccc5)CC4)CCC3(N(C)C(=O)C(=O)N(C)C)CC2)ccc1F]<br>Ethanediamide, N1-[2-[[[(4-fluoro-3-methylphenyl)methyl]amino]carbonyl]-6,7,8,9-tetrahydro-3-hydroxy-4-oxo-7-[4-(phenylmethyl)-1-piperazinyl]-7,10-ethanopyrimido[1,2-a]azepin-10(4H)-yl]-N1, N2, N2-trimethyl- | 674.5 | 2.57 | A |

TABLE 3-continued

| Example | | M + 1 observed | RT | Method |
|---|---|---|---|---|
| 167 | 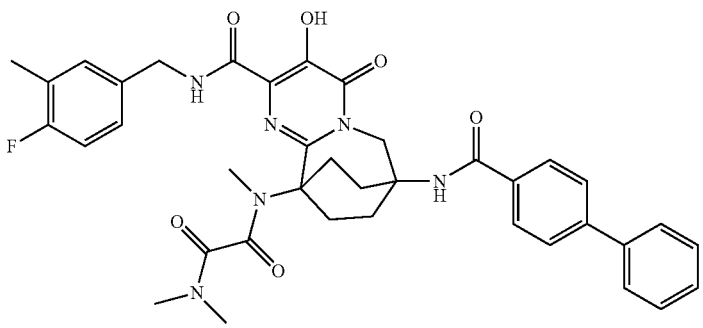 [SMILES: Cc1cc(CNC(=O)c2nc3n(c(=O)c2O)CC2(NC(=O)c4ccc(-c5ccccc5)cc4)CCC3(N(C)C(=O)C(=O)N(C)C)CC2)ccc1F]<br>Ethanediamide, N1-[7-[([1,1'-biphenyl]-4-ylcarbonyl)amino]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N1, N2, N2-trimethyl- | 695.3 | 2.66 | E |
| 168 | 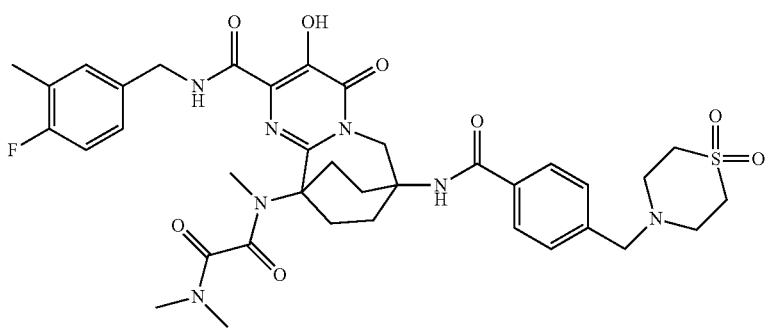 [SMILES: Cc1cc(CNC(=O)c2nc3n(c(=O)c2O)CC2(NC(=O)c4ccc(CN5CCS(=O)(=O)CC5)cc4)CCC3(N(C)C(=O)C(=O)N(C)C)CC2)ccc1F]<br>Ethanediamide, N1-[7-[([1,1'-biphenyl]-4-ylcarbonyl)amino]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N1, N2, N2-trimethyl- | 766.5 | 2.62 | F |
| 169 | 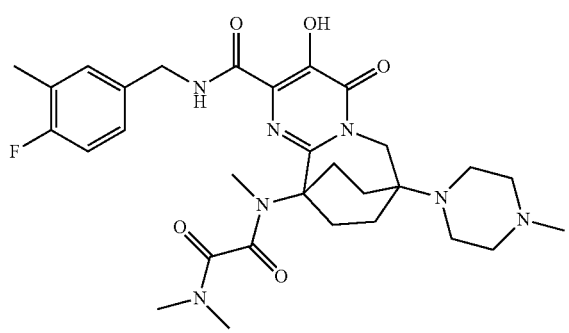 [SMILES: Cc1cc(CNC(=O)c2nc3n(c(=O)c2O)CC2(N4CCN(C)CC4)CCC3(N(C)C(=O)C(=O)N(C)C)CC2)ccc1F]<br>Ethanediamide, N-[2-[[[(4-fluoro-3-methylphenyl)methyl]amino]carbonyl]-6,7,8,9-tetrahydro-3-hydroxy-7-(4-methyl-1-piperazinyl)-4-oxo-7,10-ethanopyrimido[1,2-a]azepin-10(4H)-yl]-N,N',N'-trimethyl- | 598.5 | 2.38 | A |

TABLE 3-continued

| Example | | M + 1 observed | RT | Method |
|---|---|---|---|---|
| 170 | 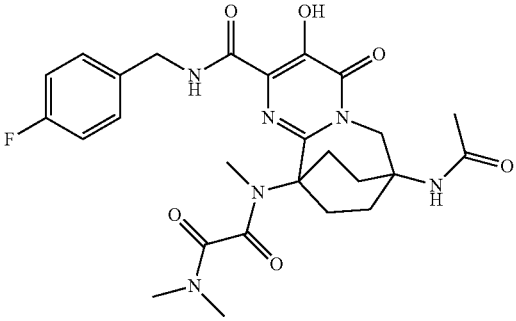 [SMILES: CC(=O)NC12CCC(N(C)C(=O)C(=O)N(C)C)(CC1)c1nc(C(=O)NCc3ccc(F)cc3)c(O)c(=O)n1C2] Ethanediamide, N-[7-(acetylamino)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 543.4 | 2.39 | A |
| 171 | 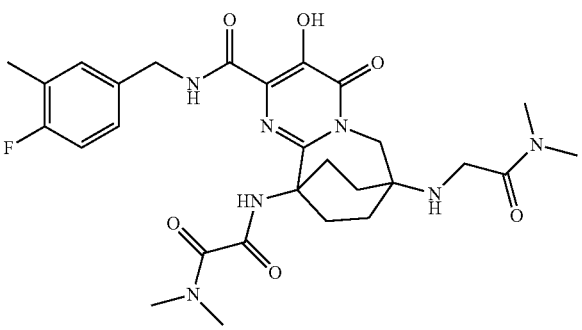 [SMILES: Cc1cc(CNC(=O)c2nc3n(c(=O)c2O)CC2(NCC(=O)N(C)C)CCC3(NC(=O)C(=O)N(C)C)CC2)ccc1F] Ethanediamide, N'-[7-[[2-(dimethylamino)-2-oxoethyl]amino]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 586.4 | 2.22 | A |
| 172 | 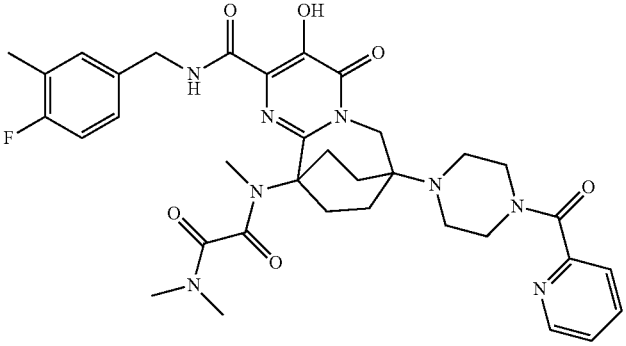 [SMILES: Cc1cc(CNC(=O)c2nc3n(c(=O)c2O)CC2(N4CCN(C(=O)c5ccccn5)CC4)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-4-oxo-7-[4-(2-pyridinylcarbonyl)-1-piperazinyl]-7,10-ethanopyrimido[1,2-a]azepin-10(4H)-yl]-N,N',N'-trimethyl- | 689.4 | 2.39 | A |

TABLE 3-continued

| Example | | M + 1 observed | RT | Method |
|---|---|---|---|---|
| 173 | 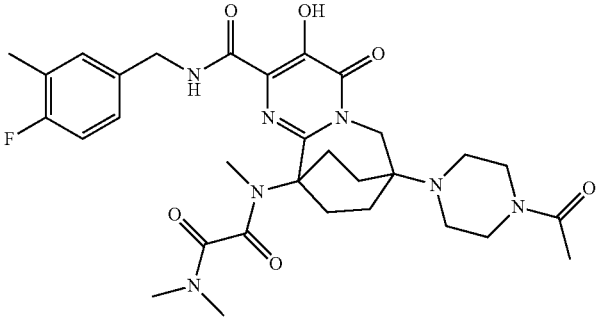 [SMILES: CC(=O)N1CCN(C23CCC(N(C)C(=O)C(=O)N(C)C)(CC2)c2nc(C(=O)NCc4ccc(F)c(C)c4)c(O)c(=O)n2C3)CC1]<br>Ethanediamide, N-[7-(4-acetyl-1-piperazinyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 626.5 | 2.39 | A |
| 174 | 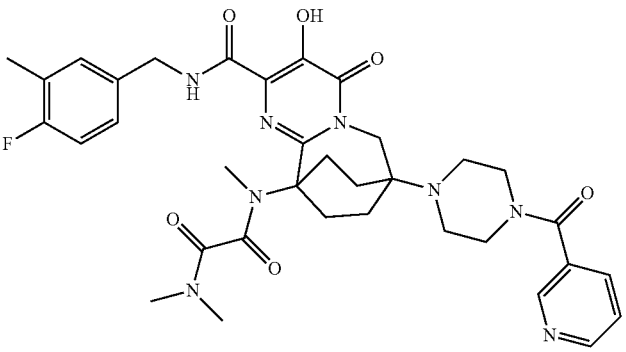 [SMILES: Cc1cc(CNC(=O)c2nc3n(c(=O)c2O)CC2(N4CCN(C(=O)c5cccnc5)CC4)CCC3(N(C)C(=O)C(=O)N(C)C)CC2)ccc1F]<br>Ethanediamide, N-[2-[[[(4-fluoro-3-methylphenyl)methyl]amino]carbonyl]-6,7,8,9-tetrahydro-3-hydroxy-4-oxo-7-[4-(3-pyridinylcarbonyl)-1-piperazinyl]-7,10-ethanopyrimido[1,2-a]azepin-10(4H)-yl]-N,N',N'-trimethyl- | 689.4 | 2.40 | A |
| 175 | 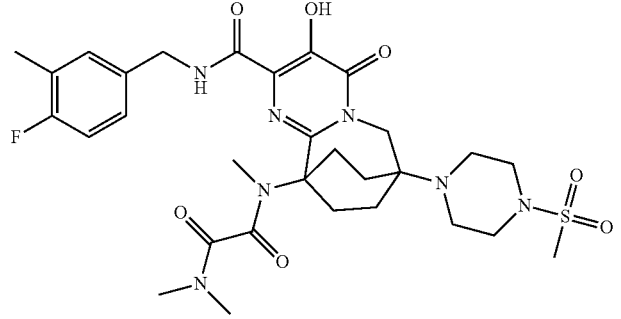 [SMILES: Cc1cc(CNC(=O)c2nc3n(c(=O)c2O)CC2(N4CCN(S(C)(=O)=O)CC4)CCC3(N(C)C(=O)C(=O)N(C)C)CC2)ccc1F]<br>Ethanediamide, N-[2-[[[(4-fluoro-3-methylphenyl)methyl]amino]carbonyl]-6,7,8,9-tetrahydro-3-hydroxy-7-[4-(methylsulfonyl)-1-pipenizinyl]-4-oxo-7,10-ethanopyrimido[1,2-a]azepin-10(4H)-yl]-N,N',N'-trimethyl- | 662.4 | 2.42 | A |

TABLE 3-continued

| Example | | M + 1 observed | RT | Method |
|---|---|---|---|---|
| 176 | 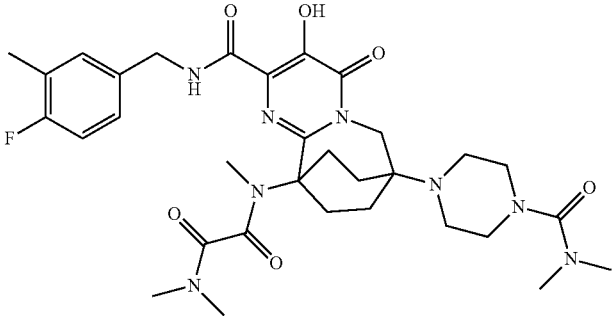 [SMILES: Cc1cc(CNC(=O)c2nc3n(c(=O)c2O)CC2(N4CCN(C(=O)N(C)C)CC4)CCC3(N(C)C(=O)C(=O)N(C)C)CC2)ccc1F] Ethanediamide, N-[7-[4-[(dimethylamino)carbonyl]-1-piperazinyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 655.5 | 2.49 | A |
| 177 | 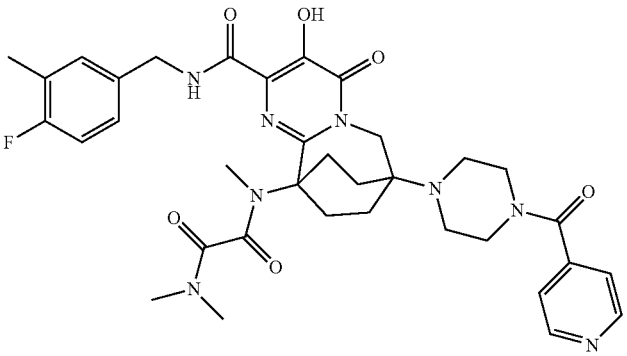 [SMILES: Cc1cc(CNC(=O)c2nc3n(c(=O)c2O)CC2(N4CCN(C(=O)c5ccncc5)CC4)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-4-oxo-7-[4-(4-pyridinylcarbonyl)-1-piperazinyl]-7,10-ethanopyrimido[1,2-a]azepin-10(4H)-yl]-N,N',N'-trimethyl- | 689.5 | 2.34 | A |
| 178 | 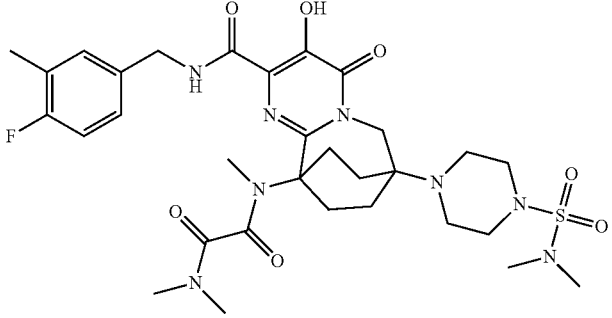 [SMILES: Cc1cc(CNC(=O)c2nc3n(c(=O)c2O)CC2(N4CCN(S(=O)(=O)N(C)C)CC4)CCC3(N(C)C(=O)C(=O)N(C)C)CC2)ccc1F] Ethanediamide, N-[7-[4-[(dimethylamino)sulfonyl]-1-piperazinyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 691.5 | 2.49 | A |

TABLE 3-continued

| Example | | M + 1 observed | RT | Method |
|---|---|---|---|---|
| 179 | 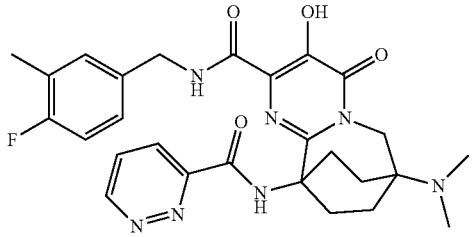 [SMILES: Cc1cc(CNC(=O)c2nc3n(c(=O)c2O)CC2(N(C)C)CCC3(NC(=O)c3cccnn3)CC2)ccc1F] 7,10-Ethanopyrimido[1,2-a]azepine-2-carboxamide, 7-(dimethylamino)-N-[(4-fluoro-3-methylphenyl)methyl]-4,6,7,8,9,10-hexahydro-3-hydroxy-4-oxo-10-[(3-pyridazinylcarbonyl)amino]- | 536.2 | 1.61 | G |
| 180 | 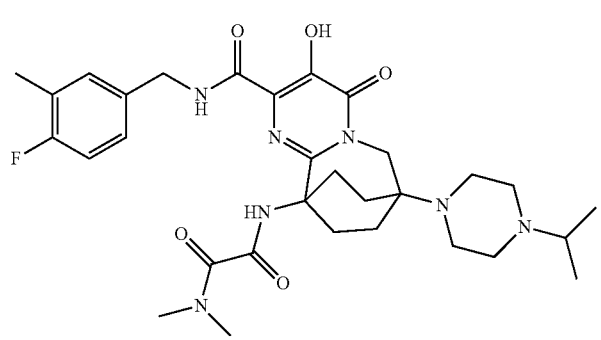 [SMILES: Cc1cc(CNC(=O)c2nc3n(c(=O)c2O)CC2(N4CCN(C(C)C)CC4)CCC3(NC(=O)C(=O)N(C)C)CC2)ccc1F] Ethanediamide, N'-[2-[[[(4-fluoro-3-methylphenyl)methyl]amino]carbonyl]-6,7,8,9-tetrahydro-3-hydroxy-7-[4-(1-methylethyl)-1-piperazinyl]-4-oxo-7,10-ethanopyrimido[1,2-a]azepin-10(4H)-yl]-N,N-dimethyl- | | | |
| 181 | 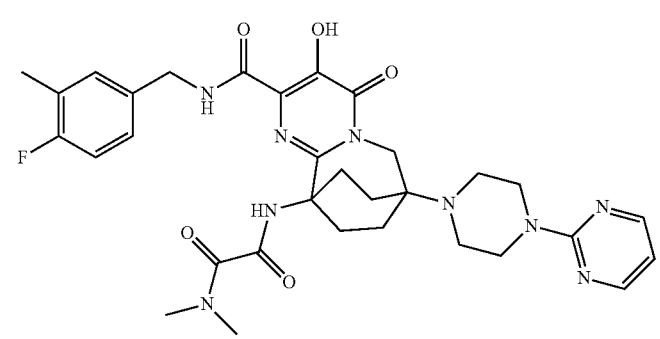 [SMILES: Cc1cc(CNC(=O)c2nc3n(c(=O)c2O)CC2(N4CCN(c5ncccn5)CC4)CCC3(NC(=O)C(=O)N(C)C)CC2)ccc1F] Ethanediamide, N'-[2-[[[(4-fluoro-3-methylphenyl)methyl]amino]carbonyl]-6,7,8,9-tetrahydro-3-hydroxy-4-oxo-7-[4-(2-pyrimidinyl)-1-piperazinyl]-7,10-ethanopyrimido[1,2-a]azepin-10(4H)-yl]-N,N-dimethyl- | 648.5 | 2.23 | A |

TABLE 3-continued

| Example | | M + 1 observed | RT | Method |
|---|---|---|---|---|
| 182 | 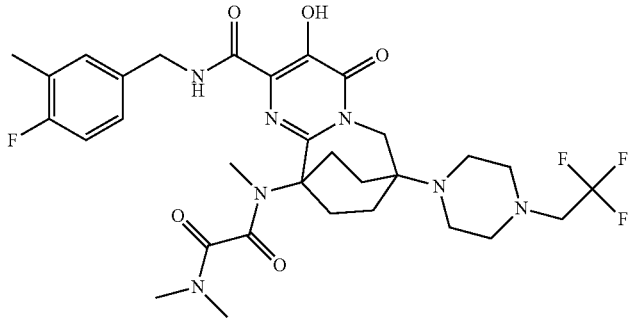 [SMILES: Cc1cc(CNC(=O)c2nc3n(c(=O)c2O)CC2(N4CCN(CC(F)(F)F)CC4)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-4-oxo-7-[4-(2,2,2-trifluoroethyl)-1-piperazinyl]-7,10-ethanopyrimido[1,2-a]azepin-10(4H)-yl]-N,N',N'-trimethyl- | 666.5 | 2.04 | A |

TABLE 3

| Example | | M + 1 Observed | RT | Method |
|---|---|---|---|---|
| 183 | 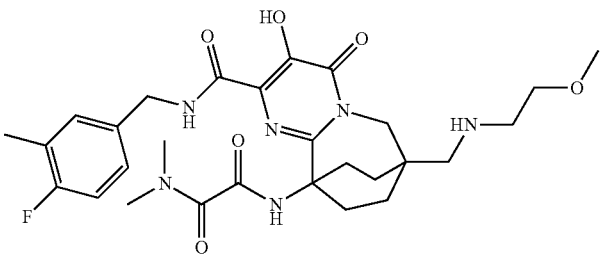 Ethanediamide, N'-[2-[[[(4-fluoro-3-methylphenyl)methyl]amino]carbonyl]-6,7,8,9-tetrahydro-3-hydroxy-7-[[(2-methoxyethyl)amino]methyl]-4-oxo-7,10-ethanopyrimido]1,2-a]azepin-10(4H)-yl]-N,N-dimethyl- | 573.3 | 2.99 | C |
| 184 | Ethanediamide, N-[2-[[[(4-fluoro-3-methylphenyl)methyl]amino]carbonyl]-6,7,8,9-tetrahydro-3-hydroxy-7-[[[(5-methyl-3-isoxazolyl)methyl]amino]methyl]-4-oxo-7,10-ethanopyrimido[1,2-a]azepin-10(4H)-yl]-N,N',N'-trimethyl- | 624.5 | 2.85 | F |

TABLE 3-continued

| Example | | M + 1 Observed | RT | Method |
|---|---|---|---|---|
| 185 | Ethanediamide, N'-[2-[[[(4-fluoro-3-methylphenyl)methyl]amino]carbonyl]-6,7,8,9-tetrahydro-3-hydroxy-7-[[(2-methoxy-1-methylethyl)amino]methyl]-4-oxo-7,10-ethanopyrimido[1,2-a]azepin-10(4H)-yl]-N,N-dimethyl- | 587.4 | 2.31 | F |
| 186 | Ethanediamide, N-[2-[[[(4-fluoro-3-methylphenyl)methyl]amino]carbonyl]-6,7,8,9-tetrahydro-3-hydroxy-4-oxo-7-(1H-1,2,4-triazol-1-ylmethyl)-7,10-ethanopyrimido[1,2-a]azepin-10(4H)-yl]-N,N',N'-trimethyl- | 581.4 | 1.40 | H |
| 187 | Ethanediamide, N'-[2-[[[(3-chloro-2-fluorophenyl)methyl]amino]carbonyl]-6,7,8,9-tetrahydro-3-hydroxy-4-oxo-7-(1H-pyrazol-1-ylmethyl)-7,10-ethanopyrimido[1,2-a]azepin-10(4H)-yl]-N,N-dimethyl- | 586.3 | 2.71 | A |
| 188 | Ethanediamide, N'-[2-[[[(3-chloro-2-fluorophenyl)methyl]amino]carbonyl]-6,7,8,9-tetrahydro-3-hydroxy-7-[[(2-methoxyethyl)amino]methyl]-4-oxo-7,10-ethanopyrimido[1,2-a]azepin-10(4H)-yl]-N,N-dimethyl- | 593.1 | 3.22 | C |

TABLE 3-continued

| Example | | M + 1 Observed | RT | Method |
|---|---|---|---|---|
| 189 | 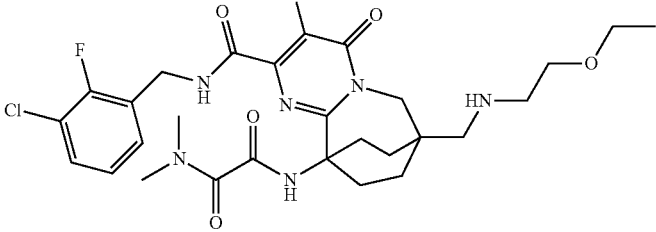 Ethanediamide, N'-[2-[[[(3-chloro-2-fluorophenyl)methyl]amino]carbonyl]-7-[[(2-ethoxyethyl)amino]methyl]-6,7,8,9-tetrahydro-3-hydroxy-4-oxo-7,10-ethanopyrimido[1,2-a]azepin-10(4H)-yl]-N,N-dimethyl- | 607.1 | 3.32 | C |
| 190 | 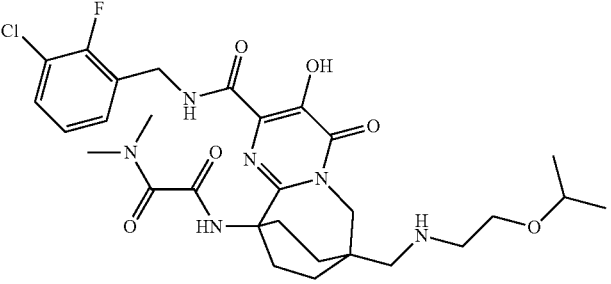 [SMILES: CC(C)OCCNCC12CCC(NC(=O)C(=O)N(C)C)(CC1)c1nc(C(=O)NCc3cccc(Cl)c3F)c(O)c(=O)n1C2] Ethanediamide, N'-[2-[[[(3-chloro-2-fluorophenyl)methyl]amino]carbonyl]-6,7,8,9-tetrahydro-3-hydroxy-7-[[[2-(1-methylethoxy)ethyl]amino]methyl]-4-oxo-7,10-ethanopyrimido[1,2-a]azepin-10(4H)-yl]-N,N-dimethyl- | 621.1 | 3.43 | C |
| 191 | 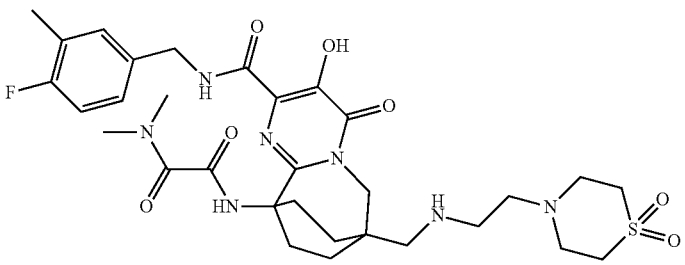 [SMILES: Cc1cc(CNC(=O)c2nc3n(c(=O)c2O)CC2(CNCCN4CCS(=O)(=O)CC4)CCC3(NC(=O)C(=O)N(C)C)CC2)ccc1F] Ethanediamide, N'-[7-[[[2-(1,1-dioxido-4-thiomorpholinyl)ethyl]amino]methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 676.4 | 2.22 | F |
| 192 | 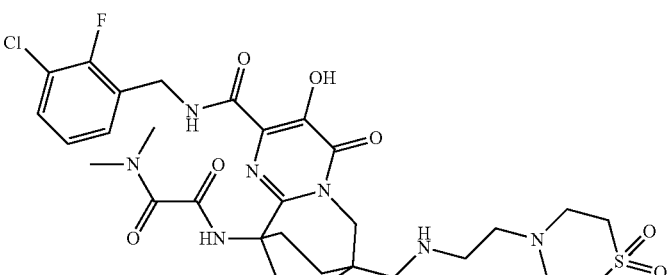 Ethanediamide, N'-[2-[[[(3-chloro-2-fluorophenyl)methyl]amino]carbonyl]-7-[[[2-(1,1-dioxido-4-thiomorpholinyl)ethyl]amino]methyl]-6,7,8,9-tetrahydro-3-hydroxy-4-oxo-7,10-ethanopyrimido[1,2-a]azepin-10(4H)-yl]-N,N-dimethyl- | 696.3 | 2.26 | F |

TABLE 3-continued

| Example | | M + 1 Observed | RT | Method |
|---|---|---|---|---|
| 193 | 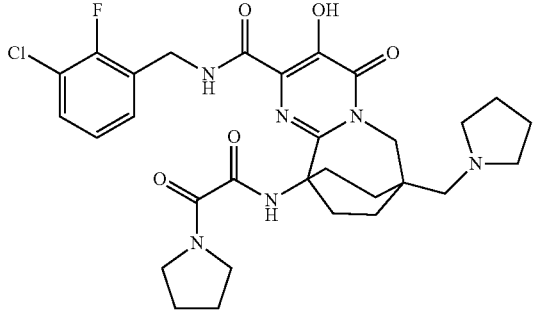 [SMILES: O=C(NC12CCC(CN3CCCC3)(CC1)Cn1c2nc(C(=O)NCc2cccc(Cl)c2F)c(O)c1=O)C(=O)N1CCCC1]<br>7,10-Ethanopyrimido[1,2-a]azepine-2-carboxamide, N-[(3-chloro-2-fluorophenyl)methyl]-10-[[1,2-dioxo-2-(1-pyrrolidinyl)ethyl]amino]-4,6,7,8,9,10-hexahydro-3-hydroxy-4-oxo-7-(1-pyrrolidinylmethyl)- | 615.4 | 2.19 | A |
| 194 | 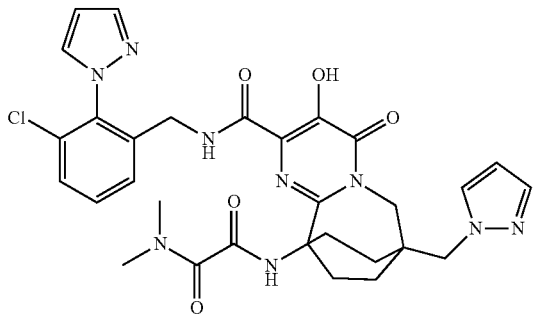 [SMILES: CN(C)C(=O)C(=O)NC12CCC(Cn3cccn3)(CC1)Cn1c2nc(C(=O)NCc2cccc(Cl)c2-n2cccn2)c(O)c1=O]<br>Ethanediamide, N'-[2-[[[[3-chloro-2-(1H-pyrazol-1-yl)phenyl]methyl]amino]carbonyl]-6,7,8,9-tetrahydro-3-hydroxy-4-oxo-7-(1H-pyrazol-1-ylmethyl)-7,10-ethanopyrimido[1,2-a]azepin-10(4H)-yl]-N,N-dimethyl- | 635.3 | 2.38 | A |
| 195 | 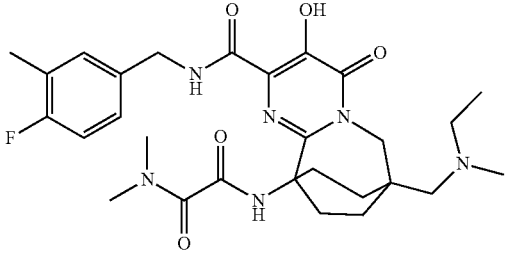<br>Ethanediamide, N'-[7-[(ethylmethylamino)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 557.4 | 2.96 | C |

| Example | | M + 1 Observed | RT | Method |
|---|---|---|---|---|
| 196 | 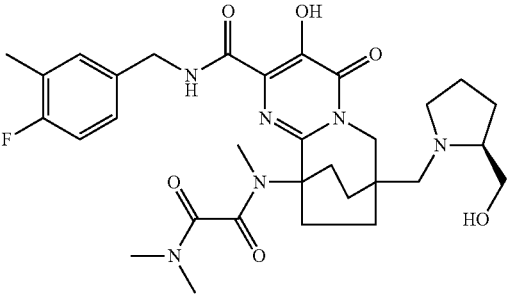 [SMILES: Cc1cc(CNC(=O)c2nc3n(c(=O)c2O)CC2(CN4CCC[C@H]4CO)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-7-[[(2S)-2-(hydroxymethyl)-1-pyrrolidinyl]methyl]-4-oxo-7,10-ethanopyrimido[1,2-a]azepin-10(4H)-yl]-N,N',N'-trimethyl- | 613.5 | 1.22 | H |
| 197 | 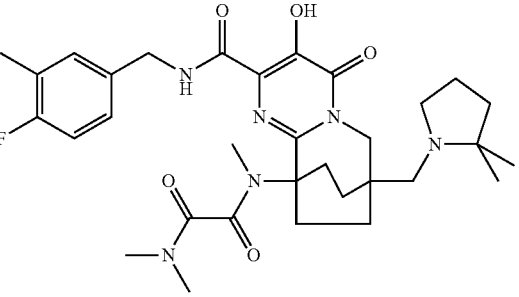 Ethanediamide, N-[7-[(2,2-dimethyl-1-pyrrolidinyl)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 611.5 | 1.28 | H |
| 198 | 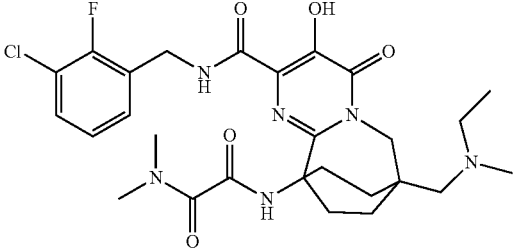 [SMILES: CCN(C)CC12CCC(NC(=O)C(=O)N(C)C)(CC1)c1nc(C(=O)NCc3cccc(Cl)c3F)c(O)c(=O)n1C2] Ethanediamide, N'-[2-[[[(3-chloro-2-fluorophenyl)methyl]amino]carbonyl]-7-[(ethylmethylamino)methyl]-6,7,8,9-tetrahydro-3-hydroxy-4-oxo-7,10-ethanopyrimido[1,2-a]azepin-10(4H)-yl]-N,N-dimethyl- | 577.4 | 2.04 | A |
| 199 | 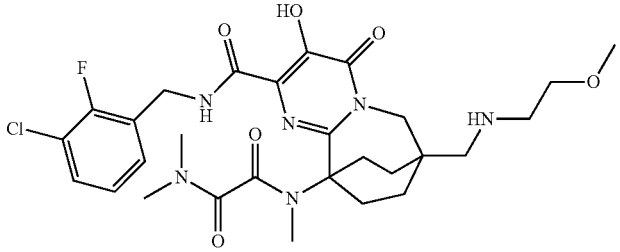 [SMILES: COCCNCC12CCC(N(C)C(=O)C(=O)N(C)C)(CC1)c1nc(C(=O)NCc3cccc(Cl)c3F)c(O)c(=O)n1C2] Ethanediamide, N-[2-[[[(3-chloro-2-fluorophenyl)methyl]amino]carbonyl]-6,7,8,9-tetrahydro-3-hydroxy-7-[[(2-methoxyethyl)amino]methyl]-4-oxo-7,10-ethanopyrimido[1,2-a]azepin-10(4H)-yl]-N,N',N'-trimethyl- | 607.1 | 3.37 | C |

TABLE 3-continued

| Example | | M + 1 Observed | RT | Method |
|---|---|---|---|---|
| 200 | Ethanediamide, N-[2-[[[(3-chloro-2-fluorophenyl)methyl]amino]carbonyl]-6,7,8,9-tetrahydro-3-hydroxy-4-oxo-7-[[(tetrahydro-2H-pyran-4-yl)amino]methyl]-7,10-ethanopyrimido[1,2-a]azepin-10(4H)-yl]-N,N',N'-trimethyl- | 633.2 | 3.37 | C |
| 201 | Ethanediamide, N'-[7-[(diethylamino)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 572.4 | 2.24 | A |
| 202 | Ethanediamide, N'-[2-[[[(4-fluoro-3-methylphenyl)methyl]amino]carbonyl]-6,7,8,9-tetrahydro-3-hydroxy-7-[[methyl(1-methylethyl)amino]methyl]-4-oxo-7,10-ethanopyrimido[1,2-a]azepin-10(4H)-yl]-N,N-dimethyl- | 571.5 | 2.28 | A |
| 203 | Ethanediamide, N-[2-[[[(3-chloro-2-fluorophenyl)methyl]amino]carbonyl]-7-[(ethylmethylamino)methyl]-6,7,8,9-tetrahydro-3-hydroxy-4-oxo-7,10-ethanopyrimido[1,2-a]azepin-10(4H)-yl]-N,N',N'-trimethyl- | 591.4 | 2.29 | A |

TABLE 3-continued

| Example | M + 1 Observed | RT | Method |
|---|---|---|---|
| 204 Ethanediamide, N'-[2-[[[(3-chloro-2-fluorophenyl)methyl]amino]carbonyl]-6,7,8,9-tetrahydro-3-hydroxy-7-[[(2S)-2-(methoxymethyl)-1-pyrrolidinyl]methyl]-4-oxo-7,10-ethanopyrimido[1,2-a]azepin-10(4H)-yl]-N,N-dimethyl- | 633.4 | 2.32 | A |
| 205 Ethanediamide, N-[2-[[[(4-fluoro-3-methylphenyl)methyl]amino]carbonyl]-6,7,8,9-tetrahydro-3-hydroxy-7-[[(3S)-3-hydroxy-1-pyrrolidinyl]methyl]-4-oxo-7,10-ethanopyrimido[1,2-a]azepin-10(4H)-yl]-N,N',N'-trimethyl- | 599.5 | 1.29 | H |
| 206 Ethanediamide, N-[2-[[[(3-chloro-2-fluorophenyl)methyl]amino]carbonyl]-6,7,8,9-tetrahydro-3-hydroxy-7-[[(2S)-2-(methoxymethyl)-1-pyrrolidinyl]methyl]-4-oxo-7,10-ethanopyrimido[1,2-a]azepin-10(4H)-yl]-N,N',N'-trimethyl- | 647.4 | 1.94 | A |
| 207 Ethanediamide, N-[2-[[[(3-chloro-2-fluorophenyl)methyl]amino]carbonyl]-7-[(dimethylamino)methyl]-6,7,8,9-tetrahydro-3-hydroxy-4-oxo-7,10-ethanopyrimido[1,2-a]azepin-10(4H)-yl]-N,N',N'-trimethyl- | 577.2 | 3.03 | C |

TABLE 3-continued

| Example | | M + 1 Observed | RT | Method |
|---|---|---|---|---|
| 208 | 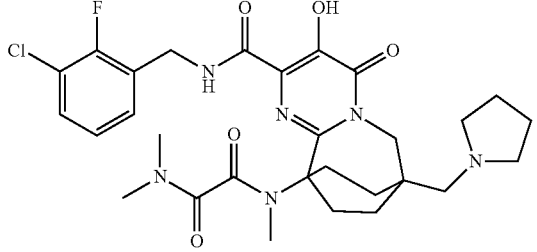 [SMILES: CN(C)C(=O)C(=O)N(C)C12CCC(CN3CCCC3)(CC1)Cn1c2nc(C(=O)NCc2cccc(Cl)c2F)c(O)c1=O]<br>Ethanediamide, N-[2-[[[(3-chloro-2-fluorophenyl)methyl]amino]carbonyl]-6,7,8,9-tetrahydro-3-hydroxy-4-oxo-7-(1-pyrrolidinylmethyl)-7,10-ethanopyrimido[1,2-a]azepin-10(4H)-yl]-N,N',N'-trimethyl- | 603.4 | 2.07 | A |
| 209 | 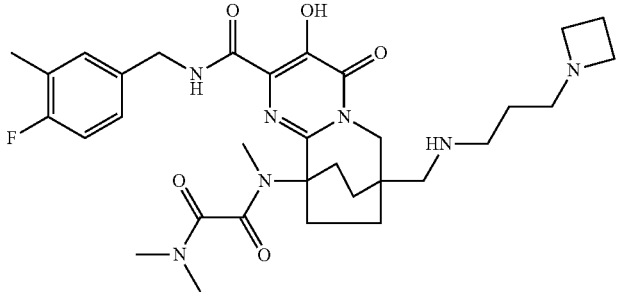 [SMILES: Cc1cc(CNC(=O)c2nc3n(c(=O)c2O)CC2(CNCCCN4CCC4)CCC3(N(C)C(=O)C(=O)N(C)C)CC2)ccc1F]<br>Ethanediamide, N-[7-[[[(3-(1-azetidinyl)propyl]amino]methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 626.5 | 1.16 | H |
| 210 | 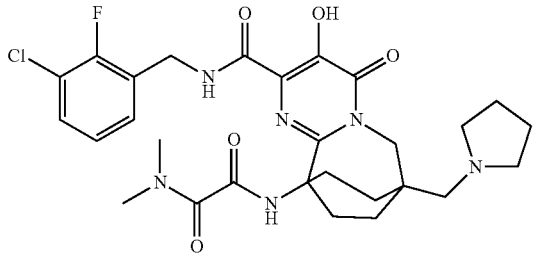 [SMILES: CN(C)C(=O)C(=O)NC12CCC(CN3CCCC3)(CC1)Cn1c2nc(C(=O)NCc2cccc(Cl)c2F)c(O)c1=O]<br>Ethanediamide, N'-[2-[[[(3-chloro-2-fluorophenyl)methyl]amino]carbonyl]-6,7,8,9-tetrahydro-3-hydroxy-4-oxo-7-(1-pyrrolidinylmethyl)-7,10-ethanopyrimido[1,2-a]azepin-10(4H)-yl]-N,N-dimethyl- | 589.4 | 2.25 | A |
| 211 | 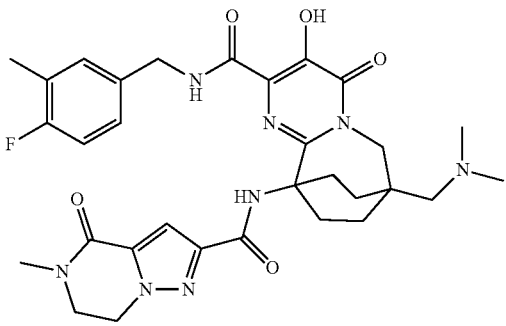<br>7,10-Ethanopyrimido[1,2-a]azepine-2-carboxamide,7-[(dimethylamino)methyl]-N-[(4-fluoro-3-methylphenyl)methyl]-4,6,7,8,9,10-hexahydro-3-hydroxy-4-oxo-10-[[(4,5,6,7-tetrahydro-5-methyl-4-oxopyrazolo[1,5-a]pyrazin-2-yl)carbonyl]amino]- | 621.5 | 2.55 | A |

TABLE 3-continued

| Example | | M + 1 Observed | RT | Method |
|---|---|---|---|---|
| 212 | 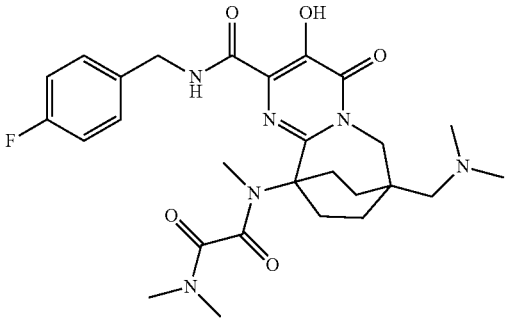 [SMILES: CN(C)CC12CCC(N(C)C(=O)C(=O)N(C)C)(CC1)c1nc(C(=O)NCc3ccc(F)cc3)c(O)c(=O)n1C2] Ethanediamide, N-[7-[dimethylamino)methyl]-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 544.5 | 2.83 | A |
| 213 | 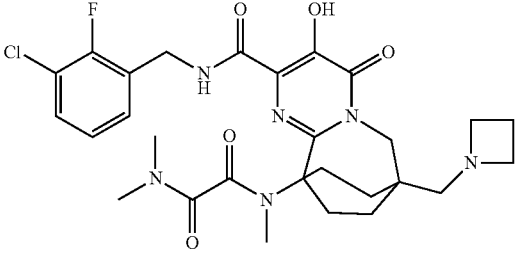 [SMILES: CN(C)C(=O)C(=O)N(C)C12CCC(CN3CCC3)(CC1)Cn1c2nc(C(=O)NCc2cccc(Cl)c2F)c(O)c1=O] Ethanediamide, N-[7-(1-azetidinylmethyl)-2-[[[(3-chloro-2-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 589.4 | 2.81 | A |
| 214 | 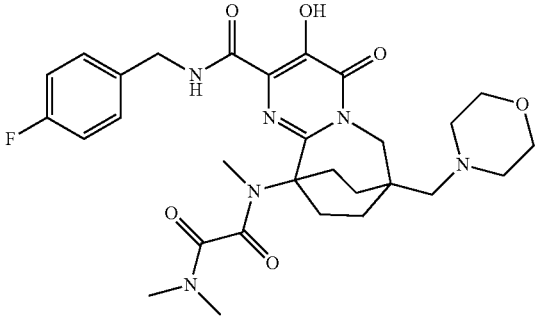 [SMILES: CN(C)C(=O)C(=O)N(C)C12CCC(CN3CCOCC3)(CC1)Cn1c2nc(C(=O)NCc2ccc(F)cc2)c(O)c1=O] Ethanediamide, N-[2-[[[(4-fluorophenyl)methyl]amino]carbonyl]-6,7,8,9-tetrahydro-3-hydroxy-7-(4-morpholinylmethyl)-4-oxo-7,10-ethanopyrimido[1,2-a]azepin-10(4H)-yl]-N,N',N'-trimethyl- | 585.4 | 2.81 | A |

TABLE 3-continued

| Example | | M + 1 Observed | RT | Method |
|---|---|---|---|---|
| 215 | 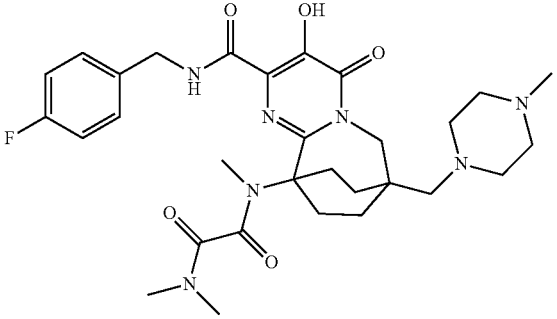 [SMILES: CN1CCN(CC23CCC(N(C)C(=O)C(=O)N(C)C)(CC2)c2nc(C(=O)NCc4ccc(F)cc4)c(O)c(=O)n2C3)CC1] Ethanediamide, N-[2-[[[(4-fluorophenyl)methyl]amino]carbonyl]-6,7,8,9-tetrahydro-3-hydroxy-7-[(4-methyl-1-piperazinyl)methyl]-4-oxo-7,10-ethanopyrimido[1,2-a]azepin-10(4H)-yl]-N,N',N'-trimethyl- | 598.5 | 2.85 | A |
| 216 | 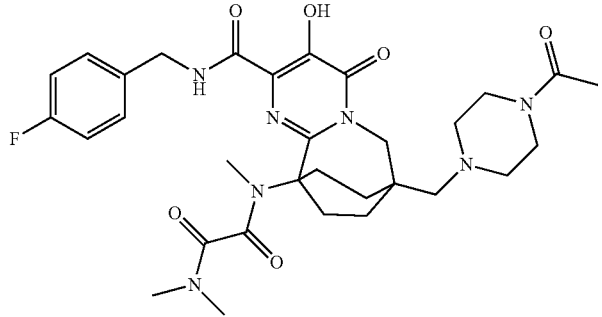 [SMILES: CC(=O)N1CCN(CC23CCC(N(C)C(=O)C(=O)N(C)C)(CC2)c2nc(C(=O)NCc4ccc(F)cc4)c(O)c(=O)n2C3)CC1] Ethanediamide, N-[7-[(4-acetyl-1-piperazinyl)methyl]-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 626.4 | 2.78 | C |
| 217 | 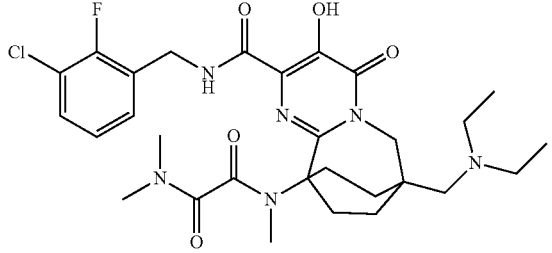 [SMILES: CCN(CC)CC12CCC(N(C)C(=O)C(=O)N(C)C)(CC1)c1nc(C(=O)NCc3cccc(Cl)c3F)c(O)c(=O)n1C2] Ethanediamide, N-[2-[[[(3-chloro-2-fluorophenyl)methyl]amino]carbonyl]-7-[(diethylamino)methyl]-6,7,8,9-tetrahydro-3-hydroxy-4-oxo-7,10-ethanopyrimido[1,2-a]azepin-10(4H)-yl]-N,N',N'-trimethyl- | 605.4 | 2.88 | A |

TABLE 3-continued

| Example | M + 1 Observed | RT | Method |
|---|---|---|---|
| 218 | 662.3 | 2.87 | C |

Ethanediamide, N-[2-[[[(4-fluorophenyl)methyl]amino]carbonyl]-6,7,8,9-tetrahydro-3-hydroxy-7-[[4-(methylsulfonyl)-1-piperazinyl]methyl]-4-oxo-7,10-ethanopyrimido[1,2-a]azepin-10(4H)-yl]-N,N',N'-trimethyl-

| | | | |
|---|---|---|---|
| 219 | 589.4 | 1.14 | H |

Ethanediamide, N'-[2-[[[(3-chloro-4-fluorophenyl)methyl]amino]carbonyl]-6,7,8,9-tetrahydro-3-hydroxy-4-oxo-7-(1-pyrrolidinylmethyl)-7,10-ethanopyrimido[1,2-a]azepin-10(4H)-yl]-N,N-dimethyl-

| | | | |
|---|---|---|---|
| 220 | 563.4 | 1.15 | H |

Ethanediamide, N'-[2-[[[(3-chloro-4-fluorophenyl)methyl]amino]carbonyl]-7-[(dimethylamino)methyl]-6,7,8,9-tetrahydro-3-hydroxy-4-oxo-7,10-ethanopyrimido[1,2-a]azepin-10(4H)-yl]-N,N-dimethyl-

| | | | |
|---|---|---|---|
| 221 | 615.4 | 1.83 | G |

Ethanediamide, N-[7-[[ethyl(2-methoxyethyl)amino]methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-

TABLE 3-continued

| Example | | M + 1 Observed | RT | Method |
|---|---|---|---|---|
| 222 | 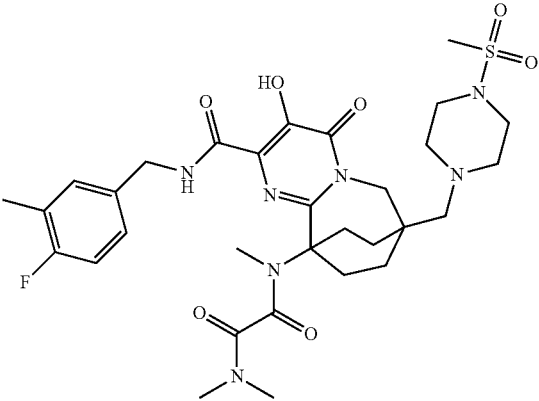 [SMILES: Cc1cc(CNC(=O)c2nc3n(c(=O)c2O)CC2(CN4CCN(S(C)(=O)=O)CC4)CCC3(N(C)C(=O)C(=O)N(C)C)CC2)ccc1F]<br>Ethanediamide, N-[2-[[[(4-fluoro-3-methylphenyl)methyl]amino]carbonyl]-6,7,8,9-tetrahydro-3-hydroxy-7-[[4-(methylsulfonyl)-1-piperazinyl]methyl]-4-oxo-7,10-ethanopyrimido[1,2-a]azepin-10(4H)-yl]-N,N',N'-trimethyl- | 676.4 | 1.78 | G |
| 223 | 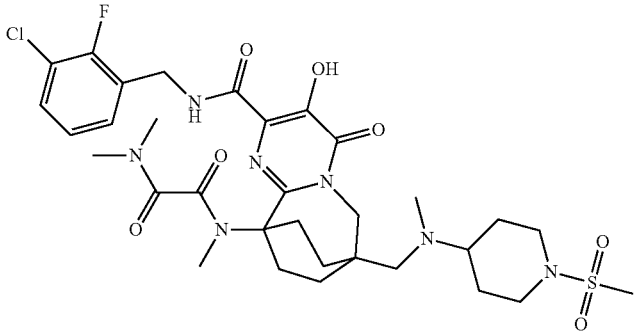 [SMILES: CN(C)C(=O)C(=O)N(C)C12CCC(CN(C)C3CCN(S(C)(=O)=O)CC3)(CC1)Cn1c2nc(C(=O)NCc2cccc(Cl)c2F)c(O)c1=O]<br>Ethanediamide, N-[2-[[[(3-chloro-2-fluorophenyl)methyl]amino]carbonyl]-6,7,8,9-tetrahydro-3-hydroxy-7-[[methyl[1-(methylsulfonyl)-4-piperidinyl]amino]methyl]-4-oxo-7,10-ethanopyrimido[1,2-a]azepin-10(4H)-yl]-N,N',N'-trimethyl- | 724.2 | 3.68 | C |
| 224 | 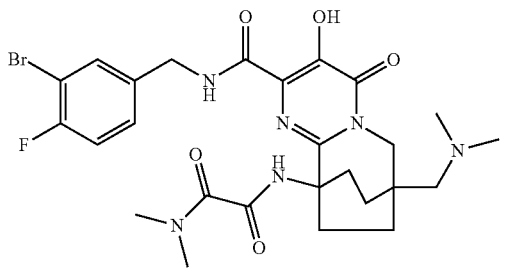<br>Ethanediamide, N'-[2-[[[(3-bromo-4-fluorophenyl)methyl]amino]carbonyl]-7-[(dimethylamino)methyl]-6,7,8,9-tetrahydro-3-hydroxy-4-oxo-7,10-ethanopyrimido[1,2-a]azepin-10(4H)-yl]-N,N-dimethyl- | 609.3 | 1.13 | H |

TABLE 3-continued

| Example | | M + 1 Observed | RT | Method |
|---|---|---|---|---|
| 225 | 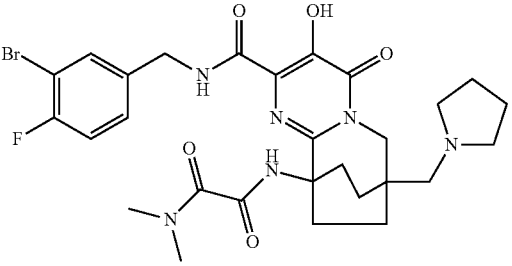 Ethanediamide, N'-[2-[[[(3-bromo-4-fluorophenyl)methyl]amino]carbonyl]-6,7,8,9-tetrahydro-3-hydroxy-4-oxo-7-(1-pyrrolidinylmethyl)-7,10-ethanopyrimido[1,2-a]azepin-10(4H)-yl]-N,N-dimethyl- | 635.3 | 1.17 | H |
| 226 | 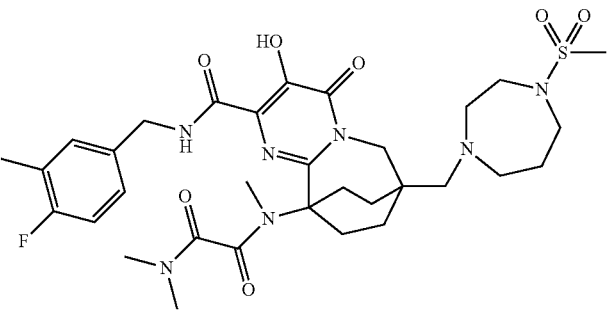 Ethanediamide, N-[2-[[[(4-fluoro-3-methylphenyl)methyl]amino]carbonyl]-7-[[hexahydro-4-(methylsulfonyl)-1H-1,4-diazepin-1-yl]methyl]-6,7,8,9-tetrahydro-3-hydroxy-4-oxo-7,10-ethanopyrimido[1,2-a]azepin-10(4H)-yl]-N,N',N'-trimethyl- | 690.4 | 1.65 | I |
| 227 | 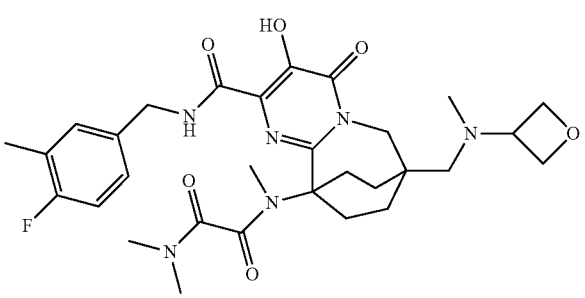 [SMILES: Cc1cc(CNC(=O)c2nc3n(c(=O)c2O)CC2(CN(C)C4COC4)CCC3(N(C)C(=O)C(=O)N(C)C)CC2)ccc1F] Ethanediamide, N-[2-[[[(4-fluoro-3-methylphenyl)methyl]amino]carbonyl]-6,7,8,9-tetrahydro-3-hydroxy-7-[(methyl-3-oxetanylamino)methyl]-4-oxo-7,10-ethanopyrimido[1,2-a]azepin-10(4H)-yl]-N,N',N'-trimethyl- | 599.4 | 1.58 | I |

TABLE 3-continued

| Example | | M + 1 Observed | RT | Method |
|---|---|---|---|---|
| 228 | Ethanediamide, N-[7-[(4-acetylhexahydro-1H-1,4-diazepin-1-yl)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 654.4 | 1.57 | I |
| 229 | Ethanediamide, N'-[2-[[[[3-chloro-4-(dimethylamino)-2-fluorophenyl]methyl]amino]carbonyl]-7-[(dimethylamino)methyl]-6,7,8,9-tetrahydro-3-hydroxy-4-oxo-7,10-ethanopyrimido[1,2-a]azepin-10(4H)-yl]-N,N-dimethyl- | 606.4 | 1.00 | H |
| 230 | Ethanediamide, N-[7-[(1,3-dihydro-2H-isoindol-2-yl)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 631.4 | 1.90 | I |

TABLE 3-continued

| Example | | M + 1 Observed | RT | Method |
|---|---|---|---|---|
| 231 | 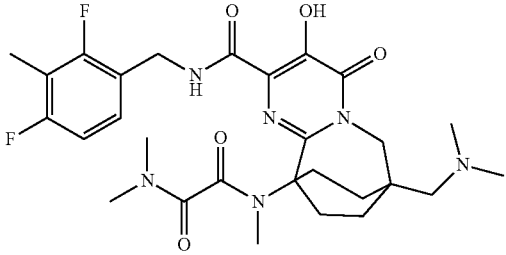 Ethanediamide, N-[2-[[[(2,4-difluoro-3-methylphenyl)methyl]amino]carbonyl]-7-[(dimethylamino)methyl]-6,7,8,9-tetrahydro-3-hydroxy-4-oxo-7,10-ethanopyrimido[1,2-a]azepin-10(4H)-yl]-N,N',N'-trimethyl- | 575.4 | 2.00 | A |
| 232 | 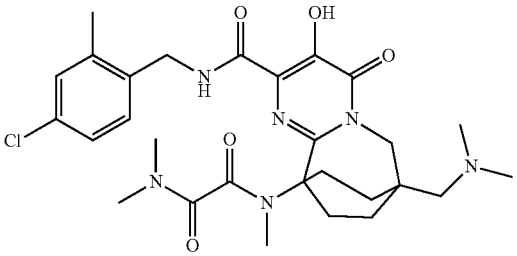 [SMILES: Cc1cc(Cl)ccc1CNC(=O)c1nc2n(c(=O)c1O)CC1(CN(C)C)CCC2(N(C)C(=O)C(=O)N(C)C)CC1] Ethanediamide, N-[2-[[[(4-chloro-2-methylphenyl)methyl]amino]carbonyl]-7-[(dimethylamino)methyl]-6,7,8,9-tetrahydro-3-hydroxy-4-oxo-7,10-ethanopyrimido[1,2-a]azepin-10(4H)-yl]-N,N',N'-trimethyl- | 573.5 | 2.12 | A |
| 233 | 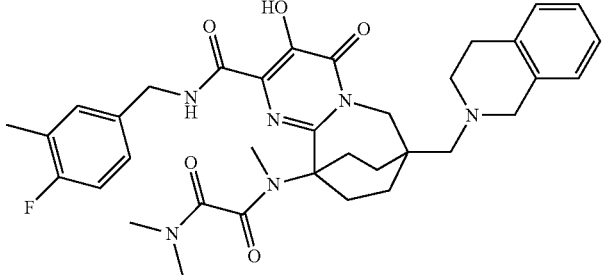 [SMILES: Cc1cc(CNC(=O)c2nc3n(c(=O)c2O)CC2(CN4CCc5ccccc5C4)CCC3(N(C)C(=O)C(=O)N(C)C)CC2)ccc1F] Ethanediamide, N-[7-[(3,4-dihydro-2(1H)-isoquinolinyl)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 645.3 | 1.74 | G |
| 234 | 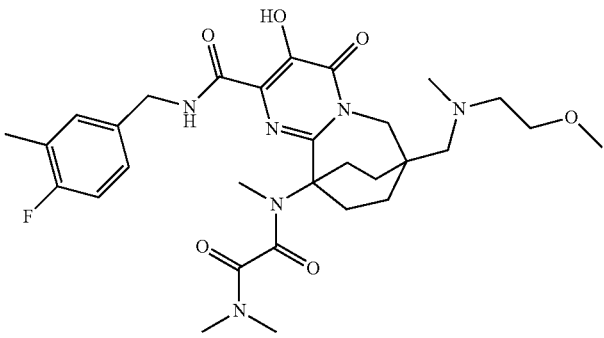 Ethanediamide, N-[2-[[[(4-fluoro-3-methylphenyl)methyl]amino]carbonyl]-6,7,8,9-tetrahydro-3-hydroxy-7-[[(2-methoxyethyl)methylamino]methyl]-4-oxo-7,10-ethanopyrimido[1,2-a]azepin-10(4H)-yl]-N,N',N'-trimethyl- | 601.3 | 1.66 | G |

TABLE 3-continued

| Example | | M + 1 Observed | RT | Method |
|---|---|---|---|---|
| 235 | Ethanediamide, N-[2-[[[(4-fluoro-3-methylphenyl)methyl]amino]carbonyl]-6,7,8,9-tetrahydro-3-hydroxy-7-[(methyl-3-pyridinylamino)methyl]-4-oxo-7,10-ethanopyrimido[1,2-a]azepin-10(4H)-yl]-N,N',N'-trimethyl- | 620.3 | 1.60 | G |
| 236 | Ethanediamide, N-[7-[(4-acetyl-1-piperazinyl)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 640.3 | 1.64 | G |
| 237 | Ethanediamide, N-[7-[(5,7-dihydro-6H-pyrrolo[3,4-b]pyridin-6-yl)methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 632.3 | 1.68 | G |
| 238 | Ethanediamide, N-[7-(5,6-dihydroimidazo[1,2-a]pyrazin-7(8H)-yl)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 661.3 | 1.81 | G |

TABLE 3-continued

| Example | | M + 1 Observed | RT | Method |
|---|---|---|---|---|
| 239 | 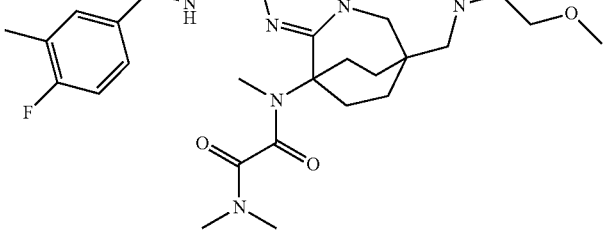 Ethanediamide, N-[2-[[[(4-fluoro-3-methylphenyl)methyl]amino]carbonyl]-6,7,8,9-tetrahydro-3-hydroxy-7-[[(2-methoxyethyl)(1-methylethyl)amino]methyl]-4-oxo-7,10-ethanopyrimido[1,2-a]azepin-10(4H)-yl]-N,N',N'-trimethyl- | 629.3 | 1.70 | G |
| 240 | 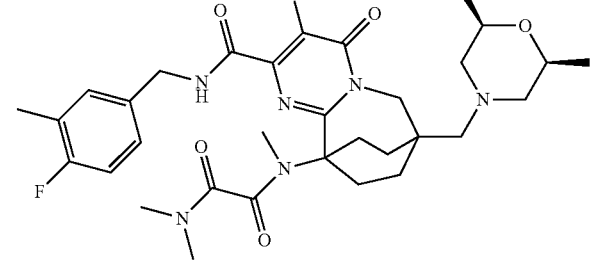 Ethanediamide, N-[7-[[(2R,6S)-2,6-dimethyl-4-morpholinyl]methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 627.3 | 1.71 | G |
| 241 | 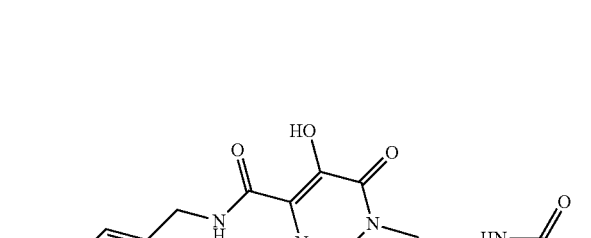 Ethanediamide, N-[2-[[[(4-fluoro-3-methylphenyl)methyl]amino]carbonyl]-6,7,8,9-tetrahydro-3-hydroxy-7-[[(methoxyacetyl)amino]methyl]-4-oxo-7,10-ethanopyrimido[1,2-a]azepin-10(4H)-yl]-N,N',N'-trimethyl- | 601.3 | 1.89 | G |

TABLE 3-continued

| Example | | M + 1 Observed | RT | Method |
|---|---|---|---|---|
| 242 | 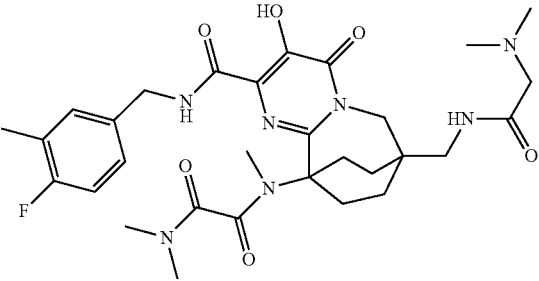<br>Ethanediamide, N-[7-[[[(dimethylamino)acetyl]amino]methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 614.3 | 1.68 | G |
| 243 | 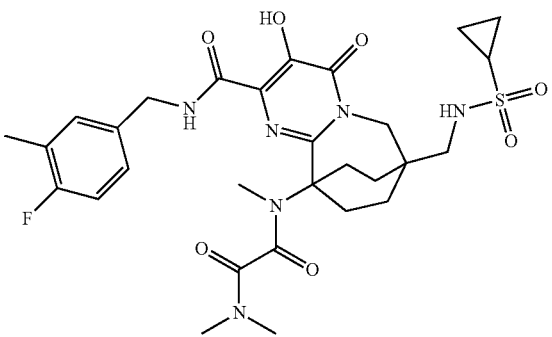 [SMILES: Cc1cc(CNC(=O)c2nc3n(c(=O)c2O)CC2(CNS(=O)(=O)C4CC4)CCC3(N(C)C(=O)C(=O)N(C)C)CC2)ccc1F]<br>Ethanediamide, N-[7-[[[(cyclopropylsulfonyl)amino]methyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 633.2 | 1.65 | G |
| 244 | 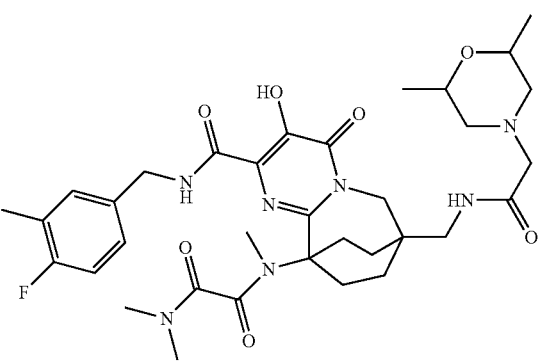<br>Ethanediamide, N-[2-[[[(4-fluoro-3-methylphenyl)methyl]amino]carbonyl]-6,7,8,9-tetrahydro-3-hydroxy-7-[[[(1H-imidazol-1-ylacetyl)amino]methyl]-4-oxo-7,10-ethanopyrimido[1,2-a]azepin-10(4H)-yl]-N,N',N'-trimethyl- | 684.5 | 2.76 | A |

TABLE 3-continued

| Example | M + 1 Observed | RT | Method |
|---|---|---|---|
| 245 | 919.7 | 3.19 | F |

Ethanediamide, N1-[2-[[[(4-fluoro-3-methylphenyl)methyl]amino]carbonyl]-6,7,8,9-tetrahydro-3-hydroxy-4-oxo-7-[[[(3alpha, 5beta, 7alpha,12alpha, 20xi)-3,7,12-trihydroxy-24-oxocholan-24-yl]amino]methyl]-7,10-ethanopyrimido[1,2-a]azepin-10(4H)-yl]-N1, N2, N2-trimethyl-

| 246 | 669.4 | 3.47 | C |

Ethanediamide, N-[2-[[[(4-fluoro-3-methylphenyl)methyl]amino]carbonyl]-6,7,8,9-tetrahydro-3-hydroxy-7-[[[(4-methyl-1-piperazinyl)acetyl]amino]methyl]-4-oxo-7,10-ethanopyrimido[1,2-a]azepin-10(4H)-yl]-N,N',N'-trimethyl-

| 247 | 705.5 | 2.10 | F |

N-(4-((4-fluoro-3-methylbenzyl)carbamoyl)-5-hydroxy-6-oxo-9-(((((2S,3S,4S,5R,6R)-3,4,5,6-tetrahydroxytetrahydro-2H-pyran-2-yl)carbonyl)amino)methyl)-3,7-diazatricyclo[7.2.2.0~2,7~]trideca-2,4-dien-1-yl)-N,N',N'-trimethylethanediamide TABLE 3-continued

| Example | | M + 1 Observed | RT | Method |
|---|---|---|---|---|
| 248 | 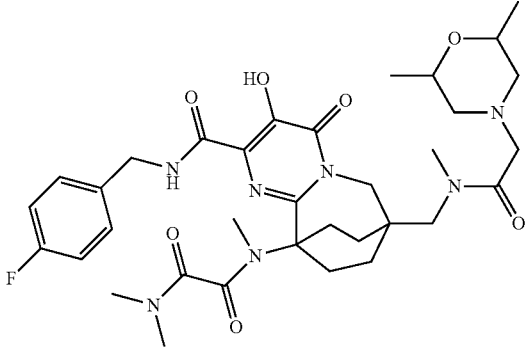 [SMILES: CC1CN(CC(=O)N(C)CC23CCC(N(C)C(=O)C(=O)N(C)C)(CC2)c2nc(C(=O)NCc4ccc(F)cc4)c(O)c(=O)n2C3)CC(C)O1] Ethanediamide, N-[7-[[[(2,6-dimethyl-4-morpholinyl)acetyl]methylamino]methyl]-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 684.4 | 3.42 | C |
| 249 | 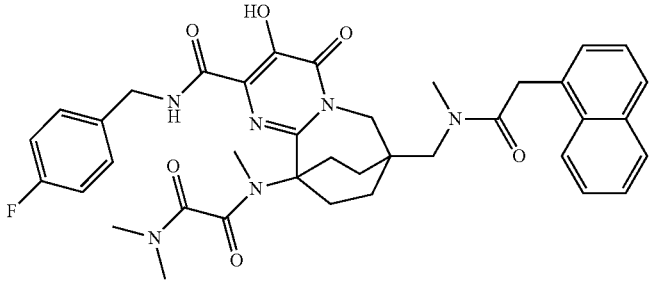 [SMILES: CN(C)C(=O)C(=O)N(C)C12CCC(CN(C)C(=O)Cc3cccc4ccccc34)(CC1)Cn1c2nc(C(=O)NCc2ccc(F)cc2)c(O)c1=O] Ethanediamide, N-[2-[[[(4-fluorophenyl)methyl]amino]carbonyl]-6,7,8,9-tetrahydro-3-hydroxy-7-[[methyl(1-naphthalenylacetyl)amino]methyl]-4-oxo-7,10-ethanopyrimido[1,2-a]azepin-10(4H)-yl]-N,N',N'-trimethyl- | 697.4 | 3.08 | F |
| 250 | 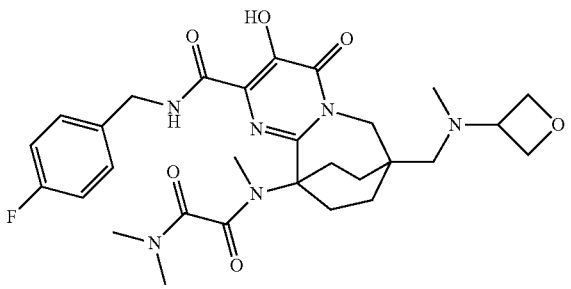 [SMILES: CN(C)C(=O)C(=O)N(C)C12CCC(CN(C)C3COC3)(CC1)Cn1c2nc(C(=O)NCc2ccc(F)cc2)c(O)c1=O] Ethanediamide, N-[2-[[[(4-fluorophenyl)methyl]amino]carbonyl]-6,7,8,9-tetrahydro-3-hydroxy-7-[(methyl-3-oxetanylamino)methyl]-4-oxo-7,10-ethanopyrimido[1,2-a]azepin-10(4H)-yl]-N,N',N'-trimethyl- | 585.4 | 1.48 | I |

TABLE 3-continued

| Example | | M + 1 Observed | RT | Method |
|---|---|---|---|---|
| 251 | | 713.6 | 3.50 | F |
| | Ethanediamide, N-[2-[[[(4-fluorophenyl)methyl]amino]carbonyl]-6,7,8,9-tetrahydro-3-hydroxy-7-[[methyl[3-(octyloxy)-1-oxopropyl]amino]methyl]-4-oxo-7,10-ethanopyrimido[1,2-a]azepin-10(4H)-yl]-N',N'-trimethyl- | | | |
| 252 | | 941.8 | 6.89 | F |
| | Carbamic acid, [[10-[[2-(dimethylamino)-1,2-dioxoethyl]methylamino]-2-[[[(4-fluorophenyl)methyl]amino]carbonyl]-4,8,9,10-tetrahydro-3-hydroxy-4-oxo-7,10-ethanopyrimido[1,2-a]azepin-7(6H)-yl]methyl]methyl-, (3beta)-cholest-5-en-3-yl ester | | | |

TABLE 5

| Example | | M + 1 Observed | RT | method |
|---|---|---|---|---|
| 253 | | 543.2 | 1.77 | G |
| | Ethanediamide, N'-[7-(3-aminopropyl)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | | | |

TABLE 5-continued

| Example | | M + 1 Observed | RT | method |
|---|---|---|---|---|
| 254 | Ethanediamide, N'-[7-(3-(dimethylamino)propyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 571.3 | 1.79 | G |
| 255 | Ethanediamide, N'-[7-(3-(dimethylamino)butyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 585.4 | 1.28 | H |
| 256 | Ethanediamide, N-[7-[3-(dimethylamino)propyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 585.4 | 1.23 | H |
| 257 | Ethanediamide, N-[2-[[[(3-chloro-2-fluorophenyl)methyl]amino]carbonyl]-7-(3,3-difluorobutyl)-6,7,8,9-tetrahydro-3-hydroxy-4-oxo-7,10-ethanopyrimido[1,2-a]azepin-10(4H)-yl]-N,N',N'-trimethyl- | 612.3 | 2.13 | G |

TABLE 5-continued

| Example | | M + 1 Observed | RT | method |
|---|---|---|---|---|
| 258 | Ethanediamide, N-[2-[[[(3-chloro-2-fluorophenyl)methyl]amino]carbonyl]-7-(2,2-difluoroethyl)-6,7,8,9-tetrahydro-3-hydroxy-4-oxo-7,10-ethanopyrimido[1,2-a]azepin-10(4H)-yl]-N,N',N'-trimethyl- | 584.2 | 2.03 | G |
| 259 | Ethanediamide, N-[2-[[[(3-chloro-2-fluorophenyl)methyl]amino]carbonyl]-7-[2-(3,3-difluoro-1-pyrrolidinyl)ethyl]-6,7,8,9-tetrahydro-3-hydroxy-4-oxo-7,10-ethanopyrimido[1,2-a]azepin-10(4H)-yl]-N,N',N'-trimethyl- | 653.4 | 1.27 | H |
| 260 | Ethanediamide, N-[2-[[[(3-chloro-2-fluorophenyl)methyl]amino]carbonyl]-7-[3-(dimethylamino)propyl]-6,7,8,9-tetrahydro-3-hydroxy-4-oxo-7,10-ethanopyrimido[1,2-a]azepin-10(4H)-yl]-N,N',N'-trimethyl- | 605.3 | 1.77 | G |
| 261 | Ethanediamide, N-[7-[2-(1-azetidinyl)ethyl]-2-[[[(3-chloro-2-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 603.4 | 1.36 | H |

TABLE 5-continued

| Example | | M + 1 Observed | RT | method |
|---|---|---|---|---|
| 262 | Ethanediamide, N'-[2-[[[(3-chloro-2-fluorophenyl)methyl]amino]carbonyl]-7-[3-(dimethylamino)propyl]-6,7,8,9-tetrahydro-3-hydroxy-4-oxo-7,10-ethanopyrimido[1,2-a]azepin-10(4H)-yl]-N,N-dimethyl- | 591.4 | 1.33 | H |
| 263 | Ethanediamide, N'-[7-[3-(dimethylamino)propyl]-2-[[[(2-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 557.5 | 1.25 | H |
| 264 | Ethanediamide, N'-[7-[2-(1-azetidinyl)ethyl]-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 569.3 | 1.71 | G |
| 265 | Ethanediamide, N'-[7-[3-(dimethylamino)propyl]-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 557.3 | 1.60 | G |

TABLE 5-continued

| Example | | M + 1 Observed | RT | method |
|---|---|---|---|---|
| 266 | Ethanediamide, N'-[7-(2,2-difluoroethyl)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 536.2 | 1.92 | G |
| 267 | Ethanediamide, N-[2-[[[(3-chloro-2-fluorophenyl)methyl]amino]carbonyl]-7-[4-(dimethylamino)butyl]-6,7,8,9-tetrahydro-3-hydroxy-4-oxo-7,10-ethanopyrimido[1,2-a]azepin-10(4H)-yl]-N,N',N'-trimethyl- | 619.4 | 1.80 | G |
| 268 | Ethanediamide, N-[2-[[[(3-chloro-2-fluorophenyl)methyl]amino]carbonyl]-7-[4-(dimethylamino)butyl]-6,7,8,9-tetrahydro-3-hydroxy-4-oxo-7,10-ethanopyrimido[1,2-a]azepin-10(4H)-yl]-N,N',N'-trimethyl- | 601.4 | 1.72 | G |
| 269 | Ethanediamide, N-[7-(2,2-difluoroethyl)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl- | 550.3 | 2.00 | G |

We claim:

1. A compound of Formula I

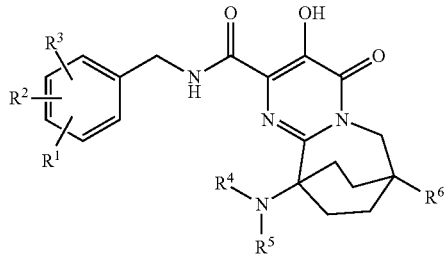

$R^1$ is hydrogen, halo, or alkyl;
$R^2$ is hydrogen, halo, or alkyl;
$R^3$ is hydrogen, halo, or alkyl;
provided that at least one of $R^1$, $R^2$, or $R^3$ is not hydrogen;
$R^4$ is alkylCO, (tetrahydropyranyl)CO, CO($Ar^1$), $CO_2R^7$, CON($R^8$)($R^9$), $COCO_2R^7$, or COCON($R^8$)($R^9$);
$R^5$ is hydrogen or alkyl;
$R^6$ is halo, cyano, N($R^8$)($R^9$), azidoalkyl, haloalkyl, cyanoalkyl, hydroxyalkyl, alkoxyalkyl, ($OCO_2R^7$)alkyl, (OCON($R^8$)($R^9$))alkyl, ($OCOCO_2R^7$)alkyl, (OCOCON($R^8$)($R^9$))alkyl, (OP(O)($OR^7$)$_2$)alkyl, (alkyl$SO_3$)alkyl, (phenyl$SO_3$)alkyl, (tolyl$SO_3$)alkyl, (N($R^8$)($R^9$))alkyl, (alkyl$CONR^8$)alkyl, (pyridinyloxy)alkyl, (alkylthio)alkyl, (N-methylimidazolylthio)alkyl, (N-methyltetrazolylthio)alkyl, (pyridinylthio)alkyl, (alkylSO)alkyl, (alkyl$SO_2$)alkyl, ($Ar^2$)alkyl, or $Ar^2$;
or $R^6$ is CO(N($R^{10}$)($R^{11}$)), CO(N($Ar^2$)($R^{11}$)), or CO(N(($Ar^2$)alkyl)($R^{11}$));
or $R^6$ is N($R^{11}$)CO($R^{12}$) or N($R^{11}$)((CO($R^{12}$)alkyl);
$R^7$ is hydrogen, alkyl, or benzyl;
$R^8$ is hydrogen, alkyl, cycloalkyl, haloalkyl, (cycloalkyl)alkyl, hydroxyalkyl, alkoxyalkyl or dialkylaminoalkyl;
$R^9$ is hydrogen, alkyl, cycloalkyl, haloalkyl, (cycloalkyl)alkyl, hydroxyalkyl, alkoxyalkyl or dialkylaminoalkyl;
or N($R^8$)($R^9$) taken together is azetidinyl, pyrrolidinyl, piperidinyl, piperazinyl, morpholinyl, or homopiperazinyl, and is substituted with 0-3 substituents selected from the group consisting of halo, alkyl, haloalkyl, hydroxy, alkylcarbonyl, and alkylsulfonyl;
or N($R^8$)($R^9$) taken together is piperazinyl substituted with 1 substituent selected from the group consisting of benzyl, $CONMe_2$, $SO_2NMe_2$, tolyl$SO_2$, $SO_2NMe_2$, $Ar_3$ and $COAr^3$;
or N($R^8$)($R^9$) taken together is selected from the group consisting of

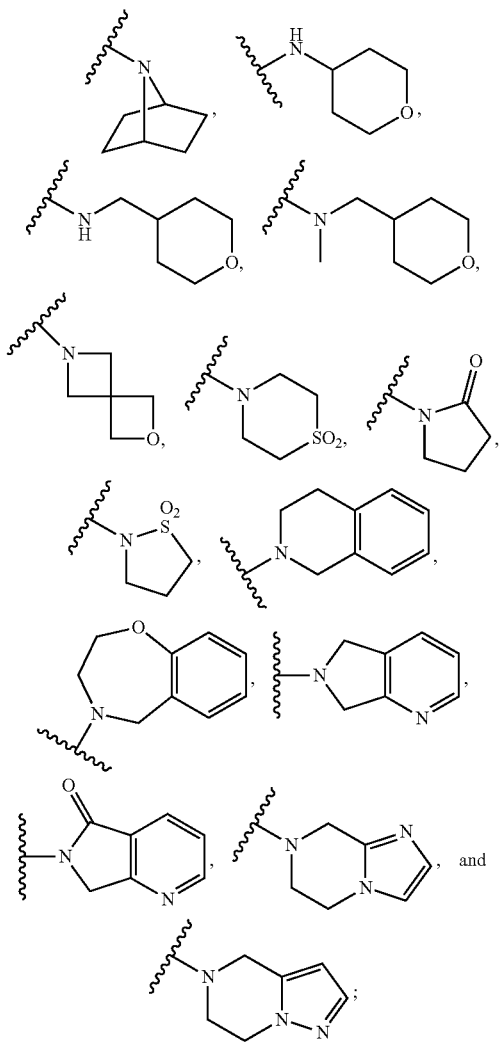

$R^{10}$ is azetidinyl, pyrrolidinyl, piperidinyl, piperazinyl, or morpholinyl, and is substituted with 0-3 substituents selected from the group consisting of halo and alkyl;
or $R^{10}$ is alkyl$SO_2$ or cycloalkyl$SO_2$;
$R^{11}$ is hydrogen or alkyl;
or N($R^{10}$)($R^{11}$) taken together is azetidinyl, pyrrolidinyl, piperidinyl, piperazinyl, or morpholinyl, and is substituted with 0-3 substituents selected from the group consisting of halo and alkyl;
$R^{12}$ is alkyl, alkoxy, N($R^8$)($R^9$), CHO, alkylCO, alkoxyCO, $CO_2R^7$, CON($R^8$)($R^9$), alkyl$SO_2$, cycloalkyl$SO_2$, or pyridinyl;
$Ar^1$ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, pyridinyl, pyridazinyl, pyrimidinyl, pyrazinyl, or hydroxypyridinyl, and is substituted with 0-3 substituents selected from the group consisting of oxo, halo, cyano, benzyl, alkyl, hydroxyl, alkoxy, N($R^8$)($R^9$), $CO_2R^7$, and CON($R^8$)($R^9$);
$Ar^2$ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, pyridinyl, pyridazinyl, or imidazolothionyl, and is substituted with 0-3 alkyl substituents; and
$Ar^3$ is triazolyl, imidazolyl, pyrazolyl, pyrrolyl, phenyl, pyridinyl, pyridazinyl, pyrimidinyl, or pyrazinyl:

or a pharmaceutically acceptable salt thereof.

2. The compound of claim 1 where
$R^1$ is hydrogen, halo, or alkyl;
$R^2$ is hydrogen, halo, or alkyl;
$R^3$ is hydrogen, halo, or alkyl;
provided that at least one of $R^1$, $R^2$, or $R^3$ is not hydrogen;
$R^4$ is alkylCO, (tetrahydropyranyl)CO, CO($Ar^1$), $CO_2R^7$, CON($R^8$)($R^9$), $COCO_2R^7$, or COCON($R^8$)($R^9$);
$R^5$ is hydrogen or alkyl;
$R^6$ is halo, cyano, N($R^8$)($R^9$), azidoalkyl, haloalkyl, cyanoalkyl, hydroxyalkyl, alkoxyalkyl, ($OCO_2R^7$)alkyl, (O CON($R^8$)($R^9$))alkyl, ($OCOCO_2R^7$)alkyl, (OCOCON($R^8$)($R^9$))alkyl, (OP(O)($OR^7$)$_2$)alkyl, (alkyl$SO_3$)alkyl, (phenyl$SO_3$)alkyl, (tolyl$SO_3$)alkyl, (N($R^8$)($R^9$))alkyl, (alkylCON$R^8$)alkyl, (pyridinyloxy)alkyl, (alkylthio)alkyl, (N-methylimidazolylthio)alkyl, (N-methyltetrazolylthio)alkyl, (pyridinylthio)alkyl, (alkylSO)alkyl, (alkyl$SO_2$)alkyl, ($Ar^2$)alkyl, or $Ar^2$;
or $R^6$ is CO(N($R^{10}$)($R^{11}$)), CO(N($Ar^2$)($R^{11}$)), or CO(N(($Ar^2$)alkyl)($R^{11}$));
or $R^6$ is N($R^{11}$)CO($R^{12}$);
$R^7$ is hydrogen, alkyl, or benzyl;
$R^8$ is hydrogen, alkyl, cycloalkyl, haloalkyl, hydroxyalkyl, alkoxyalkyl or dialkylaminoalkyl;
$R^9$ is hydrogen, alkyl, cycloalkyl, haloalkyl, hydroxyalkyl, alkoxyalkyl or dialkylaminoalkyl;
or N($R^8$)($R^9$) taken together is azetidinyl, pyrrolidinyl, piperidinyl, piperazinyl, or morpholinyl, and is substituted with 0-3 substituents selected from the group consisting of halo and alkyl;
$R^{10}$ is azetidinyl, pyrrolidinyl, piperidinyl, piperazinyl, or morpholinyl, and is substituted with 0-3 substituents selected from the group consisting of halo and alkyl;
or $R^{10}$ is alkyl$SO_2$ or cycloalkyl$SO_2$;
$R^{11}$ is hydrogen or alkyl;
or)N($R^{10}$ ($R^{11}$) taken together is azetidinyl, pyrrolidinyl, piperidinyl, piperazinyl, or morpholinyl, and is substituted with 0-3 substituents selected from the group consisting of halo and alkyl;
$R^{12}$ is alkyl, alkoxy, N($R^8$)($R^9$), $CO_2R^7$, CON($R^8$)($R^9$), alkyl$SO_2$, cycloalkyl$SO_2$, or pyridinyl;
$Ar^1$ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, pyridinyl, pyridazinyl, pyrimidinyl, pyrazinyl, or hydroxypyridinyl, and is substituted with 0-3 substituents selected from the group consisting of oxo, halo, cyano, benzyl, alkyl, alkoxy, N($R^8$)($R^9$), $CO_2R^7$, and CON($R^8$)($R^9$); and
$Ar^2$ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, or imidazolothionyl, and is substituted with 0-3 alkyl substituents;
or a pharmaceutically acceptable salt thereof.

3. The compound of claim 1 according to the following structure

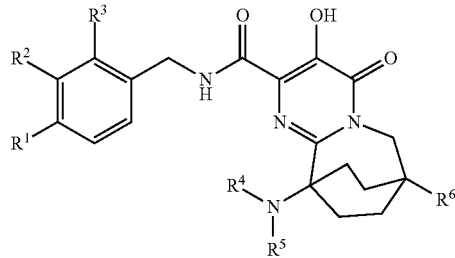

$R^1$ is hydrogen, halo, or alkyl;
$R^2$ is hydrogen, halo, or alkyl;
$R^3$ is hydrogen, halo, or alkyl;
provided that at least one of $R^1$, $R^2$, or $R^3$ is not hydrogen;
$R^4$ is alkylCO, (tetrahydropyranyl)CO, CO($Ar^1$), $CO_2R^7$, CON($R^8$)($R^9$), $COCO_2R^7$, or COCON($R^8$)($R^9$);
$R^5$ is hydrogen or alkyl;
$R^6$ is halo, cyano, N($R^8$)($R^9$), azidoalkyl, haloalkyl, cyanoalkyl, hydroxyalkyl, alkoxyalkyl, (OC(O)$R^7$)alkyl, (OCON($R^8$)($R^9$))alkyl, (OCOCON($R^8$)($R^9$))alkyl, (alkyl$SO_3$)alkyl, (phenyl$SO_3$)alkyl, (tolyl$SO_3$)alkyl, (N($R^8$)($R^9$))alkyl, (alkylCON$R^8$)alkyl, (pyridinyloxy)alkyl, (alkylthio)alkyl, (N-methylimidazolylthio)alkyl, (N-methyltetrazolylthio)alkyl, (pyridinylthio)alkyl, (alkylSO)alkyl, (alkyl$SO_2$)alkyl, ($Ar^2$)alkyl, or $Ar^2$;
or $R^6$ is CO(N($R^{10}$)($R^{11}$)), CO(N($Ar^2$)($R^{11}$)), or CO(N(($Ar^2$)alkyl)($R^{11}$));
or $R^6$ is N($R^{11}$)CO($R^{12}$);
$R^7$ is hydrogen, alkyl, or benzyl;
$R^8$ is hydrogen, alkyl, cycloalkyl, haloalkyl, hydroxyalkyl, alkoxyalkyl or dialkylaminoalkyl;
$R^9$ is hydrogen, alkyl, cycloalkyl, haloalkyl, hydroxyalkyl, alkoxyalkyl or dialkylaminoalkyl;
or N($R^8$)($R^9$) taken together is azetidinyl, pyrrolidinyl, piperidinyl, piperazinyl, or morpholinyl, and is substituted with 0-3 substituents selected from the group consisting of halo and alkyl;
$R^{10}$ is azetidinyl, pyrrolidinyl, piperidinyl, piperazinyl, or morpholinyl, and is substituted with 0-3 subtituents selected from the group consisting of halo and alkyl;
or $R^{10}$ is alkyl$SO_2$ or cycloalkyl$SO_2$;
$R^{11}$ is hydrogen or alkyl;
$R^{12}$ is alkyl, alkoxy, N($R^8$)($R^9$), $CO_2R^7$, CON($R^8$)($R^9$), alkyl$SO_2$, cycloalkyl$SO_2$, or pyridinyl;
$Ar^1$ is isoxazolyl, pyridinyl, pyridazinyl, or hydroxypyridinyl, and is substituted with 0-1 substituents selected from the group consisting of alkyl and CON($R^8$)($R^9$); and
$Ar^2$ is tetrazolyl, triazolyl, oxadiazolyl, imidazolyl, isoxazolyl or imidazolothionyl, and is substituted with 0-1 alkyl substituents;
or a pharmaceutically acceptable salt thereof.

4. The compound of claim 1 where $R^1$ is hydrogen or halo; $R^2$ is hydrogen, halo, or alkyl; and $R^3$ is hydrogen or halo; $R^4$ is COCON$Me_2$; $R^5$ is hydrogen or methyl; $R^6$ is N($R^8$)($R^9$) or (N($R^8$)($R^9$))alkyl; $R^8$ is hydrogen, alkyl, (cycloalkyl)alkyl, cycloalkyl, haloalkyl, hydroxyalkyl, alkoxyalkyl or dialkylaminoalkyl; $R^9$ is hydrogen, alkyl, (cycloalkyl)alkyl, cycloalkyl, haloalkyl, hydroxyalkyl, alkoxyalkyl or dialkylaminoalkyl; or N($R^8$)($R^9$) taken together is azetidinyl, pyrrolidinyl, piperidinyl, piperazinyl, or morpholinyl, and is substituted with 0-3 substituents selected from the group consisting of halo and alkyl.

5. The compound of claim 4 where $R^1$ is hydrogen or halo; $R^2$ is hydrogen, halo, or alkyl; and $R^3$ is hydrogen or halo; $R^4$ is COCON$Me_2$; $R^5$ is hydrogen or methyl; $R^6$ is N($R^8$)($R^9$); $R^8$ is hydrogen, alkyl, or (cycloalkyl)alkyl; $R^9$ is hydrogen, alkyl, or (cycloalkyl)alkyl; or N($R^8$)($R^9$) taken together is azetidinyl, pyrrolidinyl, piperidinyl, piperazinyl, or morpholinyl.

6. The compound of claim 1 where $R^4$ is COCON$Me_2$ and $R^5$ is hydrogen or methyl.

7. The compound of claim 6 where $R^6$ is dialkylamino, ((cycloalkyl)alkyl)(alkyl)amino, azetidinyl, pyrrolidinyl, or morpholinyl.

8. The compound of claim 7 where $R^1$ is hydrogen or halo; $R^2$ is hydrogen, halo, or methyl; and $R^3$ is hydrogen or halo.

9. The compound of claim 1 selected from the group consisting of ethanediamide, N-[7-(dimethylamino)-2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-;

ethanediamide, N-[2-[[[(4-fluoro-3-methylphenyl)methyl]amino]carbonyl]-6,7,8,9-tetrahydro-3-hydroxy-4-oxo-7-(1-pyrrolidinyl)-7,10-ethanopyrimido[1,2-a]azepin-10(4H)-yl]-N,N',N'-trimethyl-;

ethanediamide, N'-[2-[[[(3-chloro-2-fluorophenyl)methyl]amino]carbonyl]-7-(dimethylamino)-6,7,8,9-tetrahydro-3-hydroxy-4-oxo-7,10-ethanopyrimido[1,2-a]azepin-10(4H)-yl]-N,N-dimethyl-;

ethanediamide, N'-[2-[[[(4-fluoro-3-methylphenyl)methyl]amino]carbonyl]-6,7,8,9-tetrahydro-3-hydroxy-7-(4-morpholinyl)-4-oxo-7,10-ethanopyrimido[1,2-a]azepin-10(4H)-yl]-N,N-dimethyl-;

ethanediamide, N'-[2-[[[(4-fluorophenyl)methyl]amino]carbonyl]-6,7,8,9-tetrahydro-3-hydroxy-7-(4-morpholinyl)-4-oxo-7,10-ethanopyrimido[1,2-a]azepin-10(4H)-yl]-N,N-dimethyl-;

ethanediamide, N-[7-(dimethylamino)-2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-;

ethanediamide, N-[2-[[[(4-fluorophenyl)methyl]amino]carbonyl]-6,7,8,9-tetrahydro-3-hydroxy-7-(4-morpholinyl)-4-oxo-7,10-ethanopyrimido[1,2-a]azepin-10(4H)—N—N',N'-trimethyl-; and ethanediamide, N-[2-[[[(3-chloro-2-fluorophenyl)methyl]amino]carbonyl]-6,7,8,9-tetrahydro-3-hydroxy-7-(4-morpholinyl)-4-oxo-7,10-ethanopyrimido[1,2-a]azepin-10(4H)-yl]-N,N',N'-trimethyl-;

or a pharmaceutically acceptable salt thereof.

* * * * *